(12) United States Patent
Kim et al.

(10) Patent No.: US 7,517,899 B2
(45) Date of Patent: Apr. 14, 2009

(54) PHENYLAMINOPROPANOL DERIVATIVES AND METHODS OF THEIR USE

(75) Inventors: Callain Younghee Kim, Collegeville, PA (US); Paige Erin Mahaney, Pottstown, PA (US); Eugene John Trybulski, Huntingdon Valley, PA (US); Puwen Zhang, Audobon, PA (US); Eugene Anthony Terefenko, Center Valley, PA (US); Casey McComas, Phoenixville, PA (US); Michael Anthony Marella, Limerick, PA (US); Richard Dale Coghlan, Phoenixville, PA (US); Gavin David Heffernan, Florence, NJ (US); Stephen Todd Cohn, Reading, PA (US); An Thien Vu, Pottstown, PA (US); Joseph Peter Sabatucci, Collegeville, PA (US); Fei Ye, Audubon, PA (US)

(73) Assignee: Wyeth, Madison, NJ (US)

( * ) Notice: Subject to any disclaimer, the term of this patent is extended or adjusted under 35 U.S.C. 154(b) by 505 days.

(21) Appl. No.: 11/091,885

(22) Filed: Mar. 28, 2005

(65) Prior Publication Data

US 2005/0222148 A1 Oct. 6, 2005

Related U.S. Application Data

(60) Provisional application No. 60/569,863, filed on May 11, 2004, provisional application No. 60/557,651, filed on Mar. 30, 2004.

(51) Int. Cl.
*A61K 31/40* (2006.01)
*A61K 31/415* (2006.01)
*C07D 235/00* (2006.01)
*C07D 209/04* (2006.01)

(52) U.S. Cl. .................... 514/394; 514/418; 548/304.4; 548/491

(58) Field of Classification Search .............. 548/304.4, 548/491; 514/394, 418
See application file for complete search history.

(56) References Cited

U.S. PATENT DOCUMENTS

| | | | |
|---|---|---|---|
| 3,454,554 A | 7/1969 | Biel et al. ................. 260/239 |
| 4,123,543 A | 10/1978 | Jonsson et al. ............. 424/272 |
| 4,221,919 A | 9/1980 | Grimova et al. ............ 562/465 |
| 4,229,449 A | 10/1980 | Melloni et al. ........... 514/239.2 |
| 4,271,160 A | 6/1981 | Melloni et al. ........... 514/233.8 |
| 4,310,524 A | 1/1982 | Wiech et al. ............... 514/217 |
| 4,535,186 A | 8/1985 | Husbands et al. .......... 564/336 |
| 4,826,844 A | 5/1989 | Husbands et al. .......... 514/252 |
| 5,502,047 A | 3/1996 | Kavey ...................... 514/183 |
| 5,516,774 A | 5/1996 | Albright et al. ............ 514/220 |
| 5,648,511 A | 7/1997 | Ng et al. ................... 558/345 |
| 6,380,155 B1 | 4/2002 | Barazanji et al. ............. 514/2 |
| 6,703,389 B2 | 3/2004 | Wong et al. .............. 514/239.2 |
| 7,414,052 B2 * | 8/2008 | Vu et al. .................. 514/230.5 |
| 2002/0107249 A1 | 8/2002 | Wong et al. .............. 514/238.5 |
| 2003/0008860 A1 | 1/2003 | Bakker-Arkema et al. ... 514/215 |
| 2004/0019101 A1 | 1/2004 | Karlstadt et al. ............ 514/464 |
| 2004/0143008 A1 | 7/2004 | Deecher et al. ............. 514/521 |
| 2004/0152710 A1 | 8/2004 | Deecher et al. ......... 514/255.04 |
| 2004/0180879 A1 | 9/2004 | Deecher et al. .......... 514/225.8 |
| 2005/0130987 A1 | 6/2005 | Mahaney et al. ....... 514/253.05 |

FOREIGN PATENT DOCUMENTS

| | | |
|---|---|---|
| DE | 2556474 C2 | 8/2004 |
| EP | 0 065 757 B1 | 12/1982 |
| EP | 0 135 905 A2 | 4/1985 |
| EP | 0 303 961 A1 | 2/1989 |
| EP | 0 208 235 B1 | 1/1990 |
| EP | 0 636 608 A1 | 2/1995 |
| EP | 0 636 609 A1 | 2/1995 |
| EP | 0 743 064 A1 | 11/1996 |
| EP | 1 266 659 A1 | 12/2002 |
| GB | 2 362 826 A | 5/2001 |
| WO | 91/18602 A1 | 12/1991 |
| WO | WO 93/15051 A1 | 8/1993 |
| WO | WO 95/18105 A1 | 7/1995 |

(Continued)

OTHER PUBLICATIONS

Chemical Abstracts Service; 1997, Elker, A. et al., "Aminolysis of derivatives of trans-3-phenylglycidic acid with aromatic amines, IV" XP002338398 retrieved from STN Dababase accession No. 1979:420066 abstract & Archiv Der Pharmazie ((Weinheim, Germany), 312(1), 26-34, (1979).

(Continued)

*Primary Examiner*—Rei-Tsang Shiao
*Assistant Examiner*—Susannah Chung
(74) *Attorney, Agent, or Firm*—Woodcock Washburn LLP

(57) ABSTRACT

The present invention is directed to phenylaminopropanol derivatives of formula I:

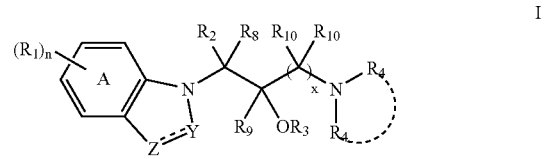

or a pharmaceutically acceptable salt thereof, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

28 Claims, 2 Drawing Sheets

FOREIGN PATENT DOCUMENTS

| WO | 96/05818 A1 | 2/1996 |
|---|---|---|
| WO | WO 97/15556 A1 | 5/1997 |
| WO | 97/35586 A1 | 10/1997 |
| WO | WO 98/14208 A1 | 4/1998 |
| WO | WO 98/25901 A1 | 6/1998 |
| WO | 99/44601 A1 | 9/1999 |
| WO | 99/55694 A1 | 11/1999 |
| WO | WO 00/02551 A1 | 1/2000 |
| WO | 00/59851 A1 | 10/2000 |
| WO | WO 00/66166 A1 | 11/2000 |
| WO | WO 00/66556 A1 | 11/2000 |
| WO | 01/01973 A2 | 1/2001 |
| WO | WO 01/55130 A2 | 8/2001 |
| WO | WO 01/55134 A2 | 8/2001 |
| WO | 01/72708 A2 | 10/2001 |
| WO | WO 02/02520 A1 | 1/2002 |
| WO | WO 02/22572 A1 | 3/2002 |
| WO | 02/064543 A2 | 8/2002 |
| WO | 02/078691 A1 | 10/2002 |
| WO | 03/010169 A1 | 2/2003 |
| WO | 03/037334 A1 | 5/2003 |
| WO | 03/053426 A1 | 7/2003 |
| WO | 03/077897 A1 | 9/2003 |
| WO | 2004/016272 A1 | 2/2004 |
| WO | 2004/089942 A2 | 10/2004 |

OTHER PUBLICATIONS

U.S. Appl. No. 10/963,458, filed Oct. 12, 2004, Mahaney et al.
U.S. Appl. No. 10/962,881, filed Oct. 12, 2004, Mahaney.
U.S. Appl. No. 10/963,064, filed Oct. 12, 2004, Trybulski et al.
U.S. Appl. No. 10/963,111, filed Oct. 12, 2004, Trybulski et al.
U.S. Appl. No. 10/962,880, filed Oct. 12, 2004, Trybulski et al.
U.S. Appl. No. 10/962,971, filed Oct. 12, 2004, Mahaney et al.
U.S. Appl. No. 10/962,897, filed Oct. 12, 2004, Deecher et al.
U.S. Appl. No. 11/013,019, filed Dec. 15, 2004, Leventhal et al.
U.S. Appl. No. 11/091,291, filed Mar. 28, 2005, Vu et al.
Acs, N. et al., "Estrogen improves impaired musculocutaneous vascular adrenergic reactivity in pharmacologically ovariectomized rats: a potential peripheral mechanism for hot flashes?" *Endocrinology*, 2001, 15: 68-73.
Ahmar, M. et al., "Enzymatic resolution of methyl 2-alkyl-2-arylacetates" *Tetrahedron Lett.*, 1989, 30(50): 7053-7056.
Ainsworth, D. P. et al., "Syntheses of Heterocyclic Compounds. Part XVI. Preparative Routes to Indoles with t-Amine Substituents in the Benzene Ring," *J. Chem. Soc.[section] C: Organic* 1967, 4:315-19.
Baker, W. et al., "Nonpeptide renin inhibitors employing a novel 3-aza(or oxa)-2,4-dialkyl glutaric acid moiety as a P2/P3 amide bond replacement," *J. Med. Chem.* 1992, 35 (10), 1722-1734.
Barberis, C. et al., "Molecular Pharmacology of AVP and OT Receptors and Therapeutic Potential," *Drug News Perspect*, Jun. 1999, 12(5):279-292.
Barlow, D. H., "Venlafaxine for hot flushes," *Lancet*, Dec. 16, 2000, 356(9247): 2025-2026.
Barton, D. et al., "Hot Flashes—Aetiology and Management," *Drugs and Aging*, 2001, 18(8): 597-606.
Berendsen, H. H. G., "Effect of tibolone and raloxifene on the tail temperature of oestrogen-deficient rats," *European Journal of Pharmacology*, 2001, 419(1): 47-54.
Berendsen, H. H. G., "Hot Flushes and serotonin," *Journal of the British Menopause Society*, Mar. 2002, 8(1): 30-34.
Berendsen, H. H. G., "The role of serotonin in hot flushes," *Maturitas*, 2000, 36(3): 155-164.
Brück, K. et al., "Adaptive changes in thermoregulation and their neuropharmacological basis" In: Schönbaum E. et al. (eds.). *Thermoregulation: Physiology and Biochemistry*, New York, Pergamon Press, (1991) pp. 255-307.
Bugle, R. C., et al., "Reduction of Azanaphthalenes by Sodium Borohydride in Trifluoroacetic Acid," *Org. Chem.* 1979, 44, 1719-1720.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Bundgaard, H. et al., "Glycolamide Esters as Biolabile Prodrugs of Carboxylic Acid Agents: Synthesis, Stabililty, Bioconversion, and Physicochemical Properties," *J. of Pharmaceutical Sciences*, Apr. 1988, 77(4):285-298.
Bundgaard, H., "Means to enhance penetration; Prodrugs as a means to improve the delivery of peptide drugs," *Advanced Drug Delivery Reviews*, 1992, 8, 1-38.
Cacchi, S. et al., "3-Aryl-2-Unsubstituted Indoles through the Palladium-Catalysed Reaction of o-Ethynyltrifluoroacetanilide with Aryl Iodides," *Synlett* 1997, 12:1363-1366.
Caliendo, G. et al., "Synthesis and Vasorelaxant Activity of New 1,4-benzoxazine Derivatives Potassium Channel Openers," *Bioorganic &Medicinal Chemistry*, 2002, 10:2663-2669.
Campaigne, E. et al., "Benzo[b ]thiophene Derivatives. XXVII. 5-Methoxy-6-halo-3-b-acetamidoethylbenzo[b ]thiophenes, Blocked Analogs of Melatonin," *J. Heterocyclic Chem.* 1983, 20, 1697-1703.
Casper, R. F. et al., "Neuroendocrinology of menopausal flushes: an hypothesis of flush mechanism," *Clinical Endocrinology*, 1985, 22: 293-312.
Cavagnol, J. C. et al., "1-Alkyl-1,2,3,4-tetrahydroquinoxalines," *J. Am. Chem. Soc.* 1947, 69, 795-799.
Clinical Trial: "Phase III Randomized Study of Medroxyprogesterone Versus Venlafaxine in Women With Symptomatic Hot Flashes", www.clinicaltrials.gov sponsored by the National Institutes of Health, Study ID Nos. CDR0000069217; NCCTG-N99C7; NCI-P02-0204, 2003, 6 pages.
Cook, G. R. et al., "Stereochemical Consequences of the Lewis Acid-Promoted 3-Aza-Cope Rearrangement of N-Alkyl-N-Allyl Enamines," *Tetrahedron*, 1994, 50(14):4105.
de Keyser, Y, et al., "Cloning and characterization of the human V3 pituitary vasopressin receptor," *FEBS Letters*, 1994, 356:215-220.
Derick, S. et al., "[1-Deamino-4-Cyclohexylalanine] Arginine Vasopressin: A Potent and Specific Agonist for Vasopressin $V_{1b}$ Receptors," *Endocrinology*, Dec. 2002, 143(12): 4655-4664.
Eliel, E. L., *Stereochemistry of Carbon Compounds*, McGraw Hill, NY (1962) Ch. 4, pp. 46-87.
El-Subbagh, H. I. et al., "Synthesis and Antitumor Activity of Some New Substituted Quinolin-4-one and 1,7-Naphthyridin-4-one Analogs," *Arch. Pharm.* 1999, 332:19-24.
Fink, G. et al., "Oestrogen and mental state," *Nature*, 1996, 383(6598): 306.
Folny, V. et al., "Pancreatic vasopressin $V_{1b}$ receptors: characterization in In-R1-G9 cells and localization in human pancreas," *Am. J. Physiol. Endocrinol. Metab.*, May 7, 2003, 285: E566-E576.
Freedman, R. R. et al., "Adrenergic mechanism in menopausal hot flushes," *Obstet Gynecol*, 1990, 76:573-578.
Freedman, R. R. et al., "Clonidine raises the sweating threshold in symptomatic but not asymptomatic postmenopausal women," *Fertility & Sterility*, 2000, 74(1): 20-3.
Freedman, R. R., "Physiology of hot flashes," *American Journal of Human Biology*, 2001, 13: 453-464.
French, N., "$\alpha_2$-Adrenoceptors and $I_2$ sites in the mammalian central nervous system," *Pharmacol. Ther.*, 1995, 68(2): 175-208.
Greene, T.W. and Wuts, P.G.M., *Protective Groups in Organic Synthesis* 2d. Ed., Wiley & Sons, 1991.
Gribble, G. W., "Reactions of Sodium Borohydride in Acidic Media; VI. Reduction of Indoles with Cyanoborohydride in Acetic Acid," *Synthesis*, 1977, 12:859-860.
Griebel, G. et al. "Anxiolytic- and antidepressant-like effects of the non-peptide vasopressin $V_{1b}$ Receptor antagonist, SSR149415, suggest an innovative approach for the treatment of stress-related disorders," *PNAS*, Apr. 30, 2002, 99(9): 6370-6375.
Griebel, G. et al., "The Vasopressin $V_{1b}$ Receptor as a Therapeutic Target in Stress-related Disorders," *Current Drug Targets- CNS Neurological Disorders*, 2003, 2:191-200.
Harrison, I. et al., "Nonsteroidal antiinflammatory agents. I. 6-substituted 2-naphthylacetic acids," *J. Med. Chem.* 1970, 13(2), 203-5.
Higuchi and Stella (eds.), *Prodrugs as Novel Drug Delivery Systems*, American Chemical Society (1975), pp. 1-115 and 196-223.

Jacques, J. et al., *Enantiomers, Racemates and Resolutions*, Wiley Interscience, NY (1981) pp. 251-434.

Janowsky, D. S. et al., "Desipramine: an overview," *Journal of Clinical Psychiatry*, 1984, 45(10 Pt 2): 3-9.

Katovich, M. J. et al., "Alpha-adrenergic mediation of the tail skin temperature response to naloxone in morphine-dependent rats," *Brain Research*, 1987, 426: 55-61.

Katovich, M. J. et al., *Proceedings of the Society for Experimental Biology & Medicine*, 1990, 193(2): 129-35.

Kende, A. et al., "Regioselective C-3 Alkylations of Oxindole Dianion," *Synth. Comm.* 12(1): 1-10 (1982).

Kramer et al., In: Murphy et al., 3rd *Int'l Symposium on Recent Advances in Urological Cancer Diagnosis and Treatment-Proceedings*, Paris, France: SCI: 3-7 1992.

Krogsgaard-Larsen, et al., (ed). *Design and Application of Prodrugs, Textbook of Drug Design and Development*, Chapter 5, 113-191, 1991.

Kronenberg, F. et al., "Thermoregulatory Physiology of Menopausal Hot Flashes: A Review," *Can. J. Physiol. Pharmacol.*, 1987, 65:1312-1324.

Kucerovy, A. et al., "The Reduction of Indolin-2-Ones With Sodium Bis(2-Methoxyethoxy)Aluminum Hydride," *Synth. Commun.* 1992, 22:729-733.

Lászlóo, F. A. et al., "Pharmacology and Clinical Perspectives of Vasopressin Antagonists," *Pharmacol Rev*, 1991, 43(1):73-108.

Ley, S.V. et al., "Use of polymer supported reagents for clean multistep organic synthesis: preparation of amines and amine derivatives from alcohols for use in compound library generation," *J. Chem. Soc. Perkin Trans.* 1; 15; 1998; 2239-2242.

Lolait, S. J. et al., "Extrapituitary expression of the rat V1b vasopressin receptor gene," *Neurobiology*, Jul. 1995, 92, 6783-6787.

Loprinizi, C. L. et al. "Pilot Evaluation of Venlafaxine Hydrochloride for the Therapy of Hot Flashes in Cancer Survivors," *Journal of Clinical Oncology*, Jul. 1998, 16(7): 2377-2381.

Loprinzi, C.L. et al., "Venlafaxine in management of hot flashes in survivors of breast cancer: a randomized controlled trial," *Lancet*, Dec. 16, 2000, 356(9247): 2059-2063.

Mackinnon et al., "$\alpha_2$ Adrenoceptors: more subtypes but fewer functional differences," *TIPS*, 1994, 15: 119-123.

Manning, M. et al., "Discovery, development, and some uses of vasopressin and oxytocin antagonists," *J Lab Clin Med*, Dec. 1989, 114(6):617-632.

Manov et al., "Solid-Phase Synthesis of Polyamine Spider Toxins and Correlation with the Natural Products by HPLC-MS/MS," *Helvetica Chimica Acta*, 2002, 85(9):2827-2846.

Merchenthaler et al., "The effect of estrogens and antiestrogens in a rat model for hot flush," *Maturitas*, 1998, 30(3): 307-316.

Monguzzi, R. et al., "Synthesis of new $\alpha$-hydrazinoarylacetic acids and derivatives," *Farmaco, Edizione Scientifica*, 1976, 31(8), 549-60.

Moon, S. et al., "An Efficient Conversion of Chiral $\alpha$-Amino Acids to Enantiomerically Pure 3-Amino Cyclic Amines," *Synth. Commun.* 1998, 28(21), 3919-3926.

Morin, S. M., "Atomoxetine Selectively Induces Fos Expression in the Rat Prefrontal Cortex," Presented at Society for Neuroscience Annual Meeting (SFN); Nov. 2-7, 2002, Orlando, FL.

Odle, R. et al., "Conversion of 2-Halo-*N*-allylanilines to Indoles via Palladium(0) Oxidative Addition-Insertion Reactions," *J. Org. Chem.*, 1980, 45:2709-2710.

Olagbemiro, T. O. et al., "Synthesis and Reactions of 3-Phenyl-3,4-Quinoxalin-2(1H)-one and its Heterocyclic Analogues," *Bull Soc. Chim. Belg.* 1987, 96, 473-480.

Pacholczyk, T. et al., "Expression cloning of a cocaine-and antidepressant-sensitive human noradrenaline transporter," *Nature*, 1991, 350(6316): 350-4.

Panek, D.U. et al., "Effect of continuous intraventricular estrogen or catechol estrogen treatment on catecholamine turnover in various brain regions," *J. Pharmacol. Exp. Ther.*, 1986, 236(3): 646-652.

Prasad, P.D., et al., "Functional expression of the plasma membrane serotonin transporter but not the vesicular monoamine transporter in human placental trophoblasts and choriocarcinoma cells," *Placenta*, 1996, 17(4): 201-7.

Quella, S. K. et al., "Pilot evaluation of Venlafaxine for the treatment of hot flashes in men undergoing androgen ablation therapy for prostate cancer," *The Journal of Urology*, Jul. 1999, 162: 98-102.

Raucher, S. et al., "Synthesis of Substituted Indoles via Meerwein Arylation," *J. Org. Chem.* 1983, 48(12):2066-2069.

*Remington's Pharmaceutical Sciences*, 17th Ed., Gennaro, A. R. (Ed.), Mack Publishing Company, Easton, PA (1985) pp. 1409-1677.

Reneric, J-Ph. et al., "Idazoxan and 8-OH-DPAT modify the behavioral effects induced by either NA, or 5-HT, or dual NA/5-HT reuptake inhibition in the rat forced swimming test," *Nueropsychopharmacology*, Apr. 2001, 24(4): 379-390.

Robertson, D. W. et al., "Dihydropyridazinone Cardiotonics: Synthesis and Inotropic Activity of 5'-(1,4,5,6-Tetrahydro-6-oxo-3-pyridazinyl)spiro[cycloalkane-1,3'-[3*H*]indol]-2'(1'*H*)-ones," *J. Med. Chem.* 1987, 30:824-829.

Rosenberg, J. et al., "Hypothesis: pathogenesis of postmenopausal hot flush," *Medical Hypotheses*, 1991, 35: 349-350.

Saito, M. et al., "Molecular cloning and characterization of rat V1b vasopressin receptor : Evidence for its expression in extra-pituitary tissues," *Biochem. Biophys. Res. Commun.*, 1995, 212(3), 751-757.

Schmid, C. R. et al., "Synthesis of 2,3-*O*-Isopropylidene-D-glyceraldehyde in High Chemical and Optical Purity: Observations on the Development of a Practical Bulk Process," *J. Org. Chem.* 1991, 56:4056-4058.

Serradeil-Le Gal, C. et al., "Functional and Pharmacological Characterization of the First Specific Agonist and Antagonist for the V1b Receptor in Mammals," *Stress* Sep. 2003, 6(3):199-206.

Serradeil-Le Gal, C. et al., "Nonpeptide vasopressin receptor antagonists: development of selective and orally active $V_{1a}$, $V_2$ and $V_{1b}$ receptor ligands," *Progress in Brain Research*, 2002, 139:197-210.

Serradeil-Le Gal, et al., "Biological and Pharmacological Properties of SR 49059, a New, Potent, Nonpeptide Antagonist of Rat and Human Vasopressin $V_{1a}$ Receptors," *J Clin Invest*, 1993, 92(1):224-231.

Serradeil-Le Gal. C. et al., "Characterization of (2S,4R)-1-[5-Chloro-1-[(2,4-dimethyoxyphenyl)sulfonyl]-3-(2-methoxyphenyl)-2-oxo-2,3-dihydro-1H-indol-3-yl]-4-hydroxy-N,N-dimethyl-2-pyrrolidine carboxamide (SSR149415), a Selective and Orally Active Vasopressin $V_{1b}$ Receptor Antagonist," *J Pharmacol Exp Ther*, 2002, 300(3):1122-30.

Sharpless, et al., "Asymmetric Epoxidation of Allyl Alcohol: Efficient Routes to Homochiral $\beta$-Adrenergic Blocking Agents," *J. Org. Chem.* 1986, 51, 3710-3712.

Shaw, C. R., "The perimenopausal hot flash: epidemiology, physiology, and treatment," *Nurse Practitioner*, Mar. 1997, 22: 55-56, 61-66.

Stearns, V. et al., "A pilot trial assessing the efficacy of paroxetine hydrochloride (Paxil) in controlling hot flashes in breast cancer survivors," *Ann Oncol.*, 2000,11:17-22.

Stearns, V. et al., "Hot flushes," *Lancet*, Dec. 7, 2002, 360(9348): 1851-1861.

Stearns, V. et al., "Paroxetine controlled release in the treatment of menopausal hot flashes," *JAMA*, 2003, 289:2827-2834.

Sugimoto, T. et al., "Molecular Cloning and Functional Expression of a cDNA Encoding the Human $V_{1b}$ Vasopressin Receptor," *J. Biol. Chem.*, Oct. 28, 1994, 269(43) : 27088-27092.

Tahara, A. et al., "Pharmacological profile of YM087, A Novel Potent Nonpeptide Vasopressin $V_{1A}$ and $V_2$ Receptor Atagonist, in Vitro and in Vivo," *JPET*, 1997, 282(1):301-308.

Ventura, M. A. et al., "Gene and cDNA cloning and characterization of the mouse V3/V1b pituitary vasopressin receptor," *Journal of Molecular Endocrinology*, 1999, 22, 251-260.

Waldinger et al., "Treatment of hot flushes with mirtazapine: four case reports," *Maturitas*, 2000, 36(3): 165-168.

Wersinger, S. R. et al., "Vasopressin V1b receptor knockout reduces aggressive behavior in male mice," *Mol Psychiatry*, 2002, 7:975-984.

Wheeler, K. W., "Some 2-Substituted 2H-1,4-Benzoxazin-3(4H)-ones," *J. Med. Pharm. Chem.* 1962, 5:1378-1383.

Widder, et al. (ed.), *Methods in Enzymology*, vol. 112, Academic Press (1985), pp. 309-396.

Wilen, S.H. *Tables of Resolving Agents and Optical Resolutions,* pp. 268-298, E.L. Eliel, Ed., University of Notre Dame Press, Notre Dame, IN 1972.

Wilen, S.H., et al., "Strategies in optical resolutions," *Tetrahedron,* 33:2725-2736, 1977.

Wu, X-Y. et al., "Highly Enantioselective Epoxidation of α,β-Unsaturated Esters by Chiral Dioxirane," *J. Am. Chem. Soc.,* 2002, 124, 8792-8793.

Yamamura, Y. et al., "Characterization of a novel aquaretic agent, OPC-31260, as an orally effective, nonpeptide vasopressin $V_2$ receptor antagonist," *Br J Pharmacol,* 1992, 105(4):787-791.

Yang, D. et al., "Epoxidation of Olefins Using Methyl(trifluoromethyl)dioxirane Generated in Situ," *J. Org. Chem.* 1995, 60, 3887-3889.

Zhang, W. et al., "Synergistic Effects of Olanzapine and Other Antipsychotic Agents in Combination with Fluoxetine on Norepinephrine and Dopamine Release in Rat Prefrontal Cortex," *Neuropsychopharmacology,* 2000, 23(3):250-262.

Zhang, Z. et al., "A General Method for the Preparation of 4- and 6-Azaindoles," *J. Org. Chem.,* 2002, 67:2345-2347.

\* cited by examiner

PHENYLAMINOPROPANOL DERIVATIVES AND METHODS OF THEIR USE

CROSS REFERENCE TO RELATED APPLICATIONS

This application claims the benefit of U.S. Application No. 60/557,651 filed Mar. 30, 2004 and U.S. Application No. 60/569,863 filed May 11, 2004, the entire disclosures of which are herein incorporated by reference.

FIELD OF THE INVENTION

The present invention relates to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., $3^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic $\alpha_2$ receptors, i.e., are $\alpha_{2A}$, $\alpha_{2B}$, $\alpha_{2C}$ and $\alpha_{2D}$ (Mackinnon et al., TIPS, 1994, 15: 119; French, Pharmacol. Ther., 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine*, 1990, 193(2): 129-35, Freedman et al., *Fertility & Sterility*, 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the present invention is directed to compounds of formula I:

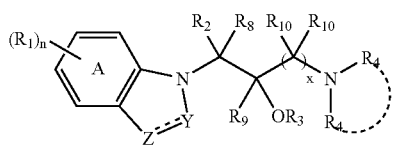

I or a pharmaceutically acceptable salt thereof;
wherein:
the dotted line between Y and Z represents an optional double bond;
the dotted line between the two $R_4$ groups represents an optional heterocyclic ring of 4 to 6 ring atoms that may be formed between the two $R_4$ groups, together with the nitrogen through which they are attached;
Y is N, $CR_6$, or C=O;
Z is N, $NR_7$, $CR_5$, or $C(R_5)_2$;
$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;
$R_2$ is aryl substituted with 0-3 $R_1$ or heteroaryl substituted with 0-3 $R_1$;
$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or
both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;
$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;
$R_6$ is H, $C_1$-$C_4$ alkyl, or cyano;
$R_7$ is H, $C_1$-$C_6$ alkyl, $C_3$-$C_6$ cycloalkyl, or aryl substituted with 0-3 $R_1$;
$R_8$ is H, or $C_1$-$C_4$ alkyl;
$R_9$ is H, or $C_1$-$C_4$ alkyl;
$R_{10}$ is, independently at each occurrence, H, or $C_1$-$C_4$ alkyl; or $R_{10}$ and $R_4$ together with the nitrogen to which $R_4$ is attached form a nitrogen-containing ring containing 3-6 carbon atoms;
n is an integer from 0 to 4;
x is an integer from 1 to 2; and
$R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;
wherein 1-3 carbon atoms in ring A may optionally be replaced with N.

In yet other embodiments, the present invention is directed to compositions, comprising:
a. at least one compound of formula I; and
b. at least one pharmaceutically acceptable carrier.

In another embodiment, the present invention is directed to methods for treating or preventing a condition ameliorated by monoamine reuptake in a subject in need thereof, comprising the step of:
administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:
administering to said subject an effective amount of at least one compound of formula I or pharmaceutically acceptable salt thereof.

In yet another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromylagia syndrome in a subject in need thereof, comprising the step of:

administering to said subject an effective amount of a compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
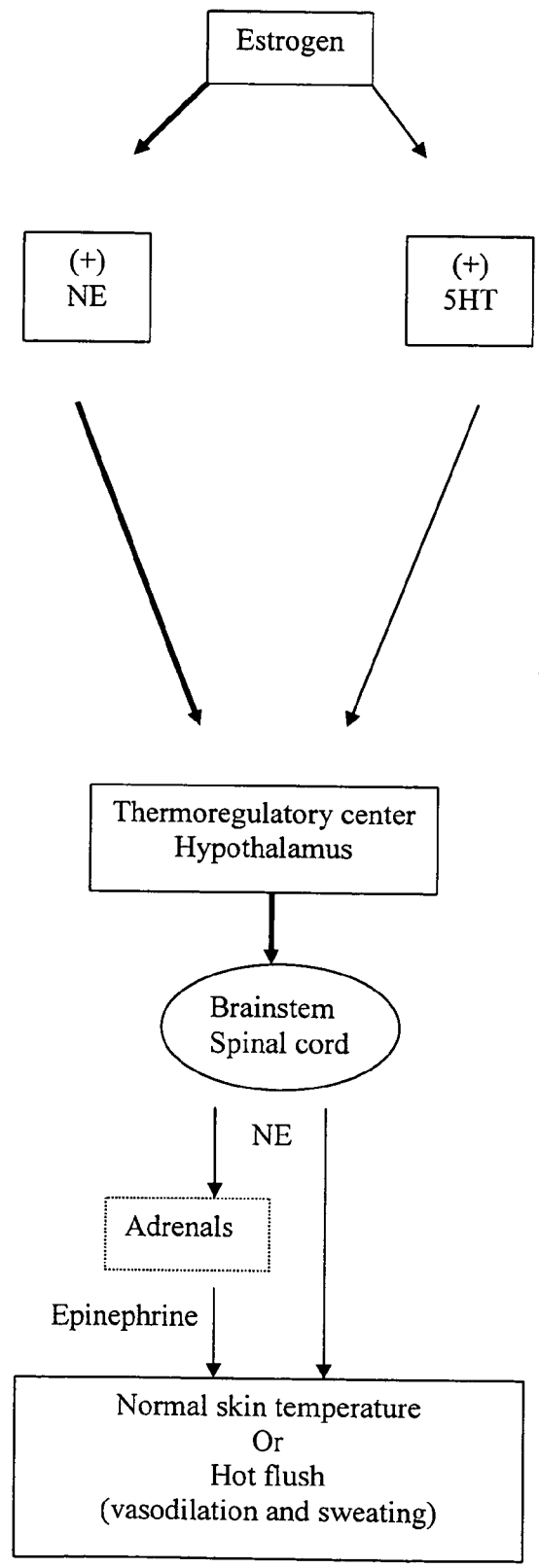
FIG. 1 is an overview of estrogen action on norepinephrine/serotonin mediated thermoregulation.

The present invention is directed to phenylaminopropanol derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value" means dose which results in 50% alleviation of the observed condition or effect (50% mean maximum endpoint).

"Norepinephrine transporter" is abbreviated NET.

"Human norepinephrine transporter" is abbreviated hNET.

"Serotonin transporter" is abbreviated SERT.

"Human serotonin transporter" is abbreviated hSERT.

"Norepinephrine reuptake inhibitor" is abbreviated NRI.

"Selective norepinephrine reuptake inhibitor" is abbreviated SNRI.

"Serotonin reuptake inhibitor" is abbreviated SRI.

"Selective serotonin reuptake inhibitor" is abbreviated SSRI.

"Norepinephrine" is abbreviated NE.

"Serotonin is abbreviated 5-HT.

"Subcutaneous" is abbreviated sc.

"Intraperitoneal" is abbreviated ip.

"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I, or a pharmaceutically acceptable salt thereof, may be administered, preferably, at a dosage of from about 0.1 mg/day to about 500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity.

The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

"Perfluorinated alkyl," as used herein, refers to an alkyl, as defined above, in which the hydrogens directly attached to the carbon atoms are completely replaced by fluorine.

"Alkenyl," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Alkoxy," as used herein, refers to the group R—O— where R is an alkyl group as defined herein.

"Aryloxy," as used herein, refers to the group R—O— where R is an aryl group, as defined herein.

"Heteroaryloxy," as used herein, refers to the group R—O— where R is a heteroaryl group, as defined herein.

"Alkanoyloxy," as used herein, refers to the group R—C(=O)—O— where R is an alkyl group of 1 to 5 carbon atoms.

"Alkylsulfoxide," as used herein, refers to as used herein, refers to —S(=O)—R, where R is alkyl, as defined above.

"Alkylsulfone," as used herein, refers to —S(=O)$_2$—R, where R is alkyl, as defined above.

"Alkylsulfonamide," as used herein, refers to —NR—S(=O)$_2$—R, where each R is independently, alkyl, as defined above or the NR part may also be NH.

"Phenylsulfonamide," as used herein, refers to —NR—S(=O)$_2$-phenyl, where R is H or alkyl, as defined above.

"Heteroarylmethyloxy," as used herein, refers to —OCH$_2$—R, where R is heteroaryl, as defined above.

"Alkylamido," as used herein, refers to —NR—C(=O)—R, where each R is independently, alkyl, as defined above, or the NR part may also be NH.

"Phenylamido," as used herein, refers to —NR—C(=O)-phenyl, where R is H or alkyl, as defined above.

"Halo," as used herein, refers to chloro, bromo, fluoro, and iodo.

In one embodiment, the present invention is directed to compounds of formula I:

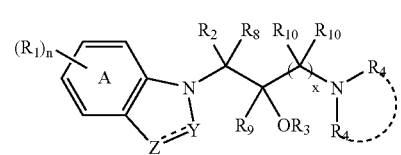

or a pharmaceutically acceptable salt thereof;

wherein:

the dotted line between Y and Z represents an optional double bond;

the dotted line between the two R$_4$ groups represents an optional heterocyclic ring of 4 to 6 ring atoms that may be formed between the two R$_4$ groups, together with the nitrogen through which they are attached;

Y is N, CR$_6$, or C=O;

Z is N, NR$_7$, CR$_5$, or C(R$_5$)$_2$;

R$_1$ is, independently at each occurrence, alkyl, alkoxy, halo, CF$_3$, OCF$_3$, arylalkyloxy substituted with 0-3 R$_{11}$, aryloxy substituted with 0-3 R$_{11}$, aryl substituted with 0-3 R$_{11}$, heteroaryl substituted with 0-3 R$_{11}$, hydroxy, alkanoyloxy, nitro, nitrile, alkenyl, alkynyl, alkylsulfoxide, phenylsulfoxide substituted with 0-3 R$_{11}$, alkylsulfone, phenylsulfone substituted with 0-3 R$_{11}$, alkylsulfonamide, phenylsulfonamide substituted with 0-3 R$_{11}$, heteroaryloxy substituted with 0-3 R$_{11}$, heteroarylmethyloxy substituted with 0-3 R$_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H, or $C_1$-$C_4$ alkyl;

$R_9$ is H, or $C_1$-$C_4$ alkyl;

$R_{10}$ is, independently at each occurrence, H, or $C_1$-$C_4$ alkyl; or $R_{10}$ and $R_4$ together with the nitrogen to which $R_4$ is attached form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N. The dotted line in the ring fused to ring A represents an optional double bond between Y and Z. The dotted line between the two $R_4$ groups represents an optional heterocyclic ring of 4 to 6 ring atoms that may be formed between the two $R_4$ groups, together with the nitrogen through which they are attached.

In certain preferred embodiments of compounds of formula I, Y is N. In certain other preferred embodiments, Y is $CR_6$, preferably CH. In certain other preferred embodiments, Y is C=O.

In certain more preferred embodiments, Z is N. In certain preferred embodiments of compounds of formula I, Z is $NR_7$. In certain other more preferred embodiments, Z is $CR_5$. In yet certain other more preferred embodiments, Z is $C(R_5)_2$. In certain even more preferred embodiments, Z is CH, $C(CH_3)$, or C(CN).

In certain preferred embodiments of compounds of formula I, $R_1$ is, independently at each occurrence, alkyl, preferably $C_1$-$C_4$ alkyl, more preferably methyl. In certain other preferred embodiments, $R_1$ is, independently at each occurrence, alkoxy. In certain other preferred embodiments of compounds, $R_1$ is, independently at each occurrence, halo, preferably F or Cl. In certain other preferred embodiments, $R_1$ is, independently at each occurrence, $CF_3$. In certain other preferred embodiments, $R_1$ is, independently at each occurrence, $OCF_3$. In certain other preferred embodiments, $R_1$ is, independently at each occurrence, benzyloxy substituted with 0-3 $R_1$. In certain other preferred embodiments, $R_1$ is, independently at each occurrence, aryloxy substituted with 0-3 $R^1$. In certain other preferred embodiments, $R_1$ is, independently at each occurrence, aryl substituted with 0-3 $R_1$. In certain other preferred embodiments, $R_1$ is, independently at each occurrence, heteroaryl substituted with 0-3 $R_1$. In certain other preferred embodiments, $R_1$ is, independently at each occurrence, hydroxy. In certain other preferred embodiments, $R_1$ is, independently at each occurrence, alkanoyloxy. In certain other preferred embodiments, $R_1$ is, independently at each occurrence, methylenedioxy. In certain other preferred embodiments, $R_1$ is, independently at each occurrence, nitro. In certain other preferred embodiments, $R_1$ is, independently at each occurrence, nitrile. In certain other preferred embodiments, $R_1$ is, independently at each occurrence, alkenyl. In certain other preferred embodiments, $R_1$ is, independently at each occurrence, alkynyl. In certain other preferred embodiments, $R_1$ is, independently at each occurrence, alkylsulfoxide. In certain other preferred embodiments, $R_1$ is, independently at each occurrence, phenylsulfoxide substituted with 0-3 $R_1$. In certain other preferred embodiments, $R_1$ is, independently at each occurrence, alkylsulfone. In certain other preferred embodiments, $R_1$ is, independently at each occurrence, phenylsulfone substituted with 0-3 $R_1$. In certain other preferred embodiments, $R_1$ is, independently at each occurrence, alkylsulfonamide. In certain other preferred embodiments, $R_1$ is, independently at each occurrence, phenylsulfonamide substituted with 0-3 $R_1$. In certain other preferred embodiments, $R_1$ is, independently at each occurrence, heteroaryloxy substituted with 0-3 $R_1$. In certain other preferred embodiments, $R_1$ is, independently at each occurrence, heteroarylmethyloxy substituted with 0-3 $R_1$. In certain other preferred embodiments, $R_1$ is, independently at each occurrence, alkylamido. In certain other preferred embodiments, $R_1$ is, independently at each occurrence, phenylamido substituted with 0-3 $R_1$.

In certain preferred embodiments of compounds of formula I, $R_2$ is aryl substituted with 0-3 $R_1$, preferably substituted with no $R_1$. In certain preferred embodiments, $R_2$ is naphthyl substituted with 0-3 $R_1$, preferably substituted with no $R_1$. In certain preferred embodiments, $R_2$ is heteroaryl substituted with 0-3 $R_1$, preferably substituted with no $R_1$.

In certain preferred embodiments of compounds of formula I, $R_3$ is H. In certain other preferred embodiments, $R_3$ is $C_1$-$C_4$ alkyl, preferably $C_1$ alkyl.

In certain preferred embodiments of compounds of formula I, $R_4$ is, independently at each occurrence, H. In certain preferred embodiments, $R_4$ is, independently at each occurrence, $C_1$-$C_4$ alkyl, preferably $C_1$-$C_3$ alkyl, more preferably methyl, ethyl, isopropyl. In certain preferred embodiments of compounds of formula I, $R_4$ is, independently at each occurrence, benzyl. In certain preferred embodiments, $R_4$ is, independently at each occurrence, heteroarylmethyl. In certain preferred embodiments, $R_4$ is, independently at each occurrence, cycloheptylmethyl, cyclohexylmethyl, cyclopentylmethyl, or cyclobutylmethyl.

In certain preferred embodiments of compounds of formula I, both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$. In certain more preferred embodiments, both $R_4$ groups, together with the nitrogen through which they are attached, form a pyridine, piperidine, piperazine, piperazine substituted with a methyl group, or morpholine ring.

In certain preferred embodiments of compounds of formula I, $R_5$ is, independently at each occurrence, H. In certain preferred embodiments of compounds, $R_5$ is, independently at each occurrence, $C_1$-$C_4$ alkyl, preferably methyl. In certain preferred embodiments of compounds, $R_5$ is, independently at each occurrence, aryl substituted with 0-3 $R_1$, preferably phenyl, tolyl, or xylyl. In certain preferred embodiments, $R_5$ is, independently at each occurrence, cyano.

In certain preferred embodiments of compounds of formula I, when two $R_5$ are present, when two $R_5$ are present, they form a carbocyclic ring of 3-7 carbons, preferably a cyclopentyl or cyclohexyl.

In certain preferred embodiments of compounds of formula I, $R_6$ is, independently at each occurrence, H. In certain preferred embodiments of compounds, $R_6$ is, independently at each occurrence, $C_1$-$C_4$ alkyl, preferably methyl. In certain preferred embodiments, $R_6$ is, independently at each occurrence, cyano.

In certain preferred embodiments of compounds of formula I, $R_7$ is, independently at each occurrence, H. In certain preferred embodiments of compounds, $R_7$ is, independently at each occurrence, $C_1$-$C_6$ alkyl, preferably $C_1$-$C_4$ alkyl, more preferably, methyl. In certain preferred embodiments of compounds, $R_7$ is, independently at each occurrence, $C_3$-$C_6$ cycloalkyl, preferably, cyclopentyl or cyclohexyl. In certain preferred embodiments of compounds, $R_5$ is, independently at each occurrence, aryl substituted with 0-3 $R_1$, preferably phenyl, tolyl, or xylyl.

In certain preferred embodiments of compounds of formula I, $R_8$ is, independently at each occurrence, H. In certain preferred embodiments of compounds, $R_8$ is, independently at each occurrence, $C_1$-$C_4$ alkyl, preferably methyl.

In certain preferred embodiments of compounds of formula I, $R_9$ is, independently at each occurrence, H. In certain preferred embodiments of compounds, $R_9$ is, independently at each occurrence, $C_1$-$C_4$ alkyl, preferably methyl.

In certain preferred embodiments of compounds of formula I, $R_{10}$ is, independently at each occurrence, H. In certain preferred embodiments of compounds, $R_{10}$ is, independently at each occurrence, $C_1$-$C_4$ alkyl, preferably methyl. In certain preferred embodiments of compounds of formula I, $R_{10}$ and $R_4$ together with the nitrogen to which $R_4$ is attached form a nitrogen-containing ring containing 3-6 carbon atoms, especially, pyrrolidinyl, pyrrolyl, piperidinyl, pyridinyl, azepanyl, and azepinyl.

In certain preferred embodiments of compounds of formula I, n is an integer from 0 to 3. More preferably, n is 0 to 2. Even more preferably, n is 0 to 1. Yet more preferably, n is 0.

In certain preferred embodiments of compounds of formula I, x is an integer from 1 to 2. More preferably, x is 1.

In certain preferred embodiments of compounds of formula 1, 1-2 carbon atoms in ring A may optionally be replaced with N. In certain preferred embodiments of compounds, one carbon atom in ring A may optionally be replaced with N. In certain preferred embodiments, no carbon atoms in ring A are replaced with N.

In certain preferred embodiments of compounds of formula I,
Y is N, $CR_6$, or C=O;
Z is N, $NR_7$, $CR_5$, or $C(R_5)_2$;
$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;
$R_2$ is aryl substituted with 0-3 $R_1$ or heteroaryl substituted with 0-3 $R_1$;
$R_3$ is H $R_4$ is, independently at each occurrence, H, or $C_1$-$C_4$ alkyl,
$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;
$R_6$ is H, C1-C4 alkyl, or cyano;
$R_7$ is H, $C_1$-$C_6$ alkyl, $C_3$-$C_6$ cycloalkyl, aryl substituted with 0-3 $R_1$;
$R_8$ is H;
$R_9$ is H;
$R_{10}$ is H;
n is an integer from 0 to 4;
x is 1;
$R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;
wherein 1-3 carbon atoms in ring A may optionally be replaced with N.

In certain preferred embodiments of compounds of formula I,
Y is $CR_6$;
Z is $CR_5$;
$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;
$R_2$ is aryl substituted with 0-3 $R_1$ or heteroaryl substituted with 0-3 $R_1$;
$R_3$ is H or $C_1$-$C_4$ alkyl;
$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;
$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;
$R_6$ is H, $C_1$-$C_4$ alkyl, or cyano;
$R_7$ is H, $C_1$-$C_6$ alkyl, $C_3$-$C_6$ cycloalkyl, or aryl substituted with 0-3 $R_1$;
$R_8$ is H or $C_1$-$C_4$ alkyl;
$R_9$ is H or $C_1$-$C_4$ alkyl;
$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;
n is an integer from 0 to 4;
x is an integer from 1 to 2; and
$R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;
wherein 1-3 carbon atoms in ring A may optionally be replaced with N.

In certain preferred embodiments of compounds of formula I,
Y is $CR_6$;
Z is $C(R_5)_2$;
$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_{11}$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$, is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

In certain preferred embodiments of compounds of formula I,

Y is C=O;

Z is $C(R_5)_2$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

In certain preferred embodiments of compounds of formula I,

Y is C=O;

Z is $NR_7$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_{11}$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or in the cases where two $R_5$ substitutions are present, they may form a carbocyclic ring of $C_3$-$C_7$;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; $R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfonamide, or alkylamido; or two adjacent $R_{11}$ also represent methylenedioxy;

wherein 1-3 carbon atoms in ring A may optionally be replaced with N.

Preferred compounds of formula I include:

1-(1H-indol-1-yl)-3-(4-methylpiperazin-1-yl)-1-phenylpropan-2-ol;

1-(5-fluoro-1H-indol-1-yl)-3-(4-methylpiperazin-1-yl)-1-phenylpropan-2-ol;

1-(1H-indol-1-yl)-3-morpholin-4-yl-1-phenylpropan-2-ol;

3-(dimethylamino)-1-(1H-indol-1-yl)-1-phenylpropan-2-ol;

3-(ethylamino)-1-(1H-indol-1-yl)-1-phenylpropan-2-ol;

1-(1H-indol-1-yl)-3-(isopropylamino)-1-phenylpropan-2-ol;

3-(benzylamino)-1-(1H-indol-1-yl)-1-phenylpropan-2-ol;

3-[(cyclohexylmethyl)amino]-1-(1H-indol-1-yl)-1-phenylpropan-2-ol;

3-[(cyclohexylmethyl)amino]-1-(3-methyl-1H-indol-1-yl)-1-phenylpropan-2-ol;

3-(isopropylamino)-1-(3-methyl-1H-indol-1-yl)-1-phenylpropan-2-ol;

1-(1H-indol-1-yl)-3-(methylamino)-1-phenylpropan-2-ol;

3-(ethylamino)-1-(3-methyl-1H-indol-1-yl)-1-phenylpropan-2-ol;

1-(1H-indol-1-yl)-1-phenyl-3-piperazin-1-ylpropan-2-ol di;

1-(1H-indol-1-yl)-1-phenyl-3-[(pyridin-4-ylmethyl) amino]propan-2-ol;

1-(5-chloro-1H-indol-1-yl)-1-phenyl-3-piperidin-1-ylpropan-2-ol;

1-(1H-indol-1-yl)-3-(methylamino)-1-phenylpropan-2-ol;

3-amino-1-(1H-indol-1-yl)-1-phenylpropan-2-ol;

3-(ethylamino)-1-(5-fluoro-1H-indol-1-yl)-1-phenylpropan-2-ol;

3-amino-1-(5-fluoro-1H-indol-1-yl)-1-phenylpropan-2-ol;

1-(5-fluoro-1H-indol-1-yl)-3-(methylamino)-1-phenylpropan-2-ol;

3-(methylamino)-1-(3-methyl-1H-indol-1-yl)-1-phenylpropan-2-ol;

1-(1H-indol-1-yl)-3-(methylamino)-1-phenylpropan-2-ol;

1-(1H-indol-1-yl)-3-(methylamino)-1-phenylpropan-2-ol;

3-amino-1-(3-methyl-1H-indol-1-yl)-1-phenylpropan-2-ol;

3-[ethyl(methyl)amino]-1-(1H-indol-1-yl)-1-phenylpropan-2-ol;

1-(5-chloro-1H-indol-1-yl)-3-(methylamino)-1-phenylpropan-2-ol;

1-(5-chloro-1H-indol-1-yl)-3-(methylamino)-1-phenylpropan-1-ol;

1-[2-hydroxy-3-(methylamino)-1-phenylpropyl]-1H-indole-3-carbonitrile;

1-(1H-indol-1-yl)-3-(methylamino)-1-phenylpropan-2-ol;

1-(1H-indol-1-yl)-3-(methylamino)-1-phenylpropan-2-ol;

3-(methylamino)-1-(3-methyl-1H-indol-1-yl)-1-phenyl propan-2-ol;

1-(3-chlorophenyl)-1-(1H-indol-1-yl)-3-(methylamino) propan-2-ol;

1-(4-chlorophenyl)-1-(1H-indol-1-yl)-3-(methylamino) propan-2-ol;

1-(1H-indol-1-yl)-3-(methylamino)-1-[3-(trifluoromethoxy)phenyl]propan-2-ol;

1-(1H-indol-1-yl)-3-(methylamino)-1-[2-(trifluoromethoxy)phenyl]propan-2-ol;

1-(1H-indol-1-yl)-3-(methylamino)-1-[2-(trifluoromethoxy)phenyl]propan-2-ol;

1-(2-chlorophenyl)-1-(1H-indol-1-yl)-3-(methylamino) propan-2-ol;

1-(1H-indol-1-yl)-3-(methylamino)-1-[4-(trifluoromethoxy)phenyl]propan-2-ol;

1-(1H-indol-1-yl)-3-(methylamino)-1-[4-(trifluoromethoxy)phenyl]propan-2-ol;

1-(1H-indol-1-yl)-3-(methylamino)-1-[4-(trifluoromethoxy)phenyl]propan-2-ol;

4-amino-1-(3-chlorophenyl)-1-(1H-indol-1-yl)butan-2-ol 1-(3-bromophenyl)-1-(1H-indol-1-yl)-3-(methylamino) propan-2-ol;

3-[2-hydroxy-1-(1H-indol-1-yl)-3-(methylamino)propyl] benzonitrile 1-(3-fluorophenyl)-1-(1H-indol-1-yl)-3-(methylamino) propan-2-ol;

1-(3-fluorophenyl)-3-(methylamino)-1-[3-(3-methylphenyl)-1H-indol-1-yl]propan-2-ol;

1-(4-fluorophenyl)-3-(methylamino)-1-(3-methyl-1H-indol-1-yl)propan-2-ol;

1-(2-fluorophenyl)-1-(1H-indol-1-yl)-3-(methylamino) propan-2-ol;

1-(4-fluorophenyl)-1-(1H-indol-1-yl)-3-(methylamino) propan-2-ol;

1-(1H-indol-1-yl)-3-(methylamino)-1-(3-methylphenyl) propan-2-ol;

1-(1H-indol-1-yl)-3-(methylamino)-1-(2-methylphenyl) propan-2-ol;

1-(1H-indol-1-yl)-3-(methylamino)-1-(2-methylphenyl) propan-2-ol;

3-(ethylamino)-1-(3-fluorophenyl)-1-(1H-indol-1-yl)propan-2-ol;

1-(3-fluorophenyl)-1-(1H-indol-1-yl)-3-morpholin-4-yl propan-2-ol;

1-(3-fluorophenyl)-1-(1H-indol-1-yl)-3-(propylamino) propan-2-ol;

1-(3-fluorophenyl)-1-(1H-indol-1-yl)-3-(4-methylpiperazin-1-yl)propan-2-ol;

1-(1H-indol-1-yl)-3-(methylamino)-1-(4-methylphenyl) propan-2-ol;

1-(2,3-dihydro-1H-indol-1-yl)-1-(3-fluorophenyl)-3-(methylamino)propan-2-ol;

1-(2,3-dihydro-1H-indol-1-yl)-3-(methylamino)-1-phenylpropan-2-ol;

1-(3-fluorophenyl)-3-(methylamino)-1-[3-(2-methylphenyl)-1H-indol-1-yl]propan-2-ol;

1-(3-fluorophenyl)-3-(methylamino)-1-(2-methyl-2,3-dihydro-1H-indol-1-yl)propan-2-ol;

1-(7-fluoro-3,3-dimethyl-2,3-dihydro-1H-indol-1-yl)-1-(3-fluorophenyl)-3-(methylamino)propan-2-ol;

1-(7-fluoro-3,3-dimethyl-2,3-dihydro-1H-indol-1-yl)-3-(methylamino)-1-phenylpropan-2-ol;

3-(methylamino)-1-(7-methyl-2,3-dihydro-1H-indol-1-yl)-1-phenylpropan-2-ol;

1-(3-fluorophenyl)-3-(methylamino)-1-(7-methyl-2,3-dihydro-1H-indol-1-yl)propan-2-ol;

1-(3-fluorophenyl)-3-(methylamino)-1-(5-methyl-2,3-dihydro-1H-indol-1-yl)propan-2-ol;

1-(1H-indol-1-yl)-1-(3-methoxyphenyl)-3-(methylamino)propan-2-ol;

1-(1H-indol-1-yl)-1-(4-methoxyphenyl)-3-(methylamino)propan-2-ol;

3-(methylamino)-1-(2-methyl-1H-indol-1-yl)-1-phenylpropan-2-ol;

1-(1H-benzimidazol-1-yl)-3-(methylamino)-1-phenylpropan-2-ol;

3-(methylamino)-1-(2-methyl-1H-benzimidazol-1-yl)-1-phenyl propan-2-ol;

1-(4-methoxy-1H-indol-1-yl)-3-(methylamino)-1-phenylpropan-2-ol;

1-(5-fluoro-1H-indol-1-yl)-3-(methylamino)-1-phenylpropan-2-ol;

1-(5-methoxy-1H-indol-1-yl)-3-(methylamino)-1-phenylpropan-2-ol;

1-(7-methoxy-1H-indol-1-yl)-3-(methylamino)-1-phenylpropan-2-ol;

1-(4-methoxy-1H-indol-1-yl)-3-(methylamino)-1-phenylpropan-2-ol;

1-(6-methoxy-1H-indol-1-yl)-3-(methylamino)-1-phenylpropan-2-ol;

1-(5-methoxy-1H-indol-1-yl)-3-(methylamino)-1-phenylpropan-2-ol;

1-(3-fluorophenyl)-1-(6-methoxy-1H-indol-1-yl)-3-(methylamino)propan-2-ol;

3-(methylamino)-1-phenyl-1-(1H-pyrrolo[2,3-b]pyridin-1-yl)propan-2-ol;

1-(5-chloro-2,3-dihydro-1H-indol-1-yl)-1-(3-fluorophenyl)-3-(methylamino)propan-2-ol;

3-(methylamino)-1-phenyl-1-(1H-pyrrolo[2,3-c]pyridin-1-yl)propan-2-ol;

1-(5-fluoro-1H-indol-1-yl)-1-(3-fluorophenyl)-3-(methylamino)propan-2-ol;

3-(methylamino)-1-(3-fluorophenyl)-1-(1H-pyrrolo[2,3-c]pyridin-1-yl)propan-2-ol;

1-(5-chloro-2,3-dihydro-1H-indol-1-yl)-3-(methylamino)-1-phenylpropan-2-ol;

3-(methylamino)-1-(6-methyl-1H-indol-1-yl)-1-phenylpropan-2-ol;

3-(methylamino)-1-(7-methyl-1H-indol-1-yl)-1-phenylpropan-2-ol;

1-(3-fluorophenyl)-3-(methylamino)-1-(5-methyl-1H-indol-1-yl)propan-2-ol;

1-(3-fluorophenyl)-3-(methylamino)-1-(7-methyl-1H-indol-1-yl)propan-2-ol;

3-(methylamino)-1-(4-methyl-1H-indol-1-yl)-1-phenylpropan-2-ol;

3-(methylamino)-1-(5-methyl-1H-indol-1-yl)-1-phenylpropan-2-ol;

1-(3-fluorophenyl)-3-(methylamino)-1-(4-methyl-1H-indol-1-yl)propan-2-ol;

1-(3-ethyl-1H-indol-1-yl)-1-(3-fluorophenyl)-3-(methylamino)propan-2-ol;

1-(3-fluorophenyl)-3-(methylamino)-1-(3-phenyl-1H-indol-1-yl)propan-2-ol;

7-fluoro-1-[2-hydroxy-3-(methylamino)-1-phenylpropyl]-3,3-dimethyl-1,3-dihydro-2H-indol-2-one;

1-[2hydroxy-3-(methylamino)-1-phenylpropyl]-3,3-dimethyl-1,3-dihydro-2H-indol-2-one;

7-fluoro-1-[1-(3-fluorophenyl)-2-hydroxy-3-(methylamino)propyl]-3,3-dimethyl-1,3-dihydro-2H-indol-2-one;

1-(1H-indol-1-yl)-3-(methylamino)-1-(2-thienyl)propan-2-ol;

1(1H-indol-1-yl)-3-(methylamino)-1-(2-thienyl)propan-2-ol;

1'-[2-hydroxy-3-(methylamino)-1-phenylpropyl]spiro[cyclohexane-1,3'-indol]-2'(1'H)-one;

2-(3-fluorophenyl)-2-(1H-indol-1-yl)-1-[(2S)-pyrrolidin-2-yl]ethanol;

2-(3-fluorophenyl)-2-(1H-indol-1-yl)-1-[pyrrolidin-2-yl]ethanol;

1'-[2hydroxy-3-(methylamino)-1-phenylpropyl]spiro[cyclobutane-1,3'-indol]-2'(1'H)-one;

1'-[2hydroxy-3-(methylamino)-1-phenylpropyl]spiro[cyclopentane-1,3'-indol]-2'(1'H)-one;

1'-[2hydroxy-3-(methylamino)-1-phenylpropyl]spiro[cyclopropane-1,3'-indol]-2'(1'H)-one;

5-fluoro-1-[2hydroxy-3-(methylamino)-1-phenylpropyl]-3,3-dimethyl-1,3-dihydro-2H-indol-2-one;

3-(cyclopropylamino)-1-(3-fluorophenyl)-1-(1H-indol-1-yl)propan-2-ol;

7'-fluoro-1'-[2hydroxy-3-(methylamino)-1-phenylpropyl]spiro[cyclohexane-1,3'-indol]-2'(1'H)-one;

5'-bromo-1'-[2hydroxy-3-(methylamino)-1-phenylpropyl]spiro[cyclohexane-1,3'-indol]-2'(1'H)-one;

1-(3-fluorophenyl)-1-[3-(2-fluorophenyl)-1H-indol-1-yl]-3-(methylamino)propan-2-ol;

1-[3-(3,4-dichlorophenyl)-1H-indol-1-yl]-1-(3-fluorophenyl)-3-(methylamino)propan-2-ol;

1-(3-fluorophenyl)-1-[3-(3-fluorophenyl)-1H-indol-1-yl]-3-(methylamino)propan-2-ol;

1-(5-fluoro-3-methyl-1H-indol-1-yl)-3-(methylamino)-1-phenylpropan-2-ol;

3-amino-1-(5-fluoro-3-methyl-1H-indol-1-yl)-1-phenylpropan-2-ol;

1-(5-chloro-3-methyl-1H-indol-1-yl)-3-(methylamino)-1-phenylpropan-2-ol;

3amino-1-(5-chloro-3-methyl-1H-indol-1-yl)-1-phenylpropan-2-ol;

[3-(5-chloro-3-methyl-1H-indol-1-yl)-2-methoxy-3-phenylpropyl]methylamine;

1-(7-chloro-3-methyl-1H-indol-1-yl)-3-(methylamino)-1-phenylpropan-2-ol;

[3-(5-fluoro-3-methyl-1H-indol-1-yl)-2-methoxy-3-phenylpropyl]methylamine;

1-(4-bromo-1H-indol-1-yl)-3-(methylamino)-1-phenylpropan-2-ol;

1-(4-bromo-1H-indol-1-yl)-1-(3-fluorophenyl)-3-(methylamino)propan-2-ol;

1-(5-bromo-1H-indol-1-yl)-3-(methylamino)-1-phenylpropan-2-ol;

1-(5-bromo-1H-indol-1-yl)-1-(3-fluorophenyl)-3-(methylamino)propan-2-ol;

1-[2-hydroxy-3-(methylamino)-1-phenylpropyl]-1H-indole-4-carbonitrile;

1-(6-bromo-1H-indol-1-yl)-3-(methylamino)-1-phenylpropan-2-ol;

1-[2-hydroxy-3-(methylamino)-1-phenylpropyl]-1H-indole-5-carbonitrile;

1-[1-(3-fluorophenyl)-2-hydroxy-3-(methylamino)propyl]-1H-indole-4-carbonitrile;

1-(6-bromo-1H-indol-1-yl)-1-(3-fluorophenyl)-3-(methylamino)propan-2-ol;

1-(6-fluoro-1H-indol-1-yl)-1-(3-fluorophenyl)-3-(methylamino)propan-2-ol;

3-amino-1-(3-fluorophenyl)-1-(1H-indol-1-yl)propan-2-ol;

1-(7-bromo-1H-indol-1-yl)-1-(3-fluorophenyl)-3-(methylamino)propan-2-ol;

1-(1H-indol-1-yl)-3-(methylamino)-1-[3-(trifluoromethyl)phenyl]propan-2-ol;

1-(3-fluorophenyl)-3-(methylamino)-1-spiro[cyclohexane-1,3'-indol]-1'(2'H)-ylpropan-2-ol;

1-(2,3-dihydro-1H-indol-1-yl)-3-(methylamino)-1-[3-(trifluoromethyl)phenyl]propan-2-ol;

1-(3-fluorophenyl)-1-(1H-indol-1-yl)-3-(methylamino)propan-2-ol;

1-(3,4-difluorophenyl)-1-(1H-indol-1-yl)-3-(methylamino)propan-2-ol;

1-(3-fluorophenyl)-3-(methylamino)-1-(3-methyl-1H-indol-1-yl)propan-2-ol;

1-(4-chloro-1H-indol-1-yl)-3-(methylamino)-1-phenylpropan-2-ol;

1-(6-chloro-1H-indol-1-yl)-3-(methylamino)-1-phenylpropan-2-ol;

1-(7-chloro-1H-indol-1-yl)-3-(methylamino)-1-phenylpropan-2-ol;

1-(7-chloro-1H-indol-1-yl)-1-(3-fluorophenyl)-3-(methylamino)propan-2-ol;

1-(4-chloro-1H-indol-1-yl)-1-(3-fluorophenyl)-3-(methylamino)propan-2-ol;

1-(6-chloro-1H-indol-1-yl)-1-(3-fluorophenyl)-3-(methylamino)propan-2-ol;

1-(5-chloro-1H-indol-1-yl)-3-(methylamino)-1-phenyl-propan-2-ol;
1-(5-chloro-1H-indol-1-yl)-1-(3-fluorophenyl)-3-(methylamino)propan-2-ol;
1-(3-isopropyl-1H-indol-1-yl)-3-(methylamino)-1-phenylpropan-2-ol;
1-(3-fluorophenyl)-1-(3-isopropyl-1H-indol-1-yl)-3-(methylamino)propan-2-ol;
1-(3,5-difluorophenyl)-1-(1H-indol-1-yl)-3-(methylamino)propan-2-ol;
1-(3,5-difluorophenyl)-1-(2,3-dihydro-1H-indol-1-yl)-3-(methylamino)propan-2-ol;
4-amino-1-(3-fluorophenyl)-1-(1H-indol-1-yl)butan-2-ol;
1-(3,3-dimethyl-2,3-dihydro-1H-indol-1-yl)-1-(3-fluorophenyl)-3-(methylamino)propan-2-ol;
1-(3,5-difluorophenyl)-1-(3,3-dimethyl-2,3-dihydro-1H-indol-1-yl)-3-(methylamino)propan-2-ol;
1-(3,3-dimethyl-2,3-dihydro-1H-indol-1-yl)-3-(methylamino)-1-phenylpropan-2-ol;
1-(3-fluorophenyl)-3-(methylamino)-1-(3-methyl-2,3-dihydro-1H-indol-1-yl)propan-2-ol;
1-(3-fluorophenyl)-3-(methylamino)-1-spiro[cyclopentane-1,3'-indol]-1'(2'H)-ylpropan-2-ol;
1-(3-fluorophenyl)-1-[3-(4-methoxyphenyl)-1H-indol-1-yl]-3-(methylamino)propan-2-ol;
1-(3-fluorophenyl)-3-(methylamino)-1-[3-(4-methylphenyl)-1H-indol-1-yl]propan-2-ol;
1-[3-(4-tert-butylphenyl)-1H-indol-1-yl]-1-(3-fluorophenyl)-3-(methylamino)propan-2-ol;
1-(3-fluorophenyl)-1-[3-(3-methoxyphenyl)-1H-indol-1-yl]-3-(methylamino)propan-2-ol;
1-(3-fluorophenyl)-3-(methylamino)-1-{3-[4-(trifluoromethyl)phenyl]-1H-indol-1-yl}propan-2-ol;
1-(3,5-difluorophenyl)-1-(6-fluoro-2,3-dihydro-1H-indol-1-yl)-3-(methylamino)propan-2-ol;
1-(3-fluorophenyl)-3-(methylamino)-1-{3-[2-(trifluoromethyl)phenyl]-1H-indol-1-yl}propan-2-ol;
1-(3-fluorophenyl)-1-[3-(2-methoxyphenyl)-1H-indol-1-yl]-3-(methylamino)propan-2-ol;
1-(3-fluorophenyl)-3-(methylamino)-1-{3-[3-(trifluoromethyl)phenyl]-1H-indol-1-yl}propan-2-ol;
3-amino-1-(3-methyl-1H-indol-1-yl)-1-phenylpropan-2-ol;
1-(7-fluoro-3-methyl-1H-indol-1-yl)-3-(methylamino)-1-phenylpropan-2-ol;
3-amino-1-(7-fluoro-3-methyl-1H-indol-1-yl)-1-phenylpropan-2-ol;
1-(7-fluoro-1H-indol-1-yl)-3-(methylamino)-1-phenylpropan-2-ol;
1-(4-fluoro-1H-indol-1-yl)-3-(methylamino)-1-phenylpropan-2-ol;
1-(7-fluoro-1H-indol-1-yl)-1-(3-fluorophenyl)-3-(methylamino)propan-2-ol;
1-(4-fluoro-1H-indol-1-yl)-1-(3-fluorophenyl)-3-(methylamino)propan-2-ol;
1-(3-fluorophenyl)-3-(methylamino)-1-[5-(trifluoromethyl)-1H-indol-1-yl]propan-2-ol;
1-(6-fluoro-1H-indol-1-yl)-3-(methylamino)-1-phenylpropan-2-ol;
3-(methylamino)-1-phenyl-1-[6-(trifluoromethyl)-1H-indol-1-yl]propan-2-ol;
3-(methylamino)-1-phenyl-1-[5-(trifluoromethyl)-1H-indol-1-yl]propan-2-ol;
1-(3-tert-butyl-1H-indol-1-yl)-1-(3-fluorophenyl)-3-(methylamino)propan-2-ol;
1-(1H-indol-1-yl)-2-methyl-3-(methylamino)-1-phenylpropan-2-ol;
3-(1H-indol-1-yl)-1-(methylamino)-3-phenylbutan-2-ol;
1-tert-butyl-3-[2hydroxy-3-(methylamino)-1-phenylpropyl]-1,3-dihydro-2H-benzimidazol-2-one;
1-[2-hydroxy-3-(methylamino)-1-phenylpropyl]-3-propyl-1,3-dihydro-2H-benzimidazol-2-one;
5-bromo-1-[2hydroxy-3-(methylamino)-1-phenylpropyl]-3,3-dimethyl-1,3-dihydro-2H-indol-2-one;
6-fluoro-1-[2hydroxy-3-(methylamino)-1-phenylpropyl]-3,3-dimethyl-1,3-dihydro-2H-indol-2-one;
4-fluoro-1-[2hydroxy-3-(methylamino)-1-phenylpropyl]-3,3-dimethyl-1,3-dihydro-2H-indol-2-one;
1-cyclobutyl-3-[2hydroxy-3-(methylamino)-1-phenylpropyl]-1,3-dihydro-2H-benzimidazol-2-one;
5-fluoro-3-[2hydroxy-3-(methylamino)-1-phenylpropyl]-1-propyl-1,3-dihydro-2H-benzimidazol-2-one;
1-ethyl-3-[1-(3-fluorophenyl)-2-hydroxy-3-(methylamino)propyl]-1,3-dihydro-2H-benzimidazol-2-one;
1-ethyl-3-[2hydroxy-3-(methylamino)-1-phenylpropyl]-1,3-dihydro-2H-benzimidazol-2-one;
4-fluoro-3-[2hydroxy-3-(methylamino)-1-phenylpropyl]-1-isopropyl-1,3-dihydro-2H-benzimidazol-2-one;
1-cyclopentyl-3-[2hydroxy-3-(methylamino)-1-phenylpropyl]-1,3-dihydro-2H-benzimidazol-2-one;
1-[2hydroxy-3-(methylamino)-1-phenylpropyl]-3-isopropyl-1,3-dihydro-2H-benzimidazol-2-one;
3-[3(ethylamino)-2-hydroxy-1-phenylpropyl]-5-fluoro-1-isopropyl-1,3-dihydro-2H-benzimidazol-2-one;
1-[2hydroxy-3-(methylamino)-1-phenylpropyl]-3-methyl-1,3-dihydro-2H-benzimidazol-2-one;
1-ethyl-5-fluoro-3-[2-hydroxy-3-(methylamino)-1-phenylpropyl]-1,3-dihydro-2H-benzimidazol-2-one;
1-ethyl-4-fluoro-3-[2-hydroxy-3-(methylamino)-1-phenylpropyl]-1,3-dihydro-2H-benzimidazol-2-one;
4-fluoro-3-[1-(3-fluorophenyl)-2-hydroxy-3-(methylamino)propyl]-1-isopropyl-1,3-dihydro-2H-benzimidazol-2-one;
1-ethyl-4-fluoro-3-[2hydroxy-3-(methylamino)-1-(3-fluorophenyl)-propyl]-1,3-dihydro-2H-benzimidazol-2-one;
1-[1-(3-fluorophenyl)-2-hydroxy-3-(methylamino)propyl]-3,3-dimethyl-1,3-dihydro-2H-indol-2-one;
1-[3-(2,3-difluorophenyl)-1H-indol-1-yl]-1-(3-fluorophenyl)-3-(methylamino)propan-2-ol;
1-[3-(2-chlorophenyl)-1H-indol-1-yl]-1-(3-fluorophenyl)-3-(methylamino)propan-2-ol; and
pharmaceutically acceptable salts thereof, particularly hydrochloride and dihydrochloride salts thereof.

Particularly preferred compounds of formula I include:
(1RS,2SR)-1-(1H-indol-1-yl)-3-(4-methylpiperazin-1-yl)-1-phenylpropan-2-ol;
(1RS,2SR)-1-(5-fluoro-1H-indol-1-yl)-3-(4-methylpiperazin-1-yl)-1-phenylpropan-2-ol;
(1RS,2SR)-1-(1H-indol-1-yl)-3-morpholin-4-yl-1-phenylpropan-2-ol;
(1RS,2SR)-3-(dimethylamino)-1-(1H-indol-1-yl)-1-phenylpropan-2-ol;
(1RS,2SR)-3-(ethylamino)-1-(1H-indol-1-yl)-1-phenylpropan-2-ol;
(1RS,2SR)-1-(1H-indol-1-yl)-3-(isopropylamino)-1-phenylpropan-2-ol;
(1RS,2SR)-3-(benzylamino)-1-(1H-indol-1-yl)-1-phenylpropan-2-ol;
(1RS,2SR)-3-[(cyclohexylmethyl)amino]-1-(1H-indol-1-yl)-1-phenylpropan-2-ol;
(1RS,2SR)-3-[(cyclohexylmethyl)amino]-1-(3-methyl-1H-indol-1-yl)-1-phenylpropan-2-ol;
(1RS,2SR)-3-(isopropylamino)-1-(3-methyl-1H-indol-1-yl)-1-phenylpropan-2-ol;

(1RS,2SR)-1-(1H-indol-1-yl)-3-(methylamino)-1-phenylpropan-2-ol;
(1RS,2SR)-3-(ethylamino)-1-(3-methyl-1H-indol-1-yl)-1-phenylpropan-2-ol;
(1RS,2SR)-1-(1H-indol-1-yl)-1-phenyl-3-piperazin-1-ylpropan-2-ol;
(1RS,2SR)-1-(1H-indol-1-yl)-1-phenyl-3-[(pyridin-4-ylmethyl) amino]propan-2-ol;
(I RS,2SR)-1-(5-chloro-1H-indol-1-yl)-1-phenyl-3-piperidin-1-ylpropan-2-ol;
(1RS,2RS)-1-(1H-indol-1-yl)-3-(methylamino)-1-phenylpropan-2-ol;
(1RS,2SR)-3-amino-1-(1H-indol-1-yl)-1-phenylpropan-2-ol;
(1RS,2SR)-3-(ethylamino)-1-(5-fluoro-1H-indol-1-yl)-1-phenylpropan-2-ol;
(1RS,2SR)-3-amino-1-(5-fluoro-1H-indol-1-yl)-1-phenylpropan-2-ol;
(1RS,2SR)-1-(5-fluoro-1H-indol-1-yl)-3-(methylamino)-1-phenylpropan-2-ol;
(1RS,2SR)-3-(methylamino)-1-(3-methyl-1H-indol-1-yl)-1-phenylpropan-2-ol;
(1R,2S)-1-(1H-indol-1-yl)-3-(methylamino)-1-phenylpropan-2-ol;
(1S,2R)-1-(1H-indol-1-yl)-3-(methylamino)-1-phenylpropan-2-ol;
(1RS,2SR)-3-amino-1-(3-methyl-1H-indol-1-yl)-1-phenylpropan-2-ol;
(1RS,2SR)-3-[ethyl(methyl)amino]-1-(1H-indol-1-yl)-1-phenylpropan-2-ol;
(1RS,2SR)-1-(5-chloro-1H-indol-1-yl)-3-(methylamino)-1-phenylpropan-2-ol;
(1RS,2RS)-1-(5-chloro-1H-indol-1-yl)-3-(methylamino)-1-phenylpropan-1-ol;
1-[(1RS,2SR)-2-hydroxy-3-(methylamino)-1-phenylpropyl]-1H-indole-3-carbonitrile;
(1R,2R)-1-(1H-indol-1-yl)-3-(methylamino)-1-phenylpropan-2-ol;
(1S,2S)-1-(1H-indol-1-yl)-3-(methylamino)-1-phenylpropan-2-ol;
(1S,2R)-3-(methylamino)-1-(3-methyl-1H-indol-1-yl)-1-phenylpropan-2-ol;
(1S,2R)-1-(3-chlorophenyl)-1-(1H-indol-1-yl)-3-(methylamino)propan-2-ol;
(1S,2R)-1-(4-chlorophenyl)-1-(1H-indol-1-yl)-3-(methylamino)propan-2-ol;
(1S,2R)-1-(1H-indol-1-yl)-3-(methylamino)-1-[3-(trifluoromethoxy)phenyl]propan-2-ol;
(1S,2R)-1-(1H-indol-1-yl)-3-(methylamino)-1-[2-(trifluoromethoxy)phenyl]propan-2-ol;
(1R,2S)-1-(1H-indol-1-yl)-3-(methylamino)-1-[2-(trifluoromethoxy)phenyl]propan-2-ol;
(1S,2R)-1-(2-chlorophenyl)-1-(1H-indol-1-yl)-3-(methylamino)propan-2-ol;
(1SR,2RS)-1-(1H-indol-1-yl)-3-(methylamino)-1-[4-(trifluoromethoxy)phenyl]propan-2-ol;
(1S,2R)-1-(1H-indol-1-yl)-3-(methylamino)-1-[4-(trifluoromethoxy)phenyl]propan-2-ol;
(1R,2S)-1-(1H-indol-1-yl)-3-(methylamino)-1-[4-(trifluoromethoxy)phenyl]propan-2-ol;
(1S,2R)-4-amino-1-(3-chlorophenyl)-1-(1H-indol-1-yl)butan-2-ol (1S,2R)-1-(3-bromophenyl)-1-(1H-indol-1-yl)-3-(methylamino)propan-2-ol;
3-[(1S,2R)-2-hydroxy-1-(1H-indol-1-yl)-3-(methylamino)propyl]benzonitrile
(1S,2R)-1-(3-fluorophenyl)-1-(1H-indol-1-yl)-3-(methylamino)propan-2-ol;
(1S,2R)-1-(3-fluorophenyl)-3-(methylamino)-1-[3-(3-methylphenyl)-1H-indol-1-yl]propan-2-ol;
(1S,2R)-1-(4-fluorophenyl)-3-(methylamino)-1-(3-methyl-1H-indol-1-yl)propan-2-ol;
(1S,2R)-1-(2-fluorophenyl)-1-(1H-indol-1-yl)-3-(methylamino)propan-2-ol;
(1S,2R)-1-(4-fluorophenyl)-1-(1H-indol-1-yl)-3-(methylamino)propan-2-ol;
(1S,2R)-1-(1H-indol-1-yl)-3-(methylamino)-1-(3-methylphenyl)propan-2-ol;
(1S,2R)-1-(1H-indol-1-yl)-3-(methylamino)-1-(2-methylphenyl)propan-2-ol;
(1R,2S)-1-(1H-indol-1-yl)-3-(methylamino)-1-(2-methylphenyl)propan-2-ol;
(1S,2R)-3-(ethylamino)-1-(3-fluorophenyl)-1-(1H-indol-1-yl)propan-2-ol;
(1S,2R)-1-(3-fluorophenyl)-1-(1H-indol-1-yl)-3-morpholin-4-ylpropan-2-ol;
(1S,2R)-1-(3-fluorophenyl)-1-(1H-indol-1-yl)-3-(propylamino)propan-2-ol;
(1S,2R)-1-(3-fluorophenyl)-1-(1H-indol-1-yl)-3-(4-methylpiperazin-1-yl)propan-2-ol;
(1S,2R)-1-(1H-indol-1-yl)-3-(methylamino)-1-(4-methylphenyl)propan-2-ol;
(1S,2R)-1-(2,3-dihydro-1H-indol-1-yl)-1-(3-fluorophenyl)-3-(methylamino)propan-2-ol;
(1S,2R)-1-(2,3-dihydro-1H-indol-1-yl)-3-(methylamino)-1-phenylpropan-2-ol;
(1S,2R)-1-(3-fluorophenyl)-3-(methylamino)-1-[3-(2-methylphenyl)-1H-indol-1-yl]propan-2-ol;
(1S,2R)-1-(3-fluorophenyl)-3-(methylamino)-1-(2-methyl-2,3-dihydro-1H-indol-1-yl)propan-2-ol;
(1S,2R)-1-(7-fluoro-3,3-dimethyl-2,3-dihydro-1H-indol-1-yl)-1-(3-fluorophenyl)-3-(methylamino)propan-2-ol;
(1S,2R)-1-(7-fluoro-3,3-dimethyl-2,3-dihydro-1H-indol-1-yl)-3-(methylamino)-1-phenylpropan-2-ol;
(1S,2R)-3-(methylamino)-1-(7-methyl-2,3-dihydro-1H-indol-1-yl)-1-phenylpropan-2-ol;
(1S,2R)-1-(3-fluorophenyl)-3-(methylamino)-1-(7-methyl-2,3-dihydro-1H-indol-1-yl)propan-2-ol;
(1S,2R)-1-(3-fluorophenyl)-3-(methylamino)-1-(5-methyl-2,3-dihydro-1H-indol-1-yl)propan-2-ol;
(1S,2R)-1-(1H-indol-1-yl)-1-(3-methoxyphenyl)-3-(methylamino)propan-2-ol;
(1SR,2RS)-1-(1H-indol-1-yl)-1-(4-methoxyphenyl)-3-(methylamino)propan-2-ol;
(1RS,2SR)-3-(methylamino)-1-(2-methyl-1H-indol-1-yl)-1-phenylpropan-2-ol;
(1RS,2SR)-1-(1H-benzimidazol-1-yl)-3-(methylamino)-1-phenylpropan-2-ol;
(1RS,2SR)-3-(methylamino)-1-(2-methyl-1H-benzimidazol-1-yl)-1-phenylpropan-2-ol;
(1RS,2SR)-1-(4-methoxy-1H-indol-1-yl)-3-(methylamino)-1-phenylpropan-2-ol;
(1S,2R)-1-(5-fluoro-1H-indol-1-yl)-3-(methylamino)-1-phenylpropan-2-ol;
(1S,2R)-1-(5-methoxy-1H-indol-1-yl)-3-(methylamino)-1-phenylpropan-2-ol;
(1S,2R)-1-(7-methoxy-1H-indol-1-yl)-3-(methylamino)-1-phenylpropan-2-ol;
(1S,2R)-1-(4-methoxy-1H-indol-1-yl)-3-(methylamino)-1-phenylpropan-2-ol;
(1S,2R)-1-(6-methoxy-1H-indol-1-yl)-3-(methylamino)-1-phenylpropan-2-ol;
(1RS,2SR)-1-(5-methoxy-1H-indol-1-yl)-3-(methylamino)-1-phenylpropan-2-ol;

(1S,2R)-1-(3-fluorophenyl)-1-(6-methoxy-1H-indol-1-yl)-3-(methylamino)propan-2-ol;
(1S,2R)-3-(methylamino)-1-phenyl-1-(1H-pyrrolo[2,3-b]pyridin-1-yl)propan-2-ol;
(1S,2R)-1-(5-chloro-2,3-dihydro-1H-indol-1-yl)-1-(3-fluorophenyl)-3-(methylamino)propan-2-ol;
(1S,2R)-3-(methylamino)-1-phenyl-1-(1H-pyrrolo[2,3-c]pyridin-1-yl)propan-2-ol;
(1S,2R)-1-(5-fluoro-1H-indol-1-yl)-1-(3-fluorophenyl)-3-(methylamino)propan-2-ol;
(1S,2R)-3-(methylamino)-1-(3-fluorophenyl)-1-(1H-pyrrolo[2,3-c]pyridin-1-yl)propan-2-ol;
(1S,2R)-1-(5-chloro-2,3-dihydro-1H-indol-1-yl)-3-(methylamino)-1-phenylpropan-2-ol;
(1S,2R)-3-(methylamino)-1-(6-methyl-1H-indol-1-yl)-1-phenylpropan-2-ol;
(1S,2R)-3-(methylamino)-1-(7-methyl-1H-indol-1-yl)-1-phenylpropan-2-ol;
(1S,2R)-1-(3-fluorophenyl)-3-(methylamino)-1-(5-methyl-1H-indol-1-yl)propan-2-ol;
(1S,2R)-1-(3-fluorophenyl)-3-(methylamino)-1-(7-methyl-1H-indol-1-yl)propan-2-ol;
(1S,2R)-3-(methylamino)-1-(4-methyl-1H-indol-1-yl)-1-phenylpropan-2-ol;
(1S,2R)-3-(methylamino)-1-(5-methyl-1H-indol-1-yl)-1-phenylpropan-2-ol;
(1S,2R)-1-(3-fluorophenyl)-3-(methylamino)-1-(4-methyl-1H-indol-1-yl)propan-2-ol;
(1S,2R)-1-(3-ethyl-1H-indol-1-yl)-1-(3-fluorophenyl)-3-(methylamino)propan-2-ol;
(1S,2R)-1-(3-fluorophenyl)-3-(methylamino)-1-(3-phenyl-1H-indol-1-yl)propan-2-ol;
7-fluoro-1-[(1S,2R)-2-hydroxy-3-(methylamino)-1-phenylpropyl]-3,3-dimethyl-1,3-dihydro-2H-indol-2-one;
1-[(1S,2R)-2-hydroxy-3-(methylamino)-1-phenylpropyl]-3,3-dimethyl-1,3-dihydro-2H-indol-2-one;
7-fluoro-1-[(1S,2R)-1-(3-fluorophenyl)-2-hydroxy-3-(methylamino)propyl]-3,3-dimethyl-1,3-dihydro-2H-indol-2-one;
(1S,2R)-1-(1H-indol-1-yl)-3-(methylamino)-1-(2-thienyl)propan-2-ol;
(1R,2R)-1-(1H-indol-1-yl)-3-(methylamino)-1-(2-thienyl)propan-2-ol;
1'-[(1S,2R)-2-hydroxy-3-(methylamino)-1-phenylpropyl]spiro[cyclohexane-1,3'-indol]-2'(1'H)-one;
(1S,2R)-2-(3-fluorophenyl)-2-(1H-indol-1-yl)-1-[(2S)-pyrrolidin-2-yl]ethanol;
(1R,2S)-2-(3-fluorophenyl)-2-(1H-indol-1-yl)-1-[(2S)-pyrrolidin-2-yl]ethanol;
1'-[(1S,2R)-2-hydroxy-3-(methylamino)-1-phenylpropyl]spiro[cyclobutane-1,3'-indol]-2'(1'H)-one;
1'-[(1S,2R)-2-hydroxy-3-(methylamino)-1-phenylpropyl]spiro[cyclopentane-1,3'-indol]-2'(1'H)-one;
1'-[(1S,2R)-2-hydroxy-3-(methylamino)-1-phenylpropyl]spiro[cyclopropane-1,3'-indol]-2'(1'H)-one;
5-fluoro-1-[(1S,2R)-2-hydroxy-3-(methylamino)-1-phenylpropyl]-3,3-dimethyl-1,3-dihydro-2H-indol-2-one;
(1S,2R)-3-(cyclopropylamino)-1-(3-fluorophenyl)-1-(1H-indol-1-yl)propan-2-ol;
7'-fluoro-1'-[(1S,2R)-2-hydroxy-3-(methylamino)-1-phenylpropyl]spiro[cyclohexane-1,3'-indol]-2'(1'H)-one;
5'-bromo-1'-[(1S,2R)-2-hydroxy-3-(methylamino)-1-phenylpropyl]spiro[cyclohexane-1,3'-indol]-2'(1'H)-one;
(1S,2R)-1-(3-fluorophenyl)-1-[3-(2-fluorophenyl)-1H-indol-1-yl]-3-(methylamino)propan-2-ol;
(1S,2R)-1-[3-(3,4-dichlorophenyl)-1H-indol-1-yl]-1-(3-fluorophenyl)-3-(methylamino)propan-2-ol;
(1S,2R)-1-(3-fluorophenyl)-1-[3-(3-fluorophenyl)-1H-indol-1-yl]-3-(methylamino)propan-2-ol;
(1S,2R)-1-(5-fluoro-3-methyl-1H-indol-1-yl)-3-(methylamino)-1-phenylpropan-2-ol;
(1S*,2R*)-3-amino-1-(5-fluoro-3-methyl-1H-indol-1-yl)-1-phenylpropan-2-ol;
(1S,2R)-1-(5-chloro-3-methyl-1H-indol-1-yl)-3-(methylamino)-1-phenylpropan-2-ol;
(1S,2R)-3-amino-1-(5-chloro-3-methyl-1H-indol-1-yl)-1-phenylpropan-2-ol;
[(2R,3S)-3-(5-chloro-3-methyl-1H-indol-1-yl)-2-methoxy-3-phenylpropyl]methylamine;
(1S,2R)-1-(7-chloro-3-methyl-1H-indol-1-yl)-3-(methylamino)-1-phenylpropan-2-ol;
[(2R,3S)-3-(5-fluoro-3-methyl-1H-indol-1-yl)-2-methoxy-3-phenylpropyl]methylamine;
(1S,2R)-1-(4-bromo-1H-indol-1-yl)-3-(methylamino)-1-phenylpropan-2-ol;
(1S,2R)-1-(4-bromo-1H-indol-1-yl)-1-(3-fluorophenyl)-3-(methylamino)propan-2-ol;
(1S,2R)-1-(5-bromo-1H-indol-1-yl)-3-(methylamino)-1-phenylpropan-2-ol;
(1S,2R)-1-(5-bromo-1H-indol-1-yl)-1-(3-fluorophenyl)-3-(methylamino)propan-2-ol;
1-[(1S,2R)-2-hydroxy-3-(methylamino)-1-phenylpropyl]-1H-indole-4-carbonitrile;
(1S,2R)-1-(6-bromo-1H-indol-1-yl)-3-(methylamino)-1-phenylpropan-2-ol;
1-[(1S,2R)-2-hydroxy-3-(methylamino)-1-phenylpropyl]-1H-indole-5-carbonitrile;
1-[(1S,2R)-1-(3-fluorophenyl)-2-hydroxy-3-(methylamino)propyl]-1H-indole-4-carbonitrile;
(1S,2R)-1-(6-bromo-1H-indol-1-yl)-1-(3-fluorophenyl)-3-(methylamino)propan-2-ol;
(1S,2R)-1-(6-fluoro-1H-indol-1-yl)-1-(3-fluorophenyl)-3-(methylamino)propan-2-ol;
(1S,2R)-3-amino-1-(3-fluorophenyl)-1-(1H-indol-1-yl)propan-2-ol;
(1S,2R)-1-(7-bromo-1H-indol-1-yl)-1-(3-fluorophenyl)-3-(methylamino)propan-2-ol;
(1S,2R)-1-(1H-indol-1-yl)-3-(methylamino)-1-[3-(trifluoromethyl)phenyl]propan-2-ol;
(1S,2R)-1-(3-fluorophenyl)-3-(methylamino)-1-spiro[cyclohexane-1,3'-indol]-1'(2'H)-ylpropan-2-ol;
(1S,2R)-1-(2,3-dihydro-1H-indol-1-yl)-3-(methylamino)-1-[3-(trifluoromethyl)phenyl]propan-2-ol;
(1S,2S)-1-(3-fluorophenyl)-1-(1H-indol-1-yl)-3-(methylamino)propan-2-ol;
(1S,2R)-1-(3,4-difluorophenyl)-1-(1H-indol-1-yl)-3-(methylamino)propan-2-ol;
(1S,2R)-1-(3-fluorophenyl)-3-(methylamino)-1-(3-methyl-1H-indol-1-yl)propan-2-ol;
(1S,2R)-1-(4-chloro-1H-indol-1-yl)-3-(methylamino)-1-phenylpropan-2-ol;
(1S,2R)-1-(6-chloro-1H-indol-1-yl)-3-(methylamino)-1-phenylpropan-2-ol;
(1S,2R)-1-(7-chloro-1H-indol-1-yl)-3-(methylamino)-1-phenylpropan-2-ol;
(1S,2R)-1-(7-chloro-1H-indol-1-yl)-1-(3-fluorophenyl)-3-(methylamino)propan-2-ol;
(1S,2R)-1-(4-chloro-1H-indol-1-yl)-1-(3-fluorophenyl)-3-(methylamino)propan-2-ol;
(1S,2R)-1-(6-chloro-1H-indol-1-yl)-1-(3-fluorophenyl)-3-(methylamino)propan-2-ol;
(1S,2R)-1-(5-chloro-1H-indol-1-yl)-3-(methylamino)-1-phenylpropan-2-ol;

(1S,2R)-1-(5-chloro-1H-indol-1-yl)-1-(3-fluorophenyl)-3-(methylamino)propan-2-ol;
(1S,2R)-1-(3-isopropyl-1H-indol-1-yl)-3-(methylamino)-1-phenylpropan-2-ol;
(1S,2R)-1-(3-fluorophenyl)-1-(3-isopropyl-1H-indol-1-yl)-3-(methylamino)propan-2-ol;
(1S,2R)-1-(3,5-difluorophenyl)-1-(1H-indol-1-yl)-3-(methylamino)propan-2-ol;
(1S,2R)-1-(3,5-difluorophenyl)-1-(2,3-dihydro-1H-indol-1-yl)-3-(methylamino)propan-2-ol;
(1S,2R)-4-amino-1-(3-fluorophenyl)-1-(1H-indol-1-yl)butan-2-ol;
(1S,2R)-1-(3,3-dimethyl-2,3-dihydro-1H-indol-1-yl)-1-(3-fluorophenyl)-3-(methylamino)propan-2-ol;
(1S,2R)-1-(3,5-difluorophenyl)-1-(3,3-dimethyl-2,3-dihydro-1H-indol-1-yl)-3-(methylamino)propan-2-ol;
(1S,2R)-1-(3,3-dimethyl-2,3-dihydro-1H-indol-1-yl)-3-(methylamino)-1-phenylpropan-2-ol;
(1S,2R)-1-(3-fluorophenyl)-3-(methylamino)-1-(3-methyl-2,3-dihydro-1H-indol-1-yl)propan-2-ol;
(1S,2R)-1-(3-fluorophenyl)-3-(methylamino)-1-spiro[cyclopentane-1,3'-indol]-1'(2'H)-ylpropan-2-ol;
(1S,2R)-1-(3-fluorophenyl)-1-[3-(4-methoxyphenyl)-1H-indol-1-yl]-3-(methylamino)propan-2-ol;
(1S,2R)-1-(3-fluorophenyl)-3-(methylamino)-1-[3-(4-methylphenyl)-1H-indol-1-yl]propan-2-ol;
(1S,2R)-1-[3-(4-tert-butylphenyl)-1H-indol-1-yl]-1-(3-fluorophenyl)-3-(methylamino)propan-2-ol;
(1S,2R)-1-(3-fluorophenyl)-1-[3-(3-methoxyphenyl)-1H-indol-1-yl]-3-(methylamino)propan-2-ol;
(1S,2R)-1-(3-fluorophenyl)-3-(methylamino)-1-{3-[4-(trifluoromethyl)phenyl]-1H-indol-1-yl}propan-2-ol;
(1S,2R)-1-(3,5-difluorophenyl)-1-(6-fluoro-2,3-dihydro-1H-indol-1-yl)-3-(methylamino)propan-2-ol;
(1S,2R)-1-(3-fluorophenyl)-3-(methylamino)-1-{3-[2-(trifluoromethyl)phenyl]-1H-indol-1-yl}propan-2-ol;
(1S,2R)-1-(3-fluorophenyl)-1-[3-(2-methoxyphenyl)-1H-indol-1-yl]-3-(methylamino)propan-2-ol;
(1S,2R)-1-(3-fluorophenyl)-3-(methylamino)-1-{3-[3-(trifluoromethyl)phenyl]-1H-indol-1-yl}propan-2-ol;
(1S,2R)-3-amino-1-(3-methyl-1H-indol-1-yl)-1-phenylpropan-2-ol;
(1S,2R)-1-(7-fluoro-3-methyl-1H-indol-1-yl)-3-(methylamino)-1-phenylpropan-2-ol;
(1S,2R)-3-amino-1-(7-fluoro-3-methyl-1H-indol-1-yl)-1-phenylpropan-2-ol;
(1S,2R)-1-(7-fluoro-1H-indol-1-yl)-3-(methylamino)-1-phenylpropan-2-ol;
(1S,2R)-1-(4-fluoro-1H-indol-1-yl)-3-(methylamino)-1-phenylpropan-2-ol;
(1S,2R)-1-(7-fluoro-1H-indol-1-yl)-1-(3-fluorophenyl)-3-(methylamino)propan-2-ol;
(1S,2R)-1-(4-fluoro-1H-indol-1-yl)-1-(3-fluorophenyl)-3-(methylamino)propan-2-ol;
(1S,2R)-1-(3-fluorophenyl)-3-(methylamino)-1-[5-(trifluoromethyl)-1H-indol-1-yl]propan-2-ol;
(1S,2R)-1-(6-fluoro-1H-indol-1-yl)-3-(methylamino)-1-phenylpropan-2-ol;
(1S,2R)-3-(methylamino)-1-phenyl-1-[6-(trifluoromethyl)-1H-indol-1-yl]propan-2-ol;
(1S,2R)-3-(methylamino)-1-phenyl-1-[5-(trifluoromethyl)-1H-indol-1-yl]propan-2-ol;
(1S,2R)-1-(3-tert-butyl-1H-indol-1-yl)-1-(3-fluorophenyl)-3-(methylamino)propan-2-ol;
(1S,2R)-1-(1H-indol-1-yl)-2-methyl-3-(methylamino)-1-phenylpropan-2-ol;
(2R,3S)-3-(1H-indol-1-yl)-1-(methylamino)-3-phenylbutan-2-ol;
1-tert-butyl-3-[(1S,2R)-2-hydroxy-3-(methylamino)-1-phenylpropyl]-1,3-dihydro-2H-benzimidazol-2-one;
1-[(1S,2R)-2-hydroxy-3-(methylamino)-1-phenylpropyl]-3-propyl-1,3-dihydro-2H-benzimidazol-2-one;
5-bromo-1-[(1S,2R)-2-hydroxy-3-(methylamino)-1-phenylpropyl]-3,3-dimethyl-1,3-dihydro-2H-indol-2-one;
6-fluoro-1-[(1S,2R)-2-hydroxy-3-(methylamino)-1-phenylpropyl]-3,3-dimethyl-1,3-dihydro-2H-indol-2-one;
4-fluoro-1-[(1S,2R)-2-hydroxy-3-(methylamino)-1-phenylpropyl]-3,3-dimethyl-1,3-dihydro-2H-indol-2-one;
1-cyclobutyl-3-[(1S,2R)-2-hydroxy-3-(methylamino)-1-phenylpropyl]-1,3-dihydro-2H-benzimidazol-2-one;
5-fluoro-3-[(1S,2R)-2-hydroxy-3-(methylamino)-1-phenylpropyl]-1-propyl-1,3-dihydro-2H-benzimidazol-2-one;
1-ethyl-3-[(1S,2R)-1-(3-fluorophenyl)-2-hydroxy-3-(methylamino)propyl]-1,3-dihydro-2H-benzimidazol-2-one;
1-ethyl-3-[(1S,2R)-2-hydroxy-3-(methylamino)-1-phenylpropyl]-1,3-dihydro-2H-benzimidazol-2-one;
4-fluoro-3-[(1S,2R)-2-hydroxy-3-(methylamino)-1-phenylpropyl]-1-isopropyl-1,3-dihydro-2H-benzimidazol-2-one;
1-cyclopentyl-3-[(1S,2R)-2-hydroxy-3-(methylamino)-1-phenylpropyl]-1,3-dihydro-2H-benzimidazol-2-one;
1-[(1S,2R)-2-hydroxy-3-(methylamino)-1-phenylpropyl]-3-isopropyl-1,3-dihydro-2H-benzimidazol-2-one;
3-[(1S,2R)-3-(ethylamino)-2-hydroxy-1-phenylpropyl]-5-fluoro-1-isopropyl-1,3-dihydro-2H-benzimidazol-2-one;
1-[(1S,2R)-2-hydroxy-3-(methylamino)-1-phenylpropyl]-3-methyl-1,3-dihydro-2H-benzimidazol-2-one;
1-ethyl-5-fluoro-3-[(1S,2R)-2-hydroxy-3-(methylamino)-1-phenylpropyl]-1,3-dihydro-2H-benzimidazol-2-one;
1-ethyl-4-fluoro-3-[(1S,2R)-2-hydroxy-3-(methylamino)-1-phenylpropyl]-1,3-dihydro-2H-benzimidazol-2-one;
4-fluoro-3-[(1S,2R)-1-(3-fluorophenyl)-2-hydroxy-3-(methylamino)propyl]-1-isopropyl-1,3-dihydro-2H-benzimidazol-2-one;
1-ethyl-4-fluoro-3-[(1S,2R)-2-hydroxy-3-(methylamino)-1-(3-fluorophenyl)-propyl]-1,3-dihydro-2H-benzimidazol-2-one;
1-[(1S,2R)-1-(3-fluorophenyl)-2-hydroxy-3-(methylamino)propyl]-3,3-dimethyl-1,3-dihydro-2H-indol-2-one;
(1S,2R)-1-[3-(2,3-difluorophenyl)-1H-indol-1-yl]-1-(3-fluorophenyl)-3-(methylamino)propan-2-ol;
(1S,2R)-1-[3-(2-chlorophenyl)-1H-indol-1-yl]-1-(3-fluorophenyl)-3-(methylamino)propan-2-ol; and
pharmaceutically acceptable salts thereof, particularly hydrochloride and dihydrochloride salts thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Race-* mates and Resolutions (Wiley Interscience, New York, 1981); Wilen, S. H., et al., *Tetrahedron*, 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature. In accordance with this invention, compounds of formula I are produced by the following reaction schemes (Scheme I-IV).

The compounds of this invention contain chiral centers, proving for various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature. In accordance with this invention, compounds of formula I are produced by the following reaction schemes (Scheme I-IV).

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

In accordance with this invention, compounds of formula I are produced by the following reaction schemes (Schemes I to IV). Depending on the desired diastereomer, the compounds can be prepared via two different synthetic routes (A and B, Schemes I and II). If it is desired to synthesize compounds of formula I-a, they can be prepared from compounds of formula 4 by selectively converting the primary alcohol into a leaving group and displacing it with a desired amine. (Route A, Scheme I) Any conventional method for the selective conversion of a primary alcohol into a leaving group, and any conventional method for displacing a primary leaving group with an amine can be utilized for this conversion. In accordance with the preferred embodiment of this invention, the diol of formula 4 is treated with para-toluenesulfonyl chloride in pyridine to form the tosylate of formula 5, which is converted to the compound of formula I-a through treatment with an excess of alcoholic amine solution, either at room temperature or heated to about 40° C. to about 80° C. in a sealed tube. Compounds of formula I-a can be converted to a pharmaceutically acceptable salt using any conventional method.

Scheme I

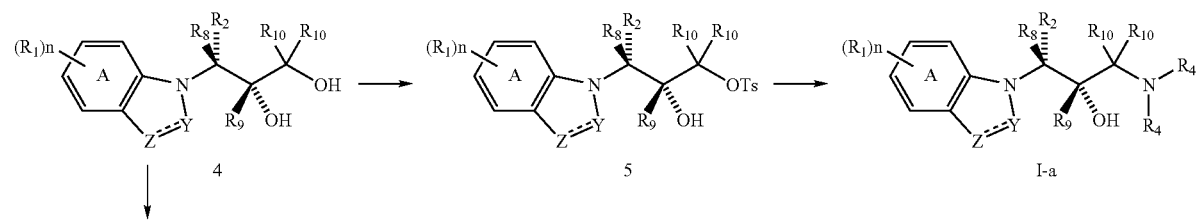

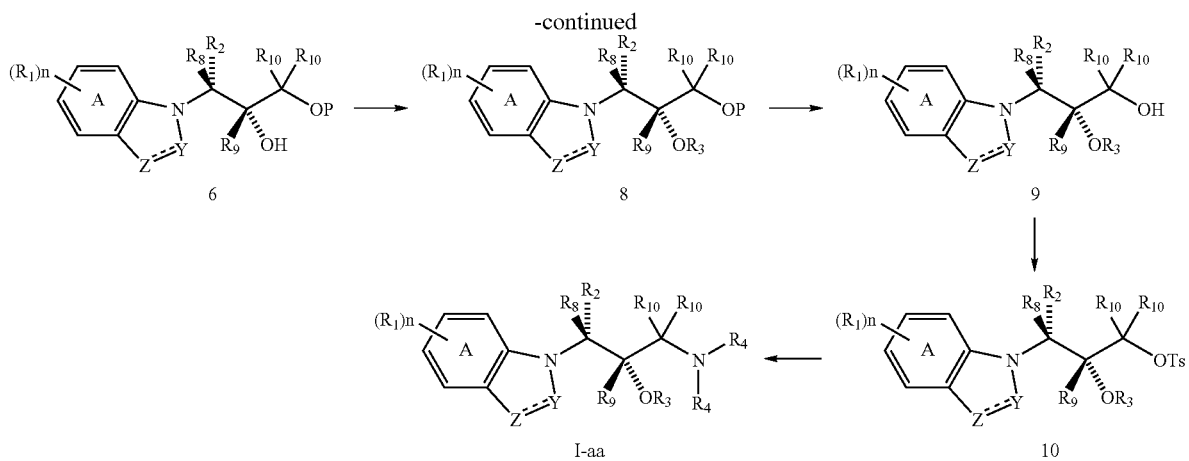

Where: A, Y, Z, R₁, n, R₂, R₄, R₈, R₉, R₁₀ are as previously described.
R³ = C₁–C₄ lower alkyl, P = protecting group; preferably trimethylsilyl, tert-butyldimethylsilyl, para-nitrobenzoyl; and OTs = paratoluenesulfonylate or any conventional leaving group If it is desired to form compounds of formula I-aa, they can be prepared from compounds of formula 4 via selective protection of the primary alcohol, followed by alkylation of the secondary alcohol, and deprotection of the primary alcohol. Any conventional alcohol protecting groups can be utilized for this conversion and any method for the selective protection of a primary alcohol can be employed. According to the preferred embodiment of this invention, the reaction is carried out at low temperature in dichloromethane with trimethylsilyl chloride and triethylamine as base to form compounds of formula 6. Alkylation of the secondary alcohol can be accomplished via any conventional method of alkylating a secondary alcohol found in the literature. According to the preferred embodiment of this invention, compounds of formula 6 are reacted with an alkyl halide using sodium hydride as base to form compounds of formula 8, which can be deprotected to form compounds of formula 9 via any conventional method for deprotection of a primary alcohol. According to the preferred embodiment of this invention, compounds of formula 8 are treated with dilute aqueous hydrochloric acid or trifluoroacetic acid in dichloromethane to form compounds of formula 9. Conversion of the primary alcohol in compounds of formula 9 to complete the synthesis of compounds of formula I-aa can be performed as previously described for the synthesis of compounds of formula I-a. Compounds of formula I-aa can be converted to a pharmaceutically acceptable salt using any conventional method.

Alternatively, compounds of formula 10 can be prepared directly from compounds of formula 5. Any method of alkylating a hydroxyl group in the presence of a tosyl group can be employed for this conversion. In accordance with the preferred embodiment of this invention, compounds of formula 5 are treated with an alkyl trifluoromethanesulfonate, e.g. methyl trifluoromethanesulfonate, in the presence of a hindered base, e.g. 2,6-di-tert-butyl-4-methylpyridine. The reaction can be performed either at room temperature or heated to about 40° C. to about 80° C. Compounds of formula 10 can be converted to compounds of formula I-aa as previously described for the synthesis of compounds of formula I-a.

Compounds of formula I-aa can be converted to a pharmaceutically acceptable salt using any conventional method.

If it is desired to form compounds of I-b, they can also be prepared from compounds of formula 4 via Route B (Scheme II). This route involves the selective protection of the primary alcohol followed by conversion of the secondary alcohol to a leaving group. Any conventional method for the selective protection of a primary alcohol, and any conventional method for converting of a secondary alcohol into a leaving group can be utilized for this conversion. In accordance with the preferred embodiment of this invention, compounds of formula 4 are treated with para-nitrobenzoyl chloride in pyridine at low temperature (preferably below about 0° C.) to form compounds of formula 11. Compounds of formula 11 can be converted to a secondary mesylate of formula 12 via reaction with methanesulfonyl chloride in dichloromethane using triethylamine as base. The reaction is preferably carried out at temperatures between about –15° C. and about 10° C. Deprotection of the primary alcohol in compounds of formula 12 allows for the formation of a primary epoxide through an $S_N2$ reaction resulting in an inversion of the stereocenter. Any conventional method for deprotection of a primary alcohol, and any conventional method for epoxide formation onto an alpha leaving group can be employed for this conversion. In accordance with the preferred embodiment of this invention, compounds of formula 12 are treated with an aqueous solution of a suitable base in organic solvent, preferably, aqueous sodium hydroxide in dioxane. The resulting epoxide of formula 13 can be ring-opened regioselectively with an amine to produce the desired aminoalcohol of formula I-b. Any conventional method for the regioselective ring opening of a primary epoxide can be employed for this conversion. In accordance with the preferred embodiment of this invention, compounds of formula 13 are treated with an excess of an alcoholic amine solution in a sealed flask, either at room temperature or heated to about 40° C. to about 90° C. Compounds of formula I-b can be converted into a pharmaceutically acceptable salt using conventional methods.

Scheme II

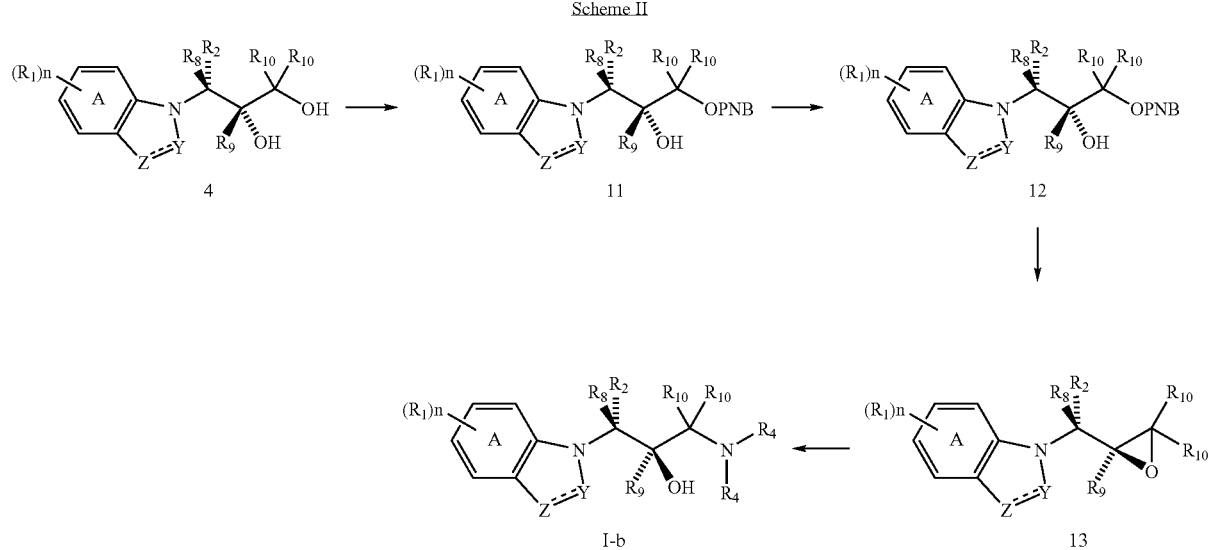

Where: A, Y, Z, $R_1$, n, $R_2$, and $R_4$, $R_8$, $R_{10}$ are as previously described
$R_9$ is H
PNB = para-nitrobenzoyl or any conventional protecting group; and
OMs = methanesulfonate or any conventional leaving group If it is desired to form compounds of formula I-bb, they can be made from compounds of formula I-b via protection of the amine, alkylation of the secondary alcohol and deprotection of the amine (Scheme III). Any conventional method for protection of an amine, alkylation of a secondary alcohol, and deprotection of an amine can be utilized for this conversion. In accordance with the preferred embodiment of this invention, compounds of formula I-b are treated with boc anhydride, where boc=tert-butoxycarbonyl, to form compounds of formula 14 which can be alkylated with an alkyl halide using sodium hydride as base to form compounds of formula 15. Deprotection is accomplished using an acid, preferably trifluoroacetic acid in dichloromethane to form compounds of formula I-bb that can be converted into a pharmaceutically acceptable salt using conventional methods.

Scheme III

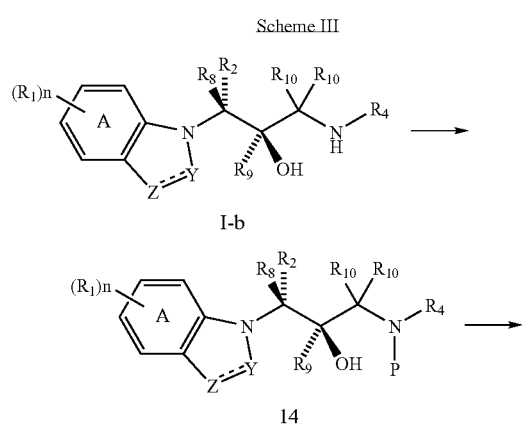

-continued

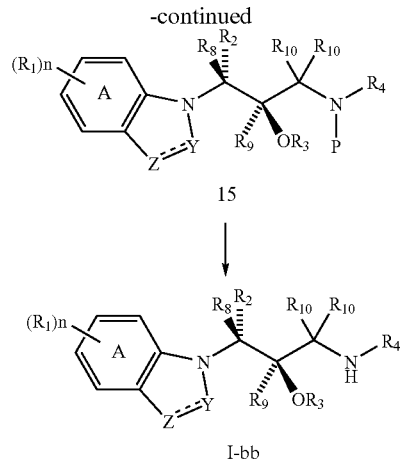

Where: A, Y, Z, $R_1$, n, $R_2$, and $R_4$, $R_8$, $R_{10}$ are as previously described
$R_9$ is H
$R_3$ = $C_1$–$C_3$ lower alkyl, P = protecting group, preferably tert-butoxycarbonyl Compounds of formula 4 are formed via a regio- and stereo-selective ring opening of an appropriately substituted epoxide of formula 17 (formed via an epoxidation of an appropriately substituted allylic alcohol) with an appropriately substituted compound of formula 16 (Scheme IV). Any conventional method for the regio- and stereo-selective ring opening of an epoxide can be employed for this conversion. In accordance with the preferred embodiment of this invention, compounds of formula 16 are treated with a base, e.g. sodium hydride, sodium tert-butoxide, potassium hydroxide, potassium tert-butoxide or potassium hydroxide, then treated with the epoxide of formula 17. The epoxide of formula 17 can be pre-treated with a Lewis acid, e.g. titanium iso-propoxide, boron-trifluoride, etc. to ensure regio-selective ring-opening.

The reaction occurs at room temperature over a duration of about 2 hours to about 72 hours. Alternatively, compounds of formula 16 that are suitably nucleophilic, e.g. indoline, can be heated with the epoxide of formula 17 at temperatures from about 50° C. to about 170° C. to form compounds of formula 4.

Epoxidation of trans-allylic alcohols can be performed either racemically or asymmetrically using methods described in the literature. In accordance with the preferred embodiment of this invention, racemic epoxidation is conducted with either peracetic acid or meta-chloroperbenzoic acid. If it is desired to produce a single enantiomer of compounds of formula I, asymmetric epoxidation of an allylic alcohol can be performed with tert-butylhydroperoxide or cumene hydroperoxide in the presence of the appropriate tartrate ester, titanium (IV) isopropoxide, and molecular sieves. This method is well established in the literature (e.g. K. B. Sharpless, et. al., *J. Org. Chem.* 1986, 51, 3710). Compounds of formula 16 and the starting allylic alcohols are either available from commercial sources or are accessible through methods well established in the literature.

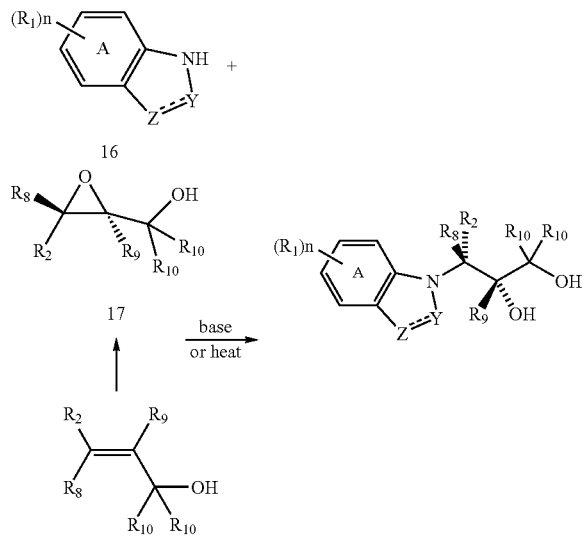

Where: A, Y, Z, $R_1$, n, $R_8$, $R_9$, $R_{10}$, and $R_2$ are as previously described.

In other embodiments, the invention is directed to pharmaceutical compositions, comprising:
a. at least compound of formula I, or pharmaceutically acceptable salt thereof; and
b. at least one pharmaceutically acceptable carrier.

Generally, the compound of formula I, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I, or pharmaceutically acceptable salt thereof, with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, non-cardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain, cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

As used herein, "pain," includes both acute pain and chronic pain, which may be centralized pain, peripheral pain, or combination thereof. The term includes many different types of pains including, but not limited to, neuropathic pain, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purpose of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

In one embodiment, the present invention is directed to methods for treating or preventing vasomotor symptoms in a subject in need thereof, comprising the step of:
administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
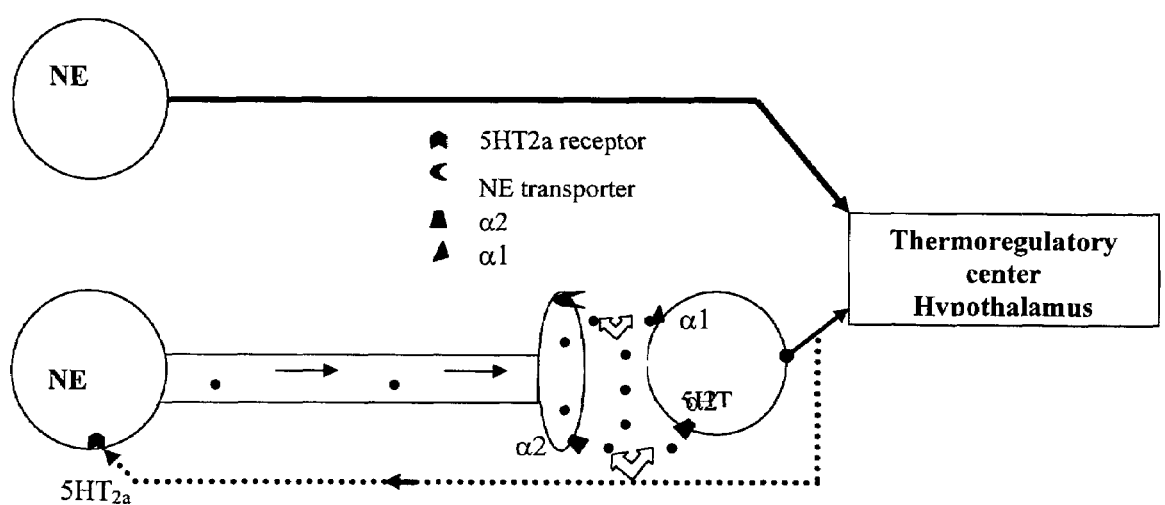
FIG. 2 is a schematic representation of the interactions of norepinephrine and serotonin and their respective receptors ($5\text{-HT}_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha 1}$ and adrenergic$_{\alpha 2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:
administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromylagia syndrome in a subject in need thereof, comprising the step of:

administering to said subject an effective amount of a compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

(1RS,2SR)-1-(1H-indol-1-yl)-3-(4-methylpiperazin-1-yl)-1-phenyl propan-2-ol dihydrochloride

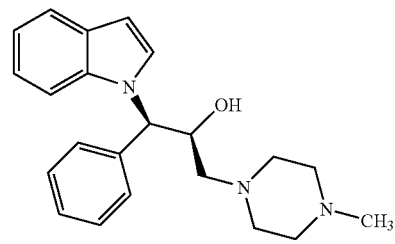

Step 1: A mixture of indole (2.34 g, 20 mmol) and pulverized solid potassium hydroxide (1.12 g, 20 mmol) was stirred for 30 minutes under nitrogen at room temperature. Trans-3-phenylglycidol (3.0 g, 20 mmol) in dimethylsulfoxide (1 mL)

was then added and the mixture was stirred at 70° C. for 2 hours until no epoxide remained. The mixture was then cooled and partitioned between water and dichloromethane. The organic layer was separated, washed with water several times, dried over anhydrous sodium sulfate, filtered, and concentrated in vacuo. The crude product was purified via Biotage chromatography (FlasH40i, silica, 10%, 20%, 30% ethyl acetate/hexane) to yield 1.92 g (36%) of (2RS,3RS)-3-indol-1-yl-3-phenyl-propane-1,2-diol as an oil. $^1$HNMR (DMSO): δ3.27 (m, 2H, CH$_2$OH), δ4.45 (m, 1H, CHOH), δ4.80 (t, 1H, CH$_2$OH), δ5.20 (d, 1H, CHOH), δ5.60 (d, 1H, CHPh); MS (ESI) m/z 268 ([M+H]$^+$).

Step 2: A solution of (2RS,3RS)-3-indol-1-yl-3-phenyl-propane-1,2-diol (1.83 g, 6.8 mmol) and p-toluenesulfonyl chloride (1.31 g, 6.8 mmol) in anhydrous pyridine (10 mL) was stirred at room temperature under nitrogen for 15 hours. The mixture was then diluted with water (10 mL), quenched with a 2N aqueous solution of hydrochloric acid in an ice/water bath until the solution was pH=3, and extracted with dichloromethane. The organic layer was washed with water again, dried over anhydrous sodium sulfate, filtered, and concentrated. The residue was purified via Biotage chromatography (FlasH40i, silica, 10%, 25% EtOAc/hexane) to yield 1.98 g (69%) of (2RS,3RS)-toluene-4-sulfonic acid 2-hydroxy-3-indol-1-yl-3-phenyl-propyl ester as a white solid. $^1$HNMR (DMSO): δ3.70 and δ3.85 (dd and dd, 2H, CH$_2$OTs), δ4.80 (m, 1H, CHOH), δ5.52 (d, 1H, CHPh), δ5.82 (d, 1H, CHOH); MS (ESI) m/z 422 ([M+H]$^+$).

Step 3: A mixture of (2RS,3RS)-toluene-4-sulfonic acid 2-hydroxy-3-indol-1-yl-3-phenyl-propyl ester (0.185 g, 0.4 mmol), 1-methyl piperazine (0.05 mL, 0.4 mmol) and potassium carbonate (0.07 g, 0.44 mmol) in acetonitrile (10 mL) was stirred at reflux under nitrogen for 24 hours. After cooling, the mixture was filtered and the filtrate was concentrated and purified via Biotage chromatography (5% methanol/dichloromethane) to give a white solid of (1RS,2SR)-1-(1H-indol-1-yl)-3-(4-methylpiperazin-1-yl)-1-phenylpropan-2-ol. The free base was dissolved in a minimum amount of ethanol and treated with a 1 N ethereal solution of hydrochloric acid until the solution was pH=3 followed by diethyl ether. The product was then crystallized by adding a minimum amount of hexane to afford the titled compound, (1RS,2SR)-1-(1H-indol-1-yl)-3-(4-methylpiperazin-1-yl)-1-phenylpropan-2-ol dihydrochloride as an off-white solid. MS m/z 350 ([M+H]$^+$); HRMS: calcd for C$_{22}$H$_{27}$N$_{30}$+H+, 350.22269; found (ESI, [M+H]+), 350.2228.

Example 2

(1RS,2SR)-1-(5-fluoro-1H-indol-1-yl)-3-(4-methylpiperazin-1-yl)-1-phenylpropan-2-ol dihydrochloride

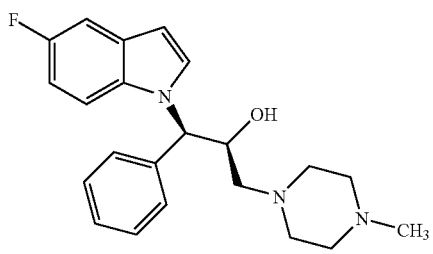

In an analogous manner to EXAMPLE 1, step 1 (2RS,3RS)-3-(5-fluoro-indol-1-yl)-3-phenyl-propane-1,2-diol was prepared from 5-fluoroindole and trans-3-phenylglycidol as an oil. MS (ESI) m/z 286 ([M+H]$^+$).

In an analogous manner to EXAMPLE 1, step 2 (2RS,3RS)-toluene-4-sulfonic acid 3-(5-fluoro-indol-1-yl)-2-hydroxy-3-phenyl-propyl ester was prepared from (2RS,3RS)-3-(5-fluoro-indol-1-yl)-3-phenyl-propane-1,2-diol. MS (ESI) m/z 440 ([M+H]$^+$).

In an analogous manner to EXAMPLE 1, step 3 (1RS,2SR)-1-(5-fluoro-1H-indol-1-yl)-3-(4-methylpiperazin-1-yl)-1-phenylpropan-2-ol dihydrochloride was prepared from (2RS,3RS)-toluene-4-sulfonic acid 3-(5-fluoro-indol-1-yl)-2-hydroxy-3-phenyl-propyl ester. MS m/z 368 ([M+H]$^+$); HRMS: calcd for C$_{22}$H$_{26}$FN$_{30}$+H+, 368.21327; found (ESI, [M+H]+), 368.213.

Example 3

(1RS,2SR)-1-(1H-indol-1-yl)-3-morpholin-4-yl-1-phenylpropan-2-ol hydrochloride

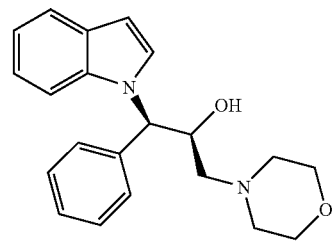

In an analogous manner to EXAMPLE 1, step 3 (1RS,2SR)-1-(1H-indol-1-yl)-3-(4-methylpiperazin-1-yl)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3) and morpholine. MS (ESI) m/z 337 ([M+H]$^+$); HRMS: calcd for C$_{21}$H$_{24}$N$_2$O$_2$+H+, 337.19105; found (ESI, [M+H]+), 337.1909.

Example 4

(1RS,2SR)-3-(dimethylamino)-1-(1H-indol-1-yl)-1-phenylpropan-2-ol hydrochloride

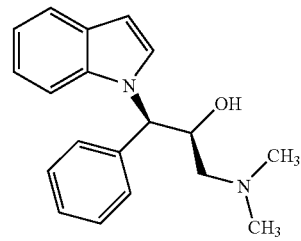

In an analogous manner to EXAMPLE 1, step 3 (1RS,2SR)-3-(dimethylamino)-1-(1H-indol-1-yl)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3) and dimethylamine hydrochloride. MS (ES) m/z 295.2 ([M+H]⁺); HRMS: calcd for $C_{19}H_{22}N_2O$+H+, 295.18049; found (ESI, [M+H]+), 295.1829.

Example 5

(1RS,2SR)-3-(ethylamino)-1-(1H-indol-1-yl)-1-phenylpropan-2-ol hydrochloride

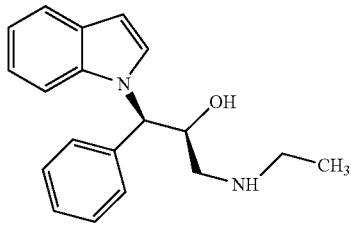

In an analogous manner to EXAMPLE 1, step 3, a solution of (2RS,3RS)-toluene-4-sulfonic acid 2-hydroxy-3-indol-1-yl-3-phenyl-propyl ester (EXAMPLE 1, step 3, 0.42 g, 1.0 mmol) and ethylamine (2 N solution in methanol, 5 mL) was stirred in a sealed flask at room temperature for 15 hours. After dilution with a saturated aqueous solution of sodium bicarbonate, the mixture was extracted with a solution of dichloromethane/isopropyl alcohol (3/1). The extract was washed with water, dried over anhydrous sodium sulfate, filtered and concentrated in vacuo. The crude product was purified on via Biotage chromatography (FlasH40i, silica, dichloromethane, 5% methanol/dichloromethane) to give an oil as free base of the expected product. The free base was dissolved in a minimum amount of ethanol and treated with a 1 N ethereal solution of hydrochloric acid until the solution was pH=3 followed by diethyl ether. The product was then crystallized by adding a minimum amount ethyl acetate to afford the titled compound, (1RS,2SR)-3-(ethylamino)-1-(1H-indol-1-yl)-1-phenylpropan-2-ol hydrochloride as a tan solid. MS (ES) m/z 295.2 ([M+H]⁺); HRMS: calcd for $C_{19}H_{22}N_2O$+H+, 295.18049; found (ESI, [M+H]+), 295.1797.

Example 6

(1RS,2SR)-1-(1H-indol-1-yl)-3-(isopropylamino)-1-phenylpropan-2-ol hydrochloride

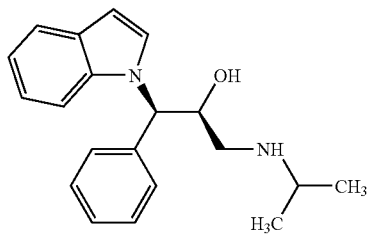

In an analogous manner to EXAMPLE 1, step 3 (1RS, 2SR)-1-(1H-indol-1-yl)-3-(isopropylamino)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3) and isopropylamine. MS (ES) m/z 309.2 ([M+H]⁺); HRMS: calcd for $C_{20}H_{24}N_2O$+H+, 309.19614; found (ESI, [M+H]+), 309.1971.

Example 7

(1RS,2SR)-3-(benzylamino)-1-(1H-indol-1-yl)-1-phenylpropan-2-ol hydrochloride

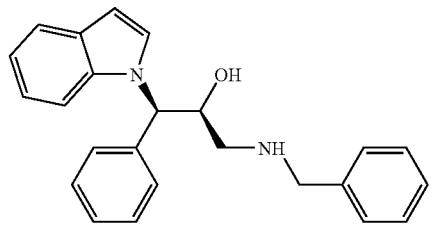

In an analogous manner to EXAMPLE 1, step 3 (1RS, 2SR)-3-(benzylamino)-1-(1H-indol-1-yl)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3) and benzylamine. MS (ES) m/z 357.2 ([M+H]⁺); HRMS: calcd for $C_{24}H_{24}N_2O$+H+, 357.19614; found (ESI, [M+H]+), 357.1962.

Example 8

(1RS,2SR)-3-[(cyclohexylmethyl)amino]-1-(1H-indol-1-yl)-1-phenylpropan-2-ol hydrochloride

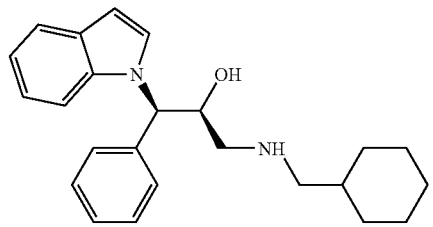

In an analogous manner to EXAMPLE 1, step 3 (1RS, 2SR)-3-[(cyclohexylmethyl)amino]-1-(1H-indol-1-yl)-1-phenylpropan-2-ol hydrochloride was prepared from (2RS, 3RS)-toluene-4-sulfonic acid 2-hydroxy-3-indol-1-yl-3-phenyl-propyl ester (EXAMPLE 1, step 3) and cyclohexyl methylamine. MS (ES) m/z 363.3 ([M+H]⁺); HRMS: calcd for $C_{24}H_{30}N_2O$+H+, 363.24309; found (ESI, [M+H]+), 363.2421.

Example 9

(1RS,2SR)-3-[(cyclohexylmethyl)amino]-1-(3-methyl-1H-indol-1-yl)-1-phenylpropan-2-ol hydrochloride

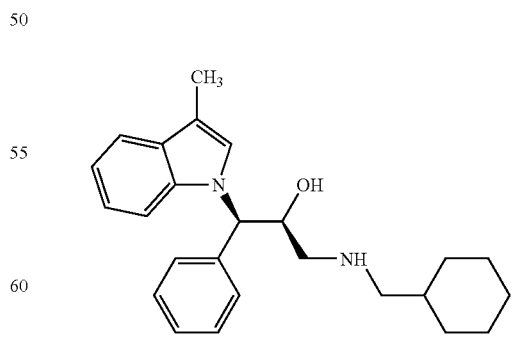

In an analogous manner to EXAMPLE 1, step 1 (2RS, 3RS)-3-(3-methyl-indol-1-yl)-3-phenyl-propane-1,2-diol was prepared from 3-methylindole and trans-3-phenylglycidol as a yellow solid. MS (ESI) m/z 282 ([M+H]⁺).

In an analogous manner to EXAMPLE 1, step 2 (2RS, 3RS)-toluene-4-sulfonic acid 3-(3-methyl-indol-1-yl)-2-hydroxy-3-phenyl-propyl ester was prepared from (2RS,3RS)-3-(3-methyl-indol-1-yl)-3-phenyl-propane-1,2-diol. MS (ESI) m/z 436 ([M+H]$^+$).

In an analogous manner to EXAMPLE 1, step 3 (1RS, 2SR)-3-[(cyclohexylmethyl)amino]-1-(3-methyl-1H-indol-1-yl)-1-phenylpropan-2-ol hydro chloride was prepared from (2RS,3RS)-toluene-4-sulfonic acid 3-(3-methyl-indol-1-yl)-2-hydroxy-3-phenyl-propyl ester and cyclohexyl methylamine. MS (ES) m/z 377.3 ([M+H]$^+$); HRMS: calcd for $C_{25}H_{32}N_2O$+H+, 377.25874; found (ESI, [M+H]+), 377.2577.

Example 10

(1RS,2SR)-3-(isopropylamino)-1-(3-methyl-1H-indol-1-yl)-1-phenylpropan-2-ol hydrochloride

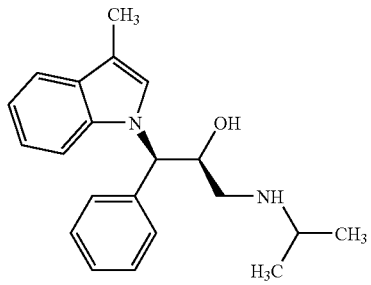

In an analogous manner to EXAMPLE 1, step 3 (1RS, 2SR)-3-(isopropylamino)-1-(3-methyl-1H-indol-1-yl)-1-phenylpropan-2-ol hydrochloride was prepared from (2RS, 3RS)-toluene-4-sulfonic acid 3-(3-methyl-indol-1-yl)-2-hydroxy-3-phenyl-propyl ester (EXAMPLE 12, step 2) and isopropylamine. MS (ES) m/z 323.2 ([M+H]$^+$); HRMS: calcd for $C_{21}H_{26}N_2O$+H+, 323.21179; found (ESI, [M+H]+), 323.2135.

Example 11

(1RS,2SR)-1-(1H-indol-1-yl)-3-(methylamino)-1-phenylpropan-2-ol hydrochloride

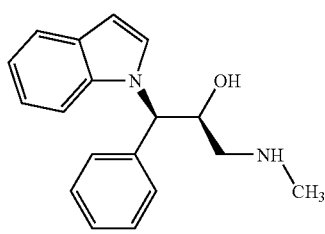

In an analogous manner to EXAMPLE 5, (1RS,2SR)-1-(1H-indol-1-yl)-3-(methylamino)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3) and methylamine (2N solution in methanol). MS (ESI) m/z 281 ([M+H]$^+$); HRMS: calcd for $C_{18}H_{20}N_2O$+H+, 281.16484; found (ESI, [M+H]+), 281.166.

Example 12

(1RS,2SR)-3-(ethylamino)-1-(3-methyl-1H-indol-1-yl)-1-phenyl propan-2-ol hydrochloride

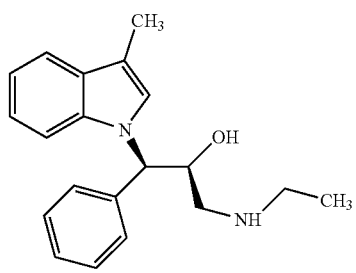

In an analogous manner to EXAMPLE 5, (1RS,2SR)-3-(ethylamino)-1-(3-methyl-1H-indol-1-yl)-1-phenylpropan-2-ol hydrochloride was prepared from (2RS,3RS)-toluene-4-sulfonic acid 3-(3-methyl-indol-1-yl-2-hydroxy-3-phenyl-propyl ester (EXAMPLE 12, step 2) and ethylamine (2N solution in methanol). MS (ESI) m/z 309 ([M+H]$^+$); HRMS: calcd for $C_{20}H_{24}N_2O$+H+, 309.19614; found (ESI, [M+H]+), 309.198.

Example 13

(1RS,2SR)-1-(1H-indol-1-yl)-1-phenyl-3-piperazin-1-ylpropan-2-ol dihydrochloride

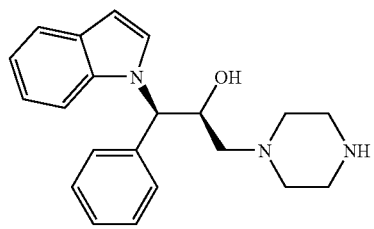

In an analogous manner to EXAMPLE 1, step 3 (2SR, 3RS)-4-(2-hydroxy-3-indol-1-yl-3-phenyl-propyl)-piperazine-1-carboxylic acid tert-butyl ester was prepared from (2RS,3RS)-toluene-4-sulfonic acid 2-hydroxy-3-indol-1-yl-3-phenyl-propyl ester (EXAMPLE 1, step 3, 0.211 g, 0.5 mmol) and tert-butyl-1-piperazine carboxylate (0.19 g, 1.0 mmol). The product was dissolved in diethyl ether (3 mL) and treated with a 4N solution of hydrochloric acid in dioxane (0.75 mL, 3.0 mmol). The reaction mixture was then stirred at room temperature for 15 hours, and the crude solid product was filtered and recrystallized from ethanol with a minimum amount of diethyl ether to give the titled compound, (1RS, 2SR)-1-(1H-indol-1-yl)-1-phenyl-3-piperazin-1-ylpropan-2-ol dihydrochloride as a tan solid. MS (ESI) m/z 336 ([M+H]$^+$); HRMS: calcd for $C_{21}H_{25}N_3O$+H+, 336.20704; found (ESI, [M+H]+), 336.2085.

Example 14

(1RS,2SR)-1-(1H-indol-1-yl)-1-phenyl-3-[(pyridin-4-ylmethyl)amino]propan-2-ol hydrochloride

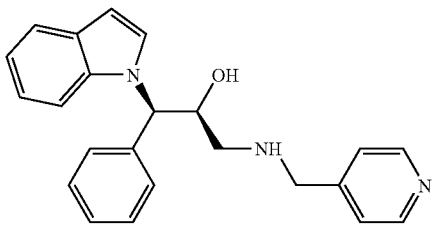

In an analogous manner to EXAMPLE 1, step 3 (1RS, 2SR)-1-(1H-indol-1-yl)-1-phenyl-3-[(pyridin-4-ylmethyl)amino]propan-2-ol hydrochloride was prepared from (2RS, 3RS)-toluene-4-sulfonic acid 2-hydroxy-3-indol-1-yl-3-phenyl-propyl ester (EXAMPLE 1, step 3) and pyridine-4-yl-methylamine. MS (ESI) m/z 358 ([M+H]$^+$); HRMS: calcd for $C_{23}H_{23}N_{3}O$+H+, 358.19139; found (ESI, [M+H]+), 358.1928.

Example 15

(1RS,2SR)-1-(5-chloro-1H-indol-1-yl)-1-phenyl-3-piperidin-1-ylpropan-2-ol hydrochloride

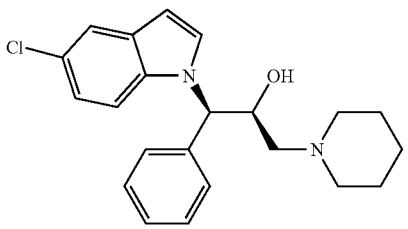

In an analogous manner to EXAMPLE 1, step 1 (2RS, 3RS)-3-(5-chloro-indol-1-yl)-3-phenyl-propane-1,2-diol was prepared from 5-chloroindole and trans-3-phenylglycidol as an oil. MS (ESI) m/z 302 ([M+H]$^+$).

In an analogous manner to EXAMPLE 1, step 2 (2RS, 3RS)-toluene-4-sulfonic acid 3-(5-chloro-indol-1-yl-2-hydroxy-3-phenyl-propyl ester was prepared from (2RS,3RS)-3-(5-chloro-indol-1-yl)-3-phenyl-propane-1,2-diol. MS (ESI) m/z 456 ([M+H]$^+$).

In an analogous manner to EXAMPLE 1, step 3 (1RS, 2SR)-1-(5-chloro-1H-indol-1-yl)-1-phenyl-3-piperidin-1-ylpropan-2-ol hydrochloride was prepared from (2RS,3RS)-toluene-4-sulfonic acid 3-(5-chloro-indol-1-yl-2-hydroxy-3-phenyl-propyl ester and piperidine. MS m/z 369 ([M+H]$^+$); HRMS: calcd for $C_{22}H_{25}ClN_{2}O$+H+, 369.17282; found (ESI, [M+H]+), 369.1725.

Example 16

(1RS,2RS)-1-(1H-indol-1-yl)-3-(methylamino)-1-phenylpropan-2-ol hydrochloride

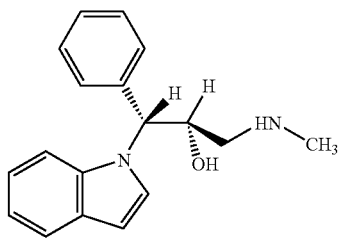

Step 2. To a solution of (2RS,3RS)-3-indol-1-yl-3-phenyl-propane-1,2-diol (EXAMPLE 1, step 1, 1.83 g, 6.9 mmol) in anhydrous pyridine (25 mL), p-nitrobenzoyl chloride (1.3 g, 6.9 mmol) in 1 mL of pyridine was added at –10° C. dropwise. After stirring for 30 minutes, the reaction mixture was cooled with an ice bath and quenched with water and a 2N aqueous solution of hydrochloric acid until the solution was pH=3 and extracted with ethyl acetate. The extract was washed with water, dried over anhydrous sodium sulfate and concentrated to give (2RS,3RS)-4-nitro-benzoic acid 2-hydroxy-3-indol-1-yl-3-phenyl-propyl ester quantitatively as a yellow solid. MS (ESI) m/z 417 ([M+H]$^+$).

Step 3. To a solution of (2RS, 3RS)-4-nitro-benzoic acid 2-hydroxy-3-indol-1-yl-3-phenyl-propyl ester and triethylamine (1.4 mL, 10.5 mmol) in dichloromethane (20 mL) was added methanesulfonyl chloride (0.59 mL, 7.6 mmol) dropwise at 0-5° C. with stirring. After stirring for 30 minutes, the mixture was washed with a 1N aqueous solution of hydrochloric acid, 5% aqueous sodium bicarbonate, and water, dried over anhydrous sodium sulfate, filtered, and concentrated to give a light yellow fluffy solid. The crude product was recrystallized from dichloromethane with a minimum amount of diethyl ether to give (2RS,3RS)-4-nitro-benzoic acid-3-indol-1-yl-2-methanesulfonyloxy-3-phenyl-propyl ester as a yellow solid. MS (ESI) m/z 495 ([M+H]$^+$).

Step 4. A solution of (2RS,3RS)-4-nitro-benzoic acid-3-indol-1-yl-2-methanesulfonyloxy-3-phenyl-propyl ester in dioxane (30 mL) and a 2N aqueous solution of sodium hydroxide (15 mL) were stirred at room temperature for 4 hours. The mixture was diluted with water and extracted with ethyl acetate. The extract was washed with 5% aqueous sodium carbonate and water, dried over anhydrous sodium sulfate, filtered, and concentrated to give (1RS,2SR)-1-(oxiranyl-phenyl-methyl)-1H-indole as an oil. MS (ESI) m/z 250 ([M+H]$^+$).

Step 5. (1RS,2SR)-1-(oxiranyl-phenyl-methyl)-1H-indole was treated with 5 mL of methylamine (2N solution in methanol) with stirring at room temperature for 15 hours. The reaction mixture was concentrated in vacuo and the crude product was recrystallized form dichloromethane. The free base of the expected product was dissolved in a minimum amount of dichloromethane, treated with a 1N ethereal solution of hydrochloric acid until the solution was pH=3. The solid product was then recrystallized by adding an additional diethyl ether to give (1RS,2RS)-1-(1H-indol-1-yl)-3-(methylamino)-1-phenylpropan-2-ol hydrochloride as a light tan solid. MS m/z 281 ([M+H]$^+$); HRMS: calcd for $C_{18}H_{20}N_{2}O$+H+, 281.16484; found (ESI, [M+H]+), 281.1654.

Example 17

(1RS,2SR)-3-amino-1-(1H-indol-1-yl)-1-phenylpropan-2-ol hydrochloride

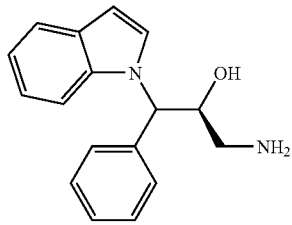

In an analogous manner to EXAMPLE 5, (1RS,2SR)-3-amino-1-(1H-indol-1-yl)-1-phenylpropan-2-ol hydrochloride was prepared from (2RS,3RS)-toluene-4-sulfonic acid 2-hydroxy-3-indol-1-yl-3-phenyl-propyl ester (EXAMPLE 1, step 3, 0.42 g, 1.0 mmol) in a minimum amount of methanol and an excess of a 30% aqueous solution of ammonium hydroxide. The crude product was dissolved in n-hexane and filtered to give a white solid as a free base. The free base of the product was dissolved in a minimum amount of ethanol and treated with a 1N solution of ethereal hydrochloric acid until the solution was pH=3 followed by diethyl ether. The product was then crystallized by adding a minimum amount of ethyl acetate to afford the titled compound as a tan solid. MS (ESI) m/z 267 ([M+H]$^+$); HRMS: calcd for $C_{17}H_{18}N_2O$+H+, 267.14919; found (ESI, [M+H]+), 267.1493.

Example 18

(1RS,2SR)-3-(ethylamino)-1-(5-fluoro-1H-indol-1-yl)-1-phenylpropan-2-ol hydrochloride

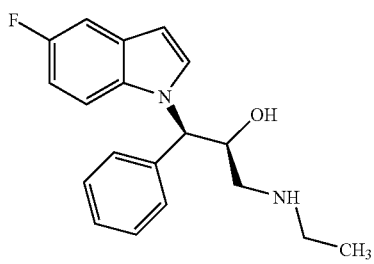

In an analogous manner to EXAMPLE 5, (1RS,2SR)-3-(ethylamino)-1-(5-fluoro-1H-indol-1-yl)-1-phenylpropan-2-ol hydrochloride was prepared from (2RS,3RS)-toluene-4-sulfon ic acid 3-(5-fluoro-indol-1-yl-2-hydroxy-3-phenyl-propyl ester (EXAMPLE 2, step 2) and ethylamine (2N solution in methanol). MS (ES) m/z 313.2 ([M+H]$^+$); HRMS: calcd for $C_{19}H_{21}FN_2O$+H+, 313.17107; found (ESI, [M+H]+), 313.1706.

Example 19

(1RS,2SR)-3-amino-1-(5-fluoro-1H-indol-1-yl)-1-phenylpropan-2-ol hydrochloride

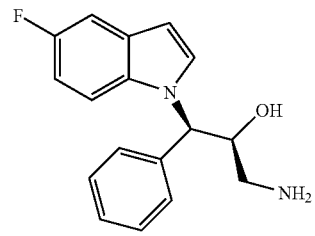

In an analogous manner to EXAMPLE 17, (1RS,2SR)-3-amino-1-(5-fluoro-1H-indol-1-yl)-1-phenylpropan-2-ol hydrochloride was prepared from (2RS, 3RS)-toluene-4-sulfonic acid 3-(5-fluoro-indol-1-yl-2-hydroxy-3-phenyl-propyl ester (EXAMPLE 2, step 2) and a 30% aqueous solution of ammonium hydroxide as a white solid. MS (ES) m/z 285.2 ([M+H]$^+$); HRMS: calcd for $C_{17}H_{17}FN_2O$+H+, 285.13977; found (ESI, [M+H]+), 285.1403.

Example 20

(1RS,2SR)-1-(5-fluoro-1H-indol-1-yl)-3-(methylamino)-1-phenylpropan-2-ol hydrochloride

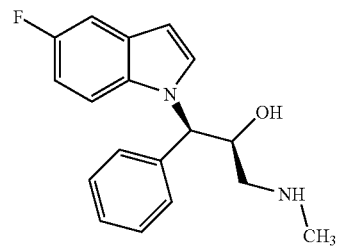

In an analogous manner to EXAMPLE 5, (1RS,2SR)-1-(5-fluoro-1H-indol-1-yl)-3-(methylamino)-1-phenylpropan-2-ol hydrochloride was prepared from (2RS,3RS)-toluene-4-sulfon ic acid 3-(5-fluoro-indol-1-yl-2-hydroxy-3-phenyl-propyl ester (EXAMPLE 2, step 2) obtained and methylamine (2N solution in methanol). MS (ESI) m/z 299 ([M+H]$^+$); HRMS: calcd for $C_{18}H_{19}FN_2O$+H+, 299.15542; found (ESI, [M+H]+), 299.1564.

Example 21

(1RS,2SR)-3-(methylamino)-1-(3-methyl-1H-indol-1-yl)-1-phenyl propan-2-ol hydrochloride

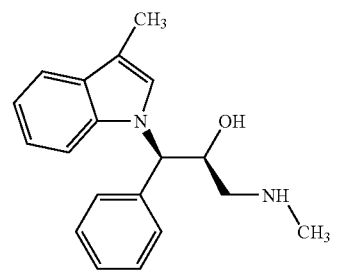

In an analogous manner to EXAMPLE 5, (1RS,2SR)-3-(methylamino)-1-(3-methyl-1H-indol-1-yl)-1-phenylpropan-2-ol hydrochloride was prepared from (2RS, 3RS)-toluene-4-sulfonic acid 3-(3-methyl-indol-1-yl-2-hydroxy-3-phenyl-propyl ester (EXAMPLE 10, step 2) and methylamine (2N solution in methanol). MS (ESI) m/z 295 ([M+H]$^+$); HRMS: calcd for $C_{19}H_{22}N_2O$+H+, 295.18049; found (ESI, [M+H]+), 295.1816.

Example 22

(1R,2S)-1-(1H-indol-1-yl)-3-(methylamino)-1-phenylpropan-2-ol hydrochloride

Chiral

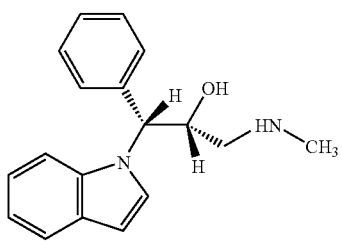

In an analogous manner to EXAMPLE 1, step 1 (2R,3R)-3-indol-1-yl-3-phenyl-propane-1,2-diol was prepared from indole and [(2S,3S)-3-phenyloxiran-2-yl]methanol as an oil. MS (ESI) m/z 286 ([M+H]$^+$).

In an analogous manner to EXAMPLE 1, step 2 (2R,3R)-toluene-4-sulfonic acid 3-indol-1-yl)-2-hydroxy-3-phenyl-propyl ester was prepared from (2R,3R)-3-indol-1-yl-3-phenyl-propane-1,2-diol. MS (ESI) m/z 440 ([M+H]$^+$).

In an analogous manner to EXAMPLE 5, (1R,2S)-1-(1H-indol-1-yl)-3-(methylamino)-1-phenylpropan-2-ol hydrochloride was prepared from (2R,3R)-toluene-4-sulfonic acid 3-indol-1-yl)-2-hydroxy-3-phenyl-propyl ester and methylamine (2N solution in methanol) as a white solid. CD/MeOH=(+); e/e=99.9% as determined by chiral HPLC; MS (ESI) m/z 281 ([M+H]$^+$); HRMS: calcd for $C_{18}H_{20}N_2O$+H+, 281.16484; found (ESI, [M+H]+), 281.1649.

Example 23

(1S,2R)-1-(1H-indol-1-yl)-3-(methylamino)-1-phenylpropan-2-ol hydrochloride

Chiral

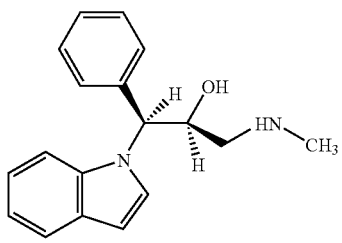

Racemic (1RS,2SR)-1-(1H-indol-1-yl)-3-(methylamino)-1-phenylpropan-2-ol (EXAMPLE 11) was dissolved in methanol. The resulting solution was injected onto the Supercritical Fluid Chromatography instrument. The baseline resolved enantiomers, using the conditions described below, were collected. The enantiomeric purity of each enantiomer was determined under the same Supercritical Fluid Chromatography conditions using a Chiralcel OJ-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702 |
| Column: | Chiralcel OJ-H; 5 u; 250 mm L × 20 mm ID (Chiral Technologies, Inc, Exton, PA, USA) |
| Column temperature: | 35° C. |
| SFC Modifier: | 20% MeOH with 1% diethylamine |
| Flow rate: | 50 mL/min |
| Outlet Pressure: | 100 bar |
| Detector: | UV at 218 nm |

(1S,2R)-1-(1H-indol-1-yl)-3-(methylamino)-1-phenylpropan-2-ol was isolated as a slower retention time peak with (−) rotation of chiral detection (CD) and e/e=99.4% as determined by chiral HPLC. The isolated free base was concentrated in vacuo, dissolved in minimum amount of ethanol and treated with a 1N ethereal solution of hydrochloric acid until the solution was pH=3 followed by diethyl ether. The product was then crystallized by adding a minimum amount of ethyl acetate to afford the titled compound as a white solid of hydrochloride salt; MS (ESI) m/z 281 ([M+H]$^+$); HRMS: calcd for C18H20N2O+H+, 281.16484; found (ESI, [M+H]+), 281.1646.

Example 24

(1RS,2SR)-3-amino-1-(3-methyl-1H-indol-1-yl)-1-phenylpropan-2-ol hydrochloride

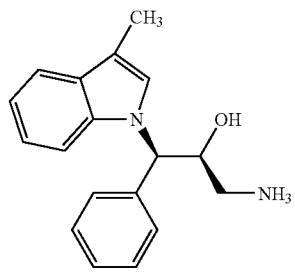

In an analogous manner to EXAMPLE 17, (1RS,2SR)-3-amino-1-(3-methyl-1H-indol-1-yl)-1-phenylpropan-2-ol hydrochloride was prepared from (2RS, 3RS)-toluene-4-sulfonic acid 3-(3-methyl-indol-1-yl-2-hydroxy-3-phenyl-propyl ester (EXAMPLE 9, step 2) and a 30% aqueous solution of ammonium hydroxide as a tan solid. MS (ES) m/z 281.1 ([M+H]$^+$); HRMS: calcd for $C_{18}H_{20}N_2O$+H+, 281.16484; found (ESI, [M+H]+), 281.1645.

Example 25

(1RS,2SR)-3-[ethyl(methyl)amino]-1-(1H-indol-1-yl)-1-phenylpropan-2-ol hydrochloride

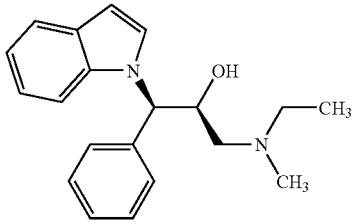

In an analogous manner to EXAMPLE 5, (1RS,2SR)-3-[ethyl(methyl)amino]-1-(1H-indol-1-yl)-1-phenylpropan-2-ol hydrochloride was prepared from (1RS,2SR)-3-(methylamino)-1-(1H-indol-1-yl)-1-phenylpropan-2-ol (EXAMPLE 11) and ethylamine (2N solution in methanol) as a tan solid. MS (ES) m/z 309.0 ([M+H]$^+$); HRMS: calcd for $C_{20}H_{24}N_{2}O$+H+, 309.19614; found (ESI, [M+H]+), 309.1955.

Example 26

(1RS,2SR)-1-(5-chloro-1H-indol-1-yl)-3-(methylamino)-1-phenylpropan-2-ol hydrochloride

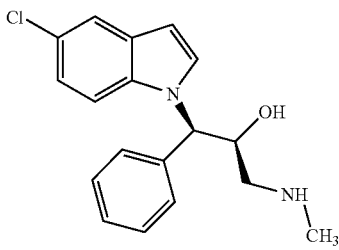

In an analogous manner to EXAMPLE 1, step 1 (2RS,3RS)-3-(5-chloro-indol-1-yl)-3-phenyl-propane-1,2-diol was prepared from 5-chloroindole and trans-3-phenylglycidol as an oil. MS (ESI) m/z 302 ([M+H]$^+$).

In an analogous manner to EXAMPLE 1, step 2 (2RS,3RS)-toluene-4-sulfonic acid 3-(5-chloro-indol-1-yl-2-hydroxy-3-phenyl-propyl ester was prepared from (2RS,3RS)-3-(5-chloro-indol-1-yl)-3-phenyl-propane-1,2-diol. MS (ESI) m/z 456 ([M+H]$^+$).

In an analogous manner to EXAMPLE 5, step 3 (1RS,2SR)-1-(5-chloro-1H-indol-1-yl)-3-(methylamino)-1-phenylpropan-2-ol hydrochloride was prepared from (2RS,3RS)-toluene-4-sulfonic acid 3-(5-chloro-indol-1-yl-2-hydroxy-3-phenyl-propyl ester and methylamine (2N solution in methanol). MS (ESI) m/z 315 ([M+H]$^+$); HRMS: calcd for $C_{18}H_{19}ClN_{2}O$+H+, 315.12587; found (ESI, [M+H]+), 315.1258.

Example 27

(1RS,2RS)-1-(5-chloro-1H-indol-1-yl)-3-(methylamino)-1-phenylpropan-1-ol hydrochloride

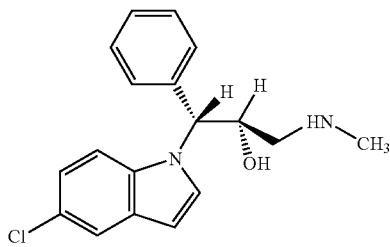

In an analogous manner to EXAMPLE 16, step 2 (2RS,3RS)-4-nitro-benzoic acid 3-(5-chloro-indol-1-yl)-2-hydroxy-3-phenyl-propyl ester was prepared from (2RS,3RS)-3-(5-chloro-indol-1-yl)-3-phenyl-propane-1,2-diol (EXAMPLE 1, step 1). MS (ESI) m/z 451 ([M+H]$^+$).

In an analogous manner to EXAMPLE 16, step 3 (2RS,3RS)-4-nitro-benzoic acid 3-(5-chloro-indol-1-yl)-2-methanesulfonyloxy-3-phenyl-propyl ester was prepared from (2RS,3RS)-4-nitro-benzoic acid 3-(5-chloro-indol-1-yl)-2-hydroxy-3-phenyl-propyl ester. MS (ESI) m/z 529 ([M+H]$^+$).

In an analogous manner to EXAMPLE 16, step 4 (1RS,2SR)-5-chloro-1-(oxiranyl-phenyl-methyl)-1H-indole was prepared from (2RS,3RS)-4-nitro-benzoic acid 3-(5-chloro-indol-1-yl)-2-methanesulfonyloxy-3-phenyl-propyl ester. MS (ESI) m/z 284 ([M+H]$^+$).

In an analogous manner to EXAMPLE 16, step 5 (1RS,2RS)-1-(5-chloro-1H-indol-1-yl)-3-(methylamino)-1-phenylpropan-2-ol hydrochloride as a tan solid. MS (ESI) m/z 315 ([M+H]$^+$); HRMS: calcd for $C_{18}H_{19}ClN_{2}O$+H+, 315.12587; found (ESI, [M+H]+), 315.1276.

Example 28

1-[(1RS,2SR)-2-hydroxy-3-(methylamino)-1-phenylpropyl]-1H-indole-3-carbonitrile hydrochloride

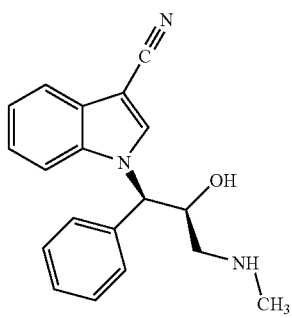

In an analogous manner to EXAMPLE 1, step 1 (2RS,3RS)-3-(3-cyano-indol-1-yl)-3-phenyl-propane-1,2-diol was prepared from 3-cyanoindole and trans-3-phenylglycidol as an oil. MS (ESI) m/z 293 ([M+H]$^+$).

In an analogous manner to EXAMPLE 1, step 2 (2RS,3RS)-toluene-4-sulfonic acid 3-(3-cyano-indol-1-yl-2-hydroxy-3-phenyl-propyl ester was prepared from (2RS,3RS)-3-(3-cyano-indol-1-yl)-3-phenyl-propane-1,2-diol. MS (ESI) m/z 447 ([M+H]$^+$).

In an analogous manner to EXAMPLE 1, step 3 (1RS,2SR)-1-(3-cyano-1H-indol-1-yl)-3-(4-methylpiperazin-1-yl)-1-phenylpropan-2-ol hydrochloride was prepared from (2RS,3RS)-toluene-4-sulfonic acid 3-(3-cyano-indol-1-yl-2-hydroxy-3-phenyl-propyl ester as a white solid. MS (ESI) m/z 306 ([M+H]$^+$); HRMS: calcd for $C_{19}H_{19}N_3O$+H+, 306.16009; found (ESI, [M+H]+), 306.1614.

Example 29

(1R,2R)-1-(1H-indol-1-yl)-3-(methylamino)-1-phenylpropan-2-ol hydrochloride

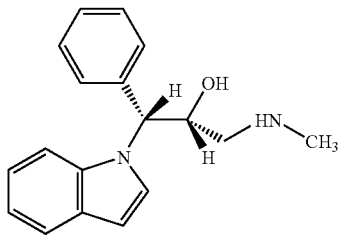

Chiral

Racemic (1RS,2RS)-1-(1H-indol-1-yl)-3-(methylamino)-1-phenylpropan-2-ol (EXAMPLE 16) was dissolved in methanol. The resulting solution was injected onto the Supercritical Fluid Chromatography instrument. The baseline resolved enantiomers, using the conditions described below, were collected. The enantiomeric purity of each enantiomer was determined under the same Supercritical Fluid Chromatography conditions using a Chiralcel OJ-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralcel OJ-H; 5 u; 250 mm L × 20 mm ID (Chiral Technologies, Inc, Exton, PA, USA) |
| Column temperature: | 35° C. |
| SFC Modifier: | 20% MeOH with 1% Ethanesulfonic acid |
| Flow rate: | 50 mL/min |
| Outlet Pressure: | 100 bar |
| Detector: | UV at 220 nm |

(1R,2R)-1-(1H-indol-1-yl)-3-(methylamino)-1-phenylpropan-2-ol was isolated as a faster retention time peak with (+) rotation of chiral detection (CD) and e/e=99.9% as determined by chiral HPLC.

In an analogous manner as EXAMPLE 23, the titled compound was afforded as an off white solid of hydrochloride salt; MS (ESI) m/z 306 ([M+H]$^+$); HRMS: calcd for C18H20N20+H+, 281.16484; found (ESI, [M+H]+), 281.1654.

Example 30

(1S,2S)-1-(1H-indol-1-yl)-3-(methylamino)-1-phenylpropan-2-ol hydrochloride

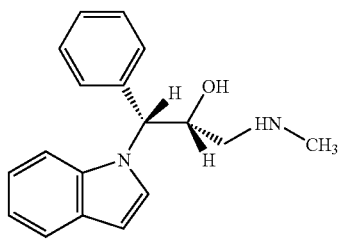

Chiral

In an analogous manner to EXAMPLE 29, (1S,2S)-1-(1H-indol-1-yl)-3-(methylamino)-1-phenylpropan-2-ol was isolated as a slower retention time peak with (−) rotation of chiral detection (CD) and e/e=99.9% as determined by chiral HPLC.

In an analogous manner as EXAMPLE 23, the titled compound was afforded as a white solid of hydrochloride salt; MS (ESI) m/z 306 ([M+H]$^+$); HRMS: calcd for C18H20N20+H+, 281.16484; found (ESI, [M+H]+), 281.1655.

Example 31

(1S,2R)-3-(methylamino)-1-(3-methyl-1H-indol-1-yl)-1-phenylpropan-2-ol hydrochloride

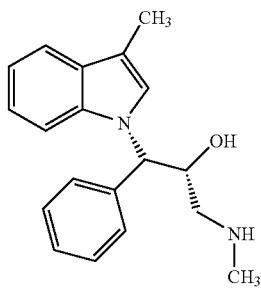

Chiral

In an analogous manner to EXAMPLE 1, step 1 (2S,3S)-3-(3-methyl-indol-1-yl)-3-phenyl-propane-1,2-diol was prepared from 3-methylindole and [(2R,3R)-3-phenyloxiran-2-yl]methanol (EXAMPLE 117, step 4) as an oil. MS (ESI) m/z 282 ([M+H]$^+$).

In an analogous manner to EXAMPLE 1, step 2 (2S,3S)-toluene-4-sulfonic acid 3-(3-methyl-indol-1-yl)-2-hydroxy-3-phenyl-propyl ester was prepared from (2S,3S)-3-(3-methyl-indol-1-yl)-3-phenyl-propane-1,2-diol. MS (ESI) m/z 436 ([M+H]$^+$).

In an analogous manner to EXAMPLE 5, (1S,2R)-1-(1H-indol-1-yl)-3-(methylamino)-1-phenylpropan-2-ol hydrochloride was prepared from (2S,3S)-toluene-4-sulfonic acid

59

3-(3-methyl-indol-1-yl)-2-hydroxy-3-phenyl-propyl ester and methylamine (2N solution in methanol) as a white solid. [□]$D^{25}$/MeOH=+116; CD/MeOH=(−); MS (ESI) m/z 295 ([M+H]$^+$); HRMS: calcd for $C_{19}H_{22}N_{2}O+H+$, 295.18049; found (ESI, [M+H]+), 295.1816.

Example 32

(1RS,2SR)-1-(2,3-dihydro-4H-1,4-benzoxazin-4-yl)-3-(methylamino)-1-phenylpropan-2-ol dihydrochloride

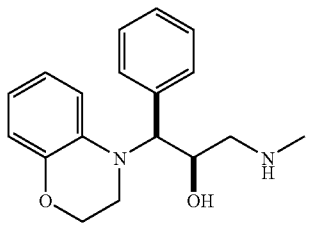

A mixture of 3,4-dihydro-2H-benzo[1,4]oxazine (2.027 g 15.00 mmol) and trans-ethyl-3-phenylglycidate (2.883 g, 15.00 mmol) was stirred at 135° C. for 12 hours. After cooling, the viscous liquid was purified via Biotage Horizon (FLASH 40 M, silica, 10%, 20%, 30% EtOAc/hexane) and recrystallized (minimal warm chloroform/hexane/−20° C.) to yield 4.261 g (87%) ethyl (2RS,3RS)-3-(2,3-dihydro-4H-1,4-benzoxazin-4-yl)-2-hydroxy-3-phenylpropanoate as a white solid. MS (ESI) m/z 328.0 ([M+H]$^+$).

A mixture of ethyl (2RS,3RS)-3-(2,3-dihydro-4H-1,4-benzoxazin-4-yl)-2-hydroxy-3-phenylpropanoate (283 mg, 0.864 mmol) and ethanolic methylamine solution (5 mL, 33% in ethanol) was stirred at 70° C. in a sealed tube for 5 hours. After cooling, all volatiles were removed under reduced pressure. The resulting yellow solid was purified via Biotage Horizon (FLASH 12 S, silica, 20%, 35%, 50% EtOAc/hexane) to yield 235 mg (87%) (2RS,3RS)-3-(2,3-dihydro-4H-1,4-benzoxazin-4-yl)-2-hydroxy-N-methyl-3 phenylpropanamide as a white solid. MS (ESI) m/z 311.0 ([M−H]$^−$).

A solution of (2RS,3RS)-3-(2,3-dihydro-4H-1,4-benzoxazin-4-yl)-2-hydroxy-N-methyl-3 phenylpropanamide (216 mg, 0.692 mmol) in dry tetrahydrofuran (3 mL) under nitrogen was treated dropwise with a solution of borane (1.0 M in tetrahydrofuran, 3.50 mL, 3.50 mmol), and the resulting solution was stirred at 70° C. for 2 hours. After cooling in an ice bath, the reaction mixture was treated with a 2N aqueous solution of hydrochloric acid (1 mL), and the resulting mixture was heated at 50° C. for 30 minutes. Tetrahydrofuran was removed under reduced pressure, and the aqueous residue was dissolved in water (5 mL) and washed with diethyl ether (10 mL). The aqueous layer was made alkaline with solid potassium carbonate and extracted with ethyl acetate (2×10 mL). The combined organic extracts were washed with brine, dried (sodium sulfate) and concentrated under reduced pressure to yield 202 mg (98%) (1RS,2SR)-1-(2,3-dihydro-4H-1,4-benzoxazin-4-yl)-3-(methylamino)-1-phenylpropan-2-ol as a colorless oil. This oil was dissolved in ethanol (1 mL) and treated with a solution of hydrochloric acid (0.5 mL, 4M in 1,4-dioxane). All volatiles were again removed under reduced pressure. The resulting white solid was recrystallized (minimal warm ethanol/ethyl ether/−20° C.) to yield 105 mg (41%) (1RS,2SR)-1-(2,3-dihydro-4H-1,4-benzoxazin-4-yl)-3-(methylamino)-1-phenylpropan-2-ol di hydrochloride as a

60 white solid. MS (ESI) m/z 299.0 ([M+H]$^+$); HRMS: calcd for $C_{18}H_{22}N_{2}O_{2}+H+$, 299.17540; found (ESI, [M+H]+), 299.1755.

Example 33

(1S,2R)-1-(3-chlorophenyl)-1-(1H-indol-1-yl)-3-(methylamino)propan-2-ol hydrochloride

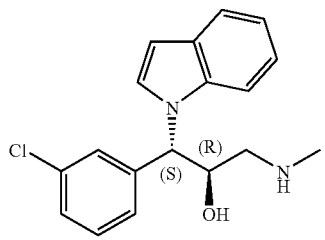

Step 1: A suspension of sodium hydride (60% in mineral oil, 4.0 g, 100 mmol) in tetrahydrofuran (600 mL) was treated dropwise with diethyl ethoxycarbonylmethylphosphonate (20 mL, 100 mmol) at 23° C. After 1 hour s,3-chlorobenzaldehyde (9.3 mL, 82 mmol) was added. After an additional 1 hour, the reaction was quenched with water (20 mL) and concentrated under vacuum to remove tetrahydrofuran. The residue was taken up in ethyl acetate (300 mL), washed with water (5×300 mL) and brine (1×300 mL), dried (magnesium sulfate) and concentrated under vacuum to provide (2E)-3-(3-chlorophenyl)-acrylic acid ethyl ester (18 g, quantitative) as a clear, pale yellow oil. MS (ESI) m/z 210 ([M+H]$^+$).

Step 2: (2E)-3-(3-Chlorophenyl)-acrylic acid ethyl ester (17.6 g, 82 mmol) was dissolved in dry dichloromethane (300 mL), cooled to −78° C. and treated with a solution of di-isobutylaluminum hydride (1.0 M solution in hexane, 250 mL, 250 mmol) over 20 minutes. After 1.5 hours total, the reaction was quenched with methanol (75 mL) at −78° C., warmed to 23° C. and treated with a saturated aqueous solution of potassium sodium tartrate (300 mL). The aqueous phase was separated and extracted with dichloromethane (2×300 mL). The combined extracts were washed with a saturated aqueous solution of sodium tartrate (450 mL), dried (sodium sulfate) and concentrated under vacuum to provide a cloudy yellow oil (14.6 g) that was pre-adsorbed on silica gel (25 g). Flash column chromatography (silica 250 g, 10%, 20% ethyl acetate/hexanes) provided (2E)-3-(3-chlorophenyl)prop-2-en-1-ol (12.4 g, 90%) as a clear, colorless oil. MS (ESI) m/z 151 ([M+H−H$_2$O]$^+$).

Step 3: In an analogous manner to EXAMPLE 117, step 4, [(2R,3R)-3-(3-chlorophenyl)oxiran-2-yl]methanol was prepared from (2E)-3-(3-chlorophenyl)prop-2-en-1-ol. MS (ESI) m/z 167 ([M+H—H$_2$O]$^+$).

Step 4 (Method A): In an analogous manner to EXAMPLE 117, step 5, (2S,3S)-3-(3-chlorophenyl)-3-(1H-indol-1-yl)propane-1,2-diol was prepared from 1H-indole and [(2R,3R)-3-(3-chlorophenyl)oxiran-2-yl]methanol. MS (ES) m/z 302 ([M+H]$^+$).

Step 4a (Method B): [(2R,3R)-3-(3-chlorophenyl)oxiran-2-yl]methanol (4.8 g, 26 mmol) and indoline (d 1.063, 2.9 mL, 26 mmol) were heated neat at 135° C. in a sealed flask. After 1.5 hours, the cooled mixture was pre-adsorbed on silica gel (25 g). Flash column chromatography (silica 375 g, 20%, 40%, 80% ethyl acetate/hexanes) provided (2S,3S)-3-

(3-chlorophenyl)-3-(2,3-dihydro-1H-indol-1-yl)propane-1, 2-diol (5.8 g, 73%) as a white solid. MS (ES) m/z 304 ([M+H]$^+$).

Step 4b (Method B): A solution of (2S,3S)-3-(3-chlorophenyl)-3-(2,3-dihydro-1H-indol-1-yl)propane-1,2-diol (5.8 g, 19 mmol) in ca. 1:1 (v/v) toluene-dichloromethane (200 mL) was treated with a solution of 2,3-dichloro-5,6-dicyano-1,4-benzoquinone (4.4 g, 19 mmol) in toluene (100 mL) at 0° C. After 30 minutes, the mixture was diluted with ethyl acetate (1 L) and washed with 5% aqueous sodium carbonate (4×1 L), water (1 L) and brine (1 L), dried (magnesium sulfate) and concentrated under vacuum to give a dark oil (5.4 g) that was pre-adsorbed on silica gel (15 g). Flash column chromatography (silica 235 g, 20%, 40% ethyl acetate/hexanes) provided (2S,3S)-3-(3-chlorophenyl)-3-(1H-indol-1-yl)propane-1,2-diol, (4.7 g, 82%) as a cloudy yellow oil. MS (ES) m/z 302 ([M+H]$^+$).

Step 5: In an analogous manner to EXAMPLE 1, step 2, (2S,3S)-toluene-4-sulfonic acid 3-(3-chlorophenyl)-2-hydroxy-3-indol-1-yl-propyl ester was prepared from (2S,3S)-3-(3-chlorophenyl)-3-(1H-indol-1-yl)propane-1,2-diol. MS (ES) m/z 456 ([M+H]$^+$).

Step 6: (2S,3S)-Toluene-4-sulfonic acid 3-(3-chlorophenyl)-2-hydroxy-3-indol-1-yl-propyl ester (0.60 g, 1.2 mmol) was treated with a solution of methylamine in methanol (2.0 M, 3 mL, 6 mmol) and the solution was stirred at 23° C. for 18 hours. At this time, the solution was concentrated under vacuum and dissolved in diethyl ether (50 mL). The organic solution was washed with a 1 N aqueous solution of sodium hydroxide (50 mL), water (50 mL) and brine (50 mL), dried (sodium sulfate) and concentrated under vacuum to provide an orange foam (0.30 g) that was purified by reverse phase HPLC (90:10 water-acetonitrile to 50:50 water-acetonitrile containing 0.1% trifluoroacetic acid @ 20 mL/min). The product fractions were concentrated under vacuum to remove acetonitrile and the aqueous solution was basified with a 2N aqueous solution of ammonium hydroxide. The resulting milky suspension was extracted with ethyl acetate (200 mL) and the organic phase was washed with water (200 mL) and brine (100 mL), dried (sodium sulfate) and concentrated under vacuum. The residue was dissolved in absolute ethanol (4 mL), treated with a 4 M hydrochloric acid in 1,4-dioxane (1.3 eq) and stirred for 10 minutes. The solution was concentrated under vacuum, then dissolved in absolute ethanol (3 mL) and left standing at 23° C. overnight. Vacuum filtration provided (1S,2R)-1-(3-chlorophenyl)-1-(1H-indol-1-yl)-3-(methylamino)propan-2-ol hydrochloride (62 mg, 5% for 3 steps) as a white crystalline solid. HRMS calcd for $C_{18}H_{19}ClN_2O+H^+$, 315.12587; found (ESI) 315.1267 ([M+H]$^+$).

Example 34

(1S,2R)-1-(4-chlorophenyl)-1-(1H-indol-1-yl)-3-(methylamino)propan-2-ol hydrochloride

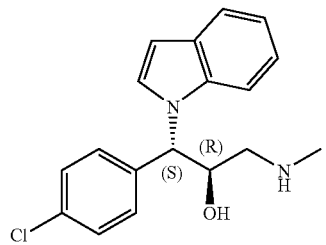

In an analogous manner to EXAMPLE 33, step 1 (2E)-3-(4-chlorophenyl)-acrylic acid ethyl ester was prepared from diethyl ethoxycarbonylmethylphosphonate and 4-chlorobenzaldehyde. MS (ESI) m/z 210 ([M+H]$^+$).

In an analogous manner to EXAMPLE 33, step 2 (2E)-3-(4-chlorophenyl)prop-2-en-1-ol was prepared from (2E)-3-(4-chlorophenyl)-acrylic acid ethyl ester. MS (ESI) m/z 151 ([M+H—H$_2$O]$^+$).

In an analogous manner to EXAMPLE 117, step 4, [(2R, 3R)-3-(4-chlorophenyl)oxiran-2-yl]methanol was prepared from (2E)-3-(4-chlorophenyl)prop-2-en-1-ol. MS (ESI) m/z 167 ([M+H—H$_2$O]$^+$); [□□$_D$+41 (c 0.0121 g/mL, DMSO); 99.2% ee.

In an analogous manner to EXAMPLE 117, step 5, (2S, 3S)-3-(4-chlorophenyl)-3-(1H-indol-1-yl)propane-1,2-diol was prepared from 1H-indole and [(2R,3R)-3-(4-chlorophenyl)oxiran-2-yl]methanol. MS (ES) m/z 302 ([M+H]$^+$).

In an analogous manner to EXAMPLE 1, step 2, (2S,3S)-toluene-4-sulfonic acid 3-(4-chlorophenyl)-2-hydroxy-3-indol-1-yl-propyl ester was prepared from (2S,3S)-3-(4-chlorophenyl)-3-(1H-indol-1-yl)propane-1,2-diol. MS (ES) m/z 456 ([M+H]$^+$).

In an analogous manner to EXAMPLE 33, step 6 (1S,2R)-1-(4-chlorophenyl)-1-(1H-indol-1-yl)-3-(methylamino)propan-2-ol hydrochloride was prepared from (2S,3S)-toluene-4-sulfonic acid 3-(4-chlorophenyl)-2-hydroxy-3-indol-1-yl-propyl ester and methylamine (2 N solution in methanol). HRMS: calcd for $C_{18}H_{19}ClN_2O+H^+$, 315.12587; found (ESI) 315.124 ([M+H]$^+$).

Example 35

(1S,2R)-1-(1H-indol-1-yl)-3-(methylamino)-1-[3-(trifluoromethoxy)phenyl]propan-2-ol hydrochloride

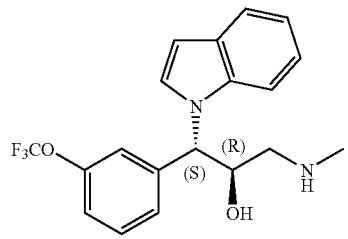

In an analogous manner to EXAMPLE 33, step 1, (2E)-3-(3-trifluoromethoxy-phenyl)-acrylic acid ethyl ester was prepared from diethyl ethoxycarbonylmethylphosphonate and 3-(trifluoromethoxy)benzaldehyde. MS (ES) m/z 261 ([M+H]$^+$).

In an analogous manner to EXAMPLE 33, step 2, (2E)-3-[3-(trifluoromethoxy)phenyl]prop-2-en-1-ol was prepared from (2E)-3-(3-trifluoromethoxy-phenyl)-acrylic acid ethyl ester. MS (ES) m/z 201 ([M+H—H$_2$O]$^+$).

In an analogous manner to EXAMPLE 117, step 4, {(2R, 3R)-3-[3-(trifluoromethoxy)phenyl]oxiran-2-yl}methanol was prepared from (2E)-3-[3-(trifluoromethoxy)phenyl]prop-2-en-1-ol. MS (ES) m/z 217 ([M+H—H$_2$O]$^+$); [□]$_D^{25}$=+30° (c=0.0118 g/mL, DMSO); 84.4% ee.

In an analogous manner to EXAMPLE 117, step 5, (2S, 3S)-3-(1H-indol-1-yl)-3-[3-(trifluoromethoxy)phenyl]propane-1,2-diol was prepared from 1H-indole and {(2R,3R)-3-[3-(trifluoromethoxy)phenyl]oxiran-2-yl}methanol. MS (ES) m/z 352 ([M+H]$^+$).

In an analogous manner to EXAMPLE 1, step 2 (2S,3S)-toluene-4-sulfonic acid 2-hydroxy-3-indol-1-yl-3-(3-trifluoromethoxy-phenyl)-propyl ester was prepared from (2S,3S)-3-(1H-indol-1-yl)-3-[3-(trifluoromethoxy)phenyl]propane-1,2-diol. MS (ES) m/z 506 ([M+H]$^+$).

In an analogous manner to EXAMPLE 33, step 6 (1S,2R)-1-(1H-indol-1-yl)-3-(methylamino)-1-[3-(trifluoromethoxy)phenyl]propan-2-ol hydrochloride was prepared from (2S,3S)-toluene-4-sulfonic acid 2-hydroxy-3-indol-1-yl-3-(3-trifluoromethoxy-phenyl)-propyl ester and methylamine (2 N in methanol). MS (ES) m/z 365 ([M+H]$^+$).

Example 36

(1S,2R)-1-(1H-indol-1-yl)-3-(methylamino)-1-[2-(trifluoromethoxy)phenyl]propan-2-ol hydrochloride

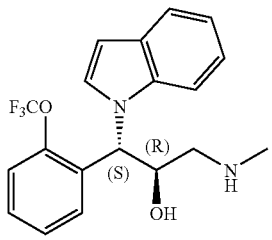

Step 1: In an analogous manner to EXAMPLE 33, step 1, (2E)-3-(2-trifluoromethoxy-phenyl)-acrylic acid ethyl ester was prepared from diethyl ethoxycarbonylmethylphosphonate and 2-(trifluoromethoxy)benzaldehyde. MS (ES) m/z 261 ([M+H]$^+$).

Step 2: In an analogous manner to EXAMPLE 33, step 2, (2E)-3-[2-(trifluoromethoxy)phenyl]prop-2-en-1-ol was prepared from (2E)-3-(2-trifluoromethoxy-phenyl)-acrylic acid ethyl ester. MS (ES) m/z 201 ([M+H—H$_2$O]$^+$).

Step 3: A solution of (2E)-3-[2-(trifluoromethoxy)phenyl]prop-2-en-1-ol (3.9 g, 18 mmol) in dichloromethane (90 mL) was treated with meta-chloroperoxybenzoic acid (77%, 8.0 g, 36 mmol) at 23° C. After 5 hours, the reaction was quenched with a 1 N aqueous solution of sodium hydroxide (200 mL) with vigorous stirring and the phases were separated. The aqueous phase was extracted with diethyl ether (2×100 mL). The combined organic phases were washed with water (3×100 mL), dried (sodium sulfate) and concentrated under vacuum to provided a clear, colorless oil (3.8 g) that was pre-adsorbed on silica gel (6 g). Flash column chromatography (silica 60 g, 10%, 20% ethyl acetate/hexanes) provided {(2RS,3RS)-3-[2-(trifluoromethoxy)phenyl]oxiran-2-yl}methanol (2.4 g, 57%) as a white solid. MS (ES) m/z 217 ([M+H—H$_2$O]$^+$).

{(2RS,3RS)-3-[2-(trifluoromethoxy)phenyl]oxiran-2-yl}methanol was dissolved in methanol. The resulting solution was injected onto the Supercritical Fluid Chromatography instrument, and the baseline resolved enantiomers were collected using the conditions described below. The enantiomeric purity of each enantiomer was determined under the same Supercritical Fluid Chromatography conditions using a Chiralpak AS-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AS-H; 5 u; 250 mm L × 20 mm ID (Chiral Technologies, Inc, Exton, PA, USA) |
| Column temperature: | 35° C. |
| SFC Modifier: | 5% IPA/95% CO2 |
| Flow rate: | 35 mL/min |
| Outlet Pressure: | 100 bar |
| Detector: | UV at 220 nm |

{(2R,3R)-3-[2-(trifluoromethoxy)phenyl]oxiran-2-yl}methanol was isolated as peak 1. MS (ES) m/z 217 ([M+H—H$_2$O]$^+$); $[\square]_D^{25}$=+19.4° (c=0.0102 g/mL, DMSO); >99.9% ee.

{(2S,3S)-3-[2-(trifluoromethoxy)phenyl]oxiran-2-yl}methanol was isolated as peak 2. MS (ES) m/z 217 ([M+H—H$_2$O]$^+$); $[\square]_D^{25}$=−15.7° (c=0.0125 g/mL, DMSO); 95.8% ee.

Step 4: In an analogous manner to EXAMPLE 117, step 5, (2S,3S)-3-(1H-indol-1-yl)-3-[2-(trifluoromethoxy)phenyl]propane-1,2-diol was prepared from 1H-indole and {(2R,3R)-3-[2-(trifluoromethoxy)phenyl]oxiran-2-yl}methanol, substituting sodium tert-butoxide in place of potassium hydride. MS (ES) m/z 352 ([M+H]$^+$).

Step 5: In an analogous manner to EXAMPLE 1, step 2, (2S,3S)-toluene-4-sulfonic acid 2-hydroxy-3-indol-1-yl-3-(2-trifluoromethoxy-phenyl)-propyl ester was prepared from (2S,3S)-3-(1H-indol-1-yl)-3-[2-(trifluoromethoxy)phenyl]propane-1,2-diol. MS (ES) m/z 506 ([M+H]$^+$).

Step 6: In an analogous manner to EXAMPLE 33, step 6 (1S,2R)-1-(1H-indol-1-yl)-3-(methylamino)-1-[2-(trifluoromethoxy)phenyl]propan-2-ol hydrochloride was prepared from (2S,3S)-toluene-4-sulfonic acid 2-hydroxy-3-indol-1-yl-3-(2-trifluoromethoxy-phenyl)-propyl ester and methylamine (2 N in methanol). MS (ES) m/z 365 ([M+H]$^+$).

Example 37

(1R,2S)-1-(1H-indol-1-yl)-3-(methylamino)-1-[2-(trifluoromethoxy)phenyl]propan-2-ol hydrochloride

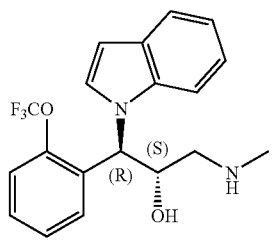

In an analogous manner to EXAMPLE 117, step 5, (2R,3R)-3-(1H-indol-1-yl)-3-[2-(trifluoromethoxy)phenyl]propane-1,2-diol was prepared from 1H-indole and {(2S,3S)-3-[2-(trifluoromethoxy)phenyl]oxiran-2-yl}methanol (EXAMPLE 36, step 3) substituting sodium tert-butoxide in place of potassium hydride. MS (ES) m/z 352 ([M+H]$^+$).

In an analogous manner to EXAMPLE 1, step 2, (2R,3R)-toluene-4-sulfonic acid 2-hydroxy-3-indol-1-yl-3-(2-trifluoromethoxy-phenyl)-propyl ester was prepared from (2R,3R)-3-(1H-indol-1-yl)-3-[2-(trifluoromethoxy)phenyl]propane-1,2-diol. MS (ES) m/z 506 ([M+H]$^+$).

In an analogous manner to EXAMPLE 33, step 6 (1R,2S)-1-(1H-indol-1-yl)-3-(methylamino)-1-[2-(trifluoromethoxy)phenyl]propan-2-ol hydrochloride was prepared from (2R,3R)-toluene-4-sulfonic acid 2-hydroxy-3-indol-1-yl-3-(2-trifluoromethoxy-phenyl)-propyl ester and methylamine (2 N in methanol). MS (ES) m/z 365 ([M+H]+).

Example 38

(1S,2R)-1-(2-chlorophenyl)-1-(1H-indol-1-yl)-3-(methylamino)propan-2-ol hydrochloride

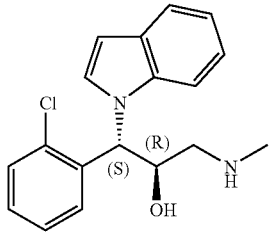

In an analogous manner to EXAMPLE 33, step 1, (2E)-3-(2-chlorophenyl)-acrylic acid ethyl ester was prepared from diethyl ethoxycarbonylmethylphosphonate and 2-chlorobenzaldehyde. MS (ESI) m/z 210 ([M+H]+).

In an analogous manner to EXAMPLE 33, step 2, (2E)-3-(2-chlorophenyl)prop-2-en-1-ol was prepared from (2E)-3-(2-chlorophenyl)-acrylic acid ethyl ester. MS (ESI) m/z 151 ([M+H—H$_2$O]+).

In an analogous manner to EXAMPLE 36, step 3, [(2RS,3RS)-3-(2-chlorophenyl)oxiran-2-yl]methanol was prepared from (2E)-3-(2-chlorophenyl)prop-2-en-1-ol.

[(2RS,3RS)-3-(2-chlorophenyl)oxiran-2-yl]methanol was dissolved in methanol. The resulting solution was injected (50 mg/injection) onto the Supercritical Fluid Chromatography instrument, and the baseline resolved enantiomers were collected using the conditions described below. The enantiomeric purity of each enantiomer was determined under the same Supercritical Fluid Chromatography conditions using a Chiralpak AD-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 20% MeOH/80% CO2 |
| Flow rate: | 50 mL/min |
| Outlet Pressure: | 100 bar |
| Detector: | UV at 220 nm |

[(2S,3S)-3-(2-chlorophenyl)oxiran-2-yl]methanol was isolated as peak 1. MS (ES) m/z 167 ([M+H—H$_2$O]+); [☐]$_D^{25}$=+2.6° (c=0.0153 g/mL, DMSO); >99.8% ee.

[(2R,3R)-3-(2-chlorophenyl)oxiran-2-yl]methanol was isolated as peak 2. MS (ES) m/z 167 ([M+H—H$_2$O]+); [☐]$_D^{25}$=−2.5° (c=0.0139 g/mL, DMSO); >99.8% ee.

In an analogous manner to EXAMPLE 117, step 5, (2S,3S)-3-(2-chlorophenyl)-3-(1H-indol-1-yl)propane-1,2-diol was prepared from 1H-indole and [(2R,3R)-3-(2-chlorophenyl)oxiran-2-yl]methanol, substituting sodium tert-butoxide in place of potassium hydride. MS (ES) m/z 302 ([M+H]+).

In an analogous manner to EXAMPLE 1, step 2, (2S,3S)-toluene-4-sulfonic acid 3-(2-chlorophenyl)-2-hydroxy-3-indol-1-yl-propyl ester was prepared from (2S,3S)-3-(2-chlorophenyl)-3-(1H-indol-1-yl)propane-1,2-diol. MS (ES) m/z 456 ([M+H]+).

In an analogous manner to EXAMPLE 33, step 6 (1S,2R)-1-(2-chlorophenyl)-1-(1H-indol-1-yl)-3-(methylamino)propan-2-ol hydrochloride was prepared from (2S,3S)-toluene-4-sulfonic acid 3-(2-chlorophenyl)-2-hydroxy-3-indol-1-yl-propyl ester and methylamine (2 N in methanol). MS (ES) m/z 315 ([M+H]+).

Example 39

(1RS,2SR)-1-(1H-indol-1-yl)-3-(methylamino)-1-[4-(trifluoromethoxy)phenyl]propan-2-ol hydrochloride

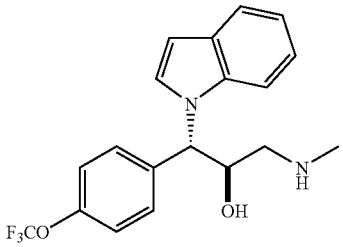

Step 1: In an analogous manner to EXAMPLE 33, step 1, (2E)-3-(4-trifluoromethoxy-phenyl)-acrylic acid ethyl ester was prepared from diethyl ethoxycarbonylmethylphosphonate and 4-(trifluoromethoxy)benzaldehyde. MS (ES) m/z 261 ([M+H]+).

Step 2: In an analogous manner to EXAMPLE 33, step 2, (2E)-3-[4-(trifluoromethoxy)phenyl]prop-2-en-1-ol was prepared from (2E)-3-(4-trifluoromethoxy-phenyl)-acrylic acid ethyl ester. MS (ES) m/z 201 ([M+H—H$_2$O]+).

Step 3: In an analogous manner to EXAMPLE 36, step 3, {(2RS,3RS)-3-[4-(trifluoromethoxy)phenyl]oxiran-2-yl}methanol was prepared from (2E)-3-[4-(trifluoromethoxy)phenyl]prop-2-en-1-ol . MS (ES) m/z 217 ([M+H—H$_2$O]+).

Step 4: In an analogous manner to EXAMPLE 33, step 4a (Method B), (2RS,3RS)-3-(2,3-dihydro-1H-indol-1-yl)-3-[4-(trifluoromethoxy)phenyl]propane-1,2-diol was prepared from indoline and {(2RS,3RS)-3-[4-(trifluoromethoxy)phenyl]oxiran-2-yl}methanol. MS (ES) m/z 354 ([M+H]+).

Step 5: In an analogous manner to EXAMPLE 33, step 4b (Method B), (2RS,3RS)-3-(1H-indol-1-yl)-3-[4-(trifluoromethoxy)phenyl]propane-1,2-diol was prepared from (2RS,3RS)-3-(2,3-dihydro-1H-indol-1-yl)-3-[4-(trifluoromethoxy)phenyl]propane-1,2-diol. MS (ES) m/z 352 ([M+H]+).

Step 6: In an analogous manner to EXAMPLE 1, step 2, (2RS,3RS)-toluene-4-sulfonic acid 2-hydroxy-3-indol-1-yl-3-(4-trifluoromethoxy-phenyl)-propyl ester was prepared from (2RS,3RS)-3-(1H-indol-1-yl)-3-[4-(trifluoromethoxy)phenyl]propane-1,2-diol . MS (ES) m/z 506 ([M+H]+).

Step 7: In an analogous manner to EXAMPLE 33, step 6 (Method B), (1RS,2SR)-1-(1H-indol-1-yl)-3-(methylamino)-1-[4-(trifluoromethoxy)phenyl]propan-2-ol hydrochloride was prepared from (2RS,3RS)-toluene-4-sulfonic acid 2-hydroxy-3-indol-1-yl-3-(4-trifluoromethoxy-phenyl)-propyl ester and methylamine (2 N in methanol). MS (ES) m/z 365 ([M+H]+).

Example 40

(1S,2R)-1-(1H-indol-1-yl)-3-(methylamino)-1-[4-(trifluoromethoxy)phenyl]propan-2-ol hydrochloride

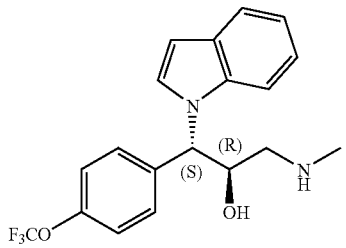

Step 1: (1RS,2SR)-1-(1H-indol-1-yl)-3-(methylamino)-1-[4-(trifluoromethoxy)phenyl]propan-2-ol hydrochloride (EXAMPLE 39, step 7) was dissolved in methanol. The resulting solution was injected (35 mg/injection) onto the Supercritical Fluid Chromatography instrument, and the baseline resolved enantiomers were collected using the conditions described below. The enantiomeric purity of each enantiomer was determined under the same Supercritical Fluid Chromatography conditions using a Chiralpak AD-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 25% MeOH w/ 1.0% DEA/75% CO2 |
| Flow rate: | 50 mL/min |
| Outlet Pressure: | 100 bar |
| Detector: | UV at 220 nm |

(1S,2R)-1-(1H-indol-1-yl)-3-(methylamino)-1-[4-(trifluoromethoxy)phenyl]propan-2-ol hydrochloride was isolated as peak 1 after neutralization and conversion of the free base to the hydrochloride salt according to EXAMPLE 33, step 6. MS (ES) m/z 365 ([M+H]$^+$); 98.4% ee.

Example 41

(1R,2S)-1-(1H-indol-1-yl)-3-(methylamino)-1-[4-(trifluoromethoxy)phenyl]propan-2-ol hydrochloride

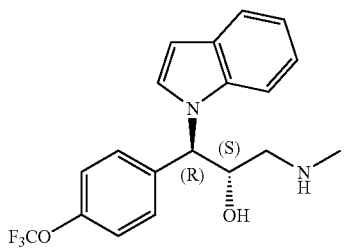

(1R,2S)-1-(1H-indol-1-yl)-3-(methylamino)-1-[4-(trifluoromethoxy)phenyl]propan-2-ol hydrochloride (EXAMPLE 40, step 1) was isolated as peak 2 after neutralization and conversion of the free base to the hydrochloride salt according to EXAMPLE 33, step 6. MS (ES) m/z 365 ([M+H]$^+$); >99.9% ee.

Example 42

(1S,2R)-4-amino-1-(3-chlorophenyl)-1-(1H-indol-1-yl)butan-2-ol hydrochloride

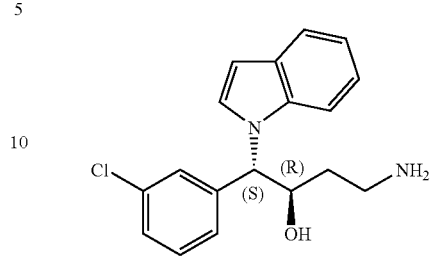

Step 1: A mixture of (2S,3S)-toluene-4-sulfonic acid 3-(3-chlorophenyl)-2-hydroxy-3-indol-1-yl-propyl ester (EXAMPLE 33, step 5, 1.9 g, 4.2 mmol) and sodium cyanide (0.23 g, 4.7 mmol) in dry dimethylsulfoxide (20 mL) was heated at 100° C. (microwave). After 15 minutes, the cooled solution was taken up in ethyl acetate (200 mL), washed with water (3×200 mL), dried (sodium sulfate) and concentrated under vacuum to give a tan foam (1.3 g) that was pre-adsorbed on silica gel (3 g). Flash column chromatography (silica 30 g, 10%, 20%, 40% ethyl acetate/hexanes) provided (3R,4S)-4-(3-chlorophenyl)-3-hydroxy-4-indol-1-yl-butyronitrile (1.2 g, 92%) as a tan foam. MS (ES) m/z 311 ([M+H]$^+$).

Step 2: A solution of (3R,4S)-4-(3-chlorophenyl)-3-hydroxy-4-indol-1-yl-butyronitrile (1.2 g, 3.9 mmol) in dry tetrahydrofuran (20 mL) was treated with diborane-tetrahydrofuran solution (1.0 M, 20 mL, 20 mmol) at 23° C. After 16 hours, the reaction was quenched with methanol (7 mL) at 23° C. and the solution was concentrated under vacuum to give an off-white foam that was partitioned between diethyl ether (200 mL) and a 1 N aqueous solution of sodium hydroxide (200 mL). The organic phase was separated, washed with brine (200 mL), dried (sodium sulfate) and concentrated under vacuum to give a yellow foam (1.2 g) that was purified via Biotage chromatography [AnaLogix silica column, 2×40 g in series, dichloromethane to 5% ammonia saturated methanol/dichloromethane] to provide (1S,2R)-4-amino-1-(3-chlorophenyl)-1-(1H-indol-1-yl)butan-2-ol (0.43 g, 36%). The free base was converted to the hydrochloride salt as described in EXAMPLE 33, step 6, to provide (1S,2R)-4-amino-1-(3-chlorophenyl)-1-(1H-indol-1-yl)butan-2-ol hydrochloride (0.47 g, 34%) as a foam. MS (ES) m/z 315 ([M+H]$^+$).

Example 43

(1S,2R)-1-(3-bromophenyl)-1-(1H-indol-1-yl)-3-(methylamino)propan-2-ol hydrochloride

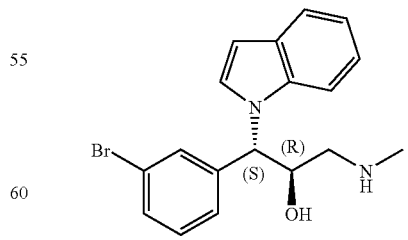

Step 1: In an analogous manner to EXAMPLE 33, step 1, (2E)-3-(3-bromophenyl)-acrylic acid ethyl ester was prepared from diethyl ethoxycarbonylmethylphosphonate and 3-bromobenzaldehyde. MS (ES) m/z 255 ([M+H]$^+$).

Step 2: In an analogous manner to EXAMPLE 33, step 2, (2E)-3-(3-bromophenyl)prop-2-en-1-ol was prepared from (2E)-3-(3-bromophenyl)-acrylic acid ethyl ester. MS (ES) m/z 195 ([M+H—H$_2$O]$^+$).

Step 3: In an analogous manner to EXAMPLE 117, step 4, [(2R,3R )-3-(3-bromophenyl)oxiran-2-yl]methanol was prepared from (2E)-3-(3-bromophenyl)prop-2-en-1-ol . MS (ES) m/z 211 ([M+H—H$_2$O]$^+$); 95% ee.

Step 4: In an analogous manner to EXAMPLE 33, step 4a (Method B), (2S,3S)-3-(3-bromophenyl)-3-(2,3-dihydro-1H-indol-1-yl)propane-1,2-diol was prepared from indoline and [(2R,3R)-3-(3-bromophenyl)oxiran-2-yl]methanol. MS (ES) m/z 348 ([M+H]$^+$).

Step 5: In an analogous manner to EXAMPLE 33, step 4b (Method B), (2S,3S)-3-(3-bromophenyl)-3-(1H-indol-1-yl)propane-1,2-diol was prepared from (2S,3S)-3-(3-bromophenyl)-3-(2,3-dihydro-1H-indol-1-yl)propane-1,2-diol. MS (ES) m/z 346 ([M+H]$^+$).

Step 6: In an analogous manner to EXAMPLE 1, step 2, (2S,3S)-toluene-4-sulfonic acid 3-(3-bromophenyl)-2-hydroxy-3-indol-1-yl-propyl ester was prepared from (2S,3S)-3-(3-bromophenyl)-3-(1H-indol-1-yl)propane-1,2-diol . MS (ES) m/z 500 ([M+H]$^+$).

Step 7: In an analogous manner to EXAMPLE 33, step 6 (1S,2R)-1-(3-bromophenyl)-1-(1H-indol-1-yl)-3-(methylamino)propan-2-ol hydrochloride was prepared from (2S,3S)-toluene-4-sulfonic acid 3-(3-bromophenyl)-2-hydroxy-3-indol-1-yl-propyl ester and methylamine (2 N solution in methanol). MS (ES) m/z 359 ([M+H]$^+$).

Example 44

3-[(1S,2R)-2-hydroxy-1-(1H-indol-1-yl)-3-(methylamino)propyl]benzonitrile hydrochloride

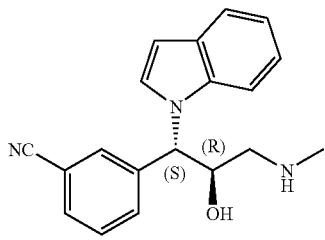

A mixture of (2S,3S)-3-(3-bromophenyl)-(1H-indol-1-yl)propane-1,2-diol (EXAMPLE 43, step 5, 1.4 g, 4.0 mmol), zinc (II) cyanide (4.7 g, 40 mmol) and tetrakis(triphenylphosphine)palladium (0) (0.46 g, 0.40 mmol) in de-gassed 1-methyl-2-pyrrolidinone (25 mL) was heated at 150° C. in a sealed flask. After 3.5 hours, the cooled brown mixture was diluted with ethyl acetate (250 mL) and filtered through Celite. The filtrate was washed with water (5×250 mL) and brine (1×250 mL), dried (sodium sulfate), and concentrated under vacuum to give an amber oil (1.6 g) that was pre-adsorbed on silica gel (6 g). Flash column chromatography (silica 70 g, 30%, 60% ethyl acetate/hexanes) provided 3-[(1S,2S)-2,3-dihydroxy-1-(1H-indol-1-yl)propyl]benzonitrile (1.0 g, 83%) as a pale yellow foam. MS (ES) m/z 293 ([M+H]$^+$).

In an analogous manner to EXAMPLE 1, step 2, (2S,3S)-toluene-4-sulfonic acid 3-(3-cyano-phenyl)-2-hydroxy-3-indol-1-yl-propyl ester was prepared from 3-[(1S,2S)-2,3-dihydroxy-1-(1H-indol-1-yl)propyl]benzonitrile. MS (ES) m/z 447 ([M+H]$^+$).

In an analogous manner to EXAMPLE 33, step 6 3-[(1S,2R)-2-hydroxy-1-(1H-indol-1-yl)-3-(methylamino)propyl]benzonitrile hydrochloride was prepared from (2S,3S)-toluene-4-sulfonic acid 3-(3-cyano-phenyl)-2-hydroxy-3-indol-1-yl-propyl ester and methylamine (2 N solution in methanol). MS (ESI) m/z 306 ([M+H]$^+$).

Example 45

(1SR,2RS)-3-(methylamino)-1-(4-methyl-3,4-dihydroquinoxalin-1 (2H)-yl)-1-phenylpropan-2-ol hydrochloride

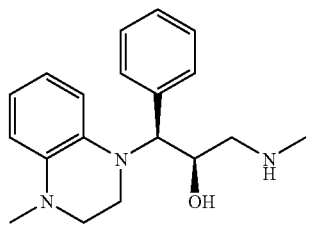

Step 1: In an analogous manner to EXAMPLE 53, step 3,3-phenylglycidol was prepared from cinnamyl alcohol as a white solid. MS (ES) m/z 151.1 ([M+H]$^+$).

Step 2: In an analogous manner to EXAMPLE 47, step 4, (2SR,3SR)-3-(4-methyl-3,4-dihydroquinoxalin-1(2H)-yl)-3-phenylpropane-1,2-diol was prepared from 1-methyl-1,2,3,4-tetrahydroquinoxaline[1] and 3-phenylglycidol as a viscous colorless oil. MS (ES) m/z 299.0 ([M+H]$^+$); HRMS: calcd for $C_{18}H_{22}N_2O_2$+H$^+$, 299.1760; found (ESI, [M+H]$^+$), 299.1739.

[1] Cavagnol, J. C.; Wiselogle, F. Y. *J. Am. Chem. Soc.* 1947, 69, 795-799.

Step 3: In an analogous manner to EXAMPLE 47, step 6, (1SR,2RS)-3-(methylamino)-1-(4-methyl-3,4-dihydroquinoxalin-1 (2H)-yl)-1-phenylpropan-2-ol hydrochloride was prepared from (2SR,3SR)-3-(4-methyl-3,4-dihydroquinoxalin-1(2H)-yl)-3-phenylpropane-1,2-diol as a white powder. MS (ES) m/z 312.0 ([M+H]$^+$); HRMS: calcd for $C_{19}H_{25}N_3O$+H$^+$, 312.2076; found (ESI, [M+H]$^+$), 312.2065.

Example 46

(1SR,2RS)-3-(methylamino)-1-phenyl-1-[4-(2,2,2-trifluoroethyl)-3,4-dihydroquinoxalin-1 (2H)-yl]propan-2-ol hydrochloride

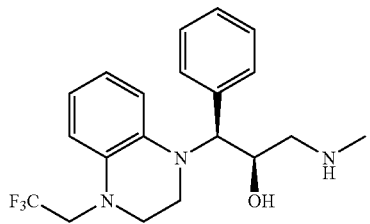

Compound 1-(2,2,2-trifluoroethyl)-1,2,3,4-tetrahydroquinoxaline was obtained as a white powder side product of the reduction reaction of quinoxaline to 1,2,3,4-tetrahydroquinoxaline using sodium borohydride in trifluoroacetic acid.[2] MS (ES) m/z 217.1 ([M+H]$^+$).

[2] Bugle, R. C.; Osteryoung, R. A. *J. Org. Chem.* 1979, 44, 1719-1720.

In an analogous manner to EXAMPLE 47, step 4, (2SR,3SR)-3-(4-(2,2,2-trfluoroethyl)-3,4-dihydroquinoxalin-1 (2H)-yl)-3-phenylpropane-1,2-diol was prepared from 1-(2,2,2-trifluoroethyl)-1,2,3,4-tetrahydroquinoxaline and 3-phenylglycidol (EXAMPLE 45, step 1) as a viscous colorless oil.

In an analogous manner to EXAMPLE 47, step 6, (1SR,2RS)-3-(methylamino)-1-phenyl-1-[4-(2,2,2-trifluoroethyl)-3,4-dihydroquinoxalin-1 (2H)-yl]propan-2-ol hydrochloride was prepared from (2SR,3SR)-3-(4-(2,2,2-trifluoroethyl)-3,4-dihydroquinoxalin-1 (2H)-yl)-3-phenylpropane-1,2-diol as a white powder. MS (ES) m/z 380.0 ([M+H]$^+$); HRMS: calcd for $C_{20}H_{24}F_3N_3O+H^+$, 380.1950; found (ESI, [M+H]$^+$), 380.1934.

Example 47

(1S,2R)-1-(3-fluorophenyl)-1-(1H-indol-1-yl)-3-(methylamino)propan-2-ol hydrochloride

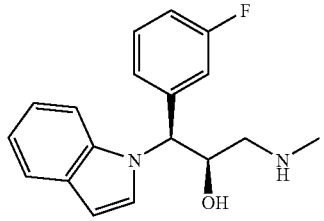

Step 1: To a mixture of trans-3-fluorocinnamic acid (50 g, 300 mmol) and iodomethane (300 mL) in acetone (1 L) was added portionwise cesium carbonate (147 g, 450 mmol, 1.5 equiv.), and the mixture was heated at 65° C. for 1.5 hours in a sealed reaction vessel. Upon cooling to room temperature, the reaction mixture was diluted with ethyl acetate (1 L), filtered through a pad of silica gel, and concentrated to give 47.33 g (87%) of trans-3-fluorocinnamic acid methyl ester as a colorless oil. MS (ES) m/z 180.0 (M$^+$).

Step 2: To a solution of trans-3-fluorocinnamic acid methyl ester (69.61 g, 386 mmol) in dry dichloromethane (1 L) at −78° C. under nitrogen was added dropwise diisobutylaluminum hydride (neat, 172 mL, 965 mmol, 2.5 equiv.) via an addition funnel. After the addition was complete, the reaction mixture was allowed to warm to −30° C. and stirred for an additional 1 hour, then quenched with methanol (150 mL). Upon warming to room temperature, the reaction mixture was treated with saturated aqueous solution of sodium/potassium tartrate (300 mL) and stirred for 30 minutes. The organic layer was washed sequentially with 1 N aqueous hydrochloric acid solution, saturated aqueous sodium bicarbonate solution, brine, and dried (anhydrous sodium sulfate). The crude oil was purified by silica gel chromatography (0-50% ethyl acetate:hexane) to give 53.07 g (90%) of trans-3-fluorocinnamyl alcohol as a colorless oil. MS (ES) m/z 152.1 (M$^+$).

Step 3: An oven-dried, 3-neck, 2-L round bottom flask fitted with two oven-dried addition funnels and a rubber septum was charged with diisopropyl D-tartrate (11.55 g, 49.3 mmol, 0.30 equiv.), 4 Å powdered, activated molecular sieves (40 g) and dry dichloromethane (800 mL) under nitrogen. After being cooled to −25° C., to the reaction mixture was added titanium isopropoxide (9.6 mL, 33 mmol, 0.20 equiv.) slowly via a hypodermic syringe. After stirring for 10 minutes, anhydrous t-butyl hydroperoxide (5.5 M in decane, 75.0 mL, 413 mmol, 2.5 equiv.) was added at a moderate rate via an addition funnel. The resulting mixture was stirred at −25° C. for 30 minutes. trans-3-Fluorocinnamyl alcohol (25.0 g, 164 mmol) in dry dichloromethane (50 mL) was added dropwise via an addition funnel while maintaining the temperature at −25° C. After the addition, the reaction mixture was stirred at −25° C. for 1 hour and at −20° C. for another 3 hours. After the reaction was complete, cooled aqueous sodium hydroxide solution (30%, 20 mL) saturated with sodium chloride was added slowly at −20° C. After diethyl ether (150 mL) was added, the cold bath was removed and the mixture was allowed to warm to ~5° C. and stirred for 1 hour. Magnesium sulfate (anhydrous, 50 g) was added and the mixture was stirred for 20 minutes, then filtered through a pad of silica gel, and washed with ether (300 mL). The filtrate was concentrated and toluene was used to azeotropically remove excess t-butyl hydroperoxide. The residual oil was purified on silica gel (0-30% ethyl acetate:hexane) to give 24.80 g (90%) of [(2R,3R)-3-(3-fluorophenyl)oxiran-2-yl]methanol as a viscous, colorless oil. Percent ee: >96.5%. MS (ESI) m/z 169.1 ([M+H]$^+$).

Step 4: A mixture of indoline (1.42 g, 11.89 mmol) and [(2R,3R)-3-(3-fluorophenyl)oxiran-2-yl]methanol (2.0 g, 11.89 mmol) was heated at 125° C. for 5 hours in a sealed reaction vial. Upon cooling, the crude product was dissolved in ethyl acetate, absorbed on Fluorocil, and purified by Biotage chromatography (FlasH40i, silica, 0-55% EtOAc/hexane) to give 2.55 g (75%) of (2S,3S)-3-(2,3-dihydro-1H-indol-1-yl)-3-(3-fluorophenyl)propane-1,2-diol as a colorless oil. MS (ESI) m/z 288.1 ([M+H]$^+$).

Step 5: A mixture of (2S,3S)-3-(2,3-dihydro-1H-indol-1-yl)-3-(3-fluorophenyl)propane-1,2-diol (2.00 g, 6.96 mmol) and activated manganese dioxide (20.0 g, 230 mmol) in dichloromethane (30 mL) was stirred at 20° C. for 3 hours. The mixture was diluted with ethyl acetate (15 mL), filtered through a pad of silica gel, and concentrated. The crude product was purified by Biotage chromatography (FlasH40i, silica, 0-70% EtOAc/hexane) to give 1.40 g (71%) of (2S,3S)-3-(3-fluorophenyl)-3-(1H-indol-1-yl)propane-1,2-diol as a colorless oil. MS (ESI) m/z 286.0 ([M+H]$^+$). HRMS: calcd for $C_{17}H_{16}FNO_2+H^+$, 286.1238; found (ESI, [M+H]$^+$), 286.1239.

Step 6: To a solution of (2S,3S)-3-(2,3-dihydro-1H-indol-1-yl)-3-(3-fluorophenyl)propane-1,2-diol (452 mg, 1.586 mmol) in dichloromethane (3 mL) under nitrogen was added triethylamine (1.1 mL, 7.93 mmol). The mixture was cooled to 0° C., and para-toluenesulfonyl chloride (423 mg, 2.22 mmol) was added portionwise. The reaction mixture was stirred at 0° C. for 1 hour and stored at 0° C. overnight. Methylamine in absolute ethanol (8 M, 5 mL, 40 mmol) was added and the reaction mixture was sealed, and stirred overnight while warming to room temperature. All volatiles were removed under reduced pressure. The oil residue was dissolved in dichloromethane (20 mL), washed with aqueous potassium carbonate (5 mL), dried (anhydrous sodium sulfate), and concentrated. Purification by Biotage chromatography (FlasH12i, silica, 0-15% MeOH/dichloromethane/ 0.5% triethylamine) gave (1S,2R)-1-(3-fluorophenyl)-1-(1H-indol-1-yl)-3-(methylamino)propan-2-ol, which was dissolved dichloromethane (5 mL) and treated with a 1 M ethereal solution of hydrochloric acid (1.9 mL, 1.9 mmol). To the resulting solution was added hexane until white powder formed, which was collected, washed with hexane, and dried in vacuo to yield 209 mg (44%) of (1S,2R)-1-(3-fluorophenyl)-1-(1H-indol-1-yl)-3-(methylamino)propan-2-ol hydrochloride as a white powder. MS (ES) m/z 299.0 ([M+H]$^+$); HRMS: calcd for $C_{18}H_{19}FN_2O+H^+$, 299.1554; found (ESI, [M+H]$^+$), 299.1553.

Example 48

(1S,2R)-1-(3-fluorophenyl)-3-(methylamino)-1-[3-(3-methylphenyl)-1H-indol-1-yl]propan-2-ol hydrochloride

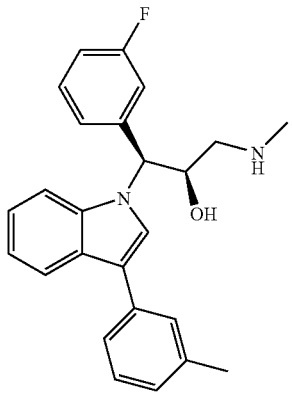

In an analogous manner to EXAMPLE 114, step 2, (2S,3S)-3-(3-fluorophenyl)-3-{3-[3-methylphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 3-methylbenzeneboronic acid.

In an analogous manner to EXAMPLE 1, step 2, (2S,3S)-toluene-4-sulfonic acid 3-(3-fluorophenyl)-3-[3-(2-chlorophenyl)-indol-1-yl]-2-hydroxy-propyl ester was prepared from (2S,3S)-3-(3-fluorophenyl)-3-{3-[3-methylphenyl]-1H-indol-1-yl}propane-1,2-diol.

In an analogous manner to EXAMPLE 5, (1S,2R)-1-(3-fluorophenyl)-3-(methylamino)-1-[3-(3-methylphenyl)-1H-indol-1-yl]propan-2-ol hydrochloride was prepared from (2S,3S)-toluene-4-sulfonic acid 3-(3-fluoro-phenyl)-3-[3-(3-methylphenyl)-indol-1-yl]-2-hydroxy-propyl ester and methylamine (2N solution in methanol). MS (ESI) m/z 389.2; HRMS: calcd for C25H25FN2O+H+, 389.20237; found (ESI, [M+H]+), 389.2005.

Example 49

(1S,2R)-1-(4-fluorophenyl)-3-(methylamino)-1-(3-methyl-1H-indol-1-yl)propan-2-ol hydrochloride

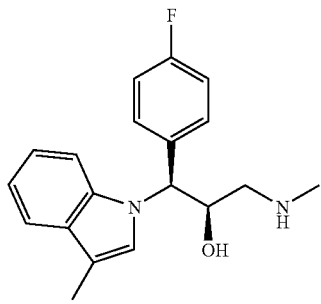

Step 1: In an analogous manner to EXAMPLE 47, step 3, [(2R,3R)-3-(4-fluorophenyl)oxiran-2-yl]methanol was prepared from trans-4-fluorocinnamyl alcohol[3] as a white solid. Percent ee: >97%. MS (ES) m/z 167.0 ([M−H]−).

[3] Takeuchi, R.; Ue, N.; Tanabe, K.; Yamashita, K.; Shiga, N. *J. Am. Chem. Soc.,* 2001, 123, 9525-9534.

Step 2: In an analogous manner to EXAMPLE 117, step 5, (2S,3S)-3-(4-fluorophenyl)-3-(3-methyl-1H-indol-1-yl)propane-1,2-diol was prepared from 3-methylindole and [(2R,3R)-3-(4-fluorophenyl)oxiran-2-yl]methanol as a viscous, colorless oil. MS (ES) m/z 300.1 ([M+H]+); HRMS: calcd for C18H18FNO2+H+, 300.1400; found (ESI, [M+H]+), 300.1406.

Step 3: In an analogous manner to EXAMPLE 47, step 6, (1S,2R)-1-(4-fluorophenyl)-3-(methylamino)-1-(3-methyl-1H-indol-1-yl)propan-2-ol hydrochloride was prepared from (2S,3S)-3-(4-fluorophenyl)-3-(3-methyl-1H-indol-1-yl)propane-1,2-diol as a white powder. MS (ESI) m/z 313.1 ([M+H]+); HRMS: calcd for C19H21FN2O+H+, 313.1711; found (ESI, [M+H]+), 313.1727.

Example 50

(1S,2R)-1-(2-fluorophenyl)-1-(1H-indol-1-yl)-3-(methylamino)propan-2-ol hydrochloride

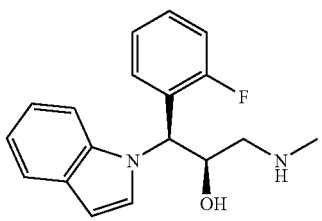

In an analogous manner to EXAMPLE 47, step 1, trans-2-fluorocinnamic acid methyl ester was prepared from trans-2-fluorocinnamic acid as a white solid. MS m/z 180.9 ([M+H]+).

In an analogous manner to EXAMPLE 47, step 2, trans-2-fluorocinnamyl alcohol was prepared from trans-2-fluorocinnamic acid methyl ester as a colorless oil. MS (ESI) m/z 152.0 [M]+; HRMS: calcd for C9H9FO, 152.0637; found (ESI, [M]+), 152.0640.

In an analogous manner to EXAMPLE 47, steps 3, [(2R,3R)-3-(2-fluorophenyl)oxiran-2-yl]methanol was prepared from trans-2-fluorocinnamyl alcohol as a white solid. MS m/z 169.0 ([M+H]+).

In an analogous manner to EXAMPLE 117, step 5, (2S,3S)-3-(2-fluorophenyl)-3-(1H-indol-1-yl)propane-1,2-diol was prepared from indole and [(2R,3R)-3-(2-fluorophenyl)oxiran-2-yl]methanol as a viscous, colorless oil. MS (ES) m/z 286.2 ([M+H]+); HRMS: calcd for C17H16FNO2+H+, 286.1238; found (ESI, [M+H]+), 286.1231.

In an analogous manner to EXAMPLE 47, step 6, (1S,2R)-1-(2-fluorophenyl)-1-(1H-indol-1-yl)-3-(methylamino)propan-2-ol hydrochloride was prepared from (2S,3S)-3-(2-fluorophenyl)-3-(3-methyl-1H-indol-1-yl)propane-1,2-diol as a white powder. MS (ES) m/z 299.1 ([M+H]+); HRMS: calcd for C18H19FN2O+H+, 299.1554; found (ESI, [M+H]+), 299.1557.

Example 51

(1S,2R)-1-(4-fluorophenyl)-1-(1H-indol-1-yl)-3-(methylamino)propan-2-ol hydrochloride

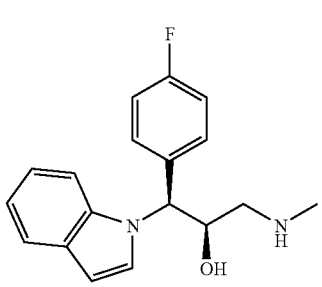

In an analogous manner to EXAMPLE 117, step 5, (2S,3S)-3-(4-fluorophenyl)-3-(1H-indol-1-yl)propane-1,2-diol was prepared from indole and [3-(4-fluorophenyl)oxiran-2-yl]methanol (EXAMPLE 49, step 1) as a viscous, colorless oil. MS (ES) m/z 286.1 ([M+H]+); HRMS: calcd for C17H16FNO2+H+, 286.1238; found (ESI, [M+H]+), 286.1230.

In an analogous manner to EXAMPLE 47, step 6, (1S,2R)-1-(4-fluorophenyl)-1-(1H-indol-1-yl)-3-(methylamino)propan-2-ol hydrochloride was prepared from (2S,3S)-3-(4-fluorophenyl)-3-(1H-indol-1-yl)propane-1,2-diol as a white powder. MS (ES) m/z 299.1 ([M+H]$^+$).

Example 52

(1S,2R)-1-(1H-indol-1-yl)-3-(methylamino)-1-(3-methylphenyl)propan-2-ol hydrochloride

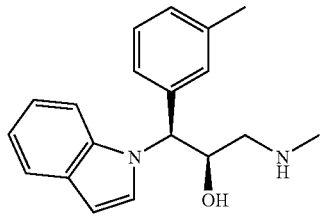

In an analogous manner to EXAMPLE 47, step 1, trans-3-methylcinnamic acid methyl ester was prepared from trans-3-methylcinnamic acid.

In an analogous manner to EXAMPLE 47, step 2, trans-3-methylcinnamyl alcohol was prepared from trans-3-methylcinnamic acid methyl ester as a colorless oil.

In an analogous manner to EXAMPLE 47, steps 3, [(2R,3R)-3-(3-methylphenyl)oxiran-2-yl]methanol was prepared from trans-3-methylcinnamyl alcohol as a colorless oil. HRMS: calcd for $C_{10}H_{12}O_2+H^+$, 165.0916; found (ESI, [M+H]$^+$), 165.0926.

In an analogous manner to EXAMPLE 117, step 5, (2S,3S)-3-(1H-indol-1-yl)-3-(3-methylphenyl)propane-1,2-diol was prepared from indole and [(2R,3R)-3-(3-methylphenyl)oxiran-2-yl]methanol as a viscous, colorless liquid. MS (ES) m/z 282.1 ([M+H]$^+$); HRMS: calcd for $C_{18}H_{19}NO_2+H^+$, 282.1494; found (ESI, [M+H]$^+$), 282.1488.

In an analogous manner to EXAMPLE 47, step 6, (1S,2R)-1-(1H-indol-1-yl)-3-(methylamino)-1-(3-methylphenyl)propan-2-ol hydrochloride was prepared from (2S,3S)-3-(1H-indol-1-yl)-3-(3-methylphenyl)propane-1,2-diol as a white powder.

MS (ES) m/z 295.3 ([M+H]$^+$); HRMS: calcd for $C_{19}H_{20}N_2O+H^+$, 295.1805; found (ESI, [M+H]$^+$), 295.1799.

Example 53

(1S,2R)-1-(1H-indol-1-yl)-3-(methylamino)-1-(2-methylphenyl)propan-2-ol hydrochloride

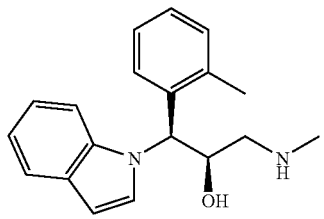

Step 1: In an analogous manner to EXAMPLE 47, step 1, trans-2-methylcinnamic acid methyl ester was prepared from trans-2-methylcinnamic acid.

Step 2: In an analogous manner to EXAMPLE 47, step 2, trans-2-methylcinnamyl alcohol was prepared from trans-2-methylcinnamic acid methyl ester as a colorless oil. MS (ES) m/z 146.9 ([M−H]$^-$).

Step 3: To a solution of trans-2-methylcinnamyl alcohol (1.50 g, 10.14 mmol) in dichloromethane (30 mL) was added sodium carbonate (1.50 g, 14.19 mmol). The mixture was cooled to 10° C. and peracetic acid (32 wt %, 2.56 mL, 12.16 mmol) was added dropwise via an addition funnel. The reaction mixture was stirred for 3 hours while warming to room temperature, and quenched with saturated aqueous sodium sulfite solution (15 mL) slowly. More dichloromethane (30 mL) was added and the mixture was extracted. The organic layer was washed with brine, dried (anhydrous sodium sulfate), and concentrated. The oil residue was purified by silica gel chromatography (10-30% EtOAc/hexane) to give 920 mg (55%) of 3-(2-methylphenyl)glycidol as a colorless oil. HRMS: calcd for $C_{10}H_{12}O_2+H^+$, 165.0916; found (ESI, [M+H]$^+$), 165.0936.

Step 4: In an analogous manner to EXAMPLE 117, step 5, (2SR,3SR)-3-(1H-indol-1-yl)-3-(2-methylphenyl)propane-1,2-diol was prepared from indole and 3-(2-methylphenyl)glycidol as a viscous, colorless liquid. MS (ES) m/z 282.2 ([M+H]$^+$); HRMS: calcd for $C_{18}H_{19}NO_2+H^+$, 282.1494; found (ESI, [M+H]$^+$), 282.1499.

Step 5: In an analogous manner to EXAMPLE 47, step 6, (1SR,2RS)-1-(1H-indol-1-yl)-3-(methylamino)-1-(2-methylphenyl)propan-2-ol was prepared from (2SR,3SR)-3-(1H-indol-1-yl)-3-(2-methylphenyl)propane-1,2-diol as an oil.

Step 6: Racemic (1SR,2RS)1-(1H-indol-1-yl)-3-(methylamino)-1-(2-methylphenyl)propan-2-ol was dissolved in ethanol (20 mg/mL). The resulting solution was stack injected onto the Supercritical Fluid Chromatography instrument at 1 mL increments. The baseline resolved enantiomers, using the conditions described below, were collected. The enantiomeric purity of each enantiomer was determined under similar Supercritical Fluid Chromatography conditions using a Chiralcel OJ-H 5u, 250 mm L×4.6 mm ID column at 1.2 mL/minutes flow rate using Analytical Supercritical Fluid Chromatography (Berger Instruments, Inc. Newark, DE USA).

| | |
|---|---|
| SFC Instrument: | Berger MultiGram Prep SFC (Berger Instruments, Inc. Newark, DE 19702. |
| Column: | Chiralcel OJ-H; 5 u; 250 mm L × 20 mm ID (Chiral Technologies, Inc., Exton, PA, USA) |
| Column temperature: | 35° C. |
| SFC Modifier: | 15% MeOH with 1.0% DEA/85% $CO_2$ |
| Flow rate: | 50 mL/min |
| Outlet Pressure: | 100 bar |
| Detector: | UV at 220 nm |

Step 7: In an analogous manner to EXAMPLE 144, step 2, (1S,2R)-1-(1H-indol-1-yl)-3-(methylamino)-1-(2-methylphenyl)propan-2-ol hydrochloride was prepared as a white solid, from (1S,2R)-1-(1H-indol-1-yl)-3-(methylamino)-1-(2-methylphenyl)propan-2-ol, which was isolated as Peak 1 of the chiral separation (step 6). Chiral purity: 100%. MS (ESI) m/z 295.3 ([M+H]$^+$); HRMS: calcd for $C_{19}H_{22}N_2O+H^+$, 295.1805; found (ESI, [M+H]$^+$), 295.1795.

Example 54

(1R,2S)-1-(1H-indol-1-yl)-3-(methylamino)-1-(2-methylphenyl)propan-2-ol hydrochloride

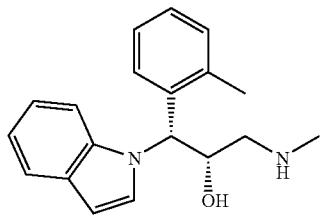

In an analogous manner to EXAMPLE 53, step 7, (1R,2S)-1-(1H-indol-1-yl)-3-(methylamino)-1-(2-methylphenyl)propan-2-ol hydrochloride was prepared as a white solid, from (1R,2S)-1-(1H-indol-1-yl)-3-(methylamino)-1-(2-methylphenyl)propan-2-ol, which was isolated as Peak 2 of the chiral separation (EXAMPLE 53, step 6). Chiral purity: 100%. MS (ESI) m/z 295.3 ([M+H]$^+$); HRMS: calcd for $C_{19}H_{22}N_2O+H^+$, 295.1805; found (ESI, [M+H]$^+$), 295.1805.

Example 55

(1S,2R)-3-(ethylamino)-1-(3-fluorophenyl)-1-(1H-indol-1-yl)propan-2-ol hydrochloride

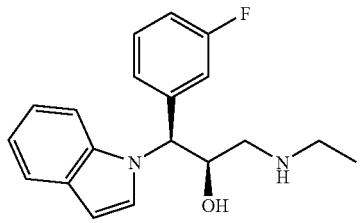

Step 1: In an analogous manner to EXAMPLE 1, step 2, (2S,3S)-3-(3-fluorophenyl)-2-hydroxy-3-(1H-indol-1-yl)propyl 4-methylbenzenesulfonate was prepared from (2S,3S)-3-(3-fluorophenyl)-3-(1H-indol-1-yl)propane-1,2-diol (EXAMPLE 47, step 5) as an ivory solid. HRMS: calcd for $C_{24}H_{22}FN_2O_4S+H^+$, 440.1326; found (ESI, [M+H]$^+$), 440.1345.

Step 2: (2S,3S)-3-(3-fluorophenyl)-2-hydroxy-3-(1H-indol-1-yl)propyl 4-methylbenzenesulfonate (200 mg, 0.456 mmol) was dissolved in a solution of ethylamine in methanol (2.0 M, 10 mL) and stirred for 12 hours in a sealed reaction vessel. All volatiles were removed under reduced pressure, and the liquid residue was dissolved in dichloromethane (15 mL), washed with a saturated aqueous solution of potassium carbonate, dried (anhydrous sodium sulfate), and concentrated. Purification of the liquid residue by Biotage chromatography (FlasH12i, silica, 0-15% MeOH/dichloromethane/0.5% triethylamine) gave (1S,2R)-1-(3-fluorophenyl)-1-(1H-indol-1-yl)-3-(ethylamino)propan-2-ol, which was used to prepare (1S,2R)-3-(ethylamino)-1-(3-fluorophenyl)-1-(1H-indol-1-yl)propan-2-ol hydrochloride as a white powder in an analogous matter to EXAMPLE 144, step 2. Yield: 99 mg (70%). MS (ES) m/z 313.1 ([M+H]$^+$); HRMS: calcd for $C_{19}H_{21}FN_2O+H^+$, 313.1716; found (ESI, [M+H]$^+$), 313.1716.

Example 56

(1S,2R)-1-(3-fluorophenyl)-1-(1H-indol-1-yl)-3-morpholin-4-ylpropan-2-ol hydrochloride

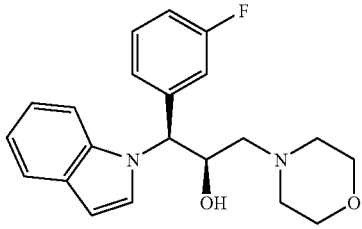

In an analogous manner to EXAMPLE 55, step 2, (1S,2R)-1-(3-fluorophenyl)-1-(1H-indol-1-yl)-3-morpholin-4-ylpropan-2-ol hydrochloride was prepared from morpholine and (2S,3S)-3-(3-fluorophenyl)-2-hydroxy-3-(1H-indol-1-yl)propyl 4-methylbenzenesulfonate (EXAMPLE 55, step 1) as a white powder. MS (ES) m/z 355.1 ([M+H]$^+$); HRMS: calcd for $C_{21}H_{23}FN_2O_2+H^+$, 355.1816; found (ESI, [M+H]$^+$), 355.1822.

Example 57

(1S,2R)-1-(3-fluorophenyl)-1-(1H-indol-1-yl)-3-(propylamino)propan-2-ol hydrochloride

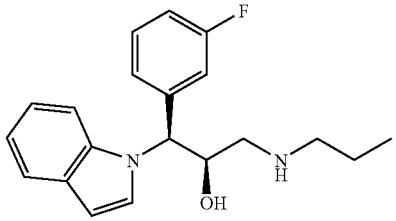

In an analogous manner to EXAMPLE 55, step 2, (1S,2R)-1-(3-fluorophenyl)-1-(1H-indol-1-yl)-3-(propylamino)propan-2-ol hydrochloride was prepared from propylamine and (2S,3S)-3-(3-fluorophenyl)-2-hydroxy-3-(1H-indol-1-yl)propyl 4-methylbenzenesulfonate (EXAMPLE 55, step 1) as a white powder. MS (ES) m/z 327.1 ([M+H]$^+$); HRMS: calcd for $C_{20}H_{23}FN_2O+H^+$, 327.1867; found (ESI, [M+H]$^+$), 327.1873.

Example 58

(1S,2R)-1-(3-fluorophenyl)-1-(1H-indol-1-yl)-3-(4-methylpiperazin-1-yl)propan-2-ol dihydrochloride

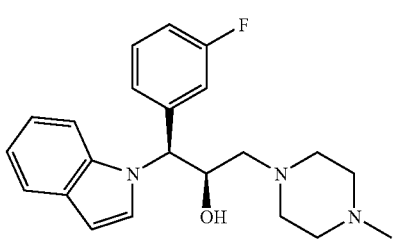

In an analogous manner to EXAMPLE 55, step 2, (1S,2R)-1-(3-fluorophenyl)-1-(1H-indol-1-yl)-3-(4-methylpiperazin-1-yl)propan-2-ol dihydrochloride was prepared from 1-methylpiperazine and (2S,3S)-3-(3-fluorophenyl)-2-hydroxy-3-(1H-indol-1-yl)propyl 4-methylbenzenesulfonate (EXAMPLE 55, step 1) as a white powder. MS (ES) m/z 368.1 ([M+H]$^+$); HRMS: calcd for $C_{22}H_{26}FN_3O+H^+$, 368.2133; found (ESI, [M+H]$^+$), 368.2138.

Example 59

(1S,2R)-1-(1H-indol-1-yl)-3-(methylamino)-1-(4-methylphenyl)propan-2-ol hydrochloride

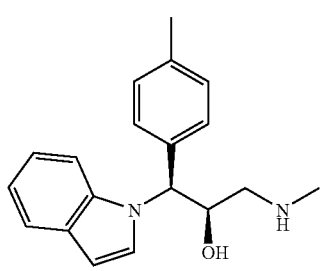

In an analogous manner to EXAMPLE 47, steps 3, [(2R,3R)-3-(4-methylphenyl)oxiran-2-yl]methanol was prepared from trans-4-methylcinnamyl alcohol[3] as a colorless oil. MS (ES) m/z 165.1 ([M+H]$^+$); HRMS: calcd for $C_{10}H_{12}O_2$+H$^+$, 165.0916; found (ESI, [M+H]$^+$), 165.0937.

In an analogous manner to EXAMPLE 117, step 5, (2S,3S)-3-(1H-indol-1-yl)-3-(4-methylphenyl)propane-1,2-diol was prepared from indole and [(2R,3R)-3-(4-methylphenyl)oxiran-2-yl]methanol as a viscous colorless liquid. MS (ES) m/z 282.1 ([M+H]$^+$); HRMS: calcd for $C_{18}H_{19}NO_2$+H$^+$, 282.1494; found (ESI, [M+H]$^+$), 282.1492.

In an analogous manner to EXAMPLE 47, step 6, (1S,2R)-1-(1H-indol-1-yl)-3-(methylamino)-1-(4-methylphenyl)propan-2-ol hydrochloride was prepared from (2S,3S)-3-(1H-indol-1-yl)-3-(4-methylphenyl)propane-1,2-diol as a white powder. MS (ES) m/z 295.1 ([M+H]$^+$); HRMS: calcd for $C_{19}H_{22}N_2O$+H$^+$, 295.1805; found (ESI, [M+H]$^+$), 295.1810.

Example 60

(1S,2R)-1-(2,3-dihydro-1H-indol-1-yl)-1-(3-fluorophenyl)-3-(methylamino)propan-2-ol hydrochloride

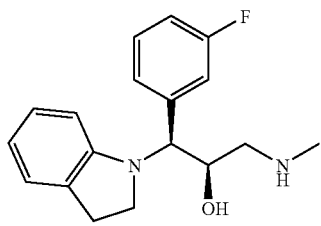

In an analogous manner to EXAMPLE 47, step 6, (1S,2R)-1-(2,3-dihydro-1H-indol-1-yl)-1-(3-fluorophenyl)-3-(methylamino)propan-2-ol hydrochloride was prepared from (2S,3S)-3-(2,3-dihydro-1H-indol-1-yl)-3-(3-fluorophenyl)propane-1,2-diol (EXAMPLE 47, step 4) as a white solid. MS (ES) m/z 301.1 ([M+H]$^+$); HRMS: calcd for $C_{18}H_{21}FN_2O$+H$^+$, 301.1711; found (ESI, [M+H]$^+$), 301.1716.

Example 61

(1S,2R)-1-(2,3-dihydro-1H-indol-1-yl)-3-(methylamino)-1-phenylpropan-2-ol hydrochloride

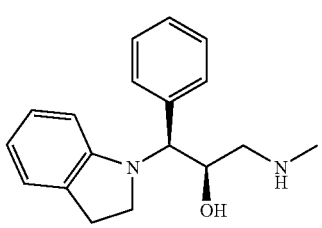

In an analogous manner to EXAMPLE 47, step 4, (2S,3S)-3-(2,3-dihydro-1H-indol-1-yl)-3-phenylpropane-1,2-diol was prepared from indoline and [(2R,3R)-3-phenyloxiran-2-yl]methanol (EXAMPLE 117, step 4) as a viscous, colorless oil. MS (ES) m/z 270.2 ([M+H]$^+$); HRMS: calcd for $C_{17}H_{20}NO_2$+H$^+$, 270.1494; found (ESI, [M+H]$^+$), 270.1493.

In an analogous manner to EXAMPLE 47, step 6, (1S,2R)-1-(2,3-dihydro-1H-indol-1-yl)-3-(methylamino)-1-phenylpropan-2-ol hydrochloride was prepared from (2S,3S)-3-(2,3-dihydro-1H-indol-1-yl)-3-phenylpropane-1,2-diol as a white solid. MS (ES) m/z 283.1 ([M+H]$^+$); HRMS: calcd for $C_{18}H_{21}N_2O$+H$^+$, 283.1805; found (ESI, [M+H]$^+$), 283.1810.

Example 63

(1S,2R)-1-(3-fluorophenyl)-3-(methylamino)-1-(2-methyl-2,3-dihydro-1H-indol-1-yl)propan-2-ol hydrochloride

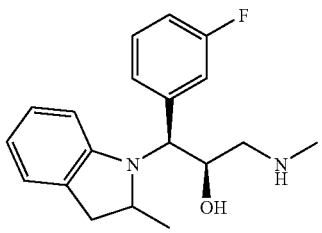

In an analogous manner to EXAMPLE 47, step 4, (2S,3S)-3-(3-fluorophenyl)-3-(2-methyl-2,3-dihydro-1H-indol-1-yl)propane-1,2-diol was prepared from 2-methylindoline and [(2R,3R)-3-(3-fluorophenyl)oxiran-2-yl]methanol (EXAMPLE 47, step 3) as a viscous, colorless oil. MS (ES) m/z 302.1 ([M+H]$^+$); HRMS: calcd for $C_{18}H_{20}FNO_2$+H$^+$, 302.1551; found (ESI, [M+H]$^+$), 302.1556.

In an analogous manner to EXAMPLE 47, step 6, (1S,2R)-1-(3-fluorophenyl)-3-(methylamino)-1-(2-methyl-2,3-dihydro-1H-indol-1-yl)propan-2-ol hydrochloride was prepared from (2S,3S)-3-(3-fluorophenyl)-3-(2-methyl-2,3-dihydro-1H-indol-1-yl)propane-1,2-diol as a white solid. MS (ES) m/z 315.0 ([M+H]$^+$); HRMS: calcd for $C_{19}H_{23}FN_2O$+H$^+$, 315.1867; found (ESI, [M+H]$^+$), 315.1850.

Example 64

(1S,2R)-1-(7-fluoro-3,3-dimethyl-2,3-dihydro-1H-indol-1-yl)-1-(3-fluorophenyl)-3-(methylamino)propan-2-ol hydrochloride

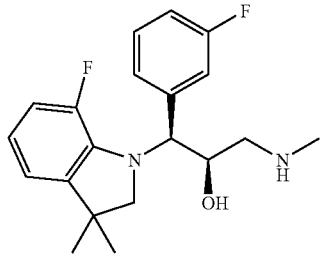

Step 1: A mixture of 7-fluoro-3,3-dimethyloxindole (EXAMPLE 99, step 5, 2.24 g 12.5 mmol) in toluene (15 mL) under nitrogen was heated at 80° C. Vitride (65 wt % in toluene, 6 mL, 19.3 mmol) was added dropwise via an addition funnel. The resulting solution was stirred at 80° C. for an additional 1.5 hours, then cooled in an ice bath. Aqueous sodium hydroxide solution (1N, 15 mL) was added slowly to quench the reaction. Water (15 mL) was added and the reaction mixture was extracted with ethyl acetate (20 mL). The organic layer was washed with brine, dried (anhydrous sodium sulfate), filtered through a pad of silica gel, and concentrated under reduced pressure to yield 1.68 g (82%) of 7-fluoro-3,3-dimethylindoline as a colorless oil. MS (ES) m/z 166.1 ([M+H]$^+$); HRMS: calcd for $C_{10}H_{12}FN+H^+$, 166.1032; found (ESI, [M+H]$^+$), 166.1040.

Step 2: In an analogous manner to EXAMPLE 47, step 4, (2S,3S)-3-(7-fluoro-3,3-dimethyl-2,3-dihydro-1H-indol-1-yl)-3-(3-fluorophenyl)propane-1,2-diol was prepared from 7-fluoro-3,3-dimethylindoline and [(2R,3R)-3-(3-fluorophenyl)oxiran-2-yl]methanol (EXAMPLE 47, step 3) as a viscous, colorless oil. MS (ES) m/z 334.1 ([M+H]$^+$); HRMS: calcd for $C_{19}H_{21}F_2NO_2+H^+$, 334.1613; found (ESI, [M+H]$^+$), 334.1616.

Step 3: In an analogous manner to EXAMPLE 47, step 6, (1S,2R)-1-(7-fluoro-3,3-dimethyl-2,3-dihydro-1H-indol-1-yl)-1-(3-fluorophenyl)-3-(methylamino)propan-2-ol hydrochloride was prepared from (2S,3S)-3-(7-fluoro-3,3-dimethyl-2,3-dihydro-1H-indol-1-yl)-3-(3-fluorophenyl)propane-1,2-diol as a white solid. MS (ES) m/z 347 ([M+H]$^+$); HRMS: calcd for $C_{20}H_{24}F_2N_2O+H^+$, 347.1929; found (ESI, [M+H]$^+$), 347.1935.

Example 65

(1S,2R)-1-(7-fluoro-3,3-dimethyl-2,3-dihydro-1H-indol-1-yl)-3-(methylamino)-1-phenylpropan-2-ol hydrochloride

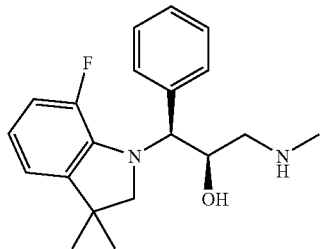

In an analogous manner to EXAMPLE 47, step 4, (2S,3S)-3-(7-fluoro-3,3-dimethyl-2,3-dihydro-1H-indol-1-yl)-3-phenylpropane-1,2-diol was prepared from 7-fluoro-3,3-dimethylindoline (EXAMPLE 64, step 1) and [(2R,3R)-3-phenyloxiran-2-yl]methanol (EXAMPLE 117, step 4) as a viscous, colorless oil. MS (ES) m/z 316.1 ([M+H]$^+$); HRMS: calcd for $C_{19}H_{22}FNO_2+H^+$, 316.1707; found (ESI, [M+H]$^+$), 316.1690.

In an analogous manner to EXAMPLE 47, step 6, (1S,2R)-1-(7-fluoro-3,3-dimethyl-2,3-dihydro-1H-indol-1-yl)-3-(methylamino)-1-phenylpropan-2-ol hydrochloride was prepared from (2S,3S)-3-(7-fluoro-3,3-dimethyl-2,3-dihydro-1H-indol-1-yl)-3-phenylpropane-1,2-diol as a white solid. HRMS: calcd for $C_{20}H_{25}FN_2O+H^+$, 329.2029; found (ESI, [M+H]$^+$), 329.2041.

Example 66

(1S,2R)-3-(methylamino)-1-(7-methyl-2,3-dihydro-1H-indol-1-yl)-1-phenylpropan-2-ol hydrochloride

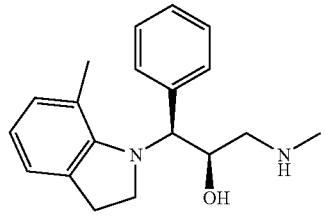

In an analogous manner to EXAMPLE 47, step 4, (2S,3S)-3-(7-methyl-2,3-dihydro-1H-indol-1-yl)-3-phenylpropane-1,2-diol was prepared from 7-methylindoline[4] and [(2R,3R)-3-phenyloxiran-2-yl]methanol (EXAMPLE 117, step 4) as a viscous, colorless oil. MS (ES) m/z 284.2 ([M+H]$^+$); HRMS: calcd for $C_{18}H_{21}NO_2+H^+$, 284.1651; found (ESI, [M+H]$^+$), 284.1650.

[4] Gribble, G. W.; Hoffman, J. H. *Synthesis* 1977, 12, 859-860.

In an analogous manner to EXAMPLE 47, step 6, (1S,2R)-3-(methylamino)-1-(7-methyl-2,3-dihydro-1H-indol-1-yl)-1-phenylpropan-2-ol hydrochloride was prepared from (2S,3S)-3-(7-methyl-2,3-dihydro-1H-indol-1-yl)-3-phenylpropane-1,2-diol as a white solid. MS (ES) m/z 297.0 ([M+H]$^+$); HRMS: calcd for $C_{19}H_{24}N_2O+H+$, 297.1961; found (ESI, [M+H]$^+$), 297.1957.

Example 67

(1S,2R)-1-(3-fluorophenyl)-3-(methylamino)-1-(7-methyl-2,3-dihydro-1H-indol-1-yl)propan-2-ol hydrochloride

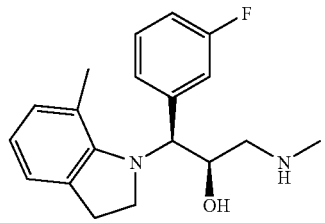

In an analogous manner to EXAMPLE 47, step 4, (2S,3S)-3-(3-fluorophenyl)-3-(7-methyl-2,3-dihydro-1H-indol-1-yl)propane-1,2-diol was prepared from 7-methylindoline[4] and [(2R,3R)-3-(3-fluorophenyl)oxiran-2-yl]methanol (EXAMPLE 47, step 3) as a viscous, colorless oil. MS (ES) m/z 302.1 ([M+H]+); HRMS: calcd for $C_{18}H_{20}FNO_2$+H+, 302.1551; found (ESI, [M+H]+), 302.1551.

In an analogous manner to EXAMPLE 47, step 6, (1S,2R)-1-(3-fluorophenyl)-3-(methylamino)-1-(7-methyl-2,3-dihydro-1H-indol-1-yl)propan-2-ol hydrochloride was prepared from (2S,3S)-3-(3-fluorophenyl)-3-(7-methyl-2,3-dihydro-1H-indol-1-yl)propane-1,2-diol as a white solid. MS (ES) m/z 315.0 ([M+H]+); HRMS: calcd for $C_{19}H_{23}FN_2O$+H+, 315.1873; found (ESI, [M+H]+), 315.1862.

Example 68

(1S,2R)-1-(3-fluorophenyl)-3-(methylamino)-1-(5-methyl-2,3-dihydro-1H-indol-1-yl)propan-2-ol hydrochloride

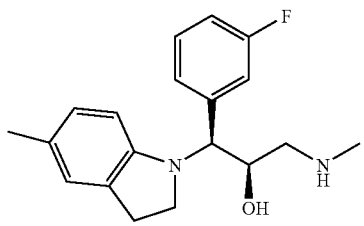

In an analogous manner to EXAMPLE 47, step 4, (2S,3S)-3-(3-fluorophenyl)-3-(5-methyl-2,3-dihydro-1H-indol-1-yl)propane-1,2-diol was prepared from 5-methylindoline and [(2R,3R)-3-(3-fluorophenyl)oxiran-2-yl]methanol (EXAMPLE 47, step 3) as a viscous, colorless oil. MS (ES) m/z 302.1 ([M+H]+); HRMS: calcd for $C_{18}H_{20}FNO_2$, 302.1551; found (ESI, [M+H]+), 302.1551.

In an analogous manner to EXAMPLE 47, step 6, (1S,2R)-1-(3-fluorophenyl)-3-(methylamino)-1-(5-methyl-2,3-dihydro-1H-indol-1-yl)propan-2-ol hydrochloride was prepared from (2S,3S)-3-(3-fluorophenyl)-3-(5-methyl-2,3-dihydro-1H-indol-1-yl)propane-1,2-diol as a white solid. MS (ES) m/z 315.0 ([M+H]+); HRMS: calcd for $C_{19}H_{23}FN_2O$+H+, 315.1873; found (ESI, [M+H]+), 315.1896.

Example 69

(1S,2R)-1-(1H-indol-1-yl)-1-(3-methoxyphenyl)-3-(methylamino)propan-2-ol hydrochloride

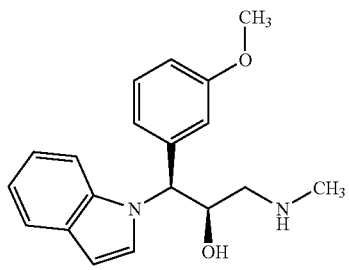

In an analogous manner to EXAMPLE 33, step 1, ethyl (2E)-3-(3-methoxyphenyl)acrylate was prepared from 3-methoxybenzaldehyde and diethyl ethoxycarbonylmethylphosphonate. 1H NMR (DMSO): □1.26 (t, 3H, $OCH_2CH_3$), □3.79 (s, 3H, $OCH_3$), □4.19 (q, 2H, $OCH_2CH_3$), □6.66 (d, 1H, CH=CHC(O)), □6.99 (m, 1H, CH=CH(CO)), □7.31 (m, 3H, ArH) and □7.62 (d, 1H, ArH).

In an analogous manner to EXAMPLE 33, step 2, (2E)-3-(3-methoxyphenyl)prop-2-en-1-ol was prepared from ethyl (2E)-3-(3-methoxyphenyl)acrylate. MS (ES) m/z 147.2 ([M+H−$H_2O$]+).

In analogous manner to EXAMPLE 117, step 4, [(2R,3R)-3-(3-methoxyphenyl)oxiran-2-yl]methanol was prepared from (2E)-3-(3-methoxyphenyl)prop-2-en-1-ol. MS (ES) m/z 222 ([M+H+$CH_3CN$]+); 93.2% ee.

In an analogous manner to EXAMPLE 117, step 5, (2S,3S)-3-(1H-indol-1-yl)-3-(3-methoxyphenyl)propane-1,2-diol was prepared from 1H-indole and [(2R,3R)-3-(3-methoxyphenyl)oxiran-2-yl]methanol. MS (ES) m/z 298.2 ([M+H]+).

In an analogous manner to EXAMPLE 1, step 2, (2S,3S)-toluene-4-sulfonic acid 2-hydroxy-3-(1H-indol-1-yl)-3-(3-methoxyphenyl)-propyl ester was prepared from (2S,3S)-3-(1H-indol-1-yl)-3-(3-methoxyphenyl)propane-1,2-diol. MS (ES) m/z 452.2 ([M+H]+).

In an analogous manner to EXAMPLE 33, step 6 (1S,2R)-1-(1H-indol-1-yl)-1-(3-methoxyphenyl)-3-(methylamino)propan-2-ol hydrochloride was prepared from (2S,3S)-toluene-4-sulfonic acid 2-hydroxy-3-(1H-indol-1-yl)-3-(3-methoxyphenyl)-propyl ester. MS (ES) m/z 311.3 ([M+H]+); HRMS: calcd for $C_{19}H_{22}N_2O_2$+H+, 311.17540; found (ESI, [M+H]+), 311.1758.

Example 70

(1SR,2RS)-1-(1H-indol-1-yl)-1-(4-methoxyphenyl)-3-(methylamino)propan-2-ol hydrochloride

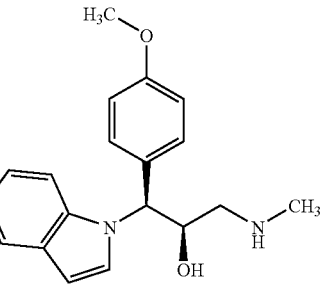

A mixture of methyl trans-3-(4-methoxyphenyl)glycidate (2.11 g, 10.1 mmol) and indoline (1.14 mL, 10.1 mmol) was heated to 135° C. in a sealed tube for 16 hours. The cooled reaction mixture was then directly purified by flash chromatography (silica, 20%, 30% ethyl acetate/hexane) to yield 2.94 g (89%) of methyl (2SR,3SR)-3-(2,3-dihydro-1H-indol-1-yl)-2-hydroxy-3-(4-methoxyphenyl) propanoate as a yellow solid. MS (ES) m/z 328.2 ([M+H]+); HRMS: calcd for $C_{19}H_{21}NO_4$+H+, 328.15434; found (ESI, [M+H]+), 328.1536.

To a solution of methyl (2SR,3SR)-3-(2,3-dihydro-1H-indol-1-yl)-2-hydroxy-3-(4-methoxyphenyl)propanoate (2.63 g, 8.0 mmol) in anhydrous toluene (50 mL) at 0° C. under nitrogen was added a solution of 2,3-dichloro-5,6-dicyano-1,4-benzoquinone (1.87 g, 8.2 mmol) in anhydrous toluene (50 mL) over 5 minutes. The reaction mixture was stirred 0° C. to room temperature for 1.5 hours then quenched by the addition of 7% w/v aqueous sodium carbonate solution (100 mL). The resulting biphasic mixture was stirred vigorously for 5 minutes then partitioned between ethyl acetate (300 mL) and 7% w/v aqueous sodium carbonate (250 mL). The organic phase was separated, washed with 7% w/v aqueous sodium carbonate solution (3×250 mL), water (250 mL) and saturated brine (250 mL), dried over anhydrous magnesium sulfate, filtered and concentrated under reduced pressure to give a lilac solid. Purification by flash chromatography (silica, 20%, 30% ethyl acetate/hexane) afforded 2.5 g (96%) of methyl (2SR,3SR)-2-hydroxy-3-(1H-indol-1-yl)-3-(4-methoxyphenyl)propanoate as a cream solid. MS (ES) m/z 326.3 ([M+H]$^+$); HRMS: calcd for $C_{19}H_{19}NO_4+H^+$, 326.13869; found (ESI, [M+H]$^+$), 326.1378.

A solution of methyl (2SR,3SR)-2-hydroxy-3-(1H-indol-1-yl)-3-(4-methoxyphenyl)propanoate (2.43 g, 7.5 mmol) in methylamine solution (33% wt. in absolute ethanol, 40 mL) was heated to 75° C. in a sealed tube for 1 hour. The cooled reaction mixture was then concentrated under reduced pressure to afford a yellow syrup. Purification by crystallization from 80% chloroform/hexane (50 mL) afforded 1.93 g (80%) of (2SR,3SR)-2-hydroxy-3-(1H-indol-1-yl)-3-(4-methoxyphenyl)-N-methylpropanamide as a white crystalline solid. MS (ES) m/z 323.2 ([M–H]$^-$); HRMS: calcd for $C_{19}H_{20}N_2O_3+H^+$, 325.15467; found (ESI, [M+H]$^+$), 325.1562.

To a solution of (2SR,3SR)-2-hydroxy-3-(1H-indol-1-yl)-3-(4-methoxyphenyl)-N-methylpropanamide (900 mg, 2.8 mmol) in anhydrous tetrahydrofuran (50 mL) at room temperature under nitrogen was added dropwise a solution of borane-tetrahydrofuran complex (1.0 M in tetrahydrofuran, 13.9 mL, 13.9 mmol) and the mixture heated to reflux for 3 hours. The reaction mixture was then cooled to 50° C., methanol (20 mL) was added, and the mixture stirred at 50° C. for 1 hour. The cooled reaction mixture was then concentrated under reduced pressure to afford a white solid. Purification by flash chromatography (silica, 15% methanol/dichloromethane) afforded 272 mg (32%) of (1SR,2RS)-1-(1H-indol-1-yl)-1-(4-methoxyphenyl)-3-(methylamino)propan-2-ol as a yellow syrup. The product was dissolved in absolute ethanol (4 mL), a solution of hydrogen chloride (4 M in 1,4-dioxane, 0.28 mL, 1.12 mmol) added, the solution stirred for 10 minutes then concentrated under reduced pressure to afford a white foam. Crystallization from 1: 1: 1 v/v absolute ethanol : diethyl ether: hexane (12 mL) at –35° C. afforded 81.3 mg (8%) of (1SR,2RS)-1-(1H-indol-1-yl)-1-(4-methoxyphenyl)-3-(methylamino)propan-2-ol hydrochloride as a hygroscopic white solid. MS (ES) m/z 311.3 ([M+H]$^+$); HRMS: calcd for C19H22N2O2+H+, 311.17540; found (ESI, [M+H]$^+$), 311.176.

Example 71

(1RS,2SR)-3-(methylamino)-1-(2-methyl-1H-indol-1-yl)-1-phenylpropan-2-ol hydrochloride

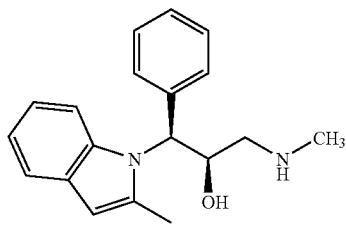

Step 1: A mixture of sodium hydride (60% in mineral oil, 0.40 g, 10 mmol) and tert-butanol (5 mL) was stirred for 15 minutes under nitrogen at room temperature. 2-Methylindole (1.31 g, 10 mmol) in methylene chloride (2 mL) was then added and the mixture was stirred for an additional 30 minutes at room temperature. A pre-mixed solution of titanium isopropoxide (3.55 mL, 12 mmol) and trans-3-phenylglycidol (1.5 g, 10 mmol) in methylene chloride (2 mL) was added, and the reaction mixture was stirred at room temperature for 15 hours until no epoxide remained as determined by tic. The mixture was filtered through a Celite pad, and the filtrate was then treated with a 2N aqueous solution of hydrochloric acid (50 mL) with stirring over 30 minutes. The organic layer was separated and the aqueous layer was extracted with methylene chloride several times. The combined extracts were washed with water, dried over anhydrous sodium sulfate, filtered, and concentrated in vacuo. The crude product was purified via Biotage Horizon (Flash 40 M, silica, gradient from 10% ethyl acetate/hexane to 65% ethyl acetate/hexane) to yield (2RS,3RS)-3-(2-methyl-indol-1-yl)-3-phenyl-propane-1,2-diol as a white solid. MS (ESI) m/z 282 ([M+H]$^+$).

In an analogous manner to EXAMPLE 1, step 2 (2RS,3RS)-toluene-4-sulfonic acid 3-(2-methyl-indol-1-yl)-2-hydroxy-3-phenyl-propyl ester was prepared from (2RS,3RS)-3-(2-methyl-indol-1-yl)-3-phenyl-propane-1,2-diol as an oil. MS (ESI) m/z 436 ([M+H]$^+$).

In an analogous manner to EXAMPLE 5, (1RS,2SR)-3-(methylamino)-1-(2-methyl-1H-indol-1-yl)-1-phenylpropan-2-ol hydrochloride was prepared from (2RS,3RS)-toluene-4-sulfonic acid 3-(2-methyl-indol-1-yl)-2-hydroxy-3-phenyl-propyl ester and methylamine (2N solution in methanol) as a tan solid. MS (ES) m/z 295.0; HRMS: calcd for C19H22N2O+H+, 295.18049; found (ESI, [M+H]$^+$), 295.1818.

Example 72

(1RS,2SR)-1-(1H-benzimidazol-1-yl)-3-(methylamino)-1-phenyl propan-2-ol hydrochloride

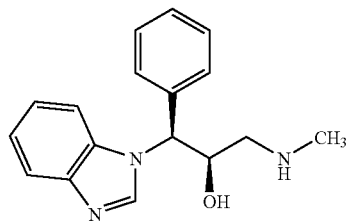

In an analogous manner to EXAMPLE 17, step 1 (2RS,3RS)-3-(1H-benzimidazol-1-yl)-3-phenyl-propane-1,2-diol was prepared from benzimidazole and trans-3-phenylglycidol as an oily solid. MS (ESI) m/z 269 ([M+H]$^+$).

In an analogous manner to EXAMPLE 1, step 2 (2RS,3RS)-toluene-4-sulfonic acid 3-benzoimidazol-1-yl-2-hydroxy-3-phenyl-propyl ester was prepared from (2RS,3RS)-1-(1H-benzimidazol-1-yl)-3-phenyl-propane-1,2-diol as a white solid. MS (ESI) m/z 423 ([M+H]$^+$).

In an analogous manner to EXAMPLE 5, (1RS,2SR)-1-(1H-benzimidazol-1-yl)-3-(methylamino)-1-phenylpropan-2-ol hydrochloride was prepared from (2RS,3RS)—toluene-4-sulfonic acid 3-benzoimidazol-1-yl-2-hydroxy-3-phenyl-propyl ester and methylamine (2N solution in methanol) as a white solid. MS (ES) m/z 282.1; HRMS: calcd for C17H19N3O+H+, 282.16009; found (ESI, [M+H]$^+$), 282.1617.

Example 73

(1RS,2SR)-3-(methylamino)-1-(2-methyl-1H-benzimidazol-1-yl)-1-phenylpropan-2-ol hydrochloride

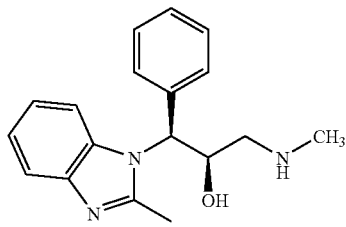

In an analogous manner to EXAMPLE 17, step 1 (2RS,3RS)-3-(2-methyl-1H-benzimidazol-1-yl)-3-phenyl-propane-1,2-diol was prepared from 2-methylbenzimidazole and trans-3-phenylglycidol as a yellow solid. MS (ESI) m/z 283 ([M+H]$^+$).

In an analogous manner to EXAMPLE 1, step 2 (2RS,3RS)-toluene-4-sulfonic acid 2-hydroxy-3-(2-methyl-benzoimidazol-1-yl)-3-phenyl-propyl ester was prepared from (2RS,3RS)-3-(2-methyl-1H-benzimidazol-1-yl)-3-phenyl-propane-1,2-diol as a white solid. MS (ESI) m/z 437 ([M+H]$^+$).

In an analogous manner to EXAMPLE 5, (1RS,2SR)-1-(2-methyl-1H-benzimidazo-1-yl)-3-(methylamino)-1-phenyl-propan-2-ol hydrochloride was prepared from (2RS,3RS)-toluene-4-sulfonic acid 2-hydroxy-3-(2-methyl-benzoimidazol-1-yl)-3-phenyl-propyl ester and methylamine as a white solid. MS (ES) m/z 296.1; SHRMS: calcd for C18H21N3O+H+, 296.17574; found (ESI, [M+H]$^+$), 296.1752.

Example 74

(1RS,2SR)-1-(4-methoxy-1H-indol-1-yl)-3-(methylamino)-1-phenyl propan-2-ol hydrochloride

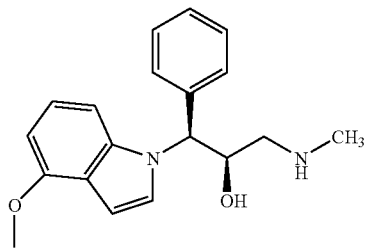

In an analogous manner to EXAMPLE 17, step 1 (2RS,3RS)-3-(4-methoxy-1H-indol-1-yl)-3-phenyl-propane-1,2-diol was prepared from 4-methoxyindole and trans-3-phenylglycidol as an oil. MS (ESI) m/z 298 ([M+H]$^+$).

In an analogous manner to EXAMPLE 1, step 2 (2RS,3RS)-toluene-4-sulfonic acid 2-hydroxy-3-(4-methoxy-indol-1-yl)-3-phenyl-propyl ester was prepared from (2RS,3RS)-3-(4-methoxy-1H-indol-1-yl)-3-phenyl-propane-1,2-diol as a white solid. MS (ESI) m/z 452 ([M+H]$^+$).

In an analogous manner to EXAMPLE 5, (1RS,2SR)-3-(4-methoxy-1H-indol-1-yl)-3-(methylamino)-1-phenylpropan-2-ol hydrochloride was prepared from (2RS,3RS)-toluene-4-sulfonic acid 2-hydroxy-3-(4-methoxy-indol-1-yl)-3-phenyl-propyl ester and methylamine as a white solid. MS (ESI) m/z 311; HRMS: calcd for C19H22N2O2+H+, 311.17540; found (ESI, [M+H]$^+$), 311.1772

Example 75

(1S,2R)-1-(5-fluoro-1H-indol-1-yl)-3-(methylamino)-1-phenylpropan-2-ol hydrochloride

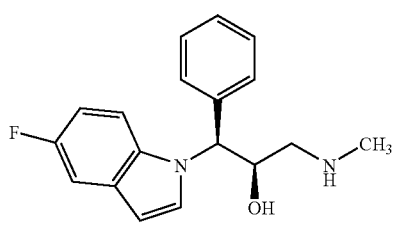

In an analogous manner to EXAMPLE 17, step 1 (2S,3S)-3-(5-fluoro-1H-indol-1-yl)-3-phenyl-propane-1,2-diol was prepared from 5-fluoroindole and [(2R,3R)-3-phenyloxiran-2-yl]methanol (EXAMPLE 117, step 4) as an oil. MS (ESI) m/z 286 ([M+H]$^+$).

In an analogous manner to EXAMPLE 1, step 2 (2S,3S)-toluene-4-sulfonic acid 3-(5-fluoro-indol-1-yl)-2-hydroxy-3-phenyl-propyl ester was prepared from (2S,3S)-3-(5-fluoro-1H-indol-1-yl)-3-phenyl-propane-1,2-diol as an oil. MS (ESI) m/z 438 ([M+H]$^+$).

In an analogous manner to EXAMPLE 5, (1S,2R)-1-(5-fluoro-1H-indol-1-yl)-3-(methylamino)-1-phenylpropan-2-ol hydrochloride was prepared from (2S,3S)-toluene-4-sulfonic acid 3-(5-fluoro-indol-1-yl)-2-hydroxy-3-phenyl-propyl ester and methylamine as a white solid. MS (ES) m/z 299.1; HRMS: calcd for C18H19FN2O+H+, 299.15542; found (ESI, [M+H]$^+$), 299.1556.

Example 76

(1S,2R)-1-(5-methoxy-1H-indol-1-yl)-3-(methylamino)-1-phenylpropan-2-ol hydrochloride

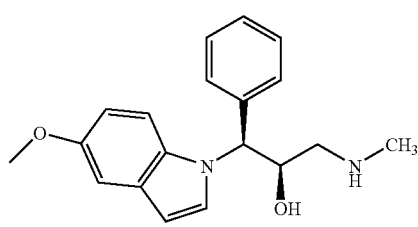

In an analogous manner to EXAMPLE 17, step 1 (2S,3S)-3-(5-methoxy-1H-indol-1-yl)-3-phenyl-propane-1,2-diol was prepared from 5-methoxyindole and [(2R,3R)-3-phenyloxiran-2-yl]methanol (EXAMPLE 117, step 4) as an oil. MS (ESI) m/z 298 ([M+H]$^+$).

In an analogous manner to EXAMPLE 1, step 2 (2S,3S)-toluene-4-sulfonic acid 3-(5-methoxy-indol-1-yl)-2-hydroxy-3-phenyl-propyl ester was prepared from (2S,3S)-3-(5-methoxy-1H-indol-1-yl)-3-phenyl-propane-1,2-diol as an oil. MS (ESI) m/z 452 ([M+H]$^+$).

In an analogous manner to EXAMPLE 5, (1S,2R)-1-(5-methoxy-1H-indol-1-yl)-3-(methylamino)-1-phenylpropan-2-ol hydrochloride was prepared from (2S,3S)-toluene-4-sulfonic acid 3-(5-methoxy-indol-1-yl)-2-hydroxy-3-phenyl-propyl ester and methylamine as a white solid. MS (ES) m/z 311.1; HRMS: calcd for C19H22N2O2+H+, 311.17540; found (ESI, [M+H]+), 311.1745.

Example 77

(1S,2R)-1-(7-methoxy-1H-indol-1-yl)-3-(methylamino)-1-phenylpropan-2-ol hydrochloride

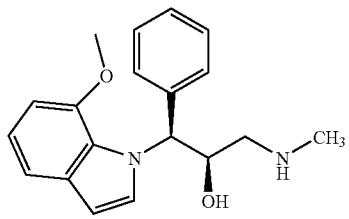

In an analogous manner to EXAMPLE 17, step 1 (2S,3S)-3-(7-methoxy-1H-indol-1-yl)-3-phenyl-propane-1,2-diol was prepared from 7-methoxyindole and [(2R,3R)-3-phenyloxiran-2-yl]methanol (EXAMPLE 117, step 4) as an oil. MS (ESI) m/z 298 ([M+H]+).

In an analogous manner to EXAMPLE 1, step 2 (2S,3S)-toluene-4-sulfonic acid 3-(7-methoxy-indol-1-yl)-2-hydroxy-3-phenyl-propyl ester was prepared from (2S,3S)-3-(7-methoxy-1H-indol-1-yl)-3-phenyl-propane-1,2-diol as an oil. MS (ESI) m/z 452 ([M+H]+).

In an analogous manner to EXAMPLE 5, (1S,2R)-1-(7-methoxy-1H-indol-1-yl)-3-(methylamino)-1-phenylpropan-2-ol hydrochloride was prepared from (2S,3S)-toluene-4-sulfonic acid 3-(7-methoxy-indol-1-yl)-2-hydroxy-3-phenyl-propyl ester and methylamine as a white solid. MS (ES) m/z 311.1; HRMS: calcd for C19H22N2O2+H+, 311.17540; found (ESI, [M+H]+), 311.1753.

Example 78

(1S,2R)-1-(4-methoxy-1H-indol-1-yl)-3-(methylamino)-1-phenyl propan-2-ol hydrochloride

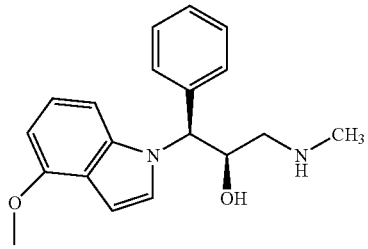

In an analogous manner to EXAMPLE 17, step 1 (2S,3S)-3-(4-methoxy-1H-indol-1-yl)-3-phenyl-propane-1,2-diol was prepared from 4-methoxyindole and [(2R,3R)-3-phenyloxiran-2-yl]methanol (EXAMPLE 117, step 4) as an oil. MS (ESI) m/z 298 ([M+H]+).

In an analogous manner to EXAMPLE 1, step 2 (2S,3S)-toluene-4-sulfonic acid 3-(4-methoxy-indol-1-yl)-2-hydroxy-3-phenyl-propyl ester was prepared from (2S,3S)-3-(4-methoxy-1H-indol-1-yl)-3-phenyl-propane-1,2-diol as an oil. MS (ESI) m/z 452 ([M+H]+).

In an analogous manner to EXAMPLE 5, (1S,2R)-1-(4-methoxy-1H-indol-1-yl)-3-(methylamino)-1-phenylpropan-2-ol hydrochloride was prepared from (2S,3S)-toluene-4-sulfonic acid 3-(4-methoxy-indol-1-yl)-2-hydroxy-3-phenyl-propyl ester and methylamine as a white solid. MS (ESI) m/z 311; HRMS: calcd for C19H22N2O2+H+, 311.17540; found (ESI, [M+H]+), 311.175.

Example 79

(1S,2R)-1-(6-methoxy-1H-indol-1-yl)-3-(methylamino)-1-phenyl propan-2-ol hydrochloride

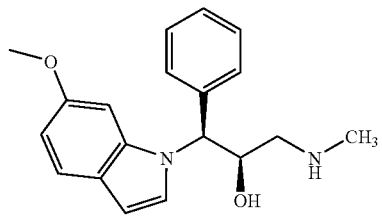

In an analogous manner to EXAMPLE 17, step 1 (2S,3S)-3-(6-methoxy-1H-indol-1-yl)-3-phenyl-propane-1,2-diol was prepared from 6-methoxyindole and [(2R,3R)-3-phenyloxiran-2-yl]methanol (EXAMPLE 117, step 4) as an oil. MS (ESI) m/z 298 ([M+H]+).

In an analogous manner to EXAMPLE 1, step 2 (2S,3S)-toluene-4-sulfonic acid 3-(6-methoxy-indol-1-yl)-2-hydroxy-3-phenyl-propyl ester was prepared from (2S,3S)-3-(6-methoxy-1H-indol-1-yl)-3-phenyl-propane-1,2-diol as an oil. MS (ESI) m/z 452 ([M+H]+).

In an analogous manner to EXAMPLE 5, (1S,2R)-1-(6-methoxy-1H-indol-1-yl)-3-(methylamino)-1-phenylpropan-2-ol hydrochloride was prepared from (2S,3S)-toluene-4-sulfonic acid 3-(6-methoxy-indol-1-yl)-2-hydroxy-3-phenyl-propyl ester and methylamine as a white solid. MS (ESI) m/z 311; HRMS: calcd for C19H22N2O2+H+, 311.17540; found (ESI, [M+H]+), 311.1757.

Example 80

(1RS,2SR)-1-(5-methoxy-1H-indol-1-yl)-3-(methylamino)-1-phenyl propan-2-ol hydrochloride

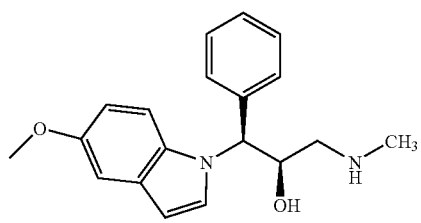

In an analogous manner to EXAMPLE 17, step 1 (2RS,3RS)-3-(5-methoxy-1H-indol-1-yl)-3-phenyl-propane-1,2-diol was prepared from 5-methoxyindole and trans-3-phenylglycidol as an oil. MS (ESI) m/z 298 ([M+H]+).

In an analogous manner to EXAMPLE 1, step 2 (2RS,3RS)-toluene-4-sulfonic acid 3-(5-methoxy-indol-1-yl)-2-hydroxy-3-phenyl-propyl ester was prepared from (2RS,3RS)-3-(5-methoxy-1H-indol-1-yl)-3-phenyl-propane-1,2-diol as an oil. MS (ESI) m/z 452 ([M+H]⁺).

In an analogous manner to EXAMPLE 5, (1RS,2SR)-1-(5-methoxy-1H-indol-1-yl)-3-(methylamino)-1-phenylpropan-2-ol hydrochloride was prepared from (2RS,3RS)-toluene-4-sulfonic acid 3-(5-methoxy-indol-1-yl)-2-hydroxy-3-phenyl-propyl ester and methylamine as a white solid. MS (ESI) m/z 311; HRMS: calcd for C19H22N2O2+H+, 311.17540; found (ESI, [M+H]⁺), 311.1756.

Example 81

(1S,2R)-1-(3-fluorophenyl)-1-(6-methoxy-1H-indol-1-yl)-3-(methyl-amino)propan-2-ol hydrochloride

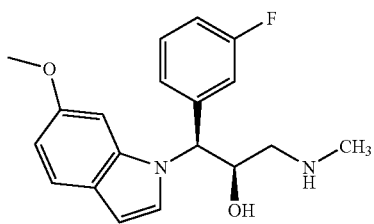

In an analogous manner to EXAMPLE 17, step 1 (2S,3S)-3-(6-methoxy-1H-indol-1-yl)-3-(3-fluorophenyl)-propane-1,2-diol was prepared from 6-methoxyindole and [(2R,3R)-3-(3-fluorophenyl)oxiran-2-yl]methanol (EXAMPLE 47, step 3) as an oil. MS (ESI) m/z 316 ([M+H]⁺).

In an analogous manner to EXAMPLE 1, step 2 (2S,3S)-toluene-4-sulfonic acid 3-(6-methoxy-indol-1-yl)-2-hydroxy-3-(3-fluorophenyl)-propyl ester was prepared from (2S,3S)-3-(6-methoxy-1H-indol-1-yl)-3-(3-fluorophenyl)-propane-1,2-diol as an oil. MS (ESI) m/z 470 ([M+H]⁺).

In an analogous manner to EXAMPLE 5, (1S,2R)-1-(3-fluorophenyl)-1-(6-methoxy-1H-indol-1-yl)-3-(methylamino)-1-phenylpropan-2-ol hydrochloride was prepared from (2S,3S)-toluene-4-sulfonic acid 3-(6-methoxy-indol-1-yl)-2-hydroxy-3-(3-fluorophenyl)-propyl ester and methylamine as a white solid. MS (ES) m/z 329.2; HRMS: calcd for C19H21FN2O2+H+, 329.16598; found (ESI, [M+H]⁺), 329.1663.

Example 82

(1S,2R)-3-(methylamino)-1-phenyl-1-(1H-pyrrolo[2,3-b]pyridin-1-yl)propan-2-ol

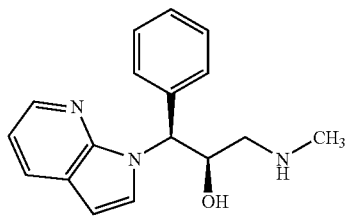

In an analogous manner to EXAMPLE 17, step 1 (2S,3S)-3-phenyl-3-(1H-pyrrolo[2,3-b]pyridin-1-yl)propane-1,2-diol was prepared from 7-azaindole and [(2R,3R)-3-phenyloxiran-2-yl]methanol (EXAMPLE 117, step 4) as a white solid. MS (ES) m/z 269.2; HRMS: calcd for C16H16N2O2+H+, 269.12845; found (ESI, [M+H]⁺), 269.13.

In an analogous manner to EXAMPLE 1, step 2 (2S,3S)-toluene-4-sulfonic acid 2-hydroxy-3-phenyl-3-pyrrolo[2,3-b]pyridin-1-yl-propyl ester was prepared from (2S,3S)-3-phenyl-3-(1H-pyrrolo[2,3-b]pyridin-1-yl)propane-1,2-diol as an oil. MS (ESI) m/z 423 ([M+H]⁺).

In an analogous manner to EXAMPLE 5, (1S,2R)-3-(methylamino)-1-phenyl-1-(1H-pyrrolo[2,3-b]pyridin-1-yl)propan-2-ol was prepared from (2S,3S)-toluene-4-sulfonic acid 2-hydroxy-3-phenyl-3-pyrrolo[2,3-b]pyridin-1-yl-propyl ester and methylamine as a white solid. MS (ES) m/z 282.3; HRMS: calcd for C17H19N3O+H+, 282.16009; found (ESI, [M+H]⁺), 282.16.

Example 83

(1S,2R)-1-(5-chloro-2,3-dihydro-1H-indol-1-yl)-1-(3-fluorophenyl)-3-(methylamino)propan-2-ol hydrochloride

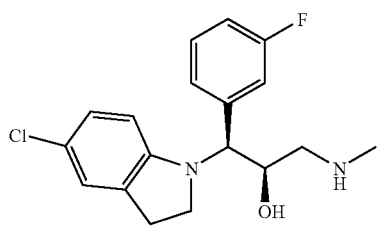

In an analogous manner to EXAMPLE 47, step 4, (2S,3S)-3-(5-chloro-2,3-dihydro-1H-indol-1-yl)-3-(3-fluorophenyl)propane-1,2-diol was prepared from 5-chloroindoline and [(2R,3R)-3-(3-fluorophenyl)oxiran-2-yl]methanol (EXAMPLE 47, step 3) as a viscous, colorless oil. MS (ES) m/z 322.1 ([M+H]⁺); HRMS: calcd for C17H17ClFNO2+H+, 322.1005; found (ESI, [M+H]⁺), 322.1005.

In an analogous manner to EXAMPLE 47, step 6, (1S,2R)-1-(5-chloro-2,3-dihydro-1H-indol-1-yl)-1-(3-fluorophenyl)-3-(methylamino)propan-2-ol hydrochloride was prepared from (2S,3S)-3-(5-chloro-2,3-dihydro-1H-indol-1-yl)-3-(3-fluorophenyl)propane-1,2-diol as a white solid. MS (ES) m/z 335.1 ([M+H]⁺); HRMS: calcd for C18H20ClFN2O+H+, 335.1326; found (ESI, [M+H]⁺), 335.1349.

Example 84

(1S,2R)-3-methylamino-1-phenyl-1-(1H-pyrrolo[2,3-c]pyridin-1-yl) propan-2-ol dihydrochloride

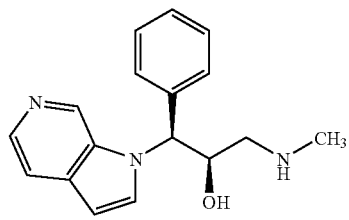

In an analogous manner to EXAMPLE 17, step 1 (2S,3S)-3-(7-chloro-1H-pyrrolo[2,3-c]pyridin-1-yl)-3-phenylpropane-1,2-diol was prepared from 7-chloro-1H-pyrrolo[2,3-c]

pyridine[5] and [(2R,3R)-3-phenyloxiran-2-yl]methanol (EXAMPLE 117, step 4) as an oil. MS (ES) m/z 303 ([M+H]+).

[5] Zhang, Z., et al., *J. Org. Chem.* 2002, 67, 2345-2347

In an analogous manner to EXAMPLE 1, step 2 (2S,3S)-toluene-4-sulfonic acid 3-(7-chloro-pyrrolo[2,3-c]pyridin-1-yl)-2-hydroxy-3-phenyl-propyl ester was prepared from (2S,3S)-3-(7-chloro-pyrrolo[2,3-c]pyridin-1-yl)-3-phenyl-propane-1,2-diol as an oil. MS (ESI) m/z 457 ([M+H]+).

In an analogous manner to EXAMPLE 5, (1S,2R)-1-(7-chloro-pyrrolo[2,3-c]pyridine-1-yl)-3-methylamino-1-phenyl-propan-2-ol was prepared from (2S,3S)-toluene-4-sulfonic acid 3-(7-chloro-pyrrolo[2,3-c]pyridin-1-yl)-2-hydroxy-3-phenyl-propyl ester and methylamine as a white solid. MS (ES) m/z 316.1 ([M+H]+).

Step 4: (1S,2R)-1-(7-chloro-pyrrolo[2,3-c]pyridine-1-yl)-3-methylamino-1-phenyl-propan-2-ol (0.12 g, 0.38 mmol) was dissolved in ethanol (20 mL) and treated with 10% palladium on carbon. The reaction mixture placed under 50 psi of hydrogen on a Parr shaker for 15 hours. The reaction mixture was filtered through a Celite pad and the filtrate was concentrated in vacuo. The crude product was purified via Biotage Horizon (Flash 25 S, silica, gradient from 30% to 100% of 0.9% ammonium hydroxide in 10% methanol-methylene chloride/methylene chloride) to give a white solid as the free base of the expected product. The free base was dissolved in a minimum amount of ethanol and treated with a 1 N ethereal solution of hydrochloric acid until the solution was pH=3 followed by diethyl ether. The product was then crystallized by adding a minimum amount of ethyl acetate to afford the titled compound, (1S,2R)-3-methylamino-1-phenyl-1-(1H-pyrrolo[2,3-c]pyrid in-1-yl)-propan-2-ol dihydrochloride as a white solid. MS (ES) m/z 282.1.

Example 85

(1S,2R)-1-(5-fluoro-1H-indol-1-yl)-1-(3-fluorophenyl)-3-(methyl-amino)propan-2-ol hydrochloride

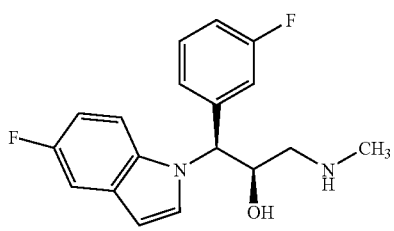

In an analogous manner to EXAMPLE 17, step 1 (2S,3S)-3-(5-fluoro-1H-indol-1-yl)-3-(3-fluorophenyl)-propane-1,2-diol was prepared from 5-fluoroindole and [(2R,3R)-3-(3-fluorophenyl)oxiran-2-yl]methanol (EXAMPLE 47, step 3) as an oil. MS (ESI) m/z 304 ([M+H]+).

In an analogous manner to EXAMPLE 1, step 2 (2S,3S)-toluene-4-sulfonic acid 3-(5-fluoro-indol-1-yl)-2-hydroxy-3-phenyl-propyl ester was prepared from (2S,3S)-3-(5-fluoro-1H-indol-1-yl)-3-(3-fluorophenyl)-propane-1,2-diol as an oil. MS (ESI) m/z 458 ([M+H]+).

In an analogous manner to EXAMPLE 5, (1S,2R)-1-(5-fluoro-1H-indol-3-yl)-1-(3-fluorophenyl)-3-(methylamino)propan-2-ol hydrochloride was prepared from (2S,3S)-toluene-4-sulfonic acid 3-(5-fluoro-indol-1-yl)-2-hydroxy-3-phenyl-propyl ester and methylamine as a light tan solid. MS (ES) m/z 317.2; HRMS: calcd for C18H18F2N2O+H+, 317.14599; found (ESI, [M+H]+), 317.1472.

Example 86

(1S,2R)-3-methylamino-1-(3-fluorophenyl)-1-(1H-pyrrolo[2,3-c]pyridin-1-yl) propan-2-ol dihydrochloride

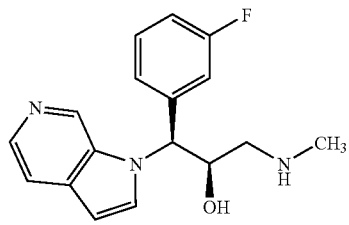

In an analogous manner to EXAMPLE 17, step 1 (2S,3S)-3-(7-chloro-pyrrolo[2,3-c]pyridin-1-yl)-3-(3-fluorophenyl)-propane-1,2-diol was prepared from 7-chloro-1H-pyrrolo[2,3-c]pyridine[5] and [(2R,3R)-3-(3-fluorophenyl)oxiran-2-yl]methanol (EXAMPLE 47, step 3) as an oil. MS (ESI) m/z 321 ([M+H]+).

In an analogous manner to EXAMPLE 1, step 2 (2S,3S)-toluene-4-sulfonic acid 3-(7-chloro-pyrrolo[2,3-c]pyridin-1-yl)-2-hydroxy-3-(3-fluorophenyl)-propyl ester was prepared from (2S,3S)-3-(7-chloro-pyrrolo[2,3-c]pyridin-1-yl)-3-(3-fluorophenyl)-propane-1,2-diol as an oil. MS (ESI) m/z 475 ([M+H]+).

In an analogous manner to EXAMPLE 5, (1S,2R)-1-(7-chloro-pyrrolo[2,3-c]pyridine-1-yl)-3-methylamino-1-(3-fluorophenyl)-propan-2-ol was prepared from (2S,3S)-toluene-4-sulfonic acid 3-(7-chloro-pyrrolo[2,3-c]pyrid in-1-yl)-2-hydroxy-3-(3-fluorophenyl)-propyl ester and methylamine as a white solid. MS (ESI) m/z 334 ([M+H]+).

In an analogous manner to EXAMPLE 84, step 4 (1S,2R)-3-methylamino-1-(3-fluorophenyl)-1-(1H-pyrrolo[2,3-c]pyridin-1-yl)-propan-2-ol dihydrochloride was prepared from (1S,2R)-1-(7-chloro-pyrrolo[2,3-c]pyridine-1-yl)-3-methylamino-1-(3-fluorophenyl)-propan-2-ol as a white solid. MS (ESI) m/z 282.1 ([M+H]+).

Example 87

(1S,2R)-1-(5-chloro-2,3-dihydro-1H-indol-1-yl)-3-(methylamino)-1-phenylpropan-2-ol hydrochloride

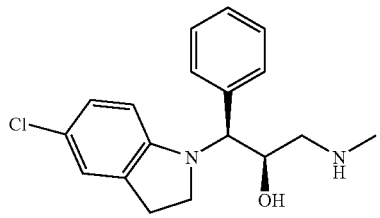

In an analogous manner to EXAMPLE 47, step 4, (2S,3S)-3-(5-chloro-2,3-dihydro-1H-indol-1-yl)-3-phenylpropane-1,2-diol was prepared from 5-chloroindoline and [(2R,3R)-3-phenyloxiran-2-yl]methanol (EXAMPLE 117, step 4) as a viscous, colorless oil. MS (ES) m/z 304.1 ([M+H]+); HRMS: calcd for $C_{17}H_{18}ClNO_2+H^+$, 304.1099; found (ESI, [M+H]+), 304.1081.

In an analogous manner to EXAMPLE 47, step 6, (1S,2R)-1-(5-chloro-2,3-dihydro-1H-indol-1-yl)-3-(methylamino)-1-phenylpropan-2-ol hydrochloride was prepared from 2S,3S)-3-(5-chloro-2,3-dihydro-1H-indol-1-yl)-3-phenylpropane-1,2-diol as a white powder. MS (ES) m/z 317.1 ([M+H]⁺); HRMS: calcd for $C_{18}H_{21}ClN_2O+H^+$, 317.1421; found (ESI, [M+H]⁺), 317.1431.

Example 88

(1S,2R)-1-(6-chloro-2,3-dihydro-4H-1,4-benzoxazin-4-yl)-1-(3,5-difluorophenyl)-3-(methylamino)propan-2-ol hydrochloride

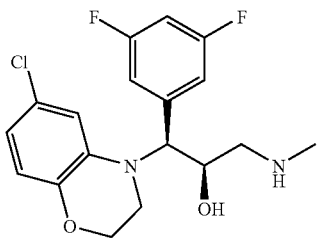

Step 1: In an analogous manner to EXAMPLE 165, step 1,6-chloro-3,4-dihydro-2H-1,4-benzoxazine was prepared from 6-chloro-2H-1,4-benzoxazin-3(4H)-one as a yellow solid. MS (ES) m/z 170.0 ([M+H]⁺); HRMS: calcd for $C_8H_8ClNO+H^+$, 170.0367; found (ESI, [M+H]⁺), 170.0365.

Step 2: In an analogous manner to EXAMPLE 47, step 4, (2S,3S)-3-(6-chloro-2,3-dihydro-4H-1,4-benzoxazin-4-yl)-3-(3,5-difluorophenyl)propane-1,2-diol was prepared from 6-chloro-3,4-dihydro-2H-1,4-benzoxazine and [(2R,3R)-3-(3,5-difluorophenyl)oxiran-2-yl]methanol (EXAMPLE 157, step 3) as a viscous, yellowish liquid. MS (ES) m/z 356.1 ([M+H]⁺); HRMS: calcd for $C_{17}H_{16}ClF_2NO_3+H^+$, 356.0860; found (ESI, [M+H]⁺), 356.0869.

Step 3: In an analogous manner to EXAMPLE 47, step 6, (1S,2R)-1-(6-chloro-2,3-dihydro-4H-1,4-benzoxazin-4-yl)-1-(3,5-difluorophenyl)-3-(methylamino)propan-2-ol hydrochloride was prepared from (2S,3S)-3-(6-chloro-2,3-dihydro-4H-1,4-benzoxazin-4-yl)-3-(3,5-difluorophenyl)propane-1,2-diol as a white powder. MS (ES) m/z 369.1 ([M+H]⁺); HRMS: calcd for $C_{18}H_{19}ClF_2N_2O_2+H^+$, 369.1176; found (ESI, [M+H]⁺), 369.1178.

Example 89

(1S,2R)-1-(3-fluorophenyl)-3-(methylamino)-1-(2-methyl-2,3-dihydro-4H-1,4-benzoxazin-4-yl)propan-2-ol hydrochloride

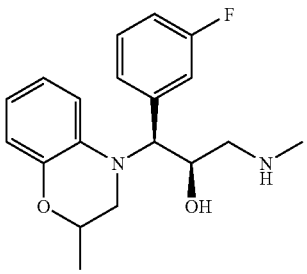

In an analogous manner to EXAMPLE 165, step 1,2-methyl-3,4-dihydro-2H-1,4-benzoxazine was prepared from 2-methyl-2H-1,4-benzoxazin-3(4H)-one⁶ as a brown oil. MS (ES) m/z 149.9 ([M+H]⁺).

[6] Wheeler, K. W. *J. Med. Pharm. Chem.* 1962, 5, 1378-1383.

In an analogous manner to EXAMPLE 47, step 4, (2S,3S)-3-(3-fluorophenyl)-3-(2-methyl-2,3-dihydro-4H-1,4-benzoxazin-4-yl)propane-1,2-diol was prepared from 2-methyl-3,4-dihydro-2H-1,4-benzoxazine and [(2R,3R)-3-(3-fluorophenyl)oxiran-2-yl]methanol (EXAMPLE 47, step 3) as a viscous, brown liquid. MS (ES) m/z 318.2 ([M+H]⁺); HRMS: calcd for $C_{18}H_{20}FNO_3+H^+$, 318.1500; found (ESI, [M+H]⁺), 318.1513.

In an analogous manner to EXAMPLE 47, step 6, (1S,2R)-1-(3-fluorophenyl)-3-(methylamino)-1-(2-methyl-2,3-dihydro-4H-1,4-benzoxazin-4-yl)propan-2-ol hydrochloride was prepared from (2S,3S)-3-(3-fluorophenyl)-3-(2-methyl-2,3-dihydro-4H-1,4-benzoxazin-4-yl)propane-1,2-diol as a white powder. MS (ES) m/z 331.0 ([M+H]⁺); HRMS: calcd for $C_{19}H_{23}FN_2O_2+H^+$, 331.1816; found (ESI, [M+H]⁺), 331.1804.

Example 90

(1S,2R)-3-(methylamino)-1-(6-methyl-1H-indol-1-yl)-1-phenylpropan-2-ol hydrochloride

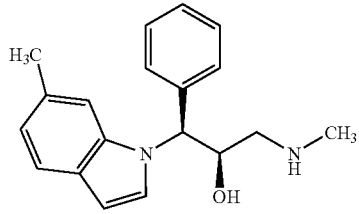

In an analogous manner to EXAMPLE 117, step 5 (2S,3S)-3-(6-methyl-1H-indol-1-yl)-3-phenylpropane-1,2-diol was prepared from 6-methylindole and 2R,3R-(+)-3-phenylglycidol as an oil. MS (ESI) m/z 282 ([M+H]⁺).

In an analogous manner to EXAMPLE 1, step 2 (2S,3S)-toluene-4-sulfonic acid 3-(6-methyl-indol-1-yl)-2-hydroxy-3-phenyl-propyl ester was prepared from (2S,3S)-3-(6-methyl-1H-indol-1-yl)-3-phenylpropane-1,2-diol MS (ESI) m/z 436 ([M+H]⁺).

In an analogous manner to EXAMPLE 5 (1S,2R)-3-(methylamino)-1-(6-methyl-1H-indol-1-yl)-1-phenylpropan-2-ol hydrochloride was prepared from (2S,3S)-toluene-4-sulfonic acid 3-(6-methyl-indol-1-yl)-2-hydroxy-3-phenyl-propyl ester and methylamine (2N solution in methanol); MS (ESI) m/z 295 ([M+H]⁺); HRMS: calcd for C19H22N2O+H+, 295.18049; found (ESI-FT/MS, [M+H]1+), 295.1809.

Example 91

(1S,2R)-3-(methylamino)-1-(7-methyl-1H-indol-1-yl)-1-phenylpropan-2-ol hydrochloride

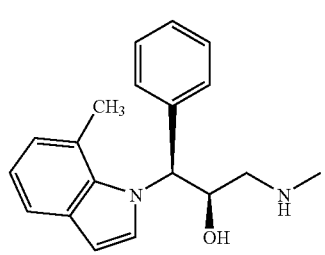

In an analogous manner to EXAMPLE 117, step 5 (2S,3S)-3-(7-methyl-1H-indol-1-yl)-3-phenylpropane-1,2-diol was prepared from 7-methylindole and 2R,3R-(+)-3-phenylglycidol as an oil. MS (ESI) m/z 282 ([M+H]⁺).

In an analogous manner to EXAMPLE 1, step 2 (2S,3S)-toluene-4-sulfonic acid 3-(7-methyl-indol-1-yl)-2-hydroxy- 3-phenyl-propyl ester was prepared from (2S,3S)-3-(7-methyl-1H-indol-1-yl)-3-phenylpropane-1,2-diol MS (ESI) m/z 436 ([M+H]+).

In an analogous manner to EXAMPLE 5 (1S,2R)-3-(methylamino)-1-(7-methyl-1H-indol-1-yl)-1-phenylpropan-2-ol hydrochloride was prepared from (2S,3S)-toluene-4-sulfonic acid 3-(7-methyl-indol-1-yl)-2-hydroxy-3-phenylpropyl ester and methylamine (2N solution in methanol); MS (ESI) m/z 295 ([M+H]+); HRMS: calcd for C19H22N2O+H+, 295.18049; found (ESI-FT/MS, [M+H]1+), 295.1809.

Example 92

((1S,2R)-1-(3-fluorophenyl)-3-(methylamino)-1-(5-methyl-1H-indol-1-yl)propan-2-ol hydrochloride

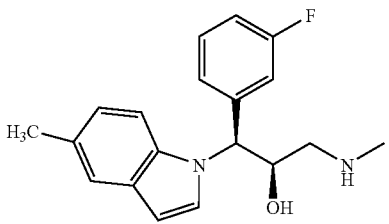

In an analogous manner to EXAMPLE 117, step 5 (2S,3S)-3-(3-fluorophenyl)-3-(5-methyl-1H-indol-1-yl)propane-1,2-diol was prepared from 5-methylindole and [(2R,3R)-3-(3-fluorophenyl)oxiran-2-yl]methanol (see EXAMPLE 47, step 3) as an oil. MS (ESI) m/z 300 ([M+H]+).

In an analogous manner to EXAMPLE 1, step 2 (2S,3S)-toluene-4-sulfonic acid 3-(3-fluorophenyl)-3-(5-methyl-indol-1-yl)-2-hydroxy-propyl ester was prepared from (2S,3S)-3-(3-fluorophenyl)-3-(5-methyl-1H-indol-1-yl)propane-1,2-diol MS (ESI) m/z 454 ([M+H]+).

In an analogous manner to EXAMPLE 5 ((1S,2R)-1-(3-fluorophenyl)-3-(methylamino)-1-(5-methyl-1H-indol-1-yl)propan-2-ol hydrochloride was prepared from (2S,3S)-toluene-4-sulfonic acid 3-(3-fluorophenyl)-3-(5-methyl-indol-1-yl)-2-hydroxy-propyl ester and methylamine (2N solution in methanol); MS (ESI) m/z 313 ([M+H]+); HRMS: calcd for C19H21FN2O+H+, 313.17107; found (ESI-FTMS, [M+H]1+), 313.17163.

Example 93

((1S,2R)-1-(3-fluorophenyl)-3-(methylamino)-1-(7-methyl-1H-indol-1-yl)propan-2-ol hydrochloride

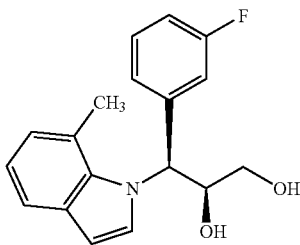

In an analogous manner to EXAMPLE 117, step 5 (2S,3S)-3-(3-fluorophenyl)-3-(7-methyl-1H-indol-1-yl)propane-1,2-diol was prepared from 7-methylindole and [(2R,3R)-3-(3-fluorophenyl)oxiran-2-yl]methanol (see EXAMPLE 47, step 3) as an oil. MS (ESI) m/z 300 ([M+H]+).

In an analogous manner to EXAMPLE 1, step 2 (2S,3S)-toluene-4-sulfonic acid 3-(3-fluorophenyl)-3-(7-methyl-indol-1-yl)-2-hydroxy-propyl ester was prepared from (2S,3S)-3-(3-fluorophenyl)-3-(7-methyl-1H-indol-1-yl)propane-1,2-diol MS (ESI) m/z 454 ([M+H]+).

In an analogous manner to EXAMPLE 5 ((1S,2R)-1-(3-fluorophenyl)-3-(methylamino)-1-(7-methyl-1H-indol-1-yl)propan-2-ol hydrochloride was prepared from (2S,3S)-toluene-4-sulfonic acid 3-(3-fluorophenyl)-3-(7-methyl-indol-1-yl)-2-hydroxy-propyl ester and methylamine (2N solution in methanol); MS (ESI) m/z 313 ([M+H]+); HRMS: calcd for C19H21FN2O+H+, 313.17107; found (ESI-FTMS, [M+H]1+), 313.17141.

Example 94

(1S,2R)-3-(methylamino)-1-(4-methyl-1H-indol-1-yl)-1-phenylpropan-2-ol hydrochloride

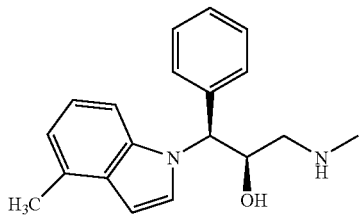

In an analogous manner to EXAMPLE 117, step 5 (2S,3S)-3-(4-methyl-1H-indol-1-yl)-3-phenylpropane-1,2-diol was prepared from 4-methylindole[7] and 2R,3R-(+)-3-phenylglycidol as an oil. MS (ESI) m/z 282 ([M+H]+).

[7] Raucher, Stanley; Koolpe, Gary A. J. Org. Chem. 1983, 48(12), 2066-9

In an analogous manner to EXAMPLE 1, step 2 (2S,3S)-toluene-4-sulfonic acid 3-(4-methyl-indol-1-yl)-2-hydroxy-3-phenyl-propyl ester was prepared from (2S,3S)-3-(4-methyl-1H-indol-1-yl)-3-phenylpropane-1,2-diol MS (ESI) m/z 436 ([M+H]+).

In an analogous manner to EXAMPLE 5 (1S,2R)-3-(methylamino)-1-(4-methyl-1H-indol-1-yl)-1-phenylpropan-2-ol hydrochloride was prepared from (2S,3S)-toluene-4-sulfonic acid 3-(4-methyl-indol-1-yl)-2-hydroxy-3-phenyl-propyl ester and methylamine (2N solution in methanol); MS (ESI) m/z 295 ([M+H]+); HRMS: calcd for C19H22N2O+H+, 295.18049; found (ESI-FT/MS, [M+H]1+), 295.1811.

Example 95

(1S,2R)-3-(methylamino)-1-(5-methyl-1H-indol-1-yl)-1-phenylpropan-2-ol hydrochloride

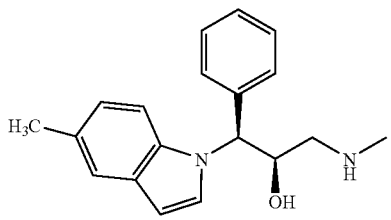

In an analogous manner to EXAMPLE 117, step 5 (2S,3S)-3-(5-methyl-1H-indol-1-yl)-3-phenylpropane-1,2-diol was prepared from 5-methylindole and 2R,3R-(+)-3-phenylglycidol as an oil. MS (ESI) m/z 282 ([M+H]+).

In an analogous manner to EXAMPLE 1, step 2 (2S,3S)-toluene-4-sulfonic acid 3-(5-methyl-indol-1-yl)-2-hydroxy-3-phenyl-propyl ester was prepared from (2S,3S)-3-(5-methyl-1H-indol-1-yl)-3-phenylpropane-1,2-diol MS (ESI) m/z 436 ([M+H]$^+$).

In an analogous manner to EXAMPLE 5 (1S,2R)-3-(methylamino)-1-(5-methyl-1H-indol-1-yl)-1-phenylpropan-2-ol hydrochloride was prepared from (2S,3S)-toluene-4-sulfonic acid 3-(5-methyl-indol-1-yl)-2-hydroxy-3-phenyl-propyl ester and methylamine (2N solution in methanol); MS (ESI) m/z 295 ([M+H]$^+$); HRMS: calcd for C19H22N2O+H+, 295.18049; found (ESI-FT/MS, [M+H]1+), 295.1812.

Example 96

((1S,2R)-1-(3-fluorophenyl)-3-(methylamino)-1-(4-methyl-1H-indol-1-yl)propan-2-ol hydrochloride

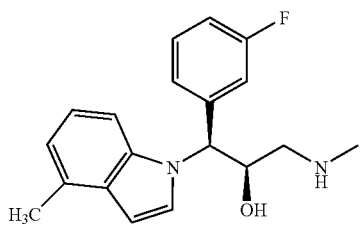

In an analogous manner to EXAMPLE 117, step 5 (2S,3S)-3-(3-fluorophenyl)-3-(4-methyl-1H-indol-1-yl)propane-1,2-diol was prepared from 4-methylindole[7] and [(2R,3R)-3-(3-fluorophenyl)oxiran-2-yl]methanol (see EXAMPLE 47, step 3) as an oil. MS (ESI) m/z 300 ([M+H]$^+$).

In an analogous manner to EXAMPLE 1, step 2 (2S,3S)-toluene-4-sulfonic acid 3-(3-fluorophenyl)-3-(4-methyl-indol-1-yl)-2-hydroxy-propyl ester was prepared from (2S,3S)-3-(3-fluorophenyl)-3-(4-methyl-1H-indol-1-yl)propane-1,2-diol MS (ESI) m/z 454 ([M+H]$^+$).

In an analogous manner to EXAMPLE 5 ((1S,2R)-1-(3-fluorophenyl)-3-(methylamino)-1-(4-methyl-1H-indol-1-yl)propan-2-ol hydrochloride was prepared from (2S,3S)-toluene-4-sulfonic acid 3-(3-fluorophenyl)-3-(4-methyl-indol-1-yl)-2-hydroxy-propyl ester and methylamine (2N solution in methanol); MS (ESI) m/z 313 ([M+H]$^+$); HRMS: calcd for C19H21FN2O+H+, 313.17107; found (ESI-FT/MS, [M+H]1+), 313.171.

Example 97

((1S,2R)-1-(3-fluorophenyl)-3-(methylamino)-1-(3-ethyl-1H-indol-1-yl)propan-2-ol hydrochloride

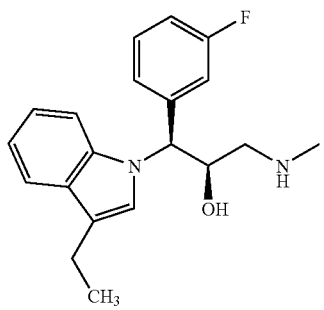

In an analogous manner to EXAMPLE 117, step 5 (2S,3S)-3-(3-fluorophenyl)-3-(3-ethyl-1H-indol-1-yl)propane-1,2-diol was prepared from 3-ethylindole[8] and [(2R,3R)-3-(3-fluorophenyl)oxiran-2-yl]methanol (see EXAMPLE 47, step 3) as an oil. MS (ESI) m/z 314 ([M+H]$^+$).

[8] Ainsworth, D. P.; Suschitzky, Hans *J. Chem Soc. [Section] C: Organic* 1967, (4), 315-19

In an analogous manner to EXAMPLE 1, step 2 (2S,3S)-toluene-4-sulfonic acid 3-(3-fluorophenyl)-3-(3-ethyl-indol-1-yl)-2-hydroxy-propyl ester was prepared from (2S,3S)-3-(3-fluorophenyl)-3-(3-ethyl-1H-indol-1-yl)propane-1,2-diol MS (ESI) m/z 468 ([M+H]$^+$).

In an analogous manner to EXAMPLE 5 ((1S,2R)-1-(3-fluorophenyl)-3-(methylamino)-1-(3-ethyl-1H-indol-1-yl)propan-2-ol hydrochloride was prepared from (2S,3S)-toluene-4-sulfonic acid 3-(3-fluorophenyl)-3-(3-ethyl-indol-1-yl)-2-hydroxy-propyl ester and methylamine (2N solution in methanol); MS (ESI) m/z 327 ([M+H]$^+$); HRMS: calcd for C20H23FN2O+H+, 327.18672; found (ESI, [M+H]$^+$), 327.1871.

Example 98

((1S,2R)-1-(3-fluorophenyl)-3-(methylamino)-1-(3-phenyl-1H-indol-1-yl)propan-2-ol hydrochloride

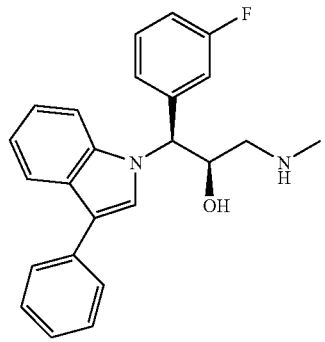

In an analogous manner to EXAMPLE 117, step 5 (2S,3S)-3-(3-fluorophenyl)-3-(3-phenyl-1H-indol-1-yl)propane-1,2-diol was prepared from 3-phenylindole[9] and [(2R,3R)-3-(3-fluorophenyl)oxiran-2-yl]methanol (see EXAMPLE 47, step 3) as an oil; MS (ESI) m/z 362 ([M+H]$^+$).

[9] Cacchi, Sandro; Fabrizi, Giancarlo; Marinelli, Fabio; Moro, Leonardo; Pace, Paola *Synlett* 1997, (12), 1363-1366.

In an analogous manner to EXAMPLE 1, step 2 (2S,3S)-toluene-4-sulfonic acid 3-(3-fluorophenyl)-3-(3-phenyl-indol-1-yl)-2-hydroxy-propyl ester was prepared from (2S,3S)-3-(3-fluorophenyl)-3-(3-phenyl-1H-indol-1-yl)propane-1,2-diol MS (ESI) m/z 516 ([M+H]$^+$).

In an analogous manner to EXAMPLE 5 ((1S,2R)-1-(3-fluorophenyl)-3-(methylamino)-1-(3-phenyl-1H-indol-1-yl)propan-2-ol hydrochloride was prepared from (2S,3S)-toluene-4-sulfonic acid 3-(3-fluorophenyl)-3-(3-phenyl-indol-1-yl)-2-hydroxy-propyl ester and methylamine (2N solution in methanol); MS (ESI) m/z 375 ([M+H]$^+$); HRMS: calcd for C$_{24}$H$_{23}$FN2O+H$^+$, 375.18672; found (ESI, [M+H]$^+$), 375.1886.

Example 99

7-fluoro-1-[(1S,2R)-2-hydroxy-3-(methylamino)-1-phenylpropyl]-3,3-dimethyl-1,3-dihydro-2H-indol-2-one hydrochloride

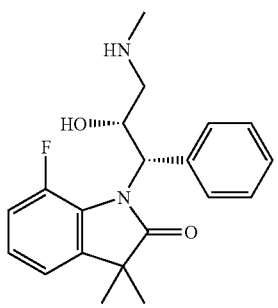

Step 1: A mixture of sodium perborate tetrahydrate (65 g, 422 mmol) in glacial acetic acid (250 mL) was stirred at 80° C. 2,6-Difluoroaniline (11.0 g, 85 mmol) in glacial acetic acid (50 mL) was added slowly to the mixture. The temperature was maintained between 80-90° C. for 1 hour. The cooled reaction mixture was poured into water and extracted twice with diethyl ether. The combined organic layers were washed with a dilute solution of sodium bicarbonate, dried over anhydrous magnesium sulfate and evaporated. The residue was purified via Biotage chromatography (FlasH90i, silica, 10% THF/hexane) and the product washed with hexane to afford 2,6-difluoronitrobenzene (7.0 g) (52%). MS (ESI) m/z 160 ([M+H]$^+$).

Step 2: To a solution of 2,6-difluoronitrobenzene (5.0 g, 31.44 mmol) in dry N,N-dimethylformamide (50 mL) was added potassium carbonate (4.41 g, 32 mmol) and dimethylmalonate (3.6 mL, 31.44 mmol). The reaction mixture was heated to 65° C. and stirred for 24 hours. After cooling to room temperature, the mixture was neutralized with a dilute aqueous solution of hydrochloric acid and extracted with diethyl ether. The ethereal layer was dried over anhydrous magnesium sulfate, and concentrated in vacuo. Crystallization from 5% ethyl acetate/hexane gave 4.6 g (54%) 2-(6-fluoro-2-nitro-phenyl)-malonic acid dimethyl ester. MS (ESI) m/z 272 [M+H]$^+$).

Step 3: 2-(6-Fluoro-2-nitro-phenyl)-malonic acid dimethyl ester (12 g, 44 mmol) in a 6N aqueous solution of hydrochloric acid (200 mL) was heated at reflux for 4 hours. The mixture was cooled, diluted with 250 mL of water and extracted with diethyl ether. The ethereal layer was dried over anhydrous magnesium sulfate, and concentrated in vacuo. Crystallization from 5% ethyl acetate/hexane gave 7.6 g of (6-fluoro-2-nitro-phenyl)-acetic acid (54%). MS (ESI) m/z 200 ([M+H]$^+$).

Step 4: A mixture of (6-fluoro-2-nitro-phenyl)-acetic acid (9.6 g, 48 mmol) and 10% palladium on carbon (1.3 g) in acetic acid (100 ml) was hydrogenated at 50 psi for 24 hours. The catalyst was removed by filtration through Celite and the solvent was evaporated. The residue was then dissolved in ethanol (100 mL) and pyridinium para-toluenesulfonate (50 mg) was added and the mixture heated at reflux for 1 hour s. The mixture was cooled, poured into water, extracted with ethyl acetate and dried over anhydrous magnesium sulfate. The solvent was filtered and concentrated in vacuo. The solid was triturated with 5% ethyl acetate/hexane to give 6.0 g (83%) 7-fluoro-1,3-dihydro-indol-2-one. MS (ESI) m/z 152, [M+H]$^+$).

Step 5: 7-Fluoro-1,3-dihydro-indol-2-one (7.3 g, 48 mmol) and lithium chloride (6.67 g, 158 mmol) were dissolved in tetrahydrofuran (200 mL). The solution was cooled to −78° C. and n-butyllithium (40 mL, 100 mmol) was added slowly over a 15 minute period. After 20 minutes at −78° C., methyl iodide (6 mL, 96 mmol) was added and the mixture allowed to warm to room temperature. After 24 hours, the mixture was poured into water and extracted with ethyl acetate. The organic layer was dried over anhydrous magnesium sulfate, and concentrated in vacuo. The crude product was purified via Biotage chromatography (Flash40i, silica, 10% then 20% ethyl acetate/hexane) gave 4.1 g (48%) 7-fluoro-3,3-dimethyl-1,3-dihydro-2H-indol-2-one. MS (ESI) m/z 180, [M+H]$^+$).

Step 6: A mixture of sodium hydride (244 mg, 6.1 mmol, 60% in mineral oil) and 7-fluoro-3,3-dimethyl-1,3-dihydro-2H-indol-2-one (1.1 g, 6.1 mmol) in dry N,N-dimethylformamide (3.5 mL) was stirred at room temperature for 20 minutes. [(2R, 3R)-3-phenyloxiran-2-yl]methanol (EXAMPLE 117, step 4, 460 mg, 3.0 mmol) was added and the mixture was heated to 60° C. under nitrogen. After 20 minutes, additional [(2R, 3R)-3-phenyloxiran-2-yl]methanol (230 mg) was added followed by another addition of [(2R, 3R)-3-phenyloxiran-2-yl]methanol (230 mg) 30 minutes later. The reaction was monitored by tlc (1:1 hexane:ethyl acetate) for the disappearance of starting epoxide. The reaction mixture was poured into a 2N aqueous solution of hydrochloric acid and diluted with ethyl acetate. The layers were separated and the organic layer was washed with water and brine. The organic layer was dried over anhydrous sodium sulfate, filtered and concentrated in vacuo to give 1.8 g of a yellow oil as crude product. The crude product was purified via Biotage chromatography (FlasH40i, silica, 6:1 to 1:1 hexane:ethyl acetate) to yield 450 mg (23%) of 1-[(1S,2S)-2,3-dihydroxy-1-phenylpropyl]-7-fluoro-3,3-dimethyl-1,3-dihydro-2H— indol-2-one as a yellow oil. MS (ESI) m/z 330 [(M+H)$^+$].

Step 7: A solution of 1-[(1S,2S)-2,3-dihydroxy-1-phenylpropyl]-7-fluoro-3,3-dimethyl-1,3-dihydro-2H-indol-2-one (870 mg, 2.6 mmol) in dry pyridine (7.5 mL) was cooled to 0° C. para-Toluenesulfonyl chloride (524 mg, 2.75 mmol) and 4-dimethylaminopyridine(50 mg) were added and the reaction was allowed to warm to room temperature and stirred overnight. The reaction was poured into an ice cold 2N aqueous solution of hydrochloric acid and extracted with ethyl acetate. The organic layer was washed with water and brine. The organic layer was dried over anhydrous sodium sulfate, filtered and concentrated in vacuo to give 1.2 g of a viscous oil. The crude product was purified via Biotage chromatography (FlasH40i, silica, 16% then 20% ethyl acetate/hexane) gave 200 mg (22%) of 1-[(1S,2S)-3-chloro-2-hydroxy-1-phenylpropyl]-7-fluoro-3,3-dimethyl-1,3-dihydro-2H-indol-2-one. MS (ESI) m/z 348 [(M+H)$^+$].

Step 8: A solution of 1-[(1S,2S)-3-chloro-2-hydroxy-1-phenylpropyl]-7-fluoro-3,3-dimethyl-1,3-dihydro-2H-indol-2-one (300 mg, 0.86 mmol), sodium iodide (10 mg), and methylamine (8M solution in ethanol) was heated to 60° C. for 1 h. The reaction was cooled to room temperature, concentrated in vacuo and pre-adsorbed onto Celite. The crude product was purified via Biotage chromatography (FlasH40i, silica, 5%, 8% and 10% methanol with ammonia/dichloromethane) to give 187 mg of the free base. The free base was dissolved in a minimum amount of dichloromethane and treated with a 1M ethereal solution of hydrochloric acid until the pH=3 followed by diethyl ether. The product was crystallized by adding a minimum of hexane to afford the title compound 7-fluoro-1-[(1S,2R)-2-hydroxy-3-(methylamino)-1-phenylpropyl]-3,3-dimethyl-1,3-dihydro-2H-indol-2-one hydrochloride as a white solid. MS (ESI) m/z 343

Example 100

1-[(1S,2R)-2-hydroxy-3-(methylamino)-1-phenyl-propyl]-3,3-dimethyl-1,3-dihydro-2H-indol-2-one hydrochloride

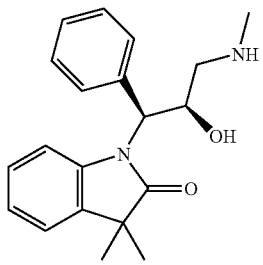

Step 1: In an analogous manner to EXAMPLE 99, step 6 1-[(1S,2S)-2,3-dihydroxy-1-phenylpropyl]-3,3-dimethyl-1,3-dihydro-2H-indol-2-one was prepared from 3,3-dimethyl-1,3-dihydro-indol-2-one[10] and [(2R, 3R)-3-phenyloxiran-2-yl]methanol (EXAMPLE 117, step 4). MS (ESI) m/z 311 ([M+H]$^+$).

[10] A. Kende, *Synth. Comm.* 1: 12 (1982)

Step 2: In an analogous manner to EXAMPLE 99, step 7 1-[(1S,2S)-3-chloro-2-hydroxy-1-phenylpropyl]-3,3-dimethyl-1,3-dihydro-2H-indol-2-one was prepared from 1-[(1S,2S)-2,3-dihydroxy-1-phenylpropyl]-3,3-dimethyl-1,3-dihydro-2H-indol-2-one. MS (ESI) m/z 330 ([M+H]$^+$.

Step 3: In an analogous manner to EXAMPLE 99, step 8 1-[(1S,2R)-2-hydroxy-3-(methylamino)-1-phenylpropyl]-3,3-dimethyl-1,3-dihydro-2H-indol-2-one hydrochloride was prepared from 1-[(1S,2S)-3-chloro-2-hydroxy-1-phenylpropyl]-3,3-dimethyl-1,3-dihydro-2H-indol-2-one. MS (ESI) m/z 325 ([M+H]$^+$], HRMS: calcd for C20H24N2O2+H$^+$, 325.19105; found (ESI-FTMS, [M+H]1$^+$), 325.19093.

Example 101

7-fluoro-1-[(1S,2R)-1-(3-fluorophenyl)-2-hydroxy-3-(methylamino)propyl]-3,3-dimethyl-1,3-dihydro-2H-indol-2-one hydrochloride

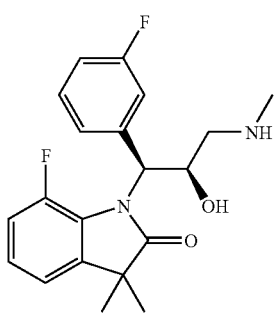

Step 1: A mixture of 7-fluoro-3,3-dimethyl-1,3-dihydro-2H-indol-2-one (EXAMPLE 99, step 5, 1.0 g; 5.58 mmol) and sodium tert-butoxide (1.0 g, 11.16 mmol) in dry dichloromethane (15 mL) was stirred at room temperature under nitrogen for 20 minutes. Titanium isopropoxide (2.0 mL, 6.70 mmol) was added to a solution of [(2R,3R)-3-(3-fluorophenyl)oxiran-2-yl]methanol (EXAMPLE 47, step 3, 844 mg, 5.02 mmol) in dry dichloromethane (6 mL) and stirred for 20 minutes at room temperature. The epoxide complex was added drop-wise to the mixture of tert-butoxide and allowed to stir for 4 days. The reaction mixture was poured into a 2N aqueous solution of hydrochloric acid and diluted with ethyl acetate. The layers were separated, and the organic layer was washed with water and brine. The organic layer was dried over anhydrous sodium sulfate, filtered and concentrated in vacuo to give 2.0 g of crude product. The crude product was purified via Isco chromatography (RediSep, silica, gradient of 0% to 100% ethyl acetate in hexane) to yield 600 mg (31%) of (2S,3S)-7-Fluoro-1-[1-(3-fluoro-phenyl)-2,3-dihydroxy-propyl]-3,3-dimethyl-1,3-dihydro-indol-2-one as an oil. MS (ESI) m/z 348 ([M+H]$^+$).

Step 2: In an analogous manner to EXAMPLE 1, step 2 (2S, 3S)-toluene-4-sulfonic acid 3-(7-fluoro-3,3-dimethyl-2-oxo-2,3-dihydro-indol-1-yl)-3-(3-fluoro-phenyl)-2-hydroxy-propyl ester was prepared from (2S,3S)-7-fluoro-1-[1-(3-fluoro-phenyl)-2,3-dihydroxy-propyl]-3,3-dimethyl-1,3-dihydro-indol-2-one. MS (ESI) m/z 502 ([M+H]$^+$).

Step 3: In an analogous manner to EXAMPLE 5 7-fluoro-1-[(1S,2R)-1-(3-fluorophenyl)-2-hydroxy-3-(methylamino)propyl]-3,3-dimethyl-1,3-dihydro-2H-indol-2-one hydrochloride was prepared from (2S,3S)-toluene-4-sulfonic acid 3-(7-fluoro-3,3-dimethyl-2-oxo-2,3-dihydro-indol-1-yl)-3-(3-fluoro-phenyl)-2-hydroxy-propyl ester. MS (ESI) m/z 360 ([M+H]$^+$), HRMS: calcd for C20H22F2N2O2+H$^+$, 361.17221; found (ESI, [M+H]$^+$), 361.1719.

Example 102

(1S,2R)-1-(1H-indol-1-yl)-3-(methylamino)-1-(2-thienyl)propan-2-ol hydrochloride

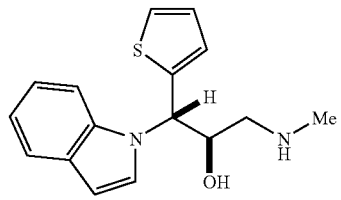

Step 1: Thiophene (2.42 mL, 30.6 mmol) was dissolved in tetrahydrofuran (50 mL), cooled to −78° C., and treated with n-butyllithium (9.2 mL, 18.4 mmol) then warmed to 25° C. The mixture was stirred for 30 minutes then cooled to −78° C. and a solution of 2,3-O-isopropylidene-D-glyceraldehyde[11] (2.00 g, 15.3 mmol) in tetrahydrofuran (15.3 mL) was added dropwise. Stirring was continued for 20 minutes then warmed to 0° C. and quenched with a saturated aqueous solution of ammonium chloride. The mixture was diluted with ethyl acetate, washed with water, and saturated brine. The organic layer was separated, dried over anhydrous magnesium sulfate, filtered, and concentrated in vacuo. The crude product was purified via Biotage chromatography (FlasH40i, silica, 10% acetone/hexane) to afford the product 1.6 g (51%) as a 2:1 mixture of (R)-[(4R)-2,2-dimethyl-1,3-dioxolan-4-yl](2-thienyl)methanol and (S)-[(4R)-2,2-dimethyl-1,3-dioxolan-4-yl](2-thienyl)methanol as an oil. HRMS: calcd for C$_{16}$H$_{18}$N$_2$OS+H+, 287.12126; found (ESI, [M+H]+), 287.1204.

[11] Schmid, C. R.; Bryant, J. D.; Dowlatzedah, M.; Phillips, J. L.; Prather, D. E.; Schantz, R. D.; Sear, N. L.; Vianco, C. S. *J. Org. Chem.* 1991, 56, 4056.

Step 2: A mixture of (R)-[(4R)-2,2-dimethyl-1,3-dioxolan-4-yl](2-thienyl)methanol and (S)-[(4R)-2,2-dimethyl-1,3-dioxolan-4-yl](2-thienyl)methanol (1.5 g, 7.0 mmol) was dissolved in tetrahydrofuran (28 mL) and sodium acetylide (2.1 g, 7.7 mmol; 18 wt % slurry in xylenes/light mineral oil) and the mixture was stirred for 2 hours. para-Toluenesulfonyl chloride (1.46 g, 7.7 mmol) was added and stirring was continued for 2 hours, then indoline (2.5 g, 21 mmol) was added followed by 2,6-lutidine (0.81 mL, 7.0 mmol). After 72 hours the mixture was quenched with a saturated aqueous solution of ammonium chloride, diluted with ethyl acetate, washed with water, and saturated brine. The organic layer was separated, dried over anhydrous magnesium sulfate, filtered, and concentrated in vacuo. The crude product was purified via Isco chromatography (Redisep, silica, gradient 1-10% ethyl acetate in hexane) to afford 590 mg that was immediately dissolved in dioxane (10 mL) and treated with dichlorodicyanobenzoquinone (552 mg, 2.4 mmol) and stirred for 30 minutes. The mixture was diluted with ethyl acetate and washed with saturated sodium bicarbonate, water, and saturated brine. The organic layer was separated, dried over anhydrous magnesium sulfate, filtered, and concentrated in vacuo. The crude product was purified via Isco chromatography (Redisep, silica, gradient 1-20% ethyl acetate in hexane) to afford 355 mg of 1-[(S)-[(4S)-2,2-dimethyl-1,3-dioxolan-4-yl](2-thienyl)methyl]-1H-indole. HRMS: calcd for $C_{18}H_{19}NO_2S+H+$, 314.12092; found (ESI-FTMS, [M+H]1+), 314.12111.

Step 3: 1-[(S)-[(4S)-2,2-dimethyl-1,3-dioxolan-4-yl](2-thienyl)methyl]-1H-indole (350 mg, 1.12 mmol) was dissolved in methanol (20 mL) and benzenesulfonic acid (17 mg, 0.11 mmol) was added. The mixture was stirred for 6 hours then diluted with ethyl acetate and washed with a saturated aqueous solution of sodium bicarbonate, water, and saturated brine. The organic layer was separated, dried over anhydrous magnesium sulfate, filtered, and concentrated in vacuo. The crude product was purified via flash column chromatography (silica, 5% methanol/chloroform) to afford 260 mg (82%) of (2S,3S)-3-(1H-indol-1-yl)-3-thien-2-ylpropane-1,2-diol. HRMS: calcd for $C_{15}H_{15}NO_2S+H+$, 274.08963; found (ESI, [M+H]+), 274.0892.

Step 4: (2S,3S)-3-(1H-indol-1-yl)-3-thien-2-ylpropane-1,2-diol (250 mg, 0.91 mmol) was dissolved in pyridine (3 mL), para-toluenesulfonyl chloride (216 mg, 1.13 mmol) was added and the mixture was stirred for 2 hours. The mixture was diluted with ethyl acetate and washed with water, a saturated aqueous solution of copper sulfate, and saturated brine. The organic layer was separated, dried over anhydrous magnesium sulfate, filtered, and concentrated in vacuo. The crude product was purified via Isco chromatography (Redisep, silica, gradient 0%-100% ethyl acetate in hexane) to afford 360 mg that was immediately dissolved in methylamine (8M solution in ethanol, 15 mL) and stirred for 16 hours. The mixture was concentrated in vacuo and purified via flash column chromatography (silica, gradient 2%-10% methanol saturated with ammonia in chloroform) to give 180 mg of (1S,2R)-1-(1H-indol-1-yl)-3-(methylamino)-1-(2-thienyl)propan-2-ol as a colorless oil. The freebase was dissolved in ether (5 mL) and treated with a 1N ethereal solution of hydrochloric acid (0.63 mL, 0.63 mmol, 1 equivalent). The white precipitate was collected and dried under vacuum to give 193 mg (60%) of (1S,2R)-1(1H-indol-1-yl)-3-(methylamino)-1-(2-thienyl)propan-2-ol hydrochloride. HRMS: calcd for $C_{16}H_{18}N_2OS+H+$, 287.12126; found (ESI, [M+H]+), 287.1204

Example 103

(1R,2R)-1-(1H-indol-1-yl)-3-(methylamino)-1-(2-thienyl)propan-2-ol hydrochloride

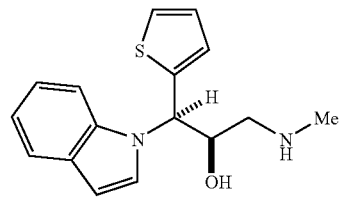

Step 1: Thiophene (2.42 mL, 30.6 mmol) was dissolved in tetrahydrofuran (50 mL), cooled to −78° C., and treated with n-butyllithium (9.2 mL, 18.4 mmol) then warmed to 25° C. The mixture was stirred for 30 minutes then cooled to −78° C. and a solution of 2,3-O-isopropylidene-D-glyceraldehyde[11] (2.00 g, 15.3 mmol) in tetrahydrofuran (15.3 mL) was added dropwise. Stirring was continued for 20 minutes then warmed to 0° C. and quenched with a saturated aqueous solution of ammonium chloride. The mixture was diluted with ethyl acetate, washed with water, and saturated brine. The organic layer was separated, dried over anhydrous magnesium sulfate, filtered, and concentrated in vacuo. The crude product was purified via Biotage chromatography (FlasH40i, silica, 10% acetone/hexane) to afford the product 1.6 g (51%) as a 2:1 mixture of (R)-[(4R)-2,2-dimethyl-1,3-dioxolan-4-yl](2-thienyl)methanol and (S)-[(4R)-2,2-dimethyl-1,3-dioxolan-4-yl](2-thienyl)methanol as an oil. HRMS: calcd for $C_{16}H_{18}N_2OS+H+$, 287.12126; found (ESI, [M+H]+), 287.1204.

Step 2: A mixture of (R)-[(4R)-2,2-dimethyl-1,3-dioxolan-4-yl](2-thienyl)methanol and (S)-[(4R)-2,2-dimethyl-1,3-dioxolan-4-yl](2-thienyl)methanol (1.5 g, 7.0 mmol) was dissolved in tetrahydrofuran (28 mL) and sodium acetylide (2.1 g, 7.7 mmol; 18 wt % slurry in xylenes/light mineral oil) and the mixture was stirred for 2 hours. para-Toluenesulfonyl chloride (1.46 g, 7.7 mmol) was added, and stirring was continued for 2 hours, then indoline (2.5 g, 21 mmol) was added followed by 2,6-lutidine (0.81 mL, 7.0 mmol). After 72 hours the mixture was quenched with a saturated aqueous solution of ammonium chloride, diluted with ethyl acetate, washed with water, and saturated brine. The organic layer was separated, dried over anhydrous magnesium sulfate, filtered, and concentrated in vacuo. The crude product was purified via Isco chromatography (Redisep, silica, gradient 1-10% ethyl acetate in hexane) to afford 590 mg that was immediately dissolved in dioxane (10 mL) and treated with dichlorodicyanobenzoquinone (552 mg, 2.4 mmol) and stirred for 30 minutes. The mixture was diluted with ethyl acetate and washed with a saturated aqueous solution of sodium bicarbonate, water, and saturated brine. The organic layer was separated, dried over anhydrous magnesium sulfate, filtered, and concentrated in vacuo. The crude product was purified via Isco chromatography (Redisep, silica, gradient 1-20% ethyl acetate in hexane) to afford 160 mg of 1-[(R)-[(4S)-2,2-dimethyl-1,3-dioxolan-4-yl](2-thienyl)methyl]-1H-indole. HRMS: calcd for $C_{18}H_{19}NO_2S+H+$, 314.12092; found (ESI-FTMS, [M+H]1+), 314.12089.

Step 3: 1-[(S )-[(4S)-2,2-dimethyl-1,3-dioxolan-4-yl](2-thienyl)methyl]-1H-indole (160 mg, 0.51 mmol) was dissolved in methanol (10 mL) and benzenesulfonic acid (10 mg, 0.06 mmol) was added. The mixture was stirred for 16 hours then diluted with ethyl acetate and washed with a saturated aqueous solution of sodium bicarbonate, water, and saturated brine. The organic layer was separated, dried over anhydrous magnesium sulfate, filtered, and concentrated in vacuo. The crude product was purified via flash column chromatography (silica, 5% methanol/chloroform) to afford 102 mg (74%) of (2S,3R)-3-(1H-indol-1-yl)-3-thien-2-ylpropane-1,2-diol that was carried directly to the next step.

Step 4: (2S,3R)-3-(1H-indol-1-yl)-3-thien-2-ylpropane-1, 2-diol (102 mg, 0.37 mmol) was dissolved in pyridine (1.5 mL), para-toluenesulfonyl chloride (88 mg, 0.46 mmol) was added and the mixture was stirred for 16 hours. The mixture was diluted with ethyl acetate and washed with water, a saturated aqueous solution of copper sulfate, and saturated brine. The organic layer was separated, dried over anhydrous magnesium sulfate, filtered, and concentrated in vacuo. The crude product was purified via Isco chromatography (Redisep, silica, gradient 0%-100% ethyl acetate in hexane) to afford 140 mg that was immediately dissolved in methylamine (8M solution in ethanol, 15 mL) and stirred for 3 hours. The mixture was concentrated in vacuo and purified via flash column chromatography (silica, gradient 2%-10% methanol saturated with ammonia in chloroform) to give 65 mg (71%) of (1R,2R)-1-(1H-indol-1-yl)-3-(methylamino)-1-(2-thienyl)propan-2-ol as a colorless oil. The freebase was dissolved in diethyl ether (5 mL) and treated with a 1 N ethereal solution of hydrochloric acid (0.23 mL, 0.23 mmol, 1 equivalent). The white precipitate was collected and dried under vacuum to give (1R,2R)-1-(1H-indol-1-yl)-3-(methylamino)-1-(2-thienyl)propan-2-ol hydrochloride. HRMS: calcd for $C_{16}H_{18}N_2OS+H+$, 287.12126; found (ESI, [M+H]+), 287.1209

Example 104

1'-[(1S,2R)-2-hydroxy-3-(methylamino)-1-phenylpropyl]spiro[cyclo-hexane-1,3'-indol]-2'(1'H)-one hydrochloride

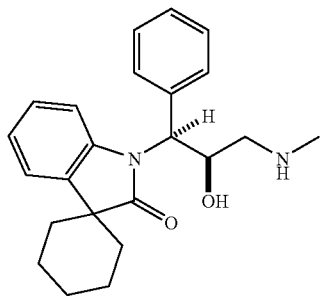

Step 1: Spiro[cyclohexane-1,3'-indol]-2'(1'H)-one[12] (0.82 g, 4.1 mmol) was dissolved in N,N-dimethylformamide (1 mL), and sodium hydride (168 mg, 4.4 mmol, 60% wt suspension in mineral oil) was added and the resulting mixture was stirred for 15 minutes. The mixture was warmed to 75° C. and trans-3-phenylglycidol (306 mg, 2.04 mmol) was added in four portions. Stirring was continued for 2 hours, then the reaction mixture was cooled and quenched with a saturated aqueous solution of ammonium chloride. The mixture was diluted with ethyl acetate, washed with water, and saturated brine. The organic layer was separated, dried over anhydrous magnesium sulfate, filtered, and concentrated in vacuo. The crude product was purified via Isco chromatography (Redisep, silica, gradient 20% to 100% ethyl acetate in hexane) to afford 290 mg (41%) of 1'-[(1S,2S)-2,3-dihydroxy-1-phenyl-propyl]spiro[cyclohexane-1,3'-indol]-2'(1'H)-one as an oil. HPLC purity 100% at 210-370 nm, 9.4 min.; Xterra RP18, 3.5u, 150×4.6 mm column, 1.2 mL/minutes, 85/15-5/95 (Ammon. Form. Buff. Ph=3.5/ACN+MeOH) for 10 minutes, hold 4 min.

[12] Fensome, A.; Miller, L. L.; Ullrich, J. W.; Bender, R. H. W.; Zhang, P.; Wrobel, J. E.; Zhi, L.; Jones, T. K.; Marschke, K. B.; Tegley, C. M. PCT Int. PCT Int. Appl. 2000,127 pp. WO2000066556

Step 2: 1'-[(1S,2S)-2,3-dihydroxy-1-phenyl-propyl]spiro [cyclohexane-1,3'-indol]-2'(1'H)-one (250 mg, 0.71 mmol) was dissolved in pyridine (2.5 mL) and para-toluenesulfonyl chloride (169 mg, 0.89 mmol) was added. The reaction was stirred for 5 hours, then the reaction mixture was diluted with ethyl acetate and washed with water, a saturated aqueous solution of copper sulfate, a 2N aqueous solution of hydrochloric acid, and saturated brine. The organic layer was separated, dried over anhydrous magnesium sulfate, filtered, and concentrated in vacuo. The crude product was immediately dissolved in methylamine (8M solution in ethanol, 15 mL) and stirred for 16 hours. The mixture was concentrated in vacuo and purified via flash column chromatography (silica, 5% methanol saturated with ammonia in chloroform) to give 85 mg (32%) 1'-[(1S,2R)-2-hydroxy-3-(methylamino)-1-phenylpropyl]spiro[cyclo-hexane-1,3'-indol]-2'(1'H)-one as a colorless oil. The freebase was dissolved in diethyl ether (5 mL) and treated with a 1 N ethereal solution of hydrochloric acid (0.23 mL, 0.23 mmol, 1 equivalent). The white precipitate was collected and dried under vacuum to give 193 mg (60%) of 1'-[(1S,2R)-2-hydroxy-3-(methylamino)-1-phenyl-propyl]spiro[cyclo-hexane-1,3'-indol]-2'(1'H)-one hydrochloride. HRMS: calcd for $C_{23}H_{28}N_2O_2+H+$, 365.22235; found ([M+H]+), 365.2226;

Example 105

(1S,2R)-2-(3-fluorophenyl)-2-(1H-indol-1-yl)-1-[(2S)-pyrrolidin-2-yl]ethanol hydrochloride

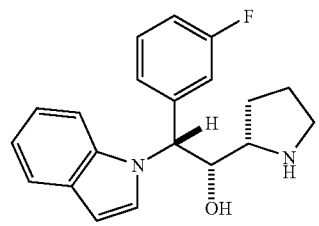

Step 1: To a suspension of 3-fluorobenzyltriphenylphosphonium bromide (6.8 g, 15 mmol) in tetrahydrofuran (50 mL) at 0° C. was added sodium hydride (0.57 g, 15 mmol, 60% wt suspension in mineral oil), and the mixture was stirred for 1 hour s. A solution of (S)-2-formyl-pyrrolidine-1-carboxylic acid tert-butyl ester[13] (2.5 g, 12.5 mmol) in tetrahydrofuran (10 mL) was added and the mixture was stirred for 1 hour then warmed to 25° C. and quenched with a saturated aqueous solution of ammonium chloride. The mixture was diluted with ethyl acetate, washed with water, and saturated brine. The organic layer was separated, dried over anhydrous magnesium sulfate, filtered, and concentrated in vacuo. The crude product was purified via Isco chromatography (Redisep, silica, 10% ethyl acetate/hexane) to afford 2.18 g (60%) of tert-butyl (2S)-2-[(E)-2-(3-fluorophenyl)vinyl] pyrrolidine-1-carboxylate as a colorless oil that crystallized on standing. HRMS: calcd for $C_{17}H_{22}FNO_2$+H+, 292.17073; found (ESI, M+H), 292.1713.

[13] Cook, G. R.; Stille, J. R. *Tetrahedron*, 1994, 50(14), 4105.

Step 2: tert-Butyl (2S)-2-[(E)-2-(3-fluorophenyl)vinyl]pyrrolidine-1-carboxylate (400 mg, 1.37 mmol) was dissolved in dichloromethane (50 mL). A saturated aqueous solution of sodium bicarbonate (50 mL) was added, followed by acetone (10 mL) and tetrabutylammonium hydrogen sulfate (46 mg, 0.14 mmol). With vigorous stirring Oxone (8.4 g, 13.7 mmol) was added over 2 hours in 8 portions (1.05 g every 15 minutes). The mixture was stirred an additional 16 hours then diluted with dichloromethane. The organic layer was separated and washed with water, and saturated brine, dried over anhydrous magnesium sulfate, filtered, and concentrated in vacuo. The crude product was purified via Isco chromatography (Redisep, silica, 20% ethyl acetate/hexane) to give 240 mg that was immediately combined with indoline (0.14 g, 1.2 mmol) and heated to 90° C. for 16 hours. The mixture was cooled and the crude orange oil was purified by Isco chromatography (Redisep, silica, gradient 0% to 25% ethyl acetate in hexane) to give 130 mg that was immediately dissolved in dichloromethane (20 mL). Manganese dioxide (0.86 g, 10 mmol) was added and the mixture was stirred for 5 hours, then diluted with dichloromethane and filtered through a pad of Celite and concentrated. The crude product was purified by Isco chromatography (Redisep, silica, gradient 0% to 50% ethyl acetate in hexane) to give 50 mg of (S)-2-[2-(R)-(3-fluoro-phenyl)-1-hydroxy-2-indol-1-yl-ethyl]-(S)-pyrrolidine-1-carboxylic acid tert-butyl ester.

Step 3: (S)-2-[2-(R)-(3-Fluoro-phenyl)-1-hydroxy-2-indol-1-yl-ethyl]-(S)-pyrrolidine-1-carboxylic acid tert-butyl ester (50 mg, 0.12 mmol) was dissolved in methanol (1 mL) and a 1N ethereal solution of hydrochloric acid (0.96 mL, 0.96 mmol) was added. After 6 hours the mixture was concentrated and purified via flash column chromatography (silica, 10% methanol saturated with ammonia in chloroform) to give 6 mg (15%) (1S,2R)-2-(3-fluorophenyl)-2-(1H-indol-1-yl)-1-[(2S)-pyrrolidin-2-yl]ethanol. The freebase was dissolved in diethyl ether (2 mL) and treated with a 1N ethereal solution of hydrochloric acid (0.02 mL, 0.02 mmol, 1 equivalent). The white precipitate was collected and dried under vacuum to give 4 mg of (1S,2R)-2-(3-fluorophenyl)-2-(1H-indol-1-yl)-1-[(2S)-pyrrolidin-2-yl]ethanol hydrochloride. HRMS: calcd for $C_{20}H_{21}FN_2O$+H+, 325.17107; found (ESI, [M+H]+), 325.1712

Example 106

(1R,2S)-2-(3-fluorophenyl)-2-(1H-indol-1-yl)-1-[(2S)-pyrrolidin-2-yl]ethanol hydrochloride

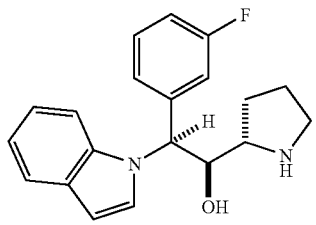

Step 1: To a suspension of 3-fluorobenzyltriphenylphosphonium bromide (6.8 g, 15 mmol) in tetrahydrofuran (50 mL) at 0° C. was added sodium hydride (0.57 g, 15 mmol, 60% wt suspension in mineral oil) and the mixture was stirred for 1 hour at room temperature. A solution of (S)-2-formyl-pyrrolidine-1-carboxylic acid tert-butyl ester[13] (2.5 g, 12.5 mmol) in tetrahydrofuran (10 mL) was added, and the mixture was stirred for 1 hour then warmed to 25° C. and quenched with a saturated aqueous solution of ammonium chloride. The mixture was diluted with ethyl acetate, washed with water, and saturated brine. The organic layer was separated, dried over anhydrous magnesium sulfate, filtered, and concentrated in vacuo. The crude product was purified via Isco chromatography (Redisep, silica, 10% ethyl acetate/hexane) to afford 2.18 g (60%) of tert-butyl (2S)-2-[(E)-2-(3-fluorophenyl)vinyl]pyrrolidine-1-carboxylate as a colorless oil that crystallized on standing. HRMS: calcd for $C_{17}H_{22}FNO_2$+H+, 292.17073; found (ESI, M+H), 292.1713.

Step 2: tert-Butyl (2S)-2-[(E)-2-(3-fluorophenyl)vinyl]pyrrolidine-1-carboxylate (400 mg, 1.37 mmol) was dissolved in dichloromethane (50 mL). A saturated aqueous solution of sodium bicarbonate (50 mL) was added, followed by acetone (10 mL) and tetrabutylammonium hydrogen sulfate (46 mg, 0.14 mmol). With vigorous stirring Oxone (8.4 g, 13.7 mmol) was added over 2 hours in 8 portions (1.05 g every 15 minutes). The mixture was stirred an additional 16 hours then diluted with dichloromethane. The organic layer was separated and washed with water, and saturated brine, dried over anhydrous magnesium sulfate, filtered, and concentrated in vacuo. The crude product was purified via Isco chromatography (Redisep, silica, 20% ethyl acetate/hexane) to give 240 mg that was immediately combined with indoline (0.14 g, 1.2 mmol) and heated to 90° C. for 16 hours. The mixture was cooled and the crude orange oil was purified by Isco chromatography (Redisep, silica, gradient 0% to 25% ethyl acetate in hexane) to give 130 mg that was immediately dissolved in dichloromethane (20 mL). Manganese dioxide (0.86 g, 10 mmol) was added and the mixture was stirred for 5 hours then diluted with dichloromethane and filtered through a pad of Celite and concentrated. The crude product was purified by Isco chromatography (Redisep, silica, gradient 0% to 50% ethyl acetate in hexane) to give 50 mg of (R)-2-[2-(S)-(3-fluoro-phenyl)-1-hydroxy-2-indol-1-yl-ethyl]-(S)-pyrrolidine-1-carboxylic acid tert-butyl ester.

Step 3: (R)-2-[2-(S)-(3-Fluoro-phenyl)-1-hydroxy-2-indol-1-yl-ethyl]-(S)-pyrrolidine-1-carboxylic acid tert-butyl ester (50 mg, 0.12 mmol) was dissolved in methanol (1 mL) and a 1N ethereal solution hydrochloric acid (1.0 mL, 1.0 mmol) was added. After 16 hours the mixture was concentrated and purified via flash column chromatography (silica, 10% methanol saturated with ammonia in chloroform) to give 19 mg (50%) (1R,2S)-2-(3-fluorophenyl)-2-(1H-indol-1-yl)-1-[(2S)-pyrrolidin-2-yl]ethanol. The freebase was dissolved in diethyl ether (2 mL) and treated with 1 N ethereal solution of hydrochloric acid (0.06 mL, 0.06 mmol, 1 equivalent). The white precipitate was collected and dried under vacuum to give 17 mg of (1R,2S)-2-(3-fluorophenyl)-2-(1H-indol-1-yl)-1-[(2S)-pyrrolidin-2-yl]ethanol hydrochloride. HRMS: calcd for $C_{20}H_{21}FN_2O$+H+, 325.17107; found (ESI, [M+H]+), 325.1711

Example 107

1'-[(1S,2R)-2-hydroxy-3-(methylamino)-1-phenyl-propyl]spiro[cyclo-butane-1,3'-indol]-2'(1'H)-one hydrochloride

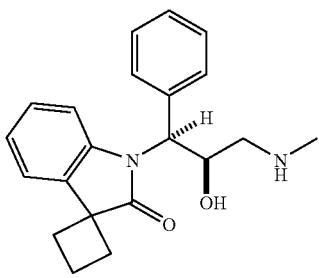

Step 1: In an analogous manner to EXAMPLE 104, step 1 1'-[(1S,2S)-2,3-dihydroxy-1-phenylpropyl]spiro[cyclobutane-1,3'-indol]-2'(1'H)-one was prepared from spiro[cyclobutane-1,3'-indol]-2'(1'H)-one[12] and trans-3-phenylglycidol. HPLC purity 100% at 210-370 nm, 8.4 min.; Xterra RP18, 3.5u, 150×4.6 mm column, 1.2 mL/minutes, 85/15-5/95 (Ammon. Form. Buff. Ph=3.5/ACN+MeOH) for 10 minutes, hold 4 min.

Step 2: In an analogous manner to EXAMPLE 104, step 2 1'-[(1S,2R)-2-hydroxy-3-(methylamino)-1-phenylpropyl]spiro[cyclo-butane-1,3'-indol]-2'(1'H)-one hydrochloride was prepared from 1'-[(1S,2S)-2,3-dihydroxy-1-phenylpropyl]spiro-[cyclobutane-1,3'-indol]-2'(1'H)-one. HRMS: calcd for $C_{21}H_{24}N_2O_2+H^+$, 337.19105; found (ESI, [M+H]+), 337.1917

Example 108

1'-[(1S,2R)-2-hydroxy-3-(methylamino)-1-phenyl-propyl]spiro-[cyclopentane-1,3'-indol]-2'(1'H)-one hydrochloride

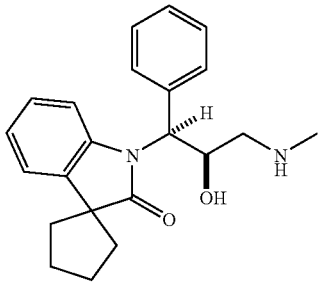

Step 1: In an analogous manner to EXAMPLE 104, step 1 1'-[(1S,2S)-2,3-dihydroxy-1-phenylpropyl]spiro[cyclopentane-1,3'-indol]-2'(1'H)-one was prepared from spiro[cyclopentane-1,3'-indol]-2'(1'H)-one[12] and trans-3-phenylglycidol. HRMS: calcd for $C_{21}H_{23}NO_3+H+$, 338.17507; found (ESI, [M+H]+), 338.1769

Step 2: In an analogous manner to EXAMPLE 104, step 2 1'-[(1S,2R)-2-hydroxy-3-(methylamino)-1-phenylpropyl]spiro-[cyclopentane-1,3'-indol]-2'(1'H)-one hydrochloride was prepared from 1'-[(1S,2S)-2,3-dihydroxy-1-phenylpropyl]spiro-[cyclopentane-1,3'-indol]-2'(1'H)-one. HRMS: calcd for $C_{22}H_{26}N_2O_2+H+$, 351.20670; found (ESI, [M+H]+), 351.2061

Example 109

1'-[(1S,2R)-2-hydroxy-3-(methylamino)-1-phenyl-propyl]spiro-[cyclopropane-1,3'-indol]-2'(1'H)-one hydrochloride

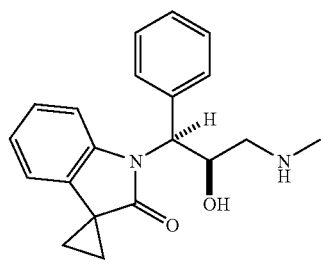

Step 1: In an analogous manner to EXAMPLE 104, step 1 1'-[(1S,2S)-2,3-dihydroxy-1-phenylpropyl]spiro[cyclopropane-1,3'-indol]-2'(1'H)-one was pre-pared from spiro[cyclopropane-1,3'-indol]-2'(1'H)-one[14] and trans-3-phenylglycidol. HPLC purity 89.1% at 210-370 nm, 7.7 min.; Xterra RP18, 3.5u, 150×4.6 mm column, 1.2 mL/minutes, 85/15-5/95 (Ammon. Form. Buff. Ph=3.5/ACN+MeOH) for 10 minutes, hold 4 min.

[14] Roberston, D. W.; Krushinski, J. H.; Pollock, G. D.; Wilson, H.; Kauffman, R. F.; Hayes, J. S. *J. Med. Chem.* 1987, 30, 824.

Step 2: In an analogous manner to EXAMPLE 104, step 2 1'-[(1S,2R)-2-hydroxy-3-(methylamino)-1-phenylpropyl] spiro-[cyclopropane-1,3'-indol]-2'(1'H)-one hydrochloride was prepared from 1'-[(1S,2S)-2,3-dihydroxy-1-phenylpropyl]-spiro[cyclopropane-1,3'-indol]-2'(1'H)-one. HRMS: calcd for $C_{20}H_{22}N_2O_2+H+$, 323.17540; found (ESI, [M+H]+), 323.1744

Example 110

5-fluoro-1-[(1S,2R)-2-hydroxy-3-(methylamino)-1-phenylpropyl]-3,3-dimethyl-1,3-dihydro-2H-indol-2-one hydrochloride

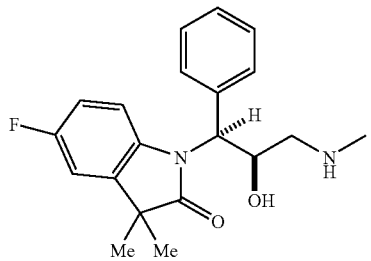

Step 1: 5-Fluoro-1,3-dihydro-indol-2-one (2.0 g, 13.2 mmol) and lithium chloride (1.39 g, 33.0 mmol) were dissolved in tetrahydrofuran (40 mL) and cooled to 0° C. n-Butyllithium (10.6 mL, 26.4 mmol) was added dropwise and the mixture was stirred 20 minutes. Methyl iodide (1.63 mL, 26.4 mmol) was added slowly and stirring was continued for 2 hours at 0° C. then warmed to 25° C. After 16 hours the reaction was quenched with a saturated aqueous solution of ammonium chloride.

The mixture was diluted with ether, washed with water, and saturated brine. The organic layer was separated, dried over anhydrous magnesium sulfate, filtered, and concentrated in vacuo. The crude product was purified via Isco chromatography (Redisep, silica, gradient 10% to 50% ethyl acetate in hexane) to afford 1.18 g (50%) of 5-fluoro-3,3-dimethyl-1,3-dihydro-2H-indol-2-one as white crystals. HPLC purity 100% at 210-370 nm, 7.1 min.; Xterra RP18, 3.5u, 150×4.6 mm column, 1.2 mL/minutes, 85/15-5/95 (Ammon. Form. Buff. Ph=3.5/ACN+MeOH) for 10 minutes, hold 4 min.

Step 2: In an analogous manner to EXAMPLE 104, step 1-[(1S,2S)-2,3-dihydroxy-1-phenylpropyl]-5-fluoro-3,3-dimethyl-1,3-dihydro-2H-indol-2-one was prepared from 5-fluoro-3,3-dimethyl-1,3-dihydro-2H-indol-2-one and trans-3-phenylglycidol. HRMS: calcd for $C_{19}H_{20}FNO_3$+H+, 330.15000; found (ESI, [M+H]+), 330.1495

Step 3: In an analogous manner to EXAMPLE 104, step 2 5-fluoro-1-[(1S,2R)-2-hydroxy-3-(methylamino)-1-phenylpropyl]-3,3-dimethyl-1,3-dihydro-2H-indol-2-one hydrochloride was prepared from 1-[(1S,2S)-2,3-dihydroxy-1-phenylpropyl]-5-fluoro-3,3-dimethyl-1,3-dihydro-2H-indol-2-one. HPLC purity 100% at 210-370 nm, 7.2 min.; Xterra RP18, 3.5u, 150×4.6 mm column, 1.2 mL/minutes, 85/15-5/95 (Ammon. Form. Buff. Ph=3.5/ACN+MeOH) for 10 minutes, hold 4 minutes. HRMS: calcd for $C_{20}H_{23}FN_2O_2$+H+, 343.18163; found (ESI, [M+H]+), 343.184

Example 111

(1S,2R)-3-(cyclopropylamino)-1-(3-fluorophenyl)-1-(1H-indol-1-yl)propan-2-ol hydrochloride

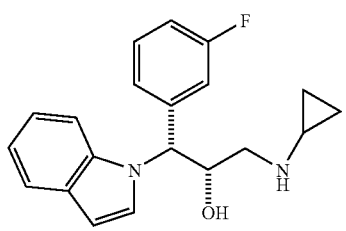

Step 1: (2S,3S)-3-(3-Fluorophenyl)-3-(1H-indol-1-yl)propane-1,2-diol (example 47, step 5) (0.6 g, 2.1 mmol) was dissolved in pyridine (5 mL) and para-toluenesulfonyl chloride (0.44 g, 2.3 mmol) was added. The mixture was stirred for 3 hours then the reaction mixture was diluted with ethyl acetate and washed with water, followed by a saturated aqueous solution of copper sulfate, a 2N aqueous solution of hydrochloric acid, and saturated brine. The organic layer was separated, dried over anhydrous magnesium sulfate, filtered, and concentrated in vacuo. The crude product was immediately dissolved in methylamine (8M solution in ethanol, 25 mL) and stirred for 16 hours. The mixture was concentrated in vacuo and purified via flash column chromatography (silica, 5% methanol saturated with ammonia in chloroform) to give (1S,2R)-3-(cyclopropylamino)-1-(3-fluorophenyl)-1-(1H-indol-1-yl)propan-2-ol as a colorless oil. The freebase was dissolved in diethyl ether (5 mL) and treated with a 1N ethereal solution of hydrochloric acid (1 equivalent). The white precipitate was collected and dried under vacuum to give 80 mg (12%) of (1S,2R)-3-(cyclopropylamino)-1-(3-fluorophenyl)-1-(1H-indol-1-yl)propan-2-ol hydrochloride. HRMS: calcd for $C_{20}H_{21}FN_2O$+H+, 325.17107; found (ESI, [M+H]+), 325.1728.

Example 112

7'-fluoro-1'-[(1S,2R)-2-hydroxy-3-(methylamino)-1-phenylpropyl]-spiro[cyclohexane-1,3'-indol]-2'(1'H)-one hydrochloride

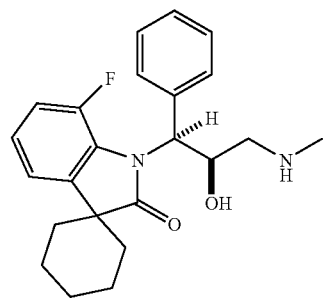

Step 1: 7-Fluoro-1,3-dihydro-indol-2-one (EXAMPLE 99, step 4) (1.16 g, 7.68 mmol) and lithium chloride (0.81 g, 19.2 mmol) were dissolved in tetrahydrofuran (50 mL) and cooled to 0° C. n-Butyllithium (6.14 mL, 15.4 mmol) was added dropwise and the mixture was stirred 15 minutes. 1,5-Dibromopentane (1.05 mL, 7.7 mmol) was added slowly and stirring was continued for 2 hours at o° C. then warmed to 25° C. After 16 hours the reaction was quenched with a saturated aqueous solution of ammonium chloride. The mixture was diluted with ether, washed with water, and saturated brine. The organic layer was separated, dried over anhydrous magnesium sulfate, filtered, and concentrated in vacuo. The crude product was purified via Isco chromatography (Redisep, silica, gradient 5% to 40% ethyl acetate in hexane) to afford 0.90 g (54%) of 7'-fluorospiro-[cyclohexane-1,3'-indol]-2'(1'H)-one. HPLC purity 95.9% at 210-370 nm, 19.2 min.; Xterra MSC18, 5u, 150×3.0 mm column, 0.5 mL/minutes, 95/5-5/95 (0.1% formic acid in $H_2O$/MeOH) for 20 minutes, hold 3 min.

Step 2: In an analogous manner to EXAMPLE 104, step 1 1'-[(1S,2S)-2,3-dihydroxy-1-phenylpropyl]-7'-fluorospiro [cyclohexane-1,3'-indol]-2'(1'H)-one was prepared from 7'-fluorospiro-[cyclohexane-1,3'-indol]-2'(1'H)-one and trans-3-phenylglycidol. HRMS: calcd for C22H24FNO3+ H+, 370.18130; found (ESI, [M+H]+), 370.1798

Step 3: In an analogous manner to EXAMPLE 104, step 2 7'-fluoro-1'-[(1S,2R)-2-hydroxy-3-(methylamino)-1-phenylpropyl]-spiro[cyclohexane-1,3'-indol]-2'(1'H)-one hydrochloride was prepared from 1'-[(1S,2S)-2,3-dihydroxy-1-phenylpropyl]-7'-fluorospiro[cyclohexane-1,3'-indol]-2' (1'H)-one. HRMS: calcd for $C_{23}H_{27}FN_2O_2$+H+, 383.21293; found (ESI, [M+H]+), 383.2109

Example 113

5'-bromo-1'-[(1S,2R)-2-hydroxy-3-(methylamino)-1-phenylpropyl]-spiro[cyclohexane-1,3'-indol]-2'(1'H)-one hydrochloride

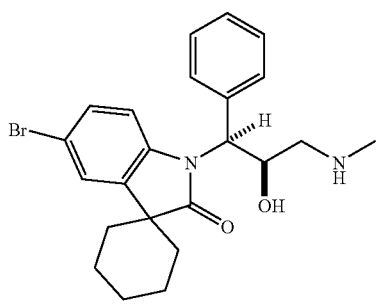

Step 1: In an analogous manner to EXAMPLE 104, step 1 5'-bromo-1'-[(1S,2S)-2,3-dihydroxy-1-phenylpropyl]spiro[cyclohexane-1,3'-indol]-2'(1'H)-one was prepared from 5'-bromospiro[cyclohexane-1,3'-indol]-2'(1'H)-one[12] and trans-3-phenylglycidol. HRMS: calcd for C22H24BrNO3+H+, 430.10123; found (ESI, [M+H]+), 430.1006

Step 2: In an analogous manner to EXAMPLE 104, step 2 5'-bromo-1'-[(1S,2R)-2-hydroxy-3-(methylamino)-1-phenylpropyl]-spiro[cyclohexane-1,3'-indol]-2'(1'H)-one hydrochloride was prepared from 5'-bromo-1'-[(1S,2S)-2,3-dihydroxy-1-phenylpropyl]spiro[cyclohexane-1,3'-indol]-2'(1'H)-one. HRMS: calcd for C23H27BrN2O2+H+, 443.13286; found (ESI, [M+H]+), 443.1333.

Example 114

(1S,2R)-1-(3-fluorophenyl)-1-[3-(2-fluorophenyl)-1H-indol-1-yl]-3-(methylamino)propan-2-ol hydrochloride

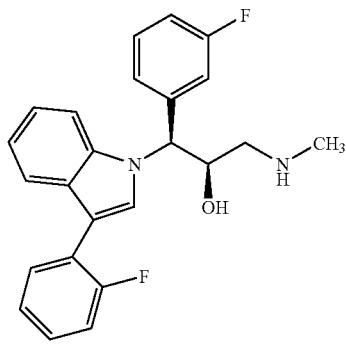

Step 1: To a solution of (2S,3S)-3-indol-1-yl-3-(3-fluorophenyl)-propane-1,2-diol (EXAMPLE 47, Step 5, 1.34 g, 4.56 mmol) in N,N-dimethylformamide (20 mL) was added pulverized solid potassium hydroxide (0.76 g, 13.68 mmol). The mixture was stirred for 15 minutes under nitrogen at room temperature, whereupon iodine (1.21 g, 4.72 mmol) was added in one portion. The mixture was stirred for 30 minutes at room temperature, then poured into 100 mL of a 5% aqueous sodium thiosulfate solution. The solution was extracted 3 times with ethyl acetate and the combined extracts were washed 3 times with water. The organic layer was dried over anhydrous sodium sulfate, filtered, and concentrated in vacuo. The crude product was purified via Biotage chromatography (FlasH40i, silica, 40% ethyl acetate/hexane) to yield 0.91 g (48%) of (2S,3S)-3-(3-fluorophenyl)-3-(3-iodo-1H-indol-1-yl)propane-1,2-diol as a dark brown oil. MS (ES) m/z 411.9.

Step 2: A mixture of (2S,3S)-3-(3-fluorophenyl)-3-(3-iodo-1H-indol-1-yl)propane-1,2-diol (0.25 g, 0.61 mmol), 2-fluorobenzeneboronic acid (0.12 g, 0.85 mmol), and potassium phosphate (0.39 g, 1.83 mmol) in N,N-dimethylformamide (10 mL) was degassed with nitrogen for 5 minutes then a catalytic amount (0.02 g) of [1,4-bis-(diphenylphosphine)butane]palladium (II) dichloride was added. The solution was heated to 90° C. for 3 hours then cooled and poured into 100 mL of water. The aqueous mixture was extracted 3 times with ethyl acetate and the combined extracts were then washed 2 times with water. The ethyl acetate was dried by filtration through a plug of silica gel then concentrated. The residue was purified by Biotage chromatography (FlasH40i, silica, 40% ethyl acetate/hexane) to yield 0.14 g of (2S,3S)-3-(3-fluorophenyl)-3-{3-[2-fluorophenyl]-1H-indol-1-yl}propane-1,2-diol as an oil, which was used in the next step without further purification.

Step 3: In an analogous manner to EXAMPLE 1, step 2 (2S,3S)-toluene-4-sulfonic acid 3-(3-fluorophenyl)-3-[3-(2-fluorophenyl)-indol-1-yl]-2-hydroxy-propyl ester was prepared from (2S,3S)-3-(3-fluorophenyl)-3-{3-[2-fluorophenyl]-1H-indol-1-yl}propane-1,2-diol.

Step 4: In an analogous manner to EXAMPLE 5, (1S,2R)-1-(3-fluorophenyl)-1-[3-(2-fluorophenyl)-1H-indol-1-yl]-3-(methylamino)propan-2-ol hydrochloride was prepared from (2S,3S)-toluene-4-sulfonic acid 3-(3-fluoro-phenyl)-3-[3-(2-fluorophenyl)-indol-1-yl]-2-hydroxy-propyl ester and methylamine (2N solution in methanol). MS (ES) m/z 393.1.

Example 115

(1S,2R)-1-[3-(3,4-dichlorophenyl)-1H-indol-1-yl]-1-(3-fluorophenyl)-3-(methylamino)propan-2-ol hydrochloride

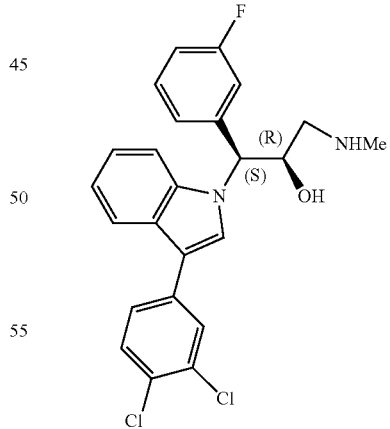

In an analogous manner to EXAMPLE 114, step 2, (2S,3S)-3-(3,4-dichlorophenyl)-3-{3-[2-fluorophenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 3,4-diclorobenzene boronic acid.

In an analogous manner to EXAMPLE 1, step 2 (2S,3S)-toluene-4-sulfonic acid 3-[3-(3,4-dichloro-phenyl)-indol-1- yl]-3-(3-fluorophenyl)-2-hydroxy-propyl ester was prepared from (2S,3S)-3-[3-(3,4-Dichloro-phenyl)-indol-1-yl]-3-(3-fluoro-phenyl)-propane-1,2-diol.

In an analogous manner to EXAMPLE 5, (1S,2R)-1-[3-(3,4-dichlorophenyl)-1H-indol-1-yl]-1-(3-fluorophenyl)-3-(methylamino)propan-2-ol hydrochloride was prepared from (2S,3S)-toluene-4-sulfonic acid 3-[3-(3,4-dichloro-phenyl)-indol-1-yl]-3-(3-fluoro-phenyl)-2-hydroxy-propyl ester and methylamine (2N solution in methanol). MS (ES) m/z 443.0.

Example 116

(1S,2R)-1-(3-fluorophenyl)-1-[3-(3-fluorophenyl)-1H-indol-1-yl]-3-(methylamino)propan-2-ol hydrochloride

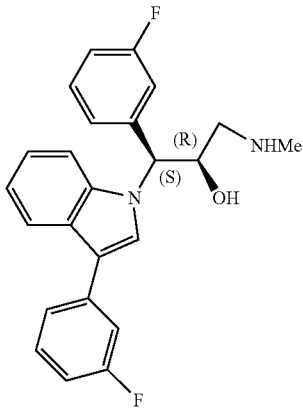

In an analogous manner to EXAMPLE 114, step 2, (2S,3S)-3-(3-fluorophenyl)-3-{3-[3-fluorophenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 3-florobenzene boronic acid.

In an analogous manner to EXAMPLE 1, step 2 (2S,3S)-toluene-4-sulfonic acid 3-(3-fluorophenyl)-3-[3-(3-fluorophenyl)-indol-1-yl]-2-hydroxy-propyl ester was prepared from (2S,3S)-3-(3-fluorophenyl)-3-{3-[3-fluorophenyl]-1H-indol-1-yl}propane-1,2-diol.

In an analogous manner to EXAMPLE 5, (1S,2R)-1-(3-fluorophenyl)-1-[3-(3-fluorophenyl)-1H-indol-1-yl]-3-(methylamino)propan-2-ol hydrochloride was prepared from (2S,3S)-toluene-4-sulfonic acid 3-(3-fluoro-phenyl)-3-[3-(3-fluorophenyl)-indol-1-yl]-2-hydroxy-propyl ester and methylamine (2N solution in methanol). MS (ESI) m/z 393.

Example 117

(1S,2R)-1-(5-fluoro-3-methyl-1H-indol-1-yl)-3-(methylamino)-1-phenylpropan-2-ol hydrochloride

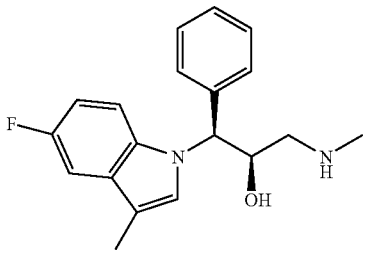

Step 1: To a mixture of 4-fluoro-phenylamine (9 g, 81 mmol), concentrated hydrochloric acid (20.4 mL), and water (35.1 mL) was added sodium nitrite (6.3 g, 89.1 mmol) dissolved in water (7.8 mL). In a separate flask ethyl 2-ethylacetoacetate (14.4 g, 89.1 mmol) in ethanol (63.6 mL) at 0° C. was treated with potassium hydroxide (5.1 g, 89.1 mmol) in water (7.5 mL) and ice and the above solution added. The pH of the reaction was adjusted to 5-6 and the reaction stirred at 0° C. for 3 hours and then stored in the freezer overnight. The reaction was then extracted with ethyl acetate (100 mL) and the organics washed with saturated brine solution (100 mL), dried with anhydrous magnesium sulfate. Most of the solvent was removed in vacuo before it was added dropwise to a 14.5% ethanolic solution of hydrochloric acid (70 mL) at 78° C. Heating was continued for 2 hours. The solvent was removed in vacuo and the residue treated with dichloromethane (300 mL) and water (100 mL). The organic layer was washed with saturated sodium chloride (200 mL), dried over sodium sulfate and concentrated in vacuo. Purification on a short wash column (silica gel, 25% ethyl acetate/hexane) gave ethyl 5-fluoro-3-methyl-1H-indole-2-carboxylate as a white solid. MS (ES) m/z 220.0

Step 2: Ethyl 5-fluoro-3-methyl-1H-indole-2-carboxylate (8.3 g, 37.5 mmol) and potassium hydroxide (6.3 g, 112.5 mmol) in a mixture of ethanol (20 mL) and water (15 mL) was heated at reflux for 1 hour. The volume was reduced to 10 mL under reduced pressure and the solution brought to an acidic pH with a 3N aqueous solution of hydrochloric acid. The resulting precipitate was filtered, washed with water (100 mL) and dried in vacuo at 80° C. overnight to afford 5-fluoro-3-methyl-1H-indole-2-carboxylic acid as a white solid. MS (ES) m/z 192.0

Step 3: 5-fluoro-3-methyl-1H-indole-2-carboxylic acid (8.49 g, 43.9 mmol) and copper metal (0.35 g, 5.5 mmol) in distilled quinoline (22 mL) was heated to reflux for 3 hours. The copper powder was filtered off and the filtrate was brought to pH 3 at 0° C. with a 6N aqueous solution of hydrochloric acid. The solution was extracted with ether (200 mL) and the organics washed with saturated sodium chloride (200 mL), dried over magnesium sulfate and concentrated in vacuo to give 5-fluoro-3-methyl-1H-indole as a brown solid. MS (ES) m/z 150.0.

Step 4: To a solution of diisopropyl D-tartrate (6 mL, 28 mmol) in methylene chloride (800 mL) at −10° C. under nitrogen was added 4A molecular sieves (15 g), titanium isopropoxide (5.9 mL, 20 mmol), and cinnamyl alcohol (27 g, 200 mmol). The mixture was allowed to age for 40 minutes at −10° C., after which time it was cooled to −20° C., and treated in a dropwise fashion with a solution of tert-butyl hydroperoxide (TBHP, ~450 mmol) in isooctane. After 18 hours at −30 to -15° C., the reaction mixture was treated with a 30% aqueous solution of sodium hydroxide (5 mL) and diethyl ether (100 mL). The cold bath was removed and the mixture was allowed to warm to ~10° C. Magnesium sulfate (anhydrous, 15 g) was added and the mixture was stirred for 20 minutes. After the solids settled, the solution was filtered through a pad of silica gel, and washed with ether (50 mL). The filtrate was concentrated in vacuo and toluene was added to azeotropically remove the unreacted TBHP. The residue was then purified using a silica gel column (hexane:ethyl acetate/3:1) and the purified product was crystallized from hexane/ethyl acetate to yield [(2R,3R)-3-phenyloxiran-2-yl] methanol as white crystal (18 g, 60%, 98.2% ee). MS (ESI) m/z 151.

Step 5: A mixture of 5-fluoro-3-methyl-1H-indole (2.91 g, 19.5 mmol) and potassium hydride 50% dispersion in mineral oil (2.8 g, 35.1 mmol) in dichloromethane (40 mL) was stirred for 10 minutes under nitrogen at room temperature. A solution of [(2R,3R)-3-phenyloxiran-2-yl]methanol (2.0 g, 13.0 mmol) and titanium isopropoxide (4.3 mL, 14.3 mmol) in dichloromethane (10 mL) was then added and the mixture was stirred at room temperature for 12 hours. After disappearance of the epoxide, the mixture was partitioned between a 1 N aqueous solution of hydrochloric acid (50 mL) and ethyl acetate (50 mL). The organic layer was separated, washed with saturated sodium bicarbonate (50 mL), dried over anhydrous sodium sulfate, filtered, and concentrated in vacuo. The crude product was purified via Biotage chromatography (FlasH40i, silica, 60% ethyl acetate/hexane) to give (2S,3S)-3-(5-fluoro-3-methyl-1H-indol-1-yl)-3-phenyl propane-1,2-diol. MS (ES I) m/z 300

Step 6: A solution of (2S,3S)-3-(5-fluoro-3-methyl-1H-indol-1-yl)-3-phenylpropane-1,2-diol (1.03 g, 3.4 mmol) and p-toluenesulfonyl chloride (0.78 g, 4.1 mmol) in anhydrous pyridine(11 ml) was stirred at room temperature under nitrogen for 12 hours. The reaction was poured into a 1N aqueous solution of hydrochloric acid (50 mL) and extracted with ethyl acetate (50 mL). The organics were dried over anhydrous sodium sulfate, filtered, and concentrated to give (2S, 3S)-toluene-4-sulfonic acid 3-(5-fluoro-3-methyl-indol-1-yl)-2-hydroxy-3-phenyl-propyl ester. The product was used in the next step without further purification. To a solution of toluene-4-sulfonic acid 3-(5-fluoro-3-methyl-indol-1-yl)-2-hydroxy-3-phenyl-propyl ester (1.6 g, 3.4 mmol) in methanol (10 mL) was added a 2N solution of methylamine in methanol (8.6 mL, 17 mmol) and the reaction stirred for 12 hours. Upon completion, the reaction was partitioned between saturated sodium bicarbonate (50 mL) and ethyl acetate (50 mL). The organic layer was separated, dried over anhydrous sodium sulfate, filtered, and concentrated in vacuo. The crude product was purified via Biotage chromatography (FlasH40i, silica, 20% MeOH/dichloromethane) to give (1S,2R)-1-(5-fluoro-3-methyl-1H-indol-1-yl)-3-(methylamino)-1-phenylpropan-2-ol as a clear oil. The free base was dissolved in a minimum amount of ethanol and treated with a 2N ethereal solution of hydrochloric acid and stirred for 1 hour. The ethanol was removed in vacuo and the clear oil was triturated with ether/dichloromethane to give (1S,2R)-1-(5-fluoro-3-methyl-1H-indol-1-yl)-3-(methylamino)-1-phenylpropan-2-ol hydrochloride as a white solid. MS (ESI) m/z 313

Example 118

(1SR,2RS)-3-amino-1-(5-fluoro-3-methyl-1H-indol-1-yl)-1-phenylpropan-2-ol hydrochloride

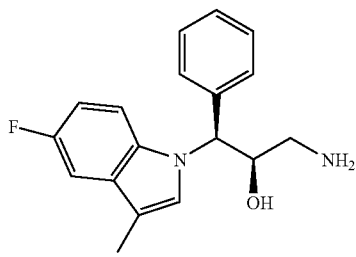

To a solution of (2S,3S)-toluene-4 sulfonic acid 3-(5-fluoro-3-methyl-indol-1-yl)-2-hydroxy-3-phenyl-propyl ester (Intermediate in EXAMPLE 117, step 6, 0.15 g, 0.33 mmol) in methanol (10 mL) was added concentrated ammonium hydroxide (20 mL), and the reaction was stirred for 12 hours. Upon completion, the reaction was partitioned between water (25 mL) and ethyl acetate (25 mL). The organic layer was separated, dried over anhydrous sodium sulfate, filtered, and concentrated in vacuo. The crude product was purified via Biotage chromatography (FlasH40i, silica, 25% MeOH/dichloromethane) to give (1SR,2RS)-3-amino-1-(5-fluoro-3-methyl-1H-indol-1-yl)-1-phenylpropan-2-ol as a clear oil. The free base was dissolved in a minimum amount of ethanol and treated with a 4N solution of hydrochloric acid in dioxane and stirred for 1 hour s. The ethanol was removed in vacuo and the clear oil was triturated with ether/dichloromethane to give (1SR,2RS)-3-amino-1-(5-fluoro-3-methyl-1H-indol-1-yl)-1-phenylpropan-2-ol hydrochloride as a white solid. MS (ES) m/z 299.0

Example 119

(1S,2R)-1-(5-chloro-3-methyl-1H-indol-1-yl)-3-(methylamino)-1-phenylpropan-2-ol hydrochloride

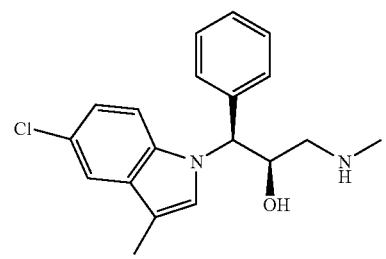

In an analogous manner to EXAMPLE 117, step 1 ethyl 5-chloro-3-methyl-1H-indole-2-carboxylate was prepared from 4-chloro-phenylamine. MS (ES) m/z 235.9

In an analogous manner to EXAMPLE 117, step 2 5-chloro-3-methyl-1H-indole-2-carboxylic acid was prepared from ethyl 5-chloro-3-methyl-1H-indole-2-carboxylate. MS (ESI) m/z 208

In an analogous manner to EXAMPLE 117, step 3 5-chloro-3-methyl-1H-indole was prepared from 5-chloro-3-methyl-1H-indole-2-carboxylic acid. MS (ESI) m/z 166.

In an analogous manner to EXAMPLE 117, step 5 (2S,3S)-3-(5-chloro-3-methyl-1H-indol-1-yl)-3-phenylpropane-1,2-diol was prepared from 5-chloro-3-methyl-1H-indole and [(2R,3R)-3-phenyloxiran-2-yl]methanol (EXAMPLE 117, step 4). MS (ES) m/z 316.0

In an analogous manner to EXAMPLE 117, step 6 (1S,2R)-1-(5-chloro-3-methyl-1H-indol-1-yl)-3-(methylamino)-1-phenylpropan-2-ol hydrochloride was prepared from (2S,3S)-3-(5-chloro-3-methyl-1H-indol-1-yl)-3-phenylpropane-1,2-diol. MS (ES) m/z 329.0

Example 120

(1S,2R)-3-amino-1-(5-chloro-3-methyl-1H-indol-1-yl)-1-phenylpropan-2-ol hydrochloride

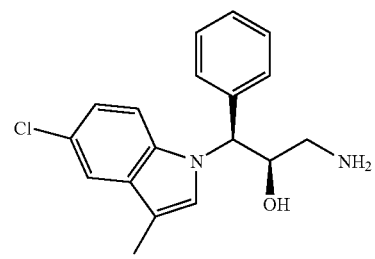

In an analogous manner to EXAMPLE 118, (1S,2R)-3-amino-1-(5-chloro-3-methyl-1H-indol-1-yl)-1-phenylpro-

121 pan-2-ol was prepared from (2S,3S)-3-(5-chloro-3-methyl-1H-indol-1-yl)-3-phenylpropane-1,2-diol (EXAMPLE 119, step 4). MS (ES) m/z 315.1

Example 121

[(2R,3S)-3-(5-chloro-3-methyl-1H-indol-1-yl)-2-methoxy-3-phenylpropyl]methylamine

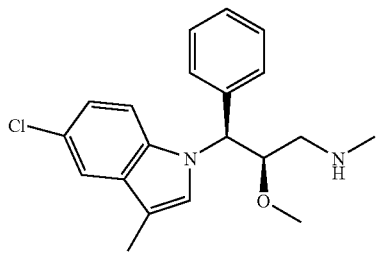

A mixture of (2S,3S)-toluene-4-sulfonic acid 3-(5-chloro-3-methyl-indol-1-yl)-2-hydroxy-3-phenyl-propyl ester (Intermediate in EXAMPLE 119, step 6, 0.52 g, 1.1 mmol), trifluoro-methanesulfonic acid methyl ester (0.6 mL, 5.5 mmol), and 2,6-di-tert-butyl-4-methyl-pyridine (1.1 g, 5.5 mmol) was heated at reflux in dichloromethane (20 mL) for 2 hours. The reaction was partitioned between ethyl acetate (25 mL) and a 1N aqueous solution of hydrochloric acid (25 mL). The organics were separated and washed with a saturated aqueous solution of sodium bicarbonate (25 mL), dried over anhydrous sodium sulfate, and concentrated in vacuo. The crude product was purified via flash column chromatography (silica, 20% ethyl acetate in hexane) to give (2S,3S)-toluene-4-sulfonic acid 3-(5-chloro-3-methyl-indol-1-yl)-2-methoxy-3-phenyl-propyl ester. To a solution of toluene-4-sulfonic acid 3-(5-chloro-3-methyl-indol-1-yl)-2-methoxy-3-phenyl-propyl ester (0.13 g, 0.27 mmol) in methanol (10 mL) was added a 2N solution of methylamine in methanol (1.4 mL, 2.7 mmol) and the reaction heated in a sealed tube for 12 hours. Upon completion, the reaction was partitioned between a saturated aqueous solution sodium bicarbonate (25 mL) and dichloromethane (25 mL). The organics were separated and removed in vacuo. The residue was taken up in diethyl ether (25 mL) and washed with a 1 N aqueous solution of hydrochloric acid (25 mL). The aqueous layer was basified to pH 8 with a saturated aqueous solution of sodium bicarbonate (50 mL). The product was extracted with diethyl ether (25 mL), dried over anhydrous sodium sulfate, and concentrated in vacuo. The free base was dissolved in a minimum amount of ethanol and treated with a 4N solution of hydrochloric acid in dioxane and stirred for 1 hour s. The ethanol was removed in vacuo to give [(2R,3S)-3-(5-chloro-3-methyl-1H-indol-1-yl)-2-methoxy-3-phenylpropyl]methylamine as a yellow oil. MS (ESI) m/z 343

122

Example 122

(1S,2R)-1-(7-chloro-3-methyl-1H-indol-1-yl)-3-(methylamino)-1-phenylpropan-2-ol hydrochloride

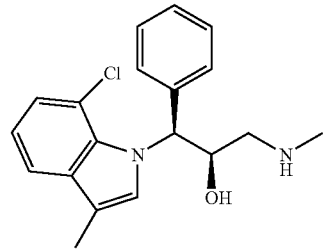

In an analogous manner to EXAMPLE 117, step 1 ethyl 7-chloro-3-methyl-1H-indole-2-carboxylate was prepared from 2-chloro-phenylamine. MS (ESI) m/z 238

In an analogous manner to EXAMPLE 117, step 2 7-chloro-3-methyl-1H-indole-2-carboxylic acid was prepared from ethyl 7-chloro-3-methyl-1H-indole-2-carboxylate. MS (ES) m/z 208.0

In an analogous manner to EXAMPLE 117, step 3 7-chloro-3-methyl-1H-indole was prepared from 7-chloro-3-methyl-1H-indole-2-carboxylic acid.

In an analogous manner to EXAMPLE 117, step 5 (2S,3S)-3-(7-chloro-3-methyl-1H-indol-1-yl)-3-phenylpropane-1,2-diol was prepared from 7-chloro-3-methyl-1H-indole and [(2R,3R)-3-phenyloxiran-2-yl]methanol (EXAMPLE 117, step 4). MS (ESI) m/z 316; MS (ESI) m/z 314.

In an analogous manner to EXAMPLE 117, step 6 (1S, 2R)-1-(7-chloro-3-methyl-1H-indol-1-yl)-3-(methylamino)-1-phenylpropan-2-ol hydrochloride was prepared from (2S, 3S)-3-(7-chloro-3-methyl-1H-indol-1-yl)-3-phenylpropane-1,2-diol. MS (ESI) m/z 329

Example 123

[(2R,3S)-3-(5-fluoro-3-methyl-1H-indol-1-yl)-2-methoxy-3-phenylpropyl]methylamine hydrochloride

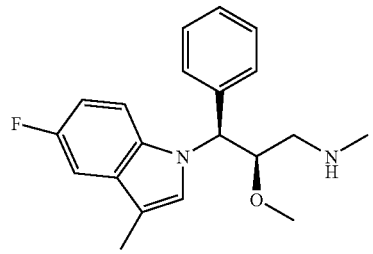

In an analogous manner to EXAMPLE 121, [(2R,3S)-3-(5-fluoro-3-methyl-1H-indol-1-yl)-2-methoxy-3-phenylpropyl]methylamine hydrochloride was prepared (2S,3S)-toluene-4-sulfonic acid 3-(5-fluoro-3-methyl-indol-1-yl)-2-hydroxy-3-phenyl-propyl ester (Intermediate in EXAMPLE 117, step 6). MS (ESI) m/z 327.

Example 124

(1S,2R)-1-(4-bromo-1H-indol-1-yl)-3-(methylamino)-1-phenylpropan-2-ol hydrochloride

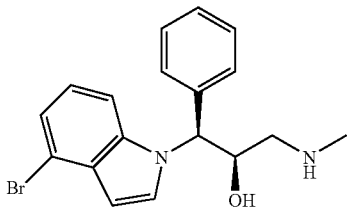

In an analogous manner to EXAMPLE 117, step 5 (2S,3S)-3-(4-bromo-1H-indol-1-yl)-3-phenylpropane-1,2-diol was prepared from 4-bromo-1H-indole and [(2R,3R)-3-phenyloxiran-2-yl]methanol (EXAMPLE 117, step 4). MS (ESI) m/z 346.

In an analogous manner to EXAMPLE 117, step 6 (1S,2R)-1-(4-bromo-1H-indol-1-yl)-3-(methylamino)-1-phenyl-propan-2-ol hydrochloride was prepared from (2S,3S)-3-(4-bromo-1H-indol-1-yl)-3-phenylpropane-1,2-diol. MS (ESI) m/z 359.

Example 125

(1S,2R)-1-(4-bromo-1H-indol-1-yl)-1-(3-fluorophenyl)-3-(methylamino)propan-2-ol hydrochloride

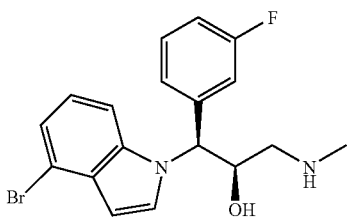

In an analogous manner to EXAMPLE 117, step 5 (2S,3S)-3-(4-bromo-1H-indol-1-yl)-3-(3-fluorophenyl)propane-1,2-diol was prepared from 4-bromo-1H-indole and [(2R,3R)-3-(3-fluorophenyl)oxiran-2-yl]methanol (EXAMPLE 47 step 3). MS (ESI) m/z 364.

In an analogous manner to EXAMPLE 117, step 6 (1S,2R)-1-(4-bromo-1H-indol-1-yl)-1-(3-fluorophenyl)-3-(methylamino)propan-2-ol hydrochloride was prepared from (2S,3S)-3-(4-bromo-1H-indol-1-yl)-3-(3-fluorophenyl)propane-1,2-diol. MS (ESI) m/z 377.

Example 126

(1S,2R)-1-(5-bromo-1H-indol-1-yl)-3-(methylamino)-1-phenylpropan-2-ol hydrochloride

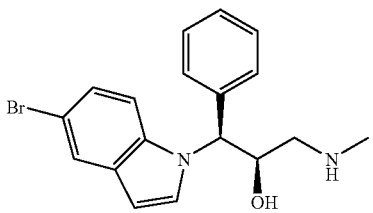

In an analogous manner to EXAMPLE 117, step 5 (2S,3S)-3-(5-bromo-1H-indol-1-yl)-3-phenylpropane-1,2-diol was prepared from 5-bromo-1H-indole and [(2R,3R)-3-phenyloxiran-2-yl]methanol (EXAMPLE 117, step 4). MS (ESI) m/z 346.

In an analogous manner to EXAMPLE 117, step 6 (1S,2R)-1-(5-bromo-1H-indol-1-yl)-3-(methylamino)-1-phenylpropan-2-ol hydrochloride was prepared from (2S,3S)-3-(5-bromo-1H-indol-1-yl)-3-phenylpropane-1,2-diol. MS (ESI) m/z 359.

Example 127

(1S,2R)-1-(5-bromo-1H-indol-1-yl)-1-(3-fluorophenyl)-3-(methylamino)propan-2-ol hydrochloride

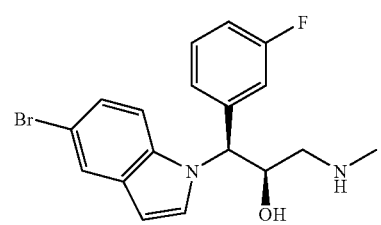

In an analogous manner to EXAMPLE 117, step 5 (2S,3S)-3-(5-bromo-1H-indol-1-yl)-3-(3-fluorophenyl)propane-1,2-diol was prepared from 5-bromo-1H-indole and [(2R,3R)-3-(3-fluorophenyl)oxiran-2-yl]methanol (EXAMPLE 47 step 3). MS (ESI) m/z 364.

In an analogous manner to EXAMPLE 117, step 6 (1S,2R)-1-(5-bromo-1H-indol-1-yl)-1-(3-fluorophenyl)-3-(methylamino)propan-2-ol hydrochloride was prepared from (2S,3S)-3-(5-bromo-1H-indol-1-yl)-3-(3-fluorophenyl)propane-1,2-diol. MS (ESI) m/z 377.

Example 128

1-[(1S,2R)-2-hydroxy-3-(methylamino)-1-phenylpropyl]-1H-indole-4-carbonitrile hydrochloride

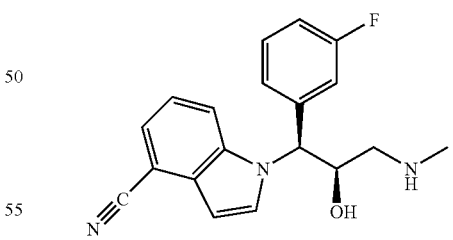

In an analogous manner to EXAMPLE 117, step 5 1-(2,3-dihydroxy-1-phenyl-propyl)-1H-indole-4-carbonitrile was prepared from 1H-Indole-4-carbonitrile and [(2R,3R)-3-phenyloxiran-2-yl]methanol (EXAMPLE 117, step 4).

In an analogous manner to EXAMPLE 117, step 6 1-[(1S,2R)-2-hydroxy-3-(methylamino)-1-phenylpropyl]-1H-indole-4-carbonitrile hydrochloride was prepared from 1-(2,3-dihydroxy-1-phenyl-propyl)-1H-indole-4-carbonitrile. MS (ESI) m/z 306.

Example 129

(1S,2R)-1-(6-bromo-1H-indol-1-yl)-3-(methylamino)-1-phenylpropan-2-ol hydrochloride

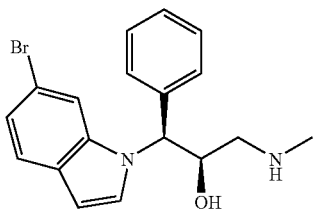

In an analogous manner to EXAMPLE 117, step 5 3-(6-bromo-indol-1-yl)-3-phenyl-propane-1,2-diol was prepared from 6-bromo-1H-indole and [(2R,3R)-3-phenyloxiran-2-yl]methanol (EXAMPLE 117, step 4).

In an analogous manner to EXAMPLE 117, step 6 (1S,2R)-1-(6-bromo-1H-indol-1-yl)-3-(methylamino)-1-phenylpropan-2-ol hydrochloride was prepared from 3-(6-bromo-indol-1-yl)-3-phenyl-propane-1,2-diol. MS (ESI) m/z 359

Example 130

1-[(1S,2R)-2-hydroxy-3-(methylamino)-1-phenylpropyl]-1H-indole-5-carbonitrile hydrochloride

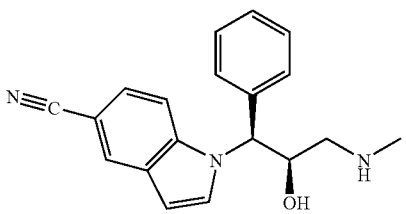

In an analogous manner to EXAMPLE 117, step 5 1-[(1S,2S)-2,3-dihydroxy-1-phenylpropyl]-1H-indole-5-carbonitrile was prepared from 1H-Indole-5-carbonitrile and [(2R,3R)-3-phenyloxiran-2-yl]methanol (EXAMPLE 117, step 4). MS (ESI) m/z 293

In an analogous manner to EXAMPLE 117, step 6 1-[(1S,2R)-2-hydroxy-3-(methylamino)-1-phenylpropyl]-1H-indole-5-carbonitrile hydrochloride was prepared from 1-[(1S,2S)-2,3-dihydroxy-1-phenylpropyl]-1H-indole-5-carbonitrile. MS (ES) m/z 306.1.

Example 131

1-[(1S,2R)-1-(3-fluorophenyl)-2-hydroxy-3-(methylamino)propyl]-1H-indole-4-carbonitrile hydrochloride

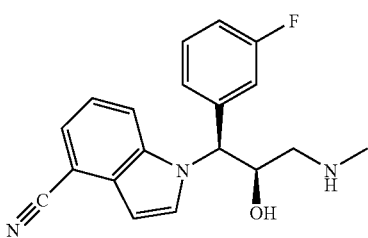

In an analogous manner to EXAMPLE 117, step 5 1-[1-(3-fluoro-phenyl)-2,3-dihydroxy-propyl]-1H-indole-4-carbonitrile was prepared from 1H-Indole-4-carbonitrile and [(2R,3R)-3-(3-fluorophenyl)oxiran-2-yl]methanol (EXAMPLE 47 step 3).

In an analogous manner to EXAMPLE 117, step 6 1-[(1S,2R)-1-(3-fluorophenyl)-2-hydroxy-3-(methylamino)propyl]-1H-indole-4-carbonitrile hydrochloride was prepared from 1-[1-(3-fluoro-phenyl)-2,3-dihydroxy-propyl]-1H-indole-4-carbonitrile. MS (ES) m/z 324.2.

Example 132

(1S,2R)-1-(6-bromo-1H-indol-1-yl)-1-(3-fluorophenyl)-3-(methylamino)propan-2-ol hydrochloride

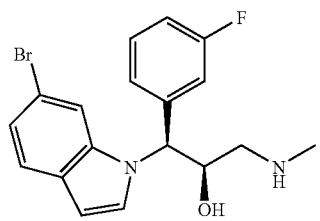

In an analogous manner to EXAMPLE 117, step 5 3-(6-bromo-indol-1-yl)-3-(3-fluoro-phenyl)-propane-1,2-diol was prepared from 6-bromo-1H-indole and [(2R,3R)-3-(3-fluorophenyl)oxiran-2-yl]methanol (EXAMPLE 47 step 3).

In an analogous manner to EXAMPLE 117, step 6 (1S,2R)-1-(6-bromo-1H-indol-1-yl)-1-(3-fluorophenyl)-3-(methylamino)propan-2-ol hydrochloride was prepared from 3-(6-bromo-indol-1-yl)-3-(3-fluoro-phenyl)-propane-1,2-diol. MS (ES) m/z 377.1.

Example 133

(1S,2R)-1-(6-fluoro-1H-indol-1-yl)-1-(3-fluorophenyl)-3-(methylamino)propan-2-ol hydrochloride

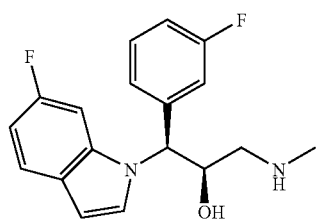

In an analogous manner to EXAMPLE 117, step 5. (2S,3S)-3-(6-fluoro-1H-indol-1-yl)-3-(3-fluorophenyl)propane-1,2-diol was prepared from 6-fluoro-1H-indole and [(2R,3R)-3-(3-fluorophenyl)oxiran-2-yl]methanol (EXAMPLE 47 step 3). MS (ESI) m/z 304.

In an analogous manner to EXAMPLE 117, step 6 (1S,2R)-1-(6-fluoro-1H-indol-1-yl)-1-(3-fluorophenyl)-3-(methylamino)propan-2-ol hydrochloride was prepared from (2S,3S)-3-(6-fluoro-1H-indol-1-yl)-3-(3-fluorophenyl)propane-1,2-diol. MS (ES) m/z 317.1.

Example 134

(1S,2R)-3-amino-1-(3-fluorophenyl)-1-(1H-indol-1-yl)propan-2-ol hydrochloride

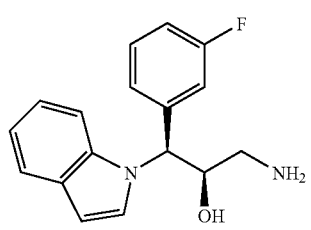

In an analogous manner to EXAMPLE 117, step 5 3-(3-fluoro-phenyl)-3-indol-1-yl-propane-1,2-diol was prepared from 1H-indole and [(2R,3R)-3-(3-fluorophenyl)oxiran-2-yl]methanol (EXAMPLE 47, step 3).

In an analogous manner to EXAMPLE 117, step 6 (1S,2R)-3-amino-1-(3-fluorophenyl)-1-(1H-indol-1-yl)propan-2-ol hydrochloride was prepared from 3-(3-fluoro-phenyl)-3-indol-1-yl-propane-1,2-diol and para-toluenesulfonic acid followed by concentrated ammonium hydroxide. MS (ES) m/z 285.2.

Example 135

(1S,2R)-1-(7-bromo-1H-indol-1-yl)-1-(3-fluorophenyl)-3-(methylamino)propan-2-ol hydrochloride

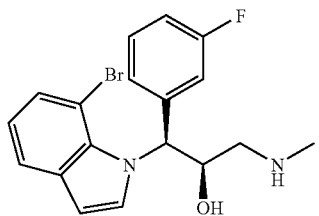

In an analogous manner to EXAMPLE 117, step 5 3-(7-bromo-indol-1-yl)-3-(3-fluoro-phenyl)-propane-1,2-diol was prepared from 7-bromo-1H-indole and [(2R,3R)-3-(3-fluorophenyl)oxiran-2-yl]methanol (EXAMPLE 47 step 3).

In an analogous manner to EXAMPLE 117, step 6 (1S,2R)-1-(7-bromo-1H-indol-1-yl)-1-(3-fluorophenyl)-3-(methylamino)propan-2-ol hydrochloride was prepared from 3-(7-bromo-indol-1-yl)-3-(3-fluoro-phenyl)-propane-1,2-diol. MS (ES) m/z 377.

Example 136

(1S,2R)-1-(1H-indol-1-yl)-3-(methylamino)-1-[3-(trifluoromethyl)phenyl]propan-2-ol hydrochloride

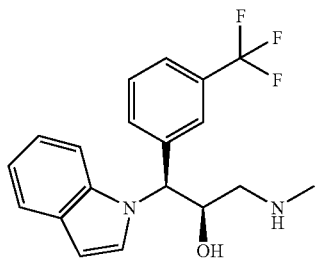

In an analogous manner to EXAMPLE 47, step 1 cinnamic acid, m-(trifluoromethyl)-, methyl ester was prepared from 3-(3-trifluoromethyl-phenyl)-acrylic acid. MS (ES) m/z 231.1

In an analogous manner to EXAMPLE 47, step 2 (2E)-3-[3-[trifluoromethyl)phenyl]prop-2-en-1-ol was prepared from cinnamic acid, m-(trifluoromethyl)-, methyl ester. MS (ES) m/z 185.1

In an analogous manner to EXAMPLE 47, step 3 {(2R,3R)-3-[3-(trifluoromethyl)phenyl]oxiran-2-yl}methanol was prepared from (2E)-3-[3-[trifluoromethyl)phenyl]prop-2-en-1-ol. MS (ES) m/z 217.3

In an analogous manner to EXAMPLE 47, step 4 (2S,3S)-3-(2,3-dihydro-1H-indol-1-yl)-3-[3-(trifluoromethyl)phenyl]propane-1,2-diol was prepared from indoline and {(2R,3R)-3-[3-(trifluoromethyl)phenyl]oxiran-2-yl}methanol. MS (ESI) m/z 338.

In an analogous manner to EXAMPLE 47, step 5 (2S,3S)-3-(1H-indol-1-yl)-3-[3-(trifluoromethyl)phenyl]propane-1,2-diol was prepared from (2S,3S)-3-(2,3-dihydro-1H-indol-1-yl)-3-[3-(trifluoromethyl)phenyl]propane-1,2-diol. MS (ESI) m/z 336.

In an analogous manner to EXAMPLE 117, step 6 (1S,2R)-1-(1H-indol-1-yl)-3-(methylamino)-1-[3-(trifluoromethyl)phenyl]propan-2-ol hydrochloride was prepared from (2S,3S)-3-(1H-indol-1-yl)-3-[3-(trifluoromethyl)phenyl]propane-1,2-diol. MS (ES) m/z 349.1.

Example 137

(1S,2R)-1-(3-fluorophenyl)-3-(methylamino)-1-spiro[cyclohexane-1,3'-indol]-1'(2'H)-ylpropan-2-ol hydrochloride

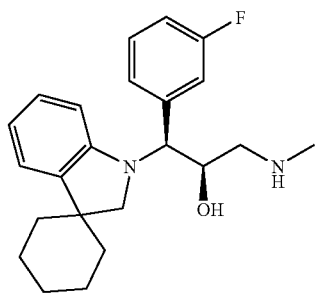

In an analogous manner to EXAMPLE 47, step 4, (2S,3S)-3-(3-fluorophenyl)-3-spiro[cyclohexane-1,3'-indol]-1'(2'H)-ylpropane-1,2-diol was prepared from 1',2'-dihydrospiro[cyclohexane-1,3'-indole][15] and [(2R,3R)-3-(3-fluorophenyl)oxiran-2-yl]methanol (EXAMPLE 47, step 3) as a white solid. MS (ES) m/z 356.2 ([M+H]$^+$); HRMS: calcd for $C_{22}H_{26}FNO_2+H^+$, 356.2020; found (ESI, [M+H]$^+$), 356.2031.

[15] Kucerovy, A.; Hathaway, J. S.; Mattner, P. G.; Repic, O. *Synth. Commun.* 1992, 22, 729-733.

In an analogous manner to EXAMPLE 47, step 6, (1S,2R)-1-(3-fluorophenyl)-3-(methylamino)-1-spiro[cyclohexane-1,3'-indol]-1'(2'H)-ylpropan-2-ol hydrochloride was prepared from (2S,3S)3-(3-fluorophenyl)-3-spiro[cyclohexane-1,3'-indol]-1'(2'H)-ylpropane-1,2-diol as a white powder. MS (ES) m/z 369.2 ([M+H]$^+$); HRMS: calcd for $C_{23}H_{29}FN_2O+H^+$, 369.2337; found (ESI, [M+H]$^+$), 369.2332.

Example 138

(1S,2R)-1-(2,3-dihydro-1H-indol-1-yl)-3-(methylamino)-1-[3-(trifluoromethyl)phenyl]propan-2-ol hydrochloride

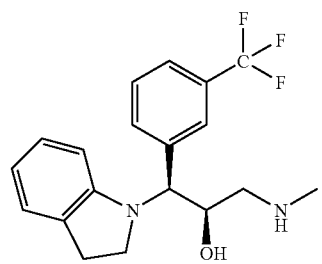

In an analogous manner to EXAMPLE 117, step 6 (1S, 2R)-1-(2,3-dihydro-1H-indol-1-yl)-3-(methylamino)-1-[3-(trifluoromethyl)phenyl]propan-2-ol was prepared from (2S, 3S)-3-(2,3-dihydro-1H-indol-1-yl)-3-[3-(trifluoromethyl) phenyl]propane-1,2-diol (EXAMPLE 136, step 4). MS (ES) m/z 351.1.

Example 139

(1S,2S)-1-(3-fluorophenyl)-1-(1H-indol-1-yl)-3-(methylamino)propan-2-ol hydrochloride

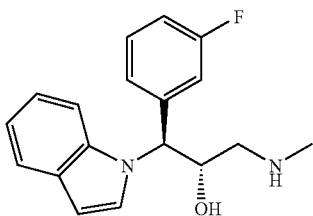

In an analogous manner to EXAMPLE 16, step 2 (2S,3S)-3-(3-fluorophenyl)-2-hydroxy-3-(1H-indol-1-yl)propyl 4-nitrobenzoate was prepared from 3-(3-fluoro-phenyl)-3-indol-1-yl-propane-1,2-diol (EXAMPLE 134, step 1). MS (ES) m/z 435.0.

In an analogous manner to EXAMPLE 16, step 3 4-nitrobenzoic acid 3-(3-fluoro-phenyl)-3-indol-1-yl-2-methanesulfonyloxy-propyl ester was prepared from (2S,3S)-3-(3-fluorophenyl)-2-hydroxy-3-(1H-indol-1-yl)propyl 4-nitrobenzoate.

In an analogous manner to EXAMPLE 16, step 4 1-{(S)-(3-fluorophenyl)[(2R)-oxiran-2-yl]methyl}-1H-indole was prepared from 4-nitro-benzoic acid 3-(3-fluoro-phenyl)-3-indol-1-yl-2-methanesulfonyloxy-propyl ester. MS (ESI) m/z 338.

In an analogous manner to EXAMPLE 16, step 5 (1S,2S)-1-(3-fluorophenyl)-1-(1H-indol-1-yl)-3-(methylamino)propan-2-ol hydrochloride was prepared from 1-{(S)-(3-fluorophenyl)[(2R)-oxiran-2-yl]methyl}-1H-indole. MS (ESI) m/z 299.

Example 140

(1S,2R)-1-(3,4-difluorophenyl)-1-(1H-indol-1-yl)-3-(methylamino)propan-2-ol hydrochloride

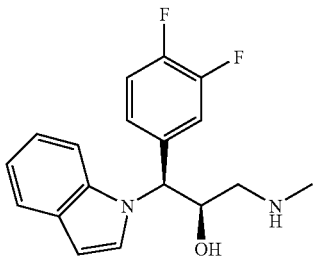

In an analogous manner to EXAMPLE 47, step 1 cinnamic acid, 3,4-difluoro-, methyl ester, (E) was prepared from 3-(3,4-difluoro-phenyl)-acrylic acid. MS (ES) m/z 199.1

In an analogous manner to EXAMPLE 47, step 2 (2E)-3-(3,4-difluorophenyl)prop-2-en-1-ol was prepared from cinnamic acid, 3,4-difluoro-, methyl ester, (E). MS (ES) m/z 153.1

In an analogous manner to EXAMPLE 47, step 3 [(2R,3R)-3-(3,4-difluorophenyl)oxiran-2-yl]methanol was prepared from (2E)-3-(3,4-difluorophenyl)prop-2-en-1-ol. MS (ES) m/z 185.1

In an analogous manner to EXAMPLE 47, step 4 (2S,3S)-3-(3,4-difluorophenyl)-3-(2,3-dihydro-1H-indol-1-yl)propane-1,2-diol was prepared from indoline and [(2R,3R)-3-(3, 4-difluorophenyl)oxiran-2-yl]methanol. MS (ES) m/z 306.1.

In an analogous manner to EXAMPLE 47, step 5 (2S,3S)-3-(3,4-difluorophenyl)-3-(1H-indol-1-yl)propane-1,2-diol was prepared from (2S,3S)-3-(3,4-difluorophenyl)-3-(2,3-dihydro-1H-indol-1-yl)propane-1,2-diol. MS (ESI) m/z 304.

In an analogous manner to EXAMPLE 117, step 6 (1S, 2R)-1-(3,4-difluorophenyl)-1-(1H-indol-1-yl)-3-(methylamino)propan-2-ol hydrochloride was prepared from (2S, 3S)-3-(3,4-difluorophenyl)-3-(1H-indol-1-yl)propane-1,2-diol. MS (ES) m/z 317.1.

Example 141

(1RS,2SR)-1-(6-chloro-2,3-dihydro-4H-1,4-benzoxazin-4-yl)-3-(methylamino)-1-phenylpropan-2-ol hydrochloride

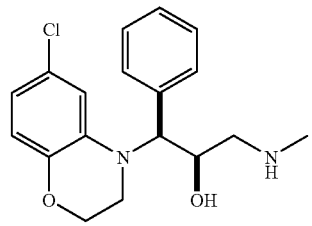

In an analogous manner to EXAMPLE 33, step 1, ethyl (2RS,3RS)-3-(6-chloro-2,3-dihydro-4H-1,4-benzoxazin-4-yl)-2-hydroxy-3-phenylpropanoate was prepared from 6-chloro-3,4-dihydro-2H-1,4-benzoxazine (EXAMPLE 88, step 1) and trans-ethyl-3-phenylglycidate as a viscous, yellow liquid. MS (ESI) m/z 362.0 ([M+H]$^+$); HRMS: calcd for $C_{19}H_{20}ClNO_4$+H$^+$, 362.1154; found (ESI, [M+H]$^+$), 362.1150.

In an analogous manner to EXAMPLE 33, step 2, (2RS, 3RS)-3-(6-chloro-2,3-dihydro-4H-1,4-benzoxazin-4-yl)-2-hydroxy-N-methyl-3-phenylpropanamide was prepared from ethyl (2RS,3RS)-3-(6-chloro-2,3-dihydro-4H-1,4-benzoxazin-4-yl)-2-hydroxy-3-phenylpropanoate as white needles. MS (ESI) m/z 344.9 ([M−H]$^-$); HRMS: calcd for $C_{18}H_{19}ClN_2O_3$+H$^+$, 347.1157; found (ESI, [M+H]$^+$), 347.1150.

In an analogous manner to EXAMPLE 33, step 3, (1RS, 2SR)-1-(6-chloro-2,3-dihydro-4H-1,4-benzoxazin-4-yl)-3-(methylamino)-1-phenylpropan-2-ol hydrochloride was prepared from (2RS,3RS)-3-(6-chloro-2,3-dihydro-4H-1,4-benzoxazin-4-yl)-2-hydroxy-N-methyl-3-phenylpropanamide as a white powder. MS (ESI) m/z 333.1 ([M+H]$^+$); HRMS: calcd for $C_{18}H_{21}ClN_2O_2$+H$^+$, 333.1370; found (ESI, [M+H]$^+$), 333.1381.

Example 142

(1RS,2SR)-3-(methylamino)-1-(6-methyl-2,3-dihydro-4H-1,4-benzoxazin-4-yl)-1-phenylpropan-2-ol hydrochloride

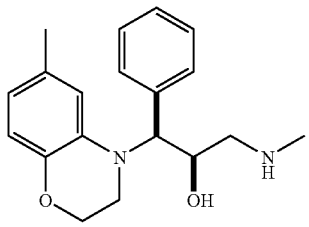

In an analogous manner to EXAMPLE 165, step 1, 6-methyl-3,4-dihydro-2H-1,4-benzoxazine was prepared from 6-methyl-2H-1,4-benzoxazin-3(4H)-one as a yellow oil. MS (ES) m/z 150.0 ([M+H]$^+$); HRMS: calcd for C$_9$H$_{11}$NO+H$^+$, 150.0919; found (ESI, [M+H]$^+$), 150.0924.

In an analogous manner to EXAMPLE 33, step 1, ethyl (2RS,3RS)-2-hydroxy-3-(6-methyl-2,3-dihydro-4H-1,4-benzoxazin-4-yl)-3-phenylpropanoate was prepared from 6-methyl-3,4-dihydro-2H-1,4-benzoxazine and trans-ethyl-3-phenylglycidate as a viscous, yellow liquid. MS (ESI) m/z 342.0 ([M+H]$^+$); HRMS: calcd for C$_{20}$H$_{23}$NO$_4$+H$^+$, 342.1700; found (ESI, [M+H]$^+$), 342.1683.

In an analogous manner to EXAMPLE 33, step 2, (2RS,3RS)-2-hydroxy-N-methyl-3-(6-methyl-2,3-dihydro-4H-1,4-benzoxazin-4-yl)-3-phenylpropanamide was prepared from ethyl (2RS,3RS)-2-hydroxy-3-(6-methyl-2,3-dihydro-4H-1,4-benzoxazin-4-yl)-3-phenylpropanoate as a white powder. MS (ESI) m/z 325.0 ([M-H]$^-$); HRMS: calcd for C$_{19}$H$_{22}$N$_2$O$_3$+H$^+$, 327.1703; found (ESI, [M+H]$^+$), 327.1703.

In an analogous manner to EXAMPLE 33, step 3, (1RS,2SR)-3-(methylamino)-1-(6-methyl-2,3-dihydro-4H-1,4-benzoxazin-4-yl)-1-phenylpropan-2-ol hydrochloride was prepared from (2RS,3RS)-2-hydroxy-N-methyl-3-(6-methyl-2,3-dihydro-4H-1,4-benzoxazin-4-yl)-3-phenylpropanamide as a white powder. MS (ESI) m/z 313.0 ([M+H]$^+$); HRMS: calcd for C$_{19}$H$_{24}$N$_2$O$_2$+H$^+$, 313.1911; found (ESI, [M+H]$^+$), 313.1908.

Example 143

(1S,2R)-1-(3-fluorophenyl)-3-(methylamino)-1-(3-methyl-1H-indol-1-yl)propan-2-ol hydrochloride

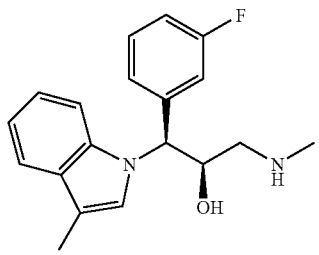

In an analogous manner to EXAMPLE 117, step 5, (2S,3S)-3-(3-fluorophenyl)-3-(3-methyl-1H-indol-1-yl)propane-1,2-diol was prepared from 3-methylindole and [(2R,3R)-3-(3-fluorophenyl)oxiran-2-yl]methanol (EXAMPLE 47, step 3) as a viscous, yellowish oil. MS (ES) m/z 300.0 ([M+H]$^+$); HRMS: calcd for C$_{18}$H$_{18}$FNO$_2$+H$^+$, 300.1400; found (ESI, [M+H]$^+$), 300.1400.

In an analogous manner to EXAMPLE 47, step 6, (1S,2R)-1-(3-fluorophenyl)-3-(methylamino)-1-(3-methyl-1H-indol-1-yl)propan-2-ol hydrochloride was prepared from (2S,3S)-3-(3-fluorophenyl)-3-(3-methyl-1H-indol-1-yl)propane-1,2-diol as a white solid. MS (ES) m/z 313.0 ([M+H]$^+$); HRMS: calcd for C$_{19}$H$_{21}$FN$_2$O+H$^+$, 313.1711; found (ESI, [M+H]$^+$), 313.1713.

Example 144

(1S,2R)-1-(6-chloro-2,3-dihydro-4H-1,4-benzoxazin-4-yl)-3-(methylamino)-1-phenylpropan-2-ol hydrochloride

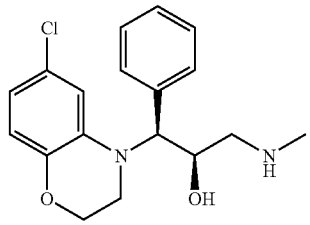

Step 1: Racemic (1RS,2SR)-1-(6-chloro-2,3-dihydro-4H-1,4-benzoxazin-4-yl)-3-(methylamino)-1-phenylpropan-2-ol (EXAMPLE 141) was dissolved in methanol. The resulting solution was injected onto the Supercritical Fluid Chromatography instrument. The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/minutes flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 40% MeOH with 0.5% DEA |
| Flow rate: | 50 mL/min |
| Outlet Pressure: | 100 bar |
| Detector: | UV at 266 nm |

Step 2: A solution of (1S,2R)-1-(6-chloro-2,3-dihydro-4H-1,4-benzoxazin-4-yl)-3-(methylamino)-1-phenylpropan-2-ol, isolated as Peak 1, (58 mg, 0.17 mmol) in dichloromethane (3 mL) was treated with an ethereal solution of hydrochloric acid (1 M, 0.2 mL, 0.2 mmol). To the resulting solution was added hexane until white powder formed, which was collected, washed with hexane, and dried in vacuo to yield 62 mg (45%) of (1S,2R)-1-(6-chloro-2,3-dihydro-4H-1,4-benzoxazin-4-yl)-3-(methylamino)-1-phenylpropan-2-ol hydrochloride. Chiral purity: >99.9%. MS (ESI) m/z 333.0 ([M+H]$^+$); HRMS: calcd for C$_{18}$H$_{21}$ClN$_2$O$_2$+H$^+$, 333.1370; found (ESI, [M+H]$^+$), 333.1372.

Example 145

(1R,2S)-1-(6-chloro-2,3-dihydro-4H-1,4-benzoxazin-4-yl)-3-(methylamino)-1-phenylpropan-2-ol hydrochloride

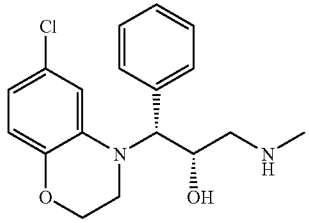

In an analogous manner to EXAMPLE 144, step 2, (1R,2S)-1-(6-chloro-2,3-dihydro-4H-1,4-benzoxazin-4-yl)-3-(methylamino)-1-phenylpropan-2-ol hydrochloride was prepared from (1R,2S)-1-(6-chloro-2,3-dihydro-4H-1,4-benzoxazin-4-yl)-3-(methylamino)-1-phenylpropan-2-ol which was isolated as Peak 2 of the chiral separation (EXAMPLE 144, step 1). Chiral purity: >99.9%. MS (ESI) m/z 333.0 ([M+H]$^+$); HRMS: calcd for C$_{18}$H$_{21}$ClN$_2$O$_2$+H$^+$, 333.1370; found (ESI, [M+H]$^+$), 333.1374.

Example 146

(1S,2R)-1-(4-chloro-1H-indol-1-yl)-3-(methylamino)-1-phenylpropan-2-ol hydrochloride

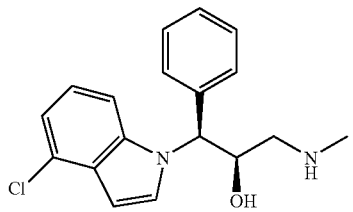

In an analogous manner to EXAMPLE 117, step 5, (2S,3S)-3-(4-chloro-1H-indol-1-yl)-3-phenylpropane-1,2-diol was prepared from 4-chloroindole and [(2R,3R)-3-phenyloxiran-2-yl]methanol (EXAMPLE 117, step 4) as a viscous, yellowish oil. MS (ES) m/z 300.0 ([M−H]$^−$).

In an analogous manner to EXAMPLE 47, step 6, (1S,2R)-1-(4-chloro-1H-indol-1-yl)-3-(methylamino)-1-phenylpropan-2-ol hydrochloride was prepared from (2S,3S)-3-(4-chloro-1H-indol-1-yl)-3-phenylpropane-1,2-diol as a white powder. MS (ES) m/z 315.0 ([M+H]$^+$); HRMS: calcd for C$_{18}$H$_{19}$ClN$_2$O+H$^+$, 315.1259; found (ESI, [M+H]$^+$), 315.1255.

Example 147

(1S,2R)-1-(6-chloro-1H-indol-1-yl)-3-(methylamino)-1-phenylpropan-2-ol hydrochloride

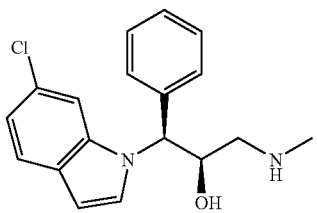

In an analogous manner to EXAMPLE 117, step 5, (2S,3S)-3-(6-chloro-1H-indol-1-yl)-3-phenylpropane-1,2-diol was prepared from 6-chloroindole and [(2R,3R)-3-phenyloxiran-2-yl]methanol (EXAMPLE 117, step 4) as a viscous, colorless oil. MS (ES) m/z 302.0 ([M+H]$^+$); HRMS: calcd for C$_{17}$H$_{16}$ClNO$_2$+H$^+$, 302.0948; found (ESI, [M+H]$^+$), 302.0946.

In an analogous manner to EXAMPLE 47, step 6, (1S,2R)-1-(6-chloro-1H-indol-1-yl)-3-(methylamino)-1-phenylpropan-2-ol hydrochloride was prepared from (2S,3S)-3-(6-chloro-1H-indol-1-yl)-3-phenylpropane-1,2-diol as a white powder. MS (ES) m/z 315.0 ([M+H]$^+$); HRMS: calcd for C$_{18}$H$_{19}$ClN$_2$O+H$^+$, 315.1259; found (ESI, [M+H]$^+$), 315.1263.

Example 148

(1S,2R)-1-(7-chloro-1H-indol-1-yl)-3-(methylamino)-1-phenylpropan-2-ol hydrochloride

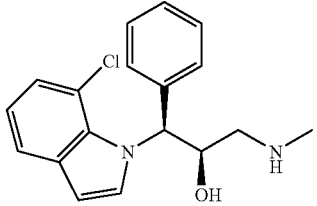

In an analogous manner to EXAMPLE 117, step 5, (2S,3S)-3-(7-chloro-1H-indol-1-yl)-3-phenylpropane-1,2-diol was prepared from 7-chloroindole and [(2R,3R)-3-phenyloxiran-2-yl]methanol (EXAMPLE 117, step 4) as a viscous, colorless oil. MS (ES) m/z 302.0 ([M+H]$^+$); HRMS: calcd for C$_{17}$H$_{16}$ClNO$_2$+H$^+$, 302.0948; found (ESI, [M+H]$^+$), 302.0949.

In an analogous manner to EXAMPLE 47, step 6, (1S,2R)-1-(7-chloro-1H-indol-1-yl)-3-(methylamino)-1-phenylpropan-2-ol hydrochloride was prepared from (2S,3S)-3-(7-chloro-1H-indol-1-yl)-3-phenylpropane-1,2-diol as a white powder. MS (ES) m/z 315.0 ([M+H]$^+$); HRMS: calcd for C$_{18}$H$_{19}$ClN$_2$O+H$^+$, 315.1259; found (ESI, [M+H]$^+$), 315.1269.

Example 149

(1S,2R)-1-(7-chloro-1H-indol-1-yl)-1-(3-fluorophenyl)-3-(methylamino)propan-2-ol hydrochloride

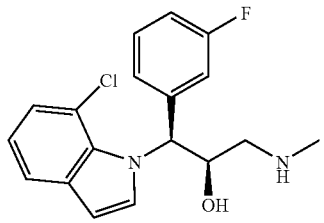

In an analogous manner to EXAMPLE 117, step 5, (2S,3S)-3-(7-chloro-1H-indol-1-yl)-3-(3-fluorophenyl)propane-1,2-diol was prepared from 7-chloroindole and [(2R,3R)-3-(3-fluorophenyl)oxiran-2-yl]methanol (EXAMPLE 47, step 3) as a viscous, colorless oil. MS (ES) m/z 320.0 ([M+H]$^+$); HRMS: calcd for $C_{17}H_{15}ClFNO_2+H^+$, 320.0848; found (ESI, [M+H]$^+$), 320.0858.

In an analogous manner to EXAMPLE 47, step 6, (1S,2R)-1-(7-chloro-1H-indol-1-yl)-1-(3-fluorophenyl)-3-(methylamino)propan-2-ol hydrochloride was prepared from (2S,3S)-3-(7-chloro-1H-indol-1-yl)-3-(3-fluorophenyl)propane-1,2-diol as a white powder. MS (ES) m/z 333.0 ([M+H]$^+$); HRMS: calcd for $C_{18}H_{18}ClFN_2O+H^+$, 333.1170; found (ESI, [M+H]$^+$), 333.1189.

Example 150

(1S,2R)-1-(4-chloro-1H-indol-1-yl)-1-(3-fluorophenyl)-3-(methylamino)propan-2-ol hydrochloride

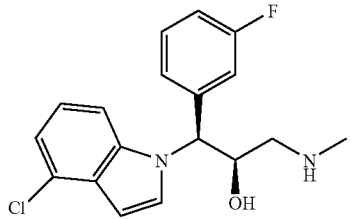

In an analogous manner to EXAMPLE 117, step 5, (2S,3S)-3-(4-chloro-1H-indol-1-yl)-3-(3-fluorophenyl)propane-1,2-diol was prepared from 4-chloroindole and [(2R,3R)-3-(3-fluorophenyl)oxiran-2-yl]methanol (EXAMPLE 47, step 3) as a viscous, colorless oil. MS (ES) m/z 320.0 ([M+H]$^+$); HRMS: calcd for $C_{17}H_{15}ClFNO_2+H^+$, 320.0848; found (ESI, [M+H]$^+$), 320.0856.

In an analogous manner to EXAMPLE 47, step 6, (1S,2R)-1-(4-chloro-1H-indol-1-yl)-1-(3-fluorophenyl)-3-(methylamino)propan-2-ol hydrochloride was prepared from (2S,3S)-3-(4-chloro-1H-indol-1-yl)-3-(3-fluorophenyl)propane-1,2-diol as a white powder. MS (ES) m/z 333.2 ([M+H]$^+$); HRMS: calcd for $C_{18}H_{18}ClFN_2O+H^+$, 333.1170; found (ESI, [M+H]$^+$), 333.1156.

Example 151

(1S,2R)-1-(6-chloro-1H-indol-1-yl)-1-(3-fluorophenyl)-3-(methylamino)propan-2-ol hydrochloride

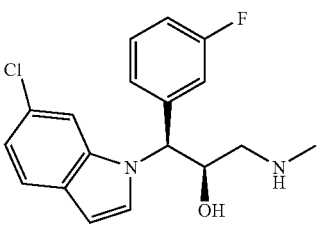

In an analogous manner to EXAMPLE 117, step 5, (2S,3S)-3-(6-chloro-1H-indol-1-yl)-3-(3-fluorophenyl)propane-1,2-diol was prepared from 6-chloroindole and [(2R,3R)-3-(3-fluorophenyl)oxiran-2-yl]methanol (EXAMPLE 47, step 3) as a viscous, colorless oil. MS (ES) m/z 320.0 ([M+H]$^+$); HRMS: calcd for $C_{17}H_{15}ClFNO_2+H^+$, 320.0848; found (ESI, [M+H]$^+$), 320.0855.

In an analogous manner to EXAMPLE 47, step 6, (1S,2R)-1-(6-chloro-1H-indol-1-yl)-1-(3-fluorophenyl)-3-(methylamino)propan-2-ol hydrochloride was prepared from (2S,3S)-3-(6-chloro-1H-indol-1-yl)-3-(3-fluorophenyl)propane-1,2-diol as a white powder. MS (ES) m/z 333.2 ([M+H]$^+$); HRMS: calcd for $C_{18}H_{18}ClFN_2O+H^+$, 333.1170; found (ESI, [M+H]$^+$), 333.1174.

Example 152

(1S,2R)-1-(5-chloro-1H-indol-1-yl)-3-(methylamino)-1-phenylpropan-2-ol hydrochloride

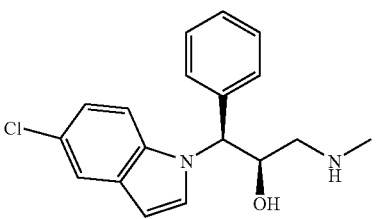

In an analogous manner to EXAMPLE 117, step 5, (2S,3S)-3-(5-chloro-1H-indol-1-yl)-3-phenylpropane-1,2-diol was prepared from 5-chloroindole and [(2R,3R)-3-phenyloxiran-2-yl]methanol (EXAMPLE 117, step 4) as a viscous, colorless oil. MS (ES) m/z 302.2 ([M+H]$^+$); HRMS: calcd for $C_{17}H_{16}ClNO_2+H^+$, 302.0948; found (ESI, [M+H]$^+$), 302.0956.

In an analogous manner to EXAMPLE 47, step 6, (1S,2R)-1-(5-chloro-1H-indol-1-yl)-3-(methylamino)-1-phenylpropan-2-ol hydrochloride was prepared from (2S,3S)-3-(5-chloro-1H-indol-1-yl)-3-phenylpropane-1,2-diol as a white powder. MS (ES) m/z 315.1 ([M+H]$^+$); HRMS: calcd for $C_{18}H_{19}ClN_2O+H^+$, 315.1259; found (ESI, [M+H]$^+$), 315.1247.

Example 153

(1S,2R)-1-(5-chloro-1H-indol-1-yl)-1-(3-fluorophenyl)-3-(methylamino)propan-2-ol hydrochloride

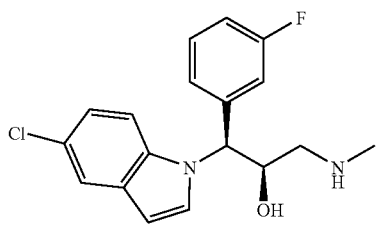

In an analogous manner to EXAMPLE 117, step 5, (2S,3S)-3-(5-chloro-1H-indol-1-yl)-3-(3-fluorophenyl)propane-1,2-diol was prepared from 5-chloroindole and [(2R,3R)-3-(3-fluorophenyl)oxiran-2-yl]methanol (EXAMPLE 47, step 3) as a viscous, colorless oil. MS (ES) m/z 320.1 ([M+H]$^+$); HRMS: calcd for $C_{17}H_{15}ClFNO_2$+H$^+$, 320.0848; found (ESI, [M+H]$^+$), 320.0854.

In an analogous manner to EXAMPLE 47, step 6, (1S,2R)-1-(5-chloro-1H-indol-1-yl)-1-(3-fluorophenyl)-3-(methylamino)propan-2-ol hydrochloride was prepared from 2S,3S)-3-(5-chloro-1H-indol-1-yl)-3-(3-fluorophenyl)propane-1,2-diol as a white powder. MS (ES) m/z 333.1 ([M+H]$^+$); HRMS: calcd for $C_{18}H_{18}ClFN_2O$+H$^+$, 333.1170; found (ESI, [M+H]$^+$), 333.1154.

Example 154

(1S,2R)-1-(3-isopropyl-1H-indol-1-yl)-3-(methylamino)-1-phenylpropan-2-ol hydrochloride

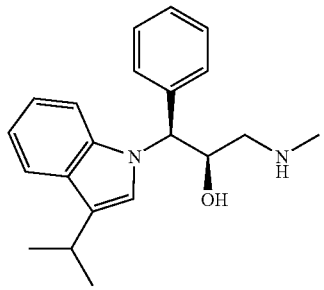

In an analogous manner to EXAMPLE 117, step 5, (2S,3S)-3-(3-isopropyl-1H-indol-1-yl)-3-phenylpropane-1,2-diol was prepared from 3-isopropylindole[16] and [(2R,3R)-3-phenyloxiran-2-yl]methanol (EXAMPLE 117, step 4) as a viscous, yellowish oil. HRMS: calcd for $C_{20}H_{23}NO_2$+H$^+$, 310.1802; found (ESI, [M+H]$^+$), 310.1793.

[16]Odle, R.; Blevins, B.; Ratcliff, M.; Hegedus, L. S. *J. Org. Chem.* 1980, 45, 2709-2710.

In an analogous manner to EXAMPLE 47, step 6, (1S,2R)-1-(3-isopropyl-1H-indol-1-yl)-3-(methylamino)-1-phenylpropan-2-ol hydrochloride was prepared from (2S,3S)-3-(3-isopropyl-1H-indol-1-yl)-3-phenylpropane-1,2-diol as a white powder. MS (ES) m/z 323.3 ([M+H]$^+$); HRMS: calcd for $C_{21}H_{26}N_2O$+H$^+$, 323.2118; found (ESI, [M+H]$^+$), 323.2117.

Example 155

(1S,2R)-1-(3-fluorophenyl)-1-(3-isopropyl-1H-indol-1-yl)-3-(methylamino)propan-2-ol hydrochloride

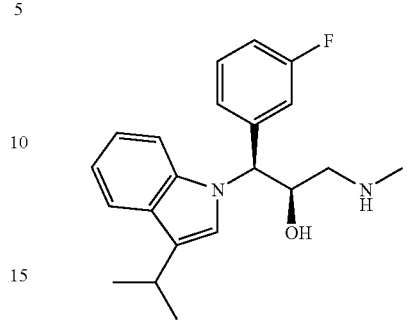

In an analogous manner to EXAMPLE 117, step 5, (2S,3S)-3-(3-fluorophenyl)-3-(3-isopropyl-1H-indol-1-yl)propane-1,2-diol was prepared from 3-isopropylindole[16] and [(2R,3R)-3-(3-fluorophenyl)oxiran-2-yl]methanol (EXAMPLE 47, step 3) as a viscous, yellowish oil. MS (ES) m/z 326.2 ([M−H]$^−$); HRMS: calcd for $C_{20}H_{22}FNO_2$+H$^+$, 328.1707; found (ESI, [M+H]$^+$), 328.1709.

In an analogous manner to EXAMPLE 47, step 6, (1S,2R)-1-(3-fluorophenyl)-1-(3-isopropyl-1H-indol-1-yl)-3-(methylamino)propan-2-ol hydrochloride was prepared from (2S,3S)-3-(3-fluorophenyl)-3-(3-isopropyl-1H-indol-1-yl)propane-1,2-diol as a white powder. MS (ES) m/z 341.3 ([M+H]$^+$); HRMS: calcd for $C_{21}H_{25}FN_2O$+H$^+$, 341.2024; found (ESI, [M+H]$^+$), 341.2025.

Example 156

(1S,2R)-1-(6-chloro-2,3-dihydro-4H-1,4-benzoxazin-4-yl)-1-(3-fluorophenyl)-3-(methylamino)propan-2-ol hydrochloride

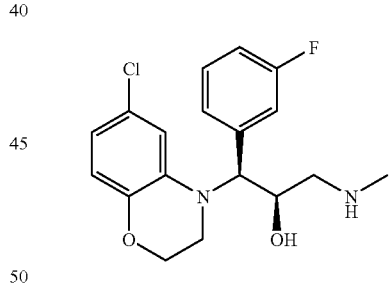

In an analogous manner to EXAMPLE 47, step 4, (2S,3S)-3-(6-chloro-2,3-dihydro-4H-1,4-benzoxazin-4-yl)-3-(3-fluorophenyl)propane-1,2-diol was prepared from 6-chloro-3,4-dihydro-2H-1,4-benzoxazine (EXAMPLE 88, step 1) and [(2R,3R)-3-(3-fluorophenyl)oxiran-2-yl]methanol (EXAMPLE 47, step 3) as a viscous, yellowish liquid. MS (ES) m/z 335.8 ([M−H]$^−$); HRMS: calcd for $C_{20}H_{22}FNO_2$+H$^+$, 338.0959; found (ESI, [M+H]$^+$), 338.0959.

In an analogous manner to EXAMPLE 47, step 6, (1S,2R)-1-(6-chloro-2,3-dihydro-4H-1,4-benzoxazin-4-yl)-1-(3-fluorophenyl)-3-(methylamino)propan-2-ol hydrochloride was prepared from (2S,3S)-3-(6-chloro-2,3-dihydro-4H-1,4-benzoxazin-4-yl)-3-(3-fluorophenyl)propane-1,2-diol as a white powder. MS (ES) m/z 351.0 ([M+H]$^+$); HRMS: calcd for $C_{18}H_{20}ClFN_2O_2$+H$^+$, 351.1276; found (ESI, [M+H]$^+$), 351.1276.

Example 157

(1S,2R)-1-(3,5-difluorophenyl)-1-(1H-indol-1-yl)-3-(methylamino)propan-2-ol hydrochloride

Step 1: In an analogous manner to EXAMPLE 47, step 1, trans-3,5-difluorocinnamic acid methyl ester was prepared from trans-3,5-difluorocinnamic acid as a white solid. MS (ESI) m/z 198.0; HRMS: calcd for $C_{10}H_8F_2O_2$, 198.0492; found (ESI, $[M]^+$), 198.0489.

Step 2: In an analogous manner to EXAMPLE 47, step 2, trans-3,5-difluorocinnamyl alcohol was prepared from trans-3,5-difluorocinnamic acid methyl ester as a colorless oil.

Step 3: In an analogous manner to EXAMPLE 47, step 3, [(2R,3R)-3-(3,5-difluorophenyl)oxiran-2-yl]methanol was prepared from trans-3,5-difluorocinnamyl alcohol as a colorless liquid. Percent ee: 97.9%. MS (ESI) m/z 186.0; HRMS: calcd for $C_9H_8F_2O_2$, 186.0492; found (ESI, $[M]^+$), 186.0501.

Step 4: In an analogous manner to EXAMPLE 47, step 4, (2S,3S)-3-(3,5-difluorophenyl)-3-(2,3-dihydro-1H-indol-1-yl)propane-1,2-diol was prepared from indoline and [(2R,3R)-3-(3,5-difluorophenyl)oxiran-2-yl]methanol as a viscous, yellowish oil. MS (ES) m/z 306.2 ($[M+H]^+$); HRMS: calcd for $C_{17}H_{17}F_2NO_2+H^+$, 306.1300; found (ESI, $[M+H]^+$), 306.1299.

Step 5: In an analogous manner to EXAMPLE 47, step 5, (2S,3S)-3-(3,5-difluorophenyl)-3-(1H-indol-1-yl)propane-1,2-diol was prepared from (2S,3S)-3-(3,5-difluorophenyl)-3-(2,3-dihydro-1H-indol-1-yl)propane-1,2-diol as a viscous, yellowish oil. MS (ES) m/z 304.0 ($[M+H]^+$); HRMS: calcd for $C_{17}H_{15}F_2NO_2+H^+$, 304.1144; found (ESI, $[M+H]^+$), 304.1146.

Step 6: In an analogous manner to EXAMPLE 47, step 6, (1S,2R)-1-(3,5-difluorophenyl)-1-(1H-indol-1-yl)-3-(methylamino)propan-2-ol hydrochloride was prepared from (2S,3S)-3-(3,5-difluorophenyl)-3-(1H-indol-1-yl)propane-1,2-diol as a white powder. MS (ES) m/z 317.0 ($[M+H]^+$); HRMS: calcd for $C_{18}H_{18}F_2N_2O+H^+$, 317.1465. Found (ESI, $[M+H]^+$), 317.1465.

Example 158

(1S,2R)-1-(3,5-difluorophenyl)-1-(2,3-dihydro-1H-indol-1-yl)-3-(methylamino)propan-2-ol hydrochloride

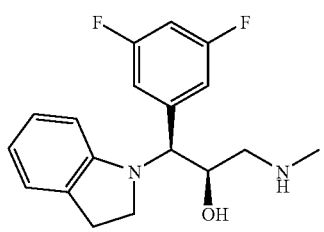

In an analogous manner to EXAMPLE 47, step 6, (1S,2R)-1-(3,5-difluorophenyl)-1-(2,3-dihydro-1H-indol-1-yl)-3-(methylamino)propan-2-ol was prepared from (2S,3S)-3-(3,5-difluorophenyl)-3-(2,3-dihydro-1H-indol-1-yl)propane-1,2-diol as a white powder. MS (ES) m/z 319.0 ($[M+H]^+$); HRMS: calcd for $C_{18}H_{20}F_2N_2O+H^+$, 319.1622; found (ESI, $[M+H]^+$), 319.1622.

Example 159

(1S,2R)-4-amino-1-(3-fluorophenyl)-1-(1H-indol-1-yl)butan-2-ol hydrochloride

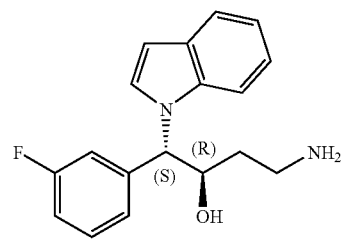

In an analogous manner to Example 1, step 2 (2S,3S)-toluene-4-sulfonic acid 3-(3-fluorophenyl)-2-hydroxy-3-indol-1-yl-propyl ester was prepared from (2S,3S)-3-(3-fluorophenyl)-3-(1H-indol-1-yl)propane-1,2-diol (Example 47, step 4). MS (ES) m/z 440 ($[M+H]^+$).

Example 160

(1S,2R)-1-(3,3-dimethyl-2,3-dihydro-1H-indol-1-yl)-1-(3-fluorophenyl)-3-(methylamino)propan-2-ol hydrochloride

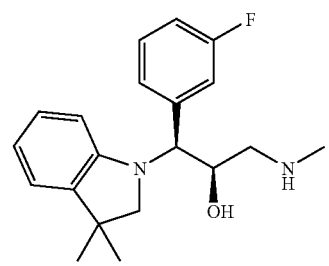

In an analogous manner to EXAMPLE 47, step 4, (2S,3S)-3-(3,3-dimethyl-2,3-dihydro-1H-indol-1-yl)-3-(3-fluorophenyl)propane-1,2-diol was prepared from 3,3-dimethylindoline[15] and [(2R,3R)-3-(3-fluorophenyl)oxiran-2-yl]methanol (EXAMPLE 47, step 3) as a viscous, brown liquid. MS (ES) m/z 316.0 ($[M+H]^+$); HRMS: calcd for $C_{19}H_{22}FNO_2+H^+$, 316.1713. Found (ESI, $[M+H]^+$), 316.1713.

In an analogous manner to EXAMPLE 47, step 6, (1S,2R)-1-(3,3-dimethyl-2,3-dihydro-1H-indol-1-yl)-1-(3-fluorophenyl)-3-(methylamino)propan-2-ol hydrochloride was prepared from (2S,3S)-3-(3,3-dimethyl-2,3-dihydro-1H-indol-1-yl)-3-(3-fluorophenyl)propane-1,2-diol as a white powder. MS (ES) m/z 329.0 ($[M+H]^+$).

Example 161

(1S,2R)-1-(3,5-difluorophenyl)-1-(3,3-dimethyl-2,3-dihydro-1H-indol-1-yl)-3-(methylamino)propan-2-ol hydrochloride

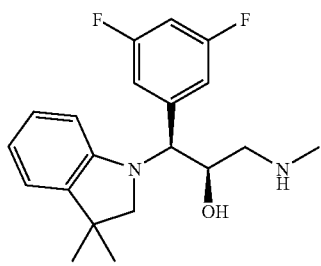

In an analogous manner to EXAMPLE 47, step 4, (2S,3S)-3-(3,5-difluorophenyl)-3-(3,3-dimethyl-2,3-dihydro-1H-indol-1-yl)propane-1,2-diol was prepared from 3,3-dimethylindoline[15] and [(2R,3R)-3-(3,5-difluorophenyl)oxiran-2-yl]methanol (EXAMPLE 157, step 3) as a viscous, brown liquid. MS (ES) m/z 334.0 ([M+H]$^+$); HRMS: calcd for $C_{19}H_{21}F_2NO_2+H^+$, 334.1619. Found (ESI, [M+H]$^+$), 334.1619.

In an analogous manner to EXAMPLE 47, step 6, (1S,2R)-1-(3,5-difluorophenyl)-1-(3,3-dimethyl-2,3-dihydro-1H-indol-1-yl)-3-(methylamino)propan-2-ol hydrochloride was prepared from (2S,3S)-3-(3,5-difluorophenyl)-3-(3,3-dimethyl-2,3-dihydro-1H-indol-1-yl)propane-1,2-diol as a white powder. MS (ES) m/z 347.0 ([M+H]$^+$); HRMS: calcd for $C_{20}H_{24}F_2N_2O+H^+$, 347.1929. Found (ESI, [M+H]$^+$), 347.1929.

Example 162

(1S,2R)-1-(3,3-dimethyl-2,3-dihydro-1H-indol-1-yl)-3-(methylamino)-1-phenylpropan-2-ol hydrochloride

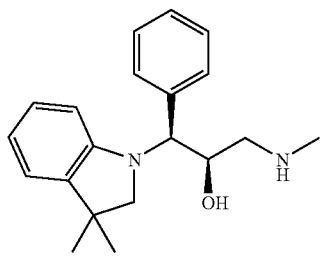

In an analogous manner to EXAMPLE 47, step 4, (2S,3S)-3-(3,3-dimethyl-2,3-dihydro-1H-indol-1-yl)-3-phenylpropane-1,2-diol was prepared from 3,3-dimethylindoline[15] and [(2R,3R)-3-phenyloxiran-2-yl]methanol (EXAMPLE 117, step 4) as a viscous, brown liquid. MS (ES) m/z 298.0 ([M+H]$^+$); HRMS: calcd for $C_{19}H_{23}NO_2+H^+$, 298.1807. Found (ESI, [M+H]$^+$), 298.1807.

In an analogous manner to EXAMPLE 47, step 6, (1S,2R)-1-(3,3-dimethyl-2,3-dihydro-1H-indol-1-yl)-3-(methylamino)-1-phenylpropan-2-ol hydrochloride was prepared from (2S,3S)-3-(3,3-dimethyl-2,3-dihydro-1H-indol-1-yl)-3-phenylpropane-1,2-diol as a white powder. MS (ES) m/z 311.0 ([M+H]$^+$); HRMS: calcd for $C_{20}H_{26}N_2O+H^+$, 311.2118. Found (ESI, [M+H]$^+$), 311.2107.

Example 163

(1S,2R)-1-(3-fluorophenyl)-3-(methylamino)-1-(3-methyl-2,3-dihydro-1H-indol-1-yl)propan-2-ol hydrochloride

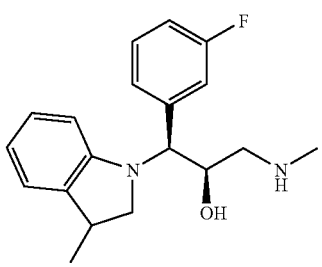

In an analogous manner to EXAMPLE 47, step 4, (2S,3S)-3-(3-fluorophenyl)-3-(3-methyl-2,3-dihydro-1H-indol-1-yl)propane-1,2-diol was prepared from 3-methylindoline[4] and [(2R,3R)-3-(3-fluorophenyl)oxiran-2-yl]methanol (EXAMPLE 47, step 3) as a viscous, yellowish liquid. MS (ES) m/z 301.8 ([M+H]$^+$); HRMS: calcd for $C_{18}H_{20}FNO_2+H^+$, 302.1551. Found (ESI, [M+H]$^+$), 302.1539.

In an analogous manner to EXAMPLE 47, step 6, (1S,2R)-1-(3-fluorophenyl)-3-(methylamino)-1-(3-methyl-2,3-dihydro-1H-indol-1-yl)propan-2-ol hydrochloride was prepared from (2S,3S)-3-(3-fluorophenyl)-3-(3-methyl-2,3-dihydro-1H-indol-1-yl)propane-1,2-diol as a white powder. MS (ES) m/z 315.2 ([M+H]$^+$); HRMS: calcd for $C_{19}H_{23}FN_2O+H^+$, 315.1873. Found (ESI, [M+H]$^+$), 315.1881.

Example 164

(1S,2R)-1-(3-fluorophenyl)-3-(methylamino)-1-spiro[cyclopentane-1,3'-indol]-1'(2'H)-ylpropan-2-ol hydrochloride

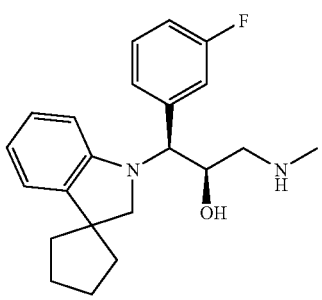

In an analogous manner to EXAMPLE 47, step 4, (2S,3S)-3-(3-fluorophenyl)-3-spiro[cyclopentane-1,3'-indol]-1'(2'H)-ylpropane-1,2-diol was prepared from 1',2'-dihydrospiro[cyclopentane-1,3'-indole][15] and [(2R,3R)-3-(3-fluorophenyl)oxiran-2-yl]methanol (EXAMPLE 47, step 3) as a viscous, yellowish liquid. MS (ES) m/z 342.2 ([M+H]$^+$).

In an analogous manner to EXAMPLE 47, step 6, (1S,2R)-1-(3-fluorophenyl)-3-(methylamino)-1-spiro[cyclopentane-1,3'-indol]-1'(2'H)-ylpropan-2-ol hydrochloride was prepared from (2S,3S)-3-(3-fluorophenyl)-3-spiro

[cyclopentane-1,3'-indol]-1'(2'H)-ylpropane-1,2-diol as a white powder. MS (ES) m/z 355.0 ([M+H]$^+$); HRMS: calcd for $C_{22}H_{27}FN_2O+H^+$, 355.2180. Found (ESI, [M+H]$^+$), 355.2178.

Example 165

(1S,2R)-1-(2,2-dimethyl-2,3-dihydro-4H-1,4-benzoxazin-4-yl)-1-(3-fluorophenyl)-3-(methylamino)propan-2-ol hydrochloride

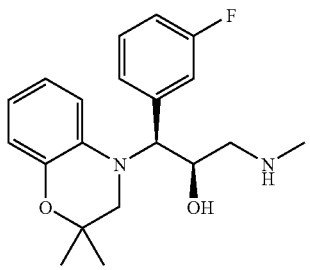

Step 1: To a solution of 2,2-dimethyl-2H-1,4-benzoxazin-3(4H)-one[17] (2.658 g, 15.0 mmol) in tetrahydrofuran (10 mL) under nitrogen was added slowly a solution of borane (1.0 M in tetrahydrofuran, 22.5 mL, 22.5 mmol) via a syringe. The resulting mixture was stirred at room temperature for 10 minutes and then at 70° C. for 1 hour s. After cooling, the reaction mixture was quenched with methanol (3 mL) slowly. All volatiles were removed under reduced pressure. A 1 N aqueous solution of hydrochloric acid (10 mL) was added to the liquid residue and the mixture was warmed to 50° C. for 10 minutes. After cooling, the reaction mixture was made alkaline using saturated sodium bicarbonate solution (15 mL), and extracted with ethyl acetate (25 mL). The organic layer was washed with water, brine, dried (anhydrous sodium sulfate), filtered through a pad of silica gel, and concentrated under reduced pressure to yield 2.310 g (94%) of 2,2-dimethyl-3,4-dihydro-2H-1,4-benzoxazine as a brown oil. MS (ES) m/z 164.0 ([M+H]$^+$).

[17]Caliendo, G.; Perissutti, E.; Santagada, V.; Fiorino, F.; Severino, B.; Bianca, R.

Step 2: In an analogous manner to EXAMPLE 47, step 4, (2S,3S)-3-(2,2-dimethyl-2,3-dihydro-4H-1,4-benzoxazin-4-yl)-3-(3-fluorophenyl)propane-1,2-diol was prepared from 2,2-dimethyl-3,4-dihydro-2H-1,4-benzoxazine and [(2R,3R)-3-(3-fluorophenyl)oxiran-2-yl]methanol (EXAMPLE 47, step 3) as a white solid. MS (ES) m/z 332.2 ([M+H]$^+$); HRMS: calcd for $C_{19}H_{22}FNO_3+H^+$, 332.1657. Found (ESI, [M+H]$^+$), 332.1648.

Step 3: In an analogous manner to EXAMPLE 47, step 6, (1S,2R)-1-(2,2-dimethyl-2,3-dihydro-4H-1,4-benzoxazin-4-yl)-1-(3-fluorophenyl)-3-(methylamino)propan-2-ol hydrochloride was prepared from (2S,3S)-3-(2,2-dimethyl-2,3-dihydro-4H-1,4-benzoxazin-4-yl)-3-(3-fluorophenyl)propane-1,2-diol as a white powder. MS (ES) m/z 345.2 ([M+H]$^+$); HRMS: calcd for $C_{20}H_{25}FN_2O_2+H^+$, 345.1978. Found (ESI, [M+H]$^+$), 345.1981.

Example 166

(1S,2R)-1-(2,2-dimethyl-2,3-dihydro-4H-1,4-benzoxazin-4-yl)-3-(methylamino)-1-phenylpropan-2-ol hydrochloride

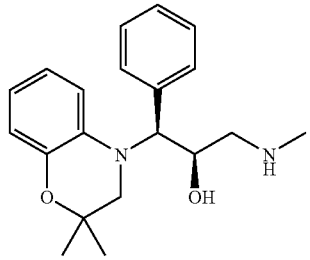

In an analogous manner to EXAMPLE 47, step 4, (2S,3S)-3-(2,2-dimethyl-2,3-dihydro-4H-1,4-benzoxazin-4-yl)-3-phenylpropane-1,2-diol was prepared from 2,2-dimethyl-3,4-dihydro-2H-1,4-benzoxazine (EXAMPLE 165, step 1) and [(2R,3R)-3-phenyloxiran-2-yl]methanol (EXAMPLE 117, step 4) as a white solid. MS (ES) m/z 314.1 ([M+H]$^+$).

In an analogous manner to EXAMPLE 47, step 6, (1S,2R)-1-(2,2-dimethyl-2,3-dihydro-4H-1,4-benzoxazin-4-yl)-3-(methylamino)-1-phenylpropan-2-ol hydrochloride was prepared from (2S,3S)-3-(2,2-dimethyl-2,3-dihydro-4H-1,4-benzoxazin-4-yl)-3-phenylpropane-1,2-diol as a white powder. MS (ES) m/z 327.2 ([M+H]$^+$); HRMS: calcd for $C_{20}H_{26}N_2O_2+H^+$, 327.2073. Found (ESI, [M+H]$^+$), 327.2082.

Example 167

(1S,2R)-1-(2,3-dihydro-4H-1,4-benzothiazin-4-yl)-1-(3-fluorophenyl)-3-(methylamino)propan-2-ol hydrochloride

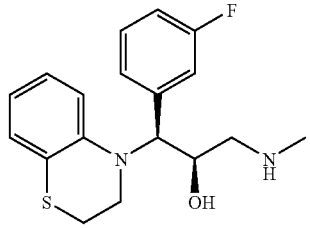

In an analogous manner to EXAMPLE 47, step 4, (2S,3S)-3-(2,3-dihydro-4H-1,4-benzothiazin-4-yl)-3-(3-fluorophenyl)propane-1,2-diol was prepared from 3,4-dihydro-2H-1,4-benzothiazine[18] and [(2R,3R)-3-(3-fluorophenyl)oxiran-2-yl]methanol (EXAMPLE 47, step 3) as a viscous, yellowish liquid. MS (ES) m/z 320.1 ([M+H]$^+$); HRMS: calcd for $C_{17}H_{18}FNO_2S+H^+$, 320.1115. Found (ESI, [M+H]$^+$), 320.1113.

[18]El-Subbagh, H. I.; Abadi, A. H.; Al-Khawad, I. E.; Al-Rashood, K. A. *Arch. Pharm.* 1999, 332, 19-24.

In an analogous manner to EXAMPLE 47, step 6, (1S,2R)-1-(2,3-dihydro-4H-1,4-benzothiazin-4-yl)-1-(3-fluorophenyl)-3-(methylamino)propan-2-ol hydrochloride was prepared from (2S,3S)-3-(2,3-dihydro-4H-1,4-benzothiazin-4-yl)-3-(3-fluorophenyl)propane-1,2-diol as a white powder.

MS (ES) m/z 333.1 ([M+H]$^+$); HRMS: calcd for C$_{18}$H$_{21}$FN$_2$OS+H$^+$, 333.1431. Found (ESI, [M+H]$^+$), 333.1420.

Example 168

(1S,2R)-1-(3-fluorophenyl)-3-(methylamino)-1-(2-phenyl-2,3-dihydro-4H-1,4-benzoxazin-4-yl)propan-2-ol hydrochloride

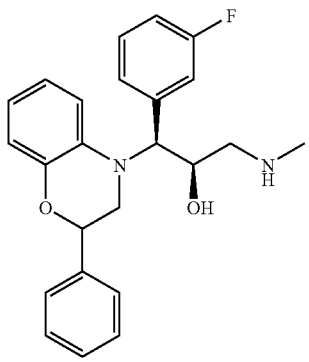

In an analogous manner to EXAMPLE 47, step 4, (2S,3S)-3-(3-fluorophenyl)-3-(2-phenyl-2,3-dihydro-4H-1,4-benzoxazin-4-yl)propane-1,2-diol was prepared from 2-phenyl-3,4-dihydro-2H-1,4-benzoxazine[19] and [(2R,3R)-3-(3-fluorophenyl)oxiran-2-yl]methanol (EXAMPLE 47, step 3) as a white solid. MS (ES) m/z 380.0 ([M+H]$^+$); HRMS: calcd for C$_{23}$H$_{22}$FNO$_3$+H$^+$, 380.1662. Found (ESI, [M+H]$^+$), 380.1661.

[19] Olagbemiro, T. O.; Nyakutse, C. A.; Lajide, L.; Agho, M. O.; Chukwu, C. E. *Bull. Soc. Chim. Belg.* 1987, 96, 473-480.

In an analogous manner to EXAMPLE 47, step 6, (1S,2R)-1-(3-fluorophenyl)-3-(methylamino)-1-(2-phenyl-2,3-dihydro-4H-1,4-benzoxazin-4-yl)propan-2-ol hydrochloride was prepared from (2S,3S)-3-(3-fluorophenyl)-3-(2-phenyl-2,3-dihydro-4H-1,4-benzoxazin-4-yl)propane-1,2-diol as a white powder. MS (ES) m/z 393.2 ([M+H]$^+$); HRMS: calcd for C$_{24}$H$_{25}$FN$_2$O$_2$+H$^+$, 393.1978. Found (ESI, [M+H]$^+$), 393.1986.

Example 169

(1S,2R)-1-(3-fluorophenyl)-1-[3-(4-methoxyphenyl)-1H-indol-1-yl]-3-(methylamino)propan-2-ol hydrochloride

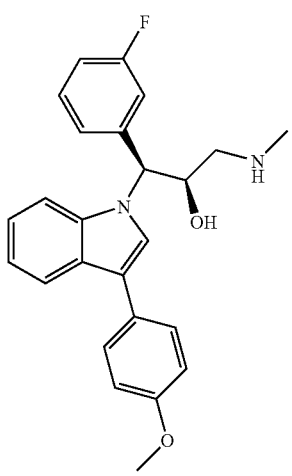

In an analogous manner to EXAMPLE 114, step 2, (2S,3S)-3-(3-fluorophenyl)-3-{3-[4-methoxyphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 4-methoxybenzeneboronic acid.

In an analogous manner to EXAMPLE 1, step 2, (2S,3S)-toluene-4-sulfonic acid 3-(3-fluorophenyl)-3-[3-(4-methoxyphenyl)-indol-1-yl]-2-hydroxy-propyl ester was prepared from (2S,3S)-3-(3-fluorophenyl)-3-{3-[4-methoxyphenyl]-1H-indol-1-yl}propane-1,2-diol.

In an analogous manner to EXAMPLE 5, (1S,2R)-1-(3-fluorophenyl)-1-[3-(4-methoxyphenyl)-1H-indol-1-yl]-3-(methylamino)propan-2-ol hydrochloride was prepared from (2S,3S)-toluene-4-sulfonic acid 3-(3-fluorophenyl)-3-[3-(4-methoxyphenyl)-indol-1-yl]-2-hydroxy-propyl ester and methylamine (2N solution in methanol). MS (ESI) m/z 405.

Example 170

(1S,2R)-1-(3-fluorophenyl)-3-(methylamino)-1-[3-(4-methylphenyl)-1H-indol-1-yl]propan-2-ol hydrochloride

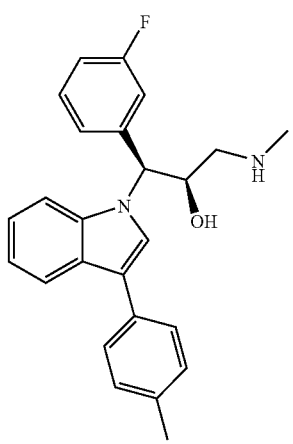

In an analogous manner to EXAMPLE 114, step 2, (2S,3S)-3-(3-fluorophenyl)-3-{3-[4-methylphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 4-methylbenzeneboronic acid.

In an analogous manner to EXAMPLE 1, step 2, (2S,3S)-toluene-4-sulfonic acid 3-(3-fluorophenyl)-3-[3-(4-methylphenyl)-indol-1-yl]-2-hydroxy-propyl ester was prepared from (2S,3S)-3-(3-fluorophenyl)-3-{3-[4-methylphenyl]-1H-indol-1-yl}propane-1,2-diol.

In an analogous manner to EXAMPLE 5, (1S,2R)-1-(3-fluorophenyl)-3-(methylamino)-1-[3-(4-methylphenyl)-1H-indol-1-yl]propan-2-ol hydrochloride was prepared from (2S,3S)-toluene-4-sulfonic acid 3-(3-fluorophenyl)-3-[3-(4-methylphenyl)-indol-1-yl]-2-hydroxy-propyl ester and methylamine (2N solution in methanol). MS (ESI) m/z 389.2.

Example 171

(1S,2R)-1-[3-(4-tert-butylphenyl)-1H-indol-1-yl]-1-(3-fluorophenyl)-3-(methylamino)propan-2-ol hydrochloride

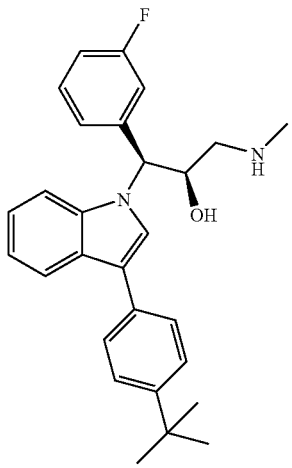

In an analogous manner to EXAMPLE 114, step 2, (2S, 3S)-3-(3-fluorophenyl)-3-{3-[4-tert-butylphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 4-tert-butylphenylboronic acid.

In an analogous manner to EXAMPLE 1, step 2, (2S,3S)-toluene-4-sulfonic acid 3-(3-fluorophenyl)-3-[3-(4-tert-butylphenyl)-indol-1-yl]-2-hydroxy-propyl ester was prepared from (2S,3S)-3-(3-fluorophenyl)-3-{3-[4-tert-butylphenyl]-1H-indol-1-yl}propane-1,2-diol.

In an analogous manner to EXAMPLE 5, (1S,2R)-1-[3-(4-tert-butylphenyl)-1H-indol-1-yl]-1-(3-fluorophenyl)-3-(methylamino)propan-2-ol hydrochloride was prepared from (2S,3S)-toluene-4-sulfonic acid 3-(3-fluorophenyl)-3-[3-(4-tert-butylphenyl)-indol-1-yl]-2-hydroxy-propyl ester and methylamine (2N solution in methanol). MS (ESI) m/z 430.9; HRMS: calcd for C28H31FN2O+H+, 431.24932. Found (ESI, [M+H]+), 431.2516.

Example 172

(1S,2R)-1-(3-fluorophenyl)-1-[3-(3-methoxyphenyl)-1H-indol-1-yl]-3-(methylamino)propan-2-ol hydrochloride

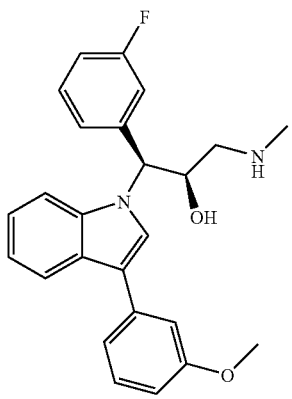

In an analogous manner to EXAMPLE 114, step 2, (2S, 3S)-3-(3-fluorophenyl)-3-{3-[3-methoxyphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 3-methoxybenzeneboronic acid.

In an analogous manner to EXAMPLE 1, step 2, (2S,3S)-toluene-4-sulfonic acid 3-(3-fluorophenyl)-3-[3-(3-methoxyphenyl)-indol-1-yl]-2-hydroxy-propyl ester was prepared from (2S,3S)-3-(3-fluorophenyl)-3-{3-[3-methoxyphenyl]-1H-indol-1-yl}propane-1,2-diol.

In an analogous manner to EXAMPLE 5, (1S,2R)-1-(3-fluorophenyl)-1-[3-(3-methoxyphenyl)-1H-indol-1-yl]-3-(methylamino)propan-2-ol hydrochloride was prepared from (2S,3S)-toluene-4-sulfonic acid 3-(3-fluorophenyl)-3-[3-(3-methoxyphenyl)-indol-1-yl]-2-hydroxy-propyl ester and methylamine (2N solution in methanol). MS (ESI) m/z 405.1; HRMS: calcd for C25H25FN2O2+H+, 405.19728. Found (ESI, [M+H]+), 405.196.

Example 173

(1S,2R)-1-(3-fluorophenyl)-3-(methylamino)-1-{3-[4-(trifluoromethyl)phenyl]-1H-indol-1-yl}propan-2-ol hydrochloride

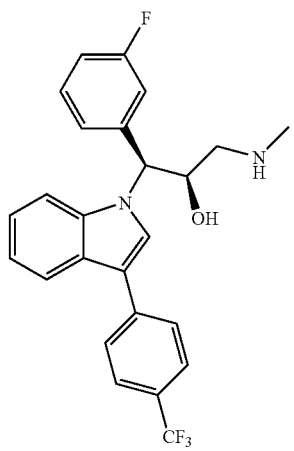

In an analogous manner to EXAMPLE 114, step 2, (2S, 3S)-3-(3-fluorophenyl)-3-{3-[4-(trifluoromethyl)phenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 4-(trifluoromethyl)benzeneboronic acid.

In an analogous manner to EXAMPLE 1, step 2 (2S,3S)-toluene-4-sulfonic acid 3-(3-fluorophenyl)-3-[3-(4-(trifluoromethyl)phenyl)-indol-1-yl]-2-hydroxy-propyl ester was prepared from (2S,3S)-3-(3-fluorophenyl)-3-{3-[4-(trifluoromethyl)phenyl]-1H-indol-1-yl}propane-1,2-diol.

In an analogous manner to EXAMPLE 5 (1S,2R)-1-(3-fluorophenyl)-3-(methylamino)-1-{3-[4-(trifluoromethyl)phenyl]-1H-indol-1-yl}propan-2-ol hydrochloride was prepared from (2S,3S)-toluene-4-sulfonic acid 3-(3-fluorophenyl)-3-[3-(4-(trifluoromethyl)phenyl)-indol-1-yl]-2-hydroxy-propyl ester and methylamine (2N solution in methanol). MS (ESI) m/z 443.1.

Example 174

(1S,2R)-1-(3,5-difluorophenyl)-1-(6-fluoro-2,3-dihydro-1H-indol-1-yl)-3-(methylamino)propan-2-ol hydrochloride

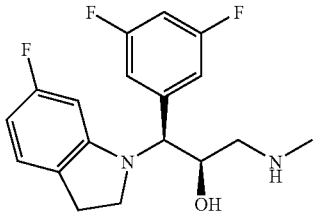

In an analogous manner to EXAMPLE 47, step 4, (2S,3S)-3-(3,5-difluorophenyl)-3-(6-fluoro-2,3-dihydro-1H-indol-1-yl)propane-1,2-diol was prepared from 6-fluoroindoline and [(2R,3R)-3-(3-fluorophenyl)oxiran-2-yl]methanol (EXAMPLE 47, step 3) as a viscous, yellowish liquid. MS (ES) m/z 324.1 ([M+H]$^+$); HRMS: calcd for $C_{17}H_{16}F_3NO_2$+H$^+$, 324.1211. Found (ESI, [M+H]$^+$), 324.1226.

In an analogous manner to EXAMPLE 47, step 6, (1S,2R)-1-(3,5-difluorophenyl)-1-(6-fluoro-2,3-dihydro-1H-indol-1-yl)-3-(methylamino)propan-2-ol hydrochloride was prepared from (2S,3S)-3-(3,5-difluorophenyl)-3-(6-fluoro-2,3-dihydro-1H-indol-1-yl)propane-1,2-diol as a white powder. MS (ES) m/z 337.3 ([M+H]$^+$); HRMS: calcd for $C_{18}H_{19}F_3N_2O$+H$^+$, 337.1522. Found (ESI, [M+H]$^+$), 337.1505.

Example 175

(1S,2R)-1-(3-fluorophenyl)-3-(methylamino)-1-{3-[2-(trifluoromethyl)phenyl]-1H-indol-1-yl}propan-2-ol hydrochloride

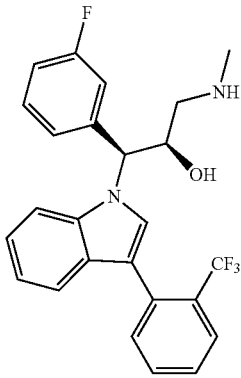

In an analogous manner to EXAMPLE 114, step 2, (2S,3S)-3-(3-fluorophenyl)-3-{3-[2-(trifluoromethyl)phenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 2-(trifluoromethyl)boronic acid.

In an analogous manner to EXAMPLE 1, step 2, (2S,3S)-toluene-4-sulfonic acid 3-(3-fluorophenyl)-2-hydroxy-3-[3-(2-(trifluoromethyl)phenyl)-indol-1-yl]-propyl ester was prepared from (2S,3S)-3-(3-fluorophenyl)-3-{3-[2-(trifluoromethyl)phenyl]-1H-indol-1-yl}propane-1,2-diol.

In an analogous manner to EXAMPLE 5, (1S,2R)-1-(3-fluorophenyl)-3-(methylamino)-1-{3-[2-(trifluoromethyl)phenyl]-1H-indol-1-yl}propan-2-ol hydrochloride was prepared from (2S,3S)-toluene-4-sulfonic acid 3-(3-fluorophenyl)-2-hydroxy-3-[3-(2-(trifluoromethyl)phenyl)-indol-1-yl]-propyl ester and methylamine (2N solution in methanol). MS (ESI) m/z 443.1; HRMS: calcd for C25H22F4N2O+H+, 443.17410. Found (ESI, [M+H]+), 443.172.

Example 176

(1S,2R)-1-(3-fluorophenyl)-1-[3-(2-methoxyphenyl)-1H-indol-1-yl]-3-(methylamino)propan-2-ol hydrochloride

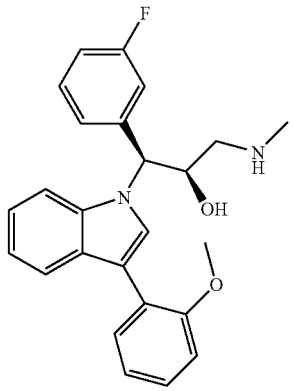

In an analogous manner to EXAMPLE 114, step 2, (2S,3S)-3-(3-fluorophenyl)-3-{3-[2-methoxyphenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 2-methoxybenzeneboronic acid.

In an analogous manner to EXAMPLE 1, step 2, (2S,3S)-toluene-4-sulfonic acid 3-(3-fluorophenyl)-3-[3-(2-methoxyphenyl)-indol-1-yl]-2-hydroxy-propyl ester was prepared from (2S,3S)-3-(3-fluorophenyl)-3-{3-[2-methoxyphenyl]-1H-indol-1-yl}propane-1,2-diol.

In an analogous manner to EXAMPLE 5, (1S,2R)-1-(3-fluorophenyl)-1-[3-(2-methoxyphenyl)-1H-indol-1-yl]-3-(methylamino)propan-2-ol hydrochloride was prepared from (2S,3S)-toluene-4-sulfonic acid 3-(3-fluorophenyl)-3-[3-(2-methoxyphenyl)-indol-1-yl]-2-hydroxy-propyl ester and methylamine (2N solution in methanol). MS (ESI) m/z 405.1; HRMS: calcd for C25H25FN2O2+H+, 405.19728. Found (ESI, [M+H]+), 405.1984.

Example 177

(1S,2R)-1-(3-fluorophenyl)-3-(methylamino)-1-{3-[3-(trifluoromethyl)phenyl]-1H-indol-1-yl}propan-2-ol hydrochloride

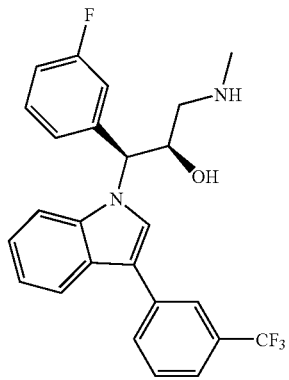

In an analogous manner to EXAMPLE 114, step 2, (2S,3S)-3-(3-fluorophenyl)-3-{3-[3-(trifluoromethyl)phenyl]-

1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 3-(trifluoromethyl)benzeneboronic acid.

In an analogous manner to EXAMPLE 1, step 2, (2S,3S)-toluene-4-sulfonic acid 3-(3-fluorophenyl)-3-[3-(3-(trifluoromethyl)phenyl)-indol-1-yl]-2-hydroxy-propyl ester was prepared from (2S,3S)-3-(3-fluorophenyl)-3-{3-[3-(trifluoromethyl)phenyl]-1H-indol-1-yl}propane-1,2-diol.

In an analogous manner to EXAMPLE 5, (1S,2R)-1-(3-fluorophenyl)-3-(methylamino)-1-{3-[3-(trifluoromethyl)phenyl]-1H-indol-1-yl}propan-2-ol hydrochloride was prepared (2S,3S)-toluene-4-sulfonic acid 3-(3-fluorophenyl)-3-[3-(3-(trifluoromethyl)phenyl)-indol-1-yl]-2-hydroxy-propyl ester and methylamine (2N solution in methanol). MS (ESI) m/z 443.1; HRMS: calcd for C25H22F4N2O+H+, 443.17410. Found (ESI, [M+H]+), 443.1764.

Example 178

(1S,2R)-3-amino-1-(3-methyl-1H-indol-1-yl)-1-phenylpropan-2-ol hydrochloride

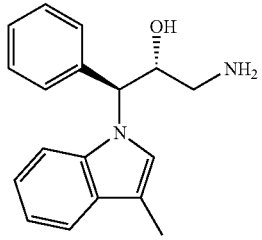

In an analogous manner to EXAMPLE 117, step 5 (2S,3S)-3-(3-methyl-indol-1-yl)-3-phenyl-propane-1,2-diol was prepared from 3-methylindole and [(2R,3R)-3-phenyloxiran-2-yl]methanol (EXAMPLE 117, step 4) as an oil. MS (ESI) m/z 282 ([M+H]+).

In an analogous manner to EXAMPLE 117, step 6 (1S,2R)-3-amino-1-(3-methyl-1H-indol-1-yl)-1-phenylpropan-2-ol hydrochloride was prepared from (2S,3S)-3-(3-methyl-indol-1-yl)-3-phenyl-propane-1,2-diol and para-toluenesulfonic acid followed by concentrated ammonium hydroxide as an off-white solid. MS (ESI) m/z 281.

Example 179

(1S,2R)-1-(7-fluoro-3-methyl-1H-indol-1-yl)-3-(methylamino)-1-phenylpropan-2-ol hydrochloride

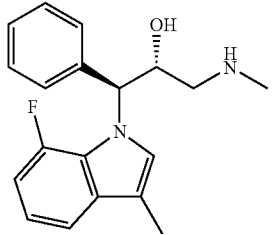

In an analogous manner to EXAMPLE 117, step 1 ethyl 7-fluoro-3-methyl-1H-indole-2-carboxylate was prepared from 2-fluoroaniline as a brownish solid. MS (ESI) m/z 221.

In an analogous manner to EXAMPLE 117, step 2 7-fluoro-3-methyl-1H-indole-2-carboxylic acid was prepared from ethyl 7-fluoro-3-methyl-1H-indole-2-carboxylate as a green solid. MS (ESI) m/z 192.

In an analogous manner to EXAMPLE 117, step 3 7-fluoro-3-methyl-1H-indole was prepared from 7-fluoro-3-methyl-1H-indole-2-carboxylic acid as a white solid. MS (ESI) m/z 150.

In an analogous manner to EXAMPLE 117, step 5 (2S,3S)-3-(7-fluoro-3-methyl-1H-indol-1-yl)-3-phenylpropane-1,2-diol was prepared from 7-fluoro-3-methyl-1H-indole and [(2R,3R)-3-phenyloxiran-2-yl]methanol (EXAMPLE 117, Step 4) as an oil. MS (ESI) m/z 300.

In an analogous manner to EXAMPLE 117, step 6 (1S,2R)-1-(7-fluoro-3-methyl-1H-indol-1-yl)-3-(methylamino)-1-phenylpropan-2-ol hydrochloride was prepared from (2S,3S)-3-(7-fluoro-3-methyl-1H-indol-1-yl)-3-phenylpropane-1,2-diol as a white solid. MS (ES) m/z 313.1.

Example 180

(1S,2R)-3-amino-1-(7-fluoro-3-methyl-1H-indol-1-yl)-1-phenylpropan-2-ol hydrochloride

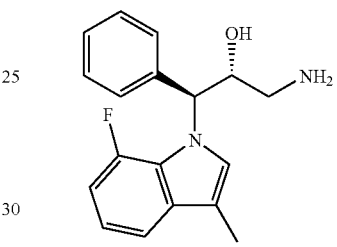

In an analogous manner to EXAMPLE 117, step 6 3-amino-1-(7-fluoro-3-methyl-1H-indol-1-yl)-1-phenylpropan-2-ol hydrochloride was prepared from (2S,3S)-3-(7-fluoro-3-methyl-1H-indol-1-yl)-3-phenylpropane-1,2-diol (EXAMPLE 179, step 4) and para-toluenesulfonic acid followed by ammonium hydroxide as a white solid. MS (ES) m/z 299.0.

Example 181

(1S,2R)-1-(7-fluoro-1H-indol-1-yl)-3-(methylamino)-1-phenylpropan-2-ol hydrochloride

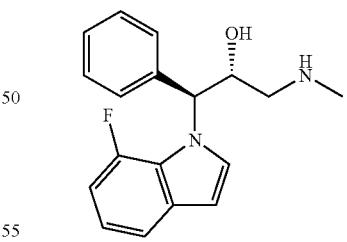

In an analogous manner to EXAMPLE 117, step 5 (2S,3S)-3-(7-fluoro-1H-indol-1-yl)-3-phenylpropane-1,2-diol was prepared from 7-fluoro-1H-indole and [(2R,3R)-3-phenyloxiran-2-yl]methanol (EXAMPLE 117, Step 4) as an oil. MS (ES) m/z 286.1.

In an analogous manner to EXAMPLE 117, step 6 (1S,2R)-1-(7-fluoro-1H-indol-1-yl)-3-(methylamino)-1-phenylpropan-2-ol hydrochloride was prepared from (2S,3S)-3-(7-fluoro-1H-indol-1-yl)-3-phenylpropane-1,2-diol as a pinkish solid. MS (ESI) m/z 299.

Example 182

(1S,2R)-1-(4-fluoro-1H-indol-1-yl)-3-(methylamino)-1-phenylpropan-2-ol hydrochloride

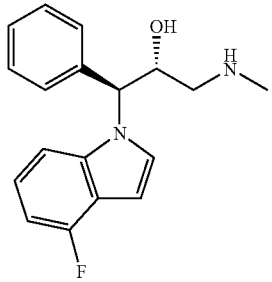

In an analogous manner to EXAMPLE 117, step 5 (2S,3S)-3-(4-fluoro-1H-indol-1-yl)-3-phenylpropane-1,2-diol was prepared from 4-fluoro-1H-indole and [(2R,3R)-3-phenyloxiran-2-yl]methanol (EXAMPLE 117, Step 4) as an oil. MS (ES) m/z 286.1.

In an analogous manner to EXAMPLE 117, step 6 (1S,2R)-1-(4-fluoro-1H-indol-1-yl)-3-(methylamino)-1-phenylpropan-2-ol hydrochloride was prepared from (2S,3S)-3-(4-fluoro-1H-indol-1-yl)-3-phenylpropane-1,2-diol as a white solid. MS (ESI) m/z 299.

Example 183

(1S,2R)-1-(7-fluoro-1H-indol-1-yl)-1-(3-fluorophenyl)-3-(methylamino)propan-2-ol hydrochloride

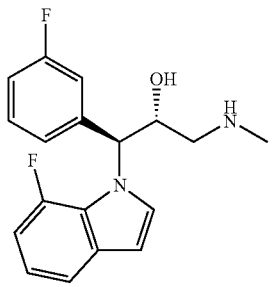

In an analogous manner to EXAMPLE 117, step 5 (2S,3S)-3-(7-fluoro-1H-indol-1-yl)-3-(3-fluorophenyl)propane-1,2-diol; was prepared from 7-fluoro-1H-indole and [(2R,3R)-3-(3-fluorophenyl)oxiran-2-yl]methanol (EXAMPLE 47, Step 3) as a brown oil. MS (ESI) m/z 304.

In an analogous manner to EXAMPLE 117, step 6 (1S,2R)-1-(7-fluoro-1H-indol-1-yl)-1-(3-fluorophenyl)-3-(methylamino)propan-2-ol hydrochloride was prepared from (2S,3S)-3-(7-fluoro-1H-indol-1-yl)-3-(3-fluorophenyl)propane-1,2-diol as a pinkish solid. MS (ESI) m/z 317.

Example 184

(1S,2R)-1-(4-fluoro-1H-indol-1-yl)-1-(3-fluorophenyl)-3-(methylamino)propan-2-ol hydrochloride

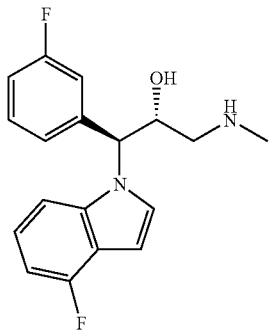

In an analogous manner to EXAMPLE 117, step 5 (2S,3S)-3-(4-fluoro-1H-indol-1-yl)-3-(3-fluorophenyl)propane-1,2-diol was prepared from 4-fluoro-1H-indole and [(2R,3R)-3-(3-fluorophenyl)oxiran-2-yl]methanol (EXAMPLE 47, Step 3) as a brown oil. MS (ESI) m/z 304.

In an analogous manner to EXAMPLE 117, step 6 (1S,2R)-1-(4-fluoro-1H-indol-1-yl)-1-(3-fluorophenyl)-3-(methylamino)propan-2-ol hydrochloride was prepared from (2S,3S)-3-(4-fluoro-1H-indol-1-yl)-3-(3-fluorophenyl)propane-1,2-diol as a white solid. MS (ESI) m/z 317.

Example 185

(1S,2R)-1-(3-fluorophenyl)-3-(methylamino)-1-[5-(trifluoromethyl)-1H-indol-1-yl]propan-2-ol hydrochloride

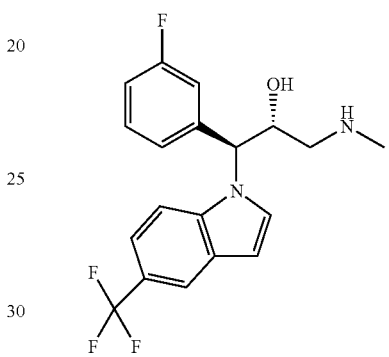

In an analogous manner to EXAMPLE 117, step 5 (2S,3S)-3-(3-fluorophenyl)-3-(5-trifluoromethyl-1H-indol-1-yl)-propane-1,2-diol was prepared from 5-trifluoromethyl-1H-indole and [(2R,3R)-3-(3-fluorophenyl)oxiran-2-yl]methanol (EXAMPLE 47, Step 3).

In an analogous manner to EXAMPLE 117, step 6 (1S,2R)-1-(3-fluorophenyl)-3-(methylamino)-1-[5-(trifluoromethyl)-1H-indol-1-yl]propan-2-ol hydrochloride was prepared from (2S,3S)-3-(3-fluorophenyl)-3-(5-trifluoromethyl-1H-indol-1-yl)-propane-1,2-diol as an off-white solid. MS (ESI) m/z 367.

Example 186

(1S,2R)-1-(6-fluoro-1H-indol-1-yl)-3-(methylamino)-1-phenylpropan-2-ol hydrochloride

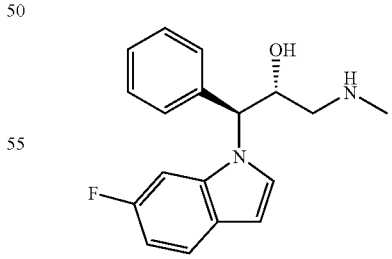

In an analogous manner to EXAMPLE 117, step 5 (2S,3S)-3-(6-fluoro-1H-indol-1-yl)-3-phenylpropane-1,2-diol was prepared from 6-fluoro-1H-indole and [(2R,3R)-3-phenyloxiran-2-yl]methanol (EXAMPLE 117, Step 4) as a brown oil. MS (ES) m/z 286.1.

In an analogous manner to EXAMPLE 117, step 6 (1S,2R)-1-(6-fluoro-1H-indol-1-yl)-3-(methylamino)-1-phenylpropan-2-ol hydrochloride was prepared from (2S,3S)-3-(6-fluoro-1H-indol-1-yl)-3-phenylpropane-1,2-diol as a white solid. MS (ESI) m/z 299.

Example 187

(1S,2R)-3-(methylamino)-1-phenyl-1-[6-(trifluoromethyl)-1H-indol-1-yl]propan-2-ol hydrochloride

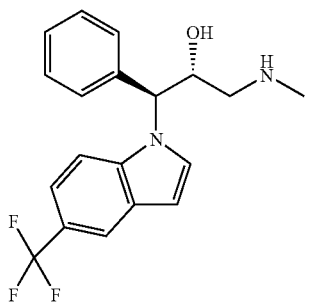

In an analogous manner to EXAMPLE 117, step 5 (2S,3S)-3-phenyl-3-[6-(trifluoromethyl)-1H-indol-1-yl]propane-1,2-diol was prepared from 6-trifluoromethyl-1H-indole and [(2R,3R)-3-phenyloxiran-2-yl]methanol (EXAMPLE 117, Step 4) as a brown oil. MS (ES) m/z 336.

In an analogous manner to EXAMPLE 117, step 6 (1S,2R)-3-(methylamino)-1-phenyl-1-[6-(trifluoromethyl)-1H-indol-1-yl]propan-2-ol hydrochloride was prepared from (2S,3S)-3-phenyl-3-[6-(trifluoromethyl)-1H-indol-1-yl]propane-1,2-diol as a white solid. MS (ESI) m/z 349.

Example 188

(1S,2R)-3-(methylamino)-1-phenyl-1-[5-(trifluoromethyl)-1H-indol-1-yl]propan-2-ol hydrochloride

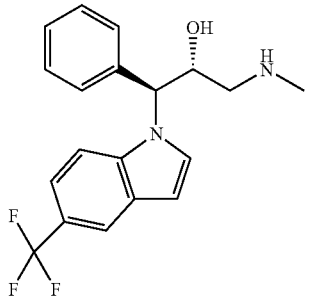

In an analogous manner to EXAMPLE 117, step 5 (2S,3S)-3-phenyl-3-[5-(trifluoromethyl)-1H-indol-1-yl]propane-1,2-diol was prepared from 5-trifluoromethyl-1H-indole and [(2R,3R)-3-phenyloxiran-2-yl]methanol (EXAMPLE 117, Step 4) as a brown oil. MS (ES) m/z 336.

In an analogous manner to EXAMPLE 117, step 6 (1S,2R)-3-(methylamino)-1-phenyl-1-[5-(trifluoromethyl)-1H-indol-1-yl]propan-2-ol hydrochloride was prepared from (2S,3S)-3-phenyl-3-[5-(trifluoromethyl)-1H-indol-1-yl]propane-1,2-diol as an off-white solid. MS (ESI) m/z 349.2.

Example 189

(1S,2R)-1-(3-tert-butyl-1H-indol-1-yl)-1-(3-fluorophenyl)-3-(methylamino)propan-2-ol

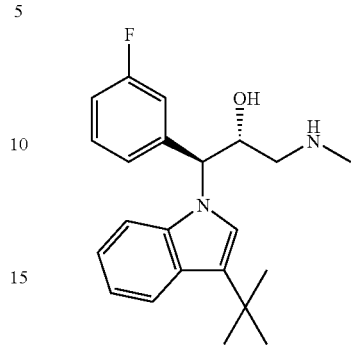

Step 1: To a mixture of indole (5 g, 42.7 mmol), zinc triflate (9.3 g, 25.6 mmol), and tetrabutylammonium iodide (7.9 g, 21.4 mmol) in anhydrous toluene (120 mL) was added diisopropylethylamine (8.2 mL, 47 mmol) at room temperature under a blanket of nitrogen. After the reaction was stirred 15 minutes at room temperature, the reaction mixture was treated with tert-butyl bromide (2.5 mL, 21.7 mmol). The reaction solution was stirred at room temperature under nitrogen for 3 hours, then poured into a saturated aqueous solution of ammonium chloride (150 mL). The organic layer was separated and the aqueous layer was extracted with ethyl acetate (3×50 mL). The combined organic layers were dried over magnesium sulfate, concentrated, and the residue was purified via flash column chromatography (silica, 10% ethyl acetate in hexane) to afford 3-tert-butyl-1H-indole as a white solid. MS (ES) m/z 174.2.

In an analogous manner to EXAMPLE 117, step 5 (2S,3S)-3-(3-tert-butyl-1H-indol-1-yl)-3-(3-fluorophenyl)propane-1,2-diol was prepared from 3-tert-butyl-1H-indole and [(2R,3R)-3-(3-fluorophenyl)oxiran-2-yl]methanol (EXAMPLE 47, step 3).

In an analogous manner to EXAMPLE 117, step 6 (1S,2R)-1-(3-tert-butyl-1H-indol-1-yl)-1-(3-fluorophenyl)-3-(methylamino)propan-2-ol was prepared from (2S,3S)-3-(3-tert-butyl-1H-indol-1-yl)-3-(3-fluorophenyl)propane-1,2-diol as a clear oil. MS (ESI) m/z 355.3.

Example 190

(1S,2R)-1-(1H-indol-1-yl)-2-methyl-3-(methylamino)-1-phenylpropan-2-ol hydrochloride

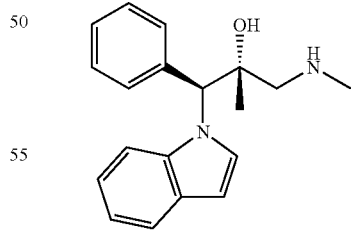

In an analogous manner to EXAMPLE 117, step 4 [(2R,3R)-2-methyl-3-phenyloxiran-2-yl]methanol was prepared from 2-methyl-3-phenylprop-2-en-1-ol as a white crystal. MS (ES) m/z 147.1.

In an analogous manner to EXAMPLE 117, step 5 (2S,3S)-2-methyl-3-phenyl-[1H-indol-1-yl]propane-1,2-diol was prepared from [(2R,3R)-2-methyl-3-phenyloxiran-2-yl]methanol (EXAMPLE 117, step 4) and indole In an analogous manner to EXAMPLE 117, step 6 (1S,2R)-1-(1H-indol- 1-yl)-2-methyl-3-(methylamino)-1-phenylpropan-2-ol hydrochloride was prepared from (2S,3S)-2-methyl-3-phenyl-[1H-indol-1-yl]propane-1,2-diol as a white solid. MS (ES) m/z 295.0.

Example 191

(2R,3S)-3-(1H-indol-1-yl)-1-(methylamino)-3-phenylbutan-2-ol hydrochloride

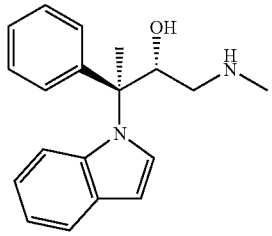

In an analogous manner to EXAMPLE 117, step 4 [(2R,3R)-3-methyl-3-phenyloxiran-2-yl]methanol was prepared from 3-methyl-3-phenylprop-2-en-1-ol as a white crystal. MS (ES) m/z 147.1.

In an analogous manner to EXAMPLE 47, step 4 (2S,3S)-3-(2,3-dihydro-1H-indol-1-yl)-3-phenylbutane-1,2-diol was prepared from [(2R,3R)-3-methyl-3-phenyloxiran-2-yl]methanol (EXAMPLE 117, step 4) and indoline as a brown solid. MS (ES) m/z 284.1.

In an analogous manner to EXAMPLE 47, step 5 (2S,3S)-3-(1H-indol-1-yl)-3-phenylbutane-1,2-diol was prepared from (2S,3S)-3-(2,3-dihydro-1H-indol-1-yl)-3-phenylbutane-1,2-diol as an off-white solid. MS (ESI) m/z 282.

In an analogous manner to EXAMPLE 117, step 6 (2R,3S)-3-(1H-indol-1-yl)-1-(methylamino)-3-phenylbutan-2-ol hydrochloride was prepared from (2S,3S)-3-(1H-indol-1-yl)-3-phenylbutane-1,2-diol as a white solid. MS (ES) m/z 295.1.

Example 192

1-tert-Butyl-3-(2-hydroxy-3-methylamino-1-phenylpropyl)-1,3-dihydro-benzoimidazol-2-one hydrochloride

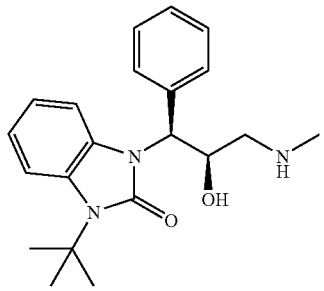

Step 1: To a solution of 1-fluoro-2-nitro-benzene (1 g, 7.1 mmol) in dimethylformamide (15 mL) was added tert-butyl amine (0.82 mL, 7.81 mmol) at room temperature, and the reaction mixture stirred for 12 hours at room temperature under nitrogen. Upon completion, the reaction mixture was poured into a saturated aqueous solution of sodium chloride (50 mL) and extracted with ethyl acetate (50 mL). The organic layer was dried over anhydrous sodium sulfate, concentrated in vacuo, and the residue was purified via flash column chromatography (silica, 1% ethyl acetate in hexane) to give tert-butyl-(2-nitrophenyl)-amine as an orange oil. MS (ES) m/z 195.2

Step 2: To a solution of tert-butyl-(2-nitrophenyl)-amine (1.27 g, 6.5 mmol), 5% palladium on carbon (0.5 g), and sodium borohydride (0.49 g, 13.1 mmol) in tetrahydrofuran (20 mL) was added methanol (10 mL) in a dropwise manner. Upon completion of the reaction, it was filtered through a pad of Celite and the filtrate was poured into a saturated aqueous solution of ammonium chloride (50 mL), and extracted with ethyl acetate (50 mL). The organic layer was dried over anhydrous magnesium sulfate, concentrated in vacuo to give N-tert-butyl-benzene-1,2-diamine which was used in the next step without further purification. A solution of N-t-butyl-benzene-1,2-diamine (1.1 g, 6.7 mmol) and carbonyldiimidazole (1.63 g, 10 mmol) in anhydrous tetrahydrofuran (50 mL) was stirred at room temperature for 12 hours. Upon completion, the reaction was poured into a 1 N aqueous solution of hydrochloric acid (50 mL) and extracted with ethyl acetate (50 mL). The organic layer was dried over anhydrous sodium sulfate and concentrated in vacuo. The crude product was purified via flash column chromatography (silica, 50% ethyl acetate in hexane) to give 1-tert-butyl-1,3-dihydro-benzimidazol-2-one as an off-white solid. MS (ES) m/z 191.1.

Step 3: A mixture of 1-tert-butyl-1,3-dihydro-benzimidazol-2-one (0.66 g, 3.5 mmol) and sodium hydride (60% dispersion in mineral oil, 0.15 g, 3.8 mmol) in anhydrous dimethylformamide (4 mL) was stirred for 10 minutes under nitrogen at room temperature. A solution of [(2R,3R)-3-phenyloxiran-2-yl]methanol (EXAMPLE 117, step 4, 1.07 g, 7.1 mmol) and titanium isopropoxide (2.14 mL, 7.1 mmol) in dimethylformamide (4 mL) that was aged for 20 minutes was then added and the mixture was stirred at room temperature under nitrogen for 12 hours. After disappearance of the epoxide, the mixture was partitioned between a 1N aqueous solution of hydrochloric acid (50 mL) and ethyl acetate (50 mL). The organic layer was separated, washed with saturated sodium bicarbonate (50 mL), dried over anhydrous sodium sulfate, filtered, and concentrated in vacuo. The residue was purified via silica gel column (60% ethyl acetate in hexane) to give 1-tert-butyl-3-[(1S,2S)-2,3-dihydroxy-1-phenyl-propyl]-1,3-dihydro-2H-benzimidazol-2-one as an oil. MS (ES) m/z 341.2.

Step 4: A solution of 1-tert-butyl-3-[(1S,2S)-2,3-dihydroxy-1-phenyl-propyl]-1,3-dihydro-2H-benzimidazol-2-one (0.55 g, 1.6 mmol) and para-toluenesulfonyl chloride (0.37 g, 1.9 mmol) in anhydrous pyridine (5 mL) was stirred at room temperature under nitrogen for 12 hours. The reaction was poured into a cold 1N aqueous solution of hydrochloric acid (50 mL) and extracted with ethyl acetate (50 mL). The organic layer was dried over anhydrous sodium sulfate, filtered, and concentrated to give (2S,3S)-toluene-4-sulfonic acid 3-(3-tert-butyl-2-oxo-2,3-dihydro-benzimidazol-1-yl)-2-hydroxy-3-phenyl-propyl ester. To a solution of (2S,3S)-toluene-4-sulfonic acid 3-(3-tert-butyl-2-oxo-2,3-dihydro-benzimidazol-1-yl)-2-hydroxy-3-phenyl-propyl ester (0.8 g, 1.6 mmol) in methanol (10 mL) was added a 2N solution of methylamine in methanol (4 mL, 8 mmol) and the reaction mixture stirred for 12 hours at room temperature in a sealed tube. Upon completion, the reaction was partitioned between a saturated aqueous solution of sodium bicarbonate (50 mL) and ethyl acetate (50 mL). The organic layer was separated, dried over anhydrous sodium sulfate, filtered, and concentrated in vacuo. The residue was purified via flash column chromatography (silica, 20% MeOH in dichloromethane) to give 1-tert-butyl-3-[(1S,2R)-2-hydroxy-3-methylamino-1-phenylpropyl]-1,3-dihydro-2H-benzimidazol-2-one as a clear oil. The free base was dissolved in a minimum amount of ethanol and treated with a 2N ethereal solution of hydrochloric acid and stirred for 1 hour s. The ethanol was removed in vacuo and the clear oil was triturated with diethyl ether/dichloromethane to give 1-tert-butyl-3-[(1S,2R)-2-hydroxy-3-(methylamino)-1-phenylpropyl]-1,3-dihydro-2H-benz-

Example 193

1-[(1S,2R)-2-hydroxy-3-(methylamino)-1-phenyl-propyl]-3-propyl-1,3-dihydro-2H-benzimidazol-2-one hydrochloride

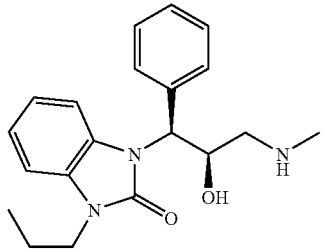

In an analogous manner to EXAMPLE 192, step 1 2-nitro-N-propylaniline was prepared from 1-fluoro-2-nitro-benzene and propyl amine. MS (ES) m/z 181.1.

In an analogous manner to EXAMPLE 192, step 2 1-propyl-1,3-dihydro-2H-benzimidazol-2-one was prepared from 2-nitro-N-propylaniline. MS (ES) m/z 177.1.

In an analogous manner to EXAMPLE 192, step 3 1-propyl-3-[(1S,2S)-2,3-dihydroxy-1-phenyl-propyl]-1,3-dihydro-2H-benzimidazol-2-one was prepared from 1-propyl-1,3-dihydro-2H-benzimidazol-2-one and [(2R,3R)-3-phenyloxiran-2-yl]methanol (EXAMPLE 117, step 4).

In an analogous manner to EXAMPLE 192, step 4 1-[(1S,2R)-2-hydroxy-3-(methylamino)-1-phenylpropyl]-3-propyl-1,3-dihydro-2H-benzimidazol-2-one hydrochloride was prepared from 1-propyl-3-[(1S,2S)-2,3-dihydroxy-1-phenyl-propyl]-1,3-dihydro-2H-benzimidazol-2-one as a white solid. HRMS: calcd for $C_{20}H_{25}N_3O_2+H^+$, 340.20195. Found (ESI, [M+H]$^+$), 340.2007

Example 194

5-bromo-1-[(1S,2R)-2-hydroxy-3-(methylamino)-1-phenylpropyl]-3,3-dimethyl-1,3-dihydro-2H-indol-2-one hydrochloride

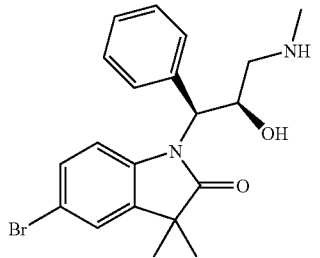

Step 1: In an analogous manner to EXAMPLE 99, step 6 5-bromo-1-[(2S,3S)-2,3-dihydroxy-1-phenylpropyl]-3,3-dimethyl-1,3-dihydro-2H-indol-2-one was prepared from 5-bromo-3,3-dimethyl-1,3-dihydro-indol-2-one[20] and [(2R, 3R)-3-phenyloxiran-2-yl]methanol (EXAMPLE 117, step 4). MS (ESI) m/z 391 ([M+H]$^+$).

[20]WO 00/66166

Step 2: In an analogous manner to EXAMPLE 1, step 2 (2S, 3S)-toluene-4-sulfonic acid 3-(5-bromo-3,3-dimethyl-2-oxo-2,3-dihydro-indol-1-yl)-2-hydroxy-3-phenyl-propyl ester was prepared from (5-bromo-1-[(2S,3S)-2,3-dihydroxy-1-phenylpropyl]-3,3-dimethyl-1,3-dihydro-2H-indol-2-one). MS (ESI) m/z 545 ([M+H]$^+$).

Step 3: In an analogous manner to EXAMPLE 5 5-bromo-1-[(1S,2R)-2-hydroxy-3-(methylamino)-1-phenylpropyl]-3,3-dimethyl-1,3-dihydro-2H-indol-2-one hydrochloride was prepared from (2S, 3S)-toluene-4-sulfonic acid 3-(5-bromo-3,3-dimethyl-2-oxo-2,3-dihydro-indol-1-yl)-2-hydroxy-3-phenyl-propyl ester. MS m/z 404 ([M+H]$^+$), HRMS: calcd for $C20H23BrN2O2+H^+$, 403.10156. Found (ESI, [M+H]$^+$), 403.0998.

Example 195

6-fluoro-1-[(1S,2R)-2-hydroxy-3-(methylamino)-1-phenylpropyl]-3,3-dimethyl-1,3-dihydro-2H-indol-2-one hydrochloride

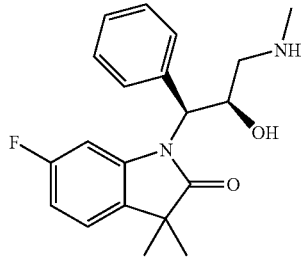

Step 1: In an analogous manner to EXAMPLE 99, step 2 dimethyl (4-fluoro-2-nitrophenyl)malonate was prepared from 2,5-difluoronitrobenzene and dimethyl malonate. MS (ESI) m/z 272 ([M+H]$^+$).

Step 2: In an analogous manner to EXAMPLE 99, step 3 (4-fluoro-2-nitrophenyl)acetic acid was prepared from dimethyl (4-fluoro-2-nitrophenyl)malonate. MS (ESI) m/z 200 ([M+H]$^+$).

Step 3: In an analogous manner to EXAMPLE 99, step 4 6-fluoro-1,3-dihydro-2H-indol-2-one was prepared from (4-fluoro-2-nitrophenyl) acetic acid. MS (ESI) m/z 152 ([M+H]$^+$)

Step 4: In an analogous manner to EXAMPLE 99, step 5 6-fluoro-3,3-dimethyl-1,3-dihydro-2H-indol-2-one was prepared from 6-fluoro-1,3-dihydro-2H-indol-2-one. MS (ESI) m/z 180 ([M+H]$^+$.

Step 5: In an analogous manner to EXAMPLE 99, step 6 (2S, 3S)-1-(2,3-dihydroxy-1-phenyl-propyl)-6-fluoro-3,3-dimethyl-1,3-dihydro-indol-2-one was prepared from 6-fluoro-3,3-dimethyl-1,3-dihydro-2H-indol-2-one and [(2R, 3R)-3-phenyloxiran-2-yl]methanol (EXAMPLE 117, step 4). MS (ESI) m/z 330 ([M+H]$^+$).

Step 6: In an analogous manner to EXAMPLE 1, step 2 (2S, 3S)-toluene-4-sulfonic acid 3-(6-fluoro-3,3-dimethyl-2-oxo-2,3-dihydro-indol-1-yl)-2-hydroxy-3-phenyl-propyl ester was prepared from (2S,3S)-1-(2,3-dihydroxy-1-phenyl-propyl)-6-fluoro-3,3-dimethyl-1,3-dihydro-indol-2-one. MS (ESI) m/z 484 ([M+H]$^+$).

Step 7: A solution of (2S, 3S)-toluene-4-sulfonic acid 3-(6-fluoro-3,3-dimethyl-2-oxo-2,3-dihydro-indol-1-yl)-2-hydroxy-3-phenyl-propyl ester (367 mg, 0.76 mmol) and methylamine (20 mL, 8M solution in ethanol) was stirred in a sealed tube for 16 hours. The solution was concentrated in vacuo to give 250 mg of the crude product. The crude product was purified via Biotage chromatography (FlasH40i, silica, 5%, 8% and 10% methanol with ammonia/dichloromethane) to give 77 mg of impure desired product. Final purification by reverse phase HPLC (X-terra MS $C_{18}$ 19×150 mm, using an isocratic mixture of 60% methanol/water with 0.05% ammonium hydroxide at a rate of 20 mL/minute at 250 nm) gave 35 mg of desired product as the free base. The free base was treated with a 1 M ethereal solution of hydrochloric acid until the solution was pH=3 followed by diethyl ether. The product was crystallized by adding a minimum of hexane to afford the title compound 6-fluoro-1-[(1S,2R)-2-hydroxy-3-(methylamino)-1-phenylpropyl]-3,3-dimethyl-1,3-dihydro-2H-indol-2-one hydrochloride. MS (ESI) m/z 343 ([M+H]$^+$); HRMS: calcd for C20H23FN2O2+H$^+$, 343.18163. Found (ESI, [M+H]$^+$), 343.18.

Example 196

4-fluoro-1-[(1S,2R)-2-hydroxy-3-(methylamino)-1-phenylpropyl]-3,3-dimethyl-1,3-dihydro-2H-indol-2-one hydrochloride

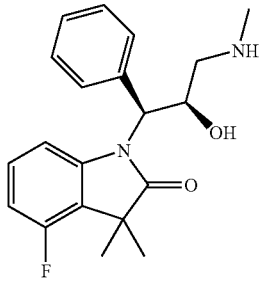

Step 1: In an analogous manner to EXAMPLE 99, step 1 1,2-difluoro-3-nitro-benzene was prepared from 2,3-Difluoro-phenylamine and a mixture of sodium perborate tetrahydrate. MS (ESI) m/z 160 ([M+H]$^+$).

Step 2: In an analogous manner to EXAMPLE 99, step 2 dimethyl (2-fluoro-6-nitrophenyl) malonate was prepared from 1,2-difluoro-3-nitro-benzene. MS (ESI) m/z 272.0576.

Step 3: In an analogous manner to EXAMPLE 99, step 3 (2-fluoro-6-nitrophenyl) acetic acid was prepared from dimethyl (2-fluoro-6-nitrophenyl)malonate. MS (ESI) m/z 200 ([M+H]$^+$).

Step 4: In an analogous manner to EXAMPLE 99, step 4 4-fluoro-1,3-dihydro-2H-indol-2-one was prepared from (2-fluoro-6-nitrophenyl)acetic acid. MS (ESI) m/z 152 ([M+H]$^+$).

Step 5: In an analogous manner to EXAMPLE 99, step 5 4-fluoro-3,3-dimethyl-1,3-dihydro-2H-indol-2-one was prepared from 4-fluoro-1,3-dihydro-2H-indol-2-one. MS (ESI) m/z 180 ([M+H]$^+$).

Step 6: In an analogous manner to EXAMPLE 99, step 6 1-[(2S,3S)-2,3-dihydroxy-1-phenylpropyl]-4-fluoro-3,3-dimethyl-1,3-dihydro-2H-indol-2-one was prepared from 4-fluoro-3,3-dimethyl-1,3-dihydro-2H-indol-2-one and [(2R, 3R)-3-phenyloxiran-2-yl]methanol (EXAMPLE 117, step 4). MS (ESI) m/z 330 ([M+H]$^+$).

Step 7: In an analogous manner to EXAMPLE 1 step 2, (2S,3S)-toluene-4-sulfonic acid 3-(4-fluoro-3,3-dimethyl-2-oxo-2,3-dihydro-indol-1-yl)-2-hydroxy-3-phenyl-propyl ester was prepared from 1-[(1S,2S)-2,3-dihydroxy-1-phenylpropyl]-4-fluoro-3,3-dimethyl-1,3-dihydro-2H-indol-2-one. MS (ESI) m/z 484 ([M+H]$^+$.

Step 8: In an analogous manner to EXAMPLE 195 step 7, 4-fluoro-1-[(1S,2R)-2-hydroxy-3-(methylamino)-1-phenylpropyl]-3,3-dimethyl-1,3-dihydro-2H-indol-2-one hydrochloride was prepared from (2S,3S)-toluene-4-sulfonic acid 3-(4-fluoro-3,3-dimethyl-2-oxo-2,3-dihydro-indol-1-yl)-2-hydroxy-3-phenyl-propyl ester. HRMS: calcd for C20H23FN2O2+H$^+$, 343.18163. Found (ESI, [M+H]$^+$), 343.1807.

Example 197

1-cyclobutyl-3-[(1S,2R)-2-hydroxy-3-(methylamino)-1-phenylpropyl]-1,3-dihydro-2H-benzimidazol-2-one hydrochloride

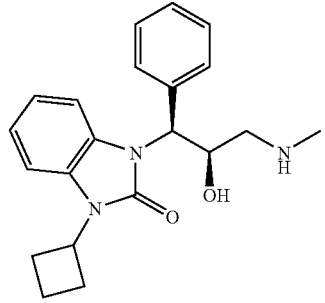

In an analogous manner to EXAMPLE 192, step 1 N-cyclobutyl-2-nitroaniline was prepared from 1-fluoro-2-nitrobenzene and cyclobutyl amine. MS (ES) m/z 193.

In an analogous manner to EXAMPLE 192, step 2 1-cyclobutyl-1,3-dihydro-2H-benzimidazol-2-one was prepared from N-cyclobutyl-2-nitroaniline. MS (ES) m/z 189.

In an analogous manner to EXAMPLE 192, step 3 1-cyclobutyl-3-[(1S,2S)-2,3-dihydroxy-1-phenyl-propyl]-1,3-dihydro-2H-benzimidazol-2-one was prepared from 1-cyclobutyl-1,3-dihydro-2H-benzimidazol-2-one and [(2R,3R)-3-phenyloxiran-2-yl]methanol (EXAMPLE 117, step 4). MS (ES) m/z 339.2.

In an analogous manner to EXAMPLE 192, step 4 1-cyclobutyl-3-[(1S,2R)-2-hydroxy-3-(methylamino)-1-phenylpropyl]-1,3-dihydro-2H-benzimidazol-2-one hydrochloride was prepared from 1-cyclobutyl-3-[(1S,2S)-2,3-dihydroxy-1-phenyl-propyl]-1,3-dihydro-2H-benzimidazol-2-one as a white solid. MS (ES) m/z 352.2. HRMS: calcd for $C_{21}H_{25}N_3O_2$+H+, 352.20195. Found (ESI, [M+H]$^+$), 352.207

Example 198

5-fluoro-3-[(1S,2R)-2-hydroxy-3-(methylamino)-1-phenylpropyl]-1-propyl-1,3-dihydro-2H-benzimidazol-2-one hydrochloride

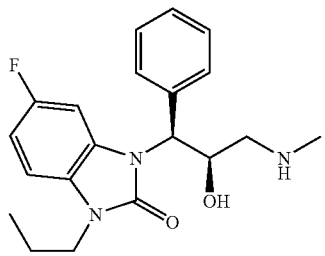

In an analogous manner to EXAMPLE 192, step 1 (4-fluoro-2-nitro-phenyl)-propyl-amine was prepared from 1,4-difluoro-2-nitro-benzene and propyl amine.

In an analogous manner to EXAMPLE 192, steps 1 and 2 5-fluoro-1-propyl-1,3-dihydro-benzimidazol-2-one was prepared from (4-fluoro-2-nitro-phenyl)-propyl-amine. MS (ES) m/z 195.2.

In an analogous manner to EXAMPLE 192, step 3 5-fluoro-3-[(1S,2S)-2,3-dihydroxy-1-phenyl-propyl]-1-propyl-1,3-dihydro-2H-benzimidazol-2-one was prepared from 5-fluoro-1-propyl-1,3-dihydro-benzimidazol-2-one and [(2R,3R)-3-phenyloxiran-2-yl]methanol (EXAMPLE 117, step 4).

In an analogous manner to EXAMPLE 192, step 4 5-fluoro-3-[(1S,2R)-2-hydroxy-3-(methylamino)-1-phenyl-propyl]-1-propyl-1,3-dihydro-2H-benzimidazol-2-one hydrochloride was prepared from 5-fluoro-3-[(1S,2S)-2,3-dihydroxy-1-phenyl-propyl]-1-propyl-1,3-dihydro-2H-benzimidazol-2-one as a white solid. MS (ES) m/z 358.2; HRMS: calcd for $C_{20}H_{24}FN_3O_2$+H+, 358.19253. Found (ESI, [M+H]+), 358.1895

Example 199

1-Ethyl-3-[1-(3-fluoro-phenyl)-2-hydroxy-3-methylamino-propyl]-1,3-dihydro-benzimidazol-2-one hydrochloride

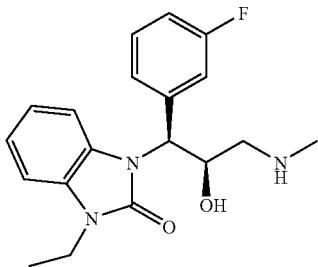

Step 1: To a solution of ethylamine in methanol (2.0 M, 150 mL, 300 mmol) was added 1-fluoro-2-nitrobenzene (8 mL, 75.7 mmol). The reaction mixture was placed in a sealed vessel and heated to 55° C. for 15 hours. The solvent was removed in vacuo and the residue was taken up in ethyl acetate (200 mL), washed with a saturated aqueous solution of sodium bicarbonate (80 mL), and dried over anhydrous sodium sulfate (50 g). After removal of solvent, ethyl-(2-nitro-phenyl)-amine (12.5 g, 75 mmol) was obtained as a brown oil. MS (ES) m/z 167.1.

Step 2: To a solution of ethyl-(2-nitro-phenyl)-amine (12.5 g, 75 mmol) in anhydrous tetrahydrofuran (150 mL) was added sodium borohydride (5.8 g, 153 mmol), and 5% palladium on carbon (150 mg). Methanol (25 mL) was then added at room temperature under nitrogen in a dropwise manner. After addition, the reaction mixture was stirred at room temperature for about 30 minutes until the reaction was complete. The reaction mixture was then filtered through a pad of Celite. The filtrate was diluted with ethyl acetate (200 mL), washed with a saturated aqueous solution of ammonium chloride (80 mL), dried over sodium sulfite, and concentrated in vacuo to afford crude N-ethyl-benzene-1,2-diamine (8.4 g, 62 mmol) which was used in next step without further purification.

Step 3: To a solution of crude N-ethyl-benzene-1,2-diamine (8.4 g, 62 mmol) in anhydrous tetrahydrofuran (200 mL) was added 1,1'-carbonyldiimidazole (10 g, 62 mmol). The mixture was stirred at room temperature under nitrogen for 12 hours and ethyl acetate (250 mL) followed by a cold 3N aqueous solution of hydrochloric acid (200 mL) were added. The organic layer was separated, dried over sodium sulfate and concentrated in vacuo to afford 1-ethyl-1,3-dihydro-benzimidazol-2-one as a white solid (8.5 g, 69% for three steps). MS (ES) m/z 163.2.

Step 4: In an analogous manner to EXAMPLE 192, step 3 1-ethyl-3-[(1S,2S)-2,3-dihydroxy-1-(3-fluorophenyl)-propyl]-1,3-dihydro-2H-benzimidazol-2-one was prepared from 1-ethyl-1,3-dihydro-benzimidazol-2-one and [(2R,3R)-3-(3-fluorophenyl)oxiran-2-yl]methanol (EXAMPLE 47, step 3).

Step 5: In an analogous manner to EXAMPLE 192, step 4 1-ethyl-3-[(1S,2R)-1-(3-fluorophenyl)-2-hydroxy-3-(methylamino)propyl]-1,3-dihydro-2H-benzimidazol-2-one hydrochloride was prepared from 1-ethyl-3-[(1S,2S)-2,3-dihydroxy-1-(3-fluorophenyl)-propyl]-1,3-dihydro-2H-benzimidazol-2-one as a white solid. MS (ES) m/z 344.2

Example 200

1-Ethyl-3-[(1S,2R)-2-hydroxy-3-(methylamino)-1-phenylpropyl]-1,3-dihydro-2H-benzimidazol-2-one hydrochloride

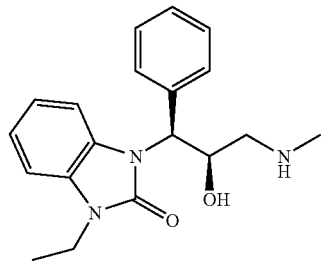

In an analogous manner to EXAMPLE 192, step 3 1-ethyl-3-[(1S,2S)-2,3-dihydroxy-1-phenyl-propyl]-1,3-dihydro-2H-benzimidazol-2-one was prepared from 1-ethyl-1,3-dihydro-benzimidazol-2-one (EXAMPLE 199, step 2) and [(2R,3R)-3-phenyloxiran-2-yl]methanol (EXAMPLE 117, step 4).

In an analogous manner to EXAMPLE 192, steps 4 and 5 1-ethyl-3-[(1S,2R)-2-hydroxy-3-(methylamino)-1-phenyl-propyl]-1,3-dihydro-2H-benzimidazol-2-one hydrochloride was prepared from 1-ethyl-3-[(1S,2S)-2,3-dihydroxy-1-phenyl-propyl]-1,3-dihydro-2H-benzimidazol-2-one as a white solid. MS (ES) m/z 326.2; HRMS: calcd for $C_{19}H_{23}N_3O_2$+H+, 326.18630. Found (ESI, [M+H]+), 326.1845.

Example 201

4-Fluoro-3-(2-hydroxy-3-methylamino-1-phenyl-propyl)-1-isopropyl-1,3-dihydro-benzimidazol-2-one hydrochloride

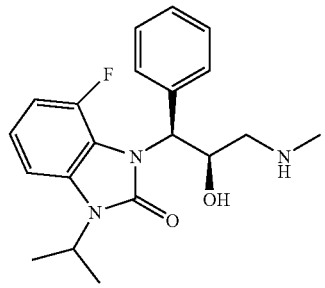

In an analogous manner to EXAMPLE 192, step 1 (3-fluoro-2-nitro-phenyl)-isopropyl-amine was prepared from 1,3-difluoro-2-nitro-benzene and iso-propylamine.

In an analogous manner to EXAMPLE 192, step 2 4-fluoro-1-isopropyl-1,3-dihydro-benzimidazol-2-one was prepared from (3-fluoro-2-nitro-phenyl)-isopropyl-amine. MS (ES) m/z 195.2.

In an analogous manner to EXAMPLE 192, step 3 4-fluoro-3-[(1S,2S)-2,3-dihydroxy-1-phenyl-propyl]-1-isopropyl-1,3-dihydro-2H-benzimidazol-2-one was prepared from 4-fluoro-1-isopropyl-1,3-dihydro-benzimidazol-2-one and [(2R,3R)-3-phenyloxiran-2-yl]methanol (EXAMPLE 117, step 4).

In an analogous manner to EXAMPLE 192, step 4 4-fluoro-3-[(1S,2R)-2-hydroxy-3-(methylamino)-1-phenyl-propyl]-1-isopropyl-1,3-dihydro-2H-benzimidazol-2-one hydrochloride was prepared from 4-fluoro-3-[(1S,2S)-2,3-dihydroxy-1-phenyl-propyl]-1-isopropyl-1,3-dihydro-2H-benzimidazol-2-one as a white solid. MS (ES) m/z 358.4.

Example 202

1-Cyclopentyl-3-[(1S,2R)-2-hydroxy-3-(methylamino)-1-phenylpropyl]-1,3-dihydro-2H-benzimidazol-2-one hydrochloride

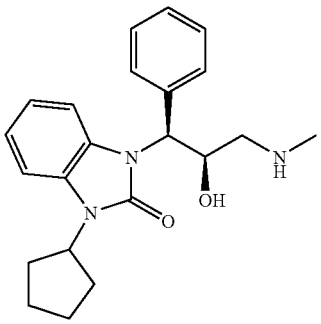

In an analogous manner to EXAMPLE 192, step 1 N-cyclopentyl-2-nitroaniline was prepared from 1-fluoro-2-nitrobenzene and cyclopentyl amine. MS (ESI) m/z 207.

In an analogous manner to EXAMPLE 192, step 2 1-cyclopentyl-1,3-dihydro-benzimidazol-2-one was prepared from N-cyclopentyl-2-nitroaniline. MS (ESI) m/z 203.

In an analogous manner to EXAMPLE 192, step 3 1-cyclopentyl-3-[(1S,2S)-2,3-dihydroxy-1-phenylpropyl]-1,3-dihydro-2H-benzimidazol-2-one was prepared from 1-cyclopentyl-1,3-dihydro-benzimidazol-2-one and [(2R,3R)-3-phenyloxiran-2-yl]methanol (EXAMPLE 117, step 4) as a white solid. MS (ES) m/z 352.9.

In an analogous manner to EXAMPLE 192, step 4 1-cyclopentyl-3-[(1S,2R)-2-hydroxy-3-(methylamino)-1-phenylpropyl]-1,3-dihydro-2H-benzimidazol-2-one hydrochloride was prepared from 1-cyclopentyl-3-[(1S,2S)-2,3-dihydroxy-1-phenylpropyl]-1,3-dihydro-2H-benzimidazol-2-one as a white solid. MS (ES) m/z MS (ESI) m/z 366.

Example 203

1-[(1S,2R)-2-hydroxy-3-(methylamino)-1-phenylpropyl]-3-isopropyl-1,3-dihydro-2H-benzimidazol-2-one hydrochloride

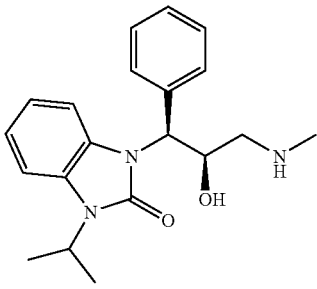

In an analogous manner to EXAMPLE 192, step 1 N-isopropyl-2-nitroaniline was prepared from 1-fluoro-2-nitrobenzene and isopropyl amine. MS (ES) m/z 181.2.

In an analogous manner to EXAMPLE 192, step 2 1-isopropyl-1,3-dihydro-2H-benzimidazol-2-one was prepared from N-isopropyl-2-nitroaniline. MS (ES) m/z 176.9.

In an analogous manner to EXAMPLE 192, step 3 1-[(1S,2S)-2,3-dihydroxy-1-phenylpropyl]-3-isopropyl-1,3-dihydro-2H-benzimidazol-2-one was prepared from 1-isopropyl-1,3-dihydro-2H-benzimidazol-2-one and [(2R,3R)-3-phenyloxiran-2-yl]methanol (EXAMPLE 117, step 4) as a white solid.

In an analogous manner to EXAMPLE 192, step 4 1-[(1S,2R)-2-hydroxy-3-(methylamino)-1-phenylpropyl]-3-isopropyl-1,3-dihydro-2H-benzimidazol-2-one hydrochloride was prepared from 1-[(1S,2S)-2,3-dihydroxy-1-phenylpropyl]-3-isopropyl-1,3-dihydro-2H-benzimidazol-2-one as a white solid. MS (ES) m/z MS (ES) m/z 340.3; HRMS: calcd for $C_{20}H_{25}N_3O_2+H^+$, 340.20195. Found (ESI, $[M+H]^+$), 340.2012.

Example 204

3-[(1S,2R)-3-(ethylamino)-2-hydroxy-1-phenylpropyl]-5-fluoro-1-isopropyl-1,3-dihydro-2H-benzimidazol-2-one hydrochloride

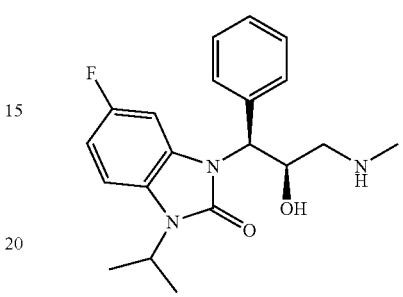

In an analogous manner to EXAMPLE 192, step 1 4-fluoro-N-isopropyl-2-nitroaniline was prepared from 1,4-difluoro-2-nitro-benzene and isopropyl amine. MS (ES) m/z 199.1.

In an analogous manner to EXAMPLE 192, step 2 5-fluoro-1-isopropyl-1,3-dihydro-2H-benzimidazol-2-one was prepared from 4-fluoro-N-isopropyl-2-nitroaniline. MS (ES) m/z 195.1.

In an analogous manner to EXAMPLE 192, step 3 5-fluoro-1-[(1S,2S)-2,3-dihydroxy-1-phenylpropyl]-3-isopropyl-1,3-dihydro-2H-benzimidazol-2-one was prepared from 5-fluoro-1-isopropyl-1,3-dihydro-2H-benzimidazol-2-one and [(2R,3R)-3-phenyloxiran-2-yl]methanol (EXAMPLE 117, step 4) as a white solid.

In an analogous manner to EXAMPLE 192, step 4 3-[(1S,2R)-3-(ethylamino)-2-hydroxy-1-phenylpropyl]-5-fluoro-1-isopropyl-1,3-dihydro-2H-benzimidazol-2-one hydrochloride was prepared from 5-fluoro-1-[(1S,2S)-2,3-dihydroxy-1-phenylpropyl]-3-isopropyl-1,3-dihydro-2H-benzimidazol-2-one and para-toluenesulfonic acid followed by ethylamine as a white solid. MS (ESI) m/z 372.21; HRMS: calcd for $C_{21}H_{26}FN_3O_2+H+$, 372.20818. Found (ESI, $[M+H]^+$), 372.2099.

Example 205

1-[(1S,2R)-2-hydroxy-3-(methylamino)-1-phenylpropyl]-3-methyl-1,3-dihydro-2H-benzimidazol-2-one hydrochloride

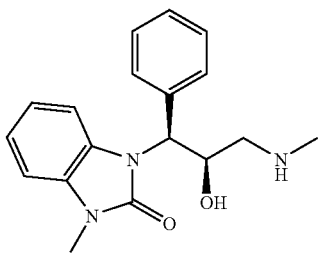

In an analogous manner to EXAMPLE 192, step 3 1-[(1S,2S)-2,3-dihydroxy-1-phenylpropyl]-3-methyl-1,3-dihydro-2H-benzimidazol-2-one was prepared from 1-methyl-1,3-dihydro-benzimidazol-2-one and [(2R,3R)-3-phenyloxiran-2-yl]methanol (EXAMPLE 117, step 4) as a white solid.

In an analogous manner to EXAMPLE 192, step 4 1-[(1S,2R)-2-hydroxy-3-(methylamino)-1-phenylpropyl]-3-methyl-1,3-dihydro-2H-benzimidazol-2-one hydrochloride was prepared from 1-[(1S,2S)-2,3-dihydroxy-1-phenylpropyl]-3-methyl-1,3-dihydro-2H-benzimidazol-2-one as a white solid. MS (ES) m/z 312.3; HRMS: calcd for $C_{18}H_{21}N_3O_2+H+$, 312.17065. Found (ESI, [M+H]$^+$), 312.17.

Example 206

1-Ethyl-5-fluoro-3-[(1S,2R)-2-hydroxy-3-(methylamino)-1-phenylpropyl]-1,3-dihydro-2H-benzimidazol-2-one hydrochloride

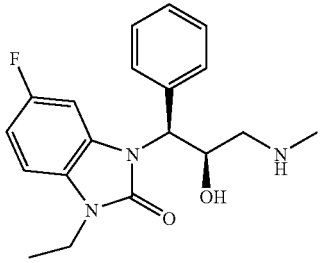

In an analogous manner to EXAMPLE 199, step 1 ethyl-(4-fluoro-2-nitro-phenyl)-amine was prepared from 1,4-difluoro-2-nitroaniline and ethylamine.

In an analogous manner to EXAMPLE 199, step 2 N-ethyl-4-fluoro-benzene-1,2-diamine was prepared from ethyl-(4-fluoro-2-nitro-phenyl)-amine.

In an analogous manner to EXAMPLE 199, step 3 1-ethyl-5-fluoro-1,3-dihydro-2H-benzimidazol-2-one was prepared from N-ethyl-4-fluoro-benzene-1,2-diamine. MS (ES) m/z 181.2.

In an analogous manner to EXAMPLE 192, step 3 3-[(1S,2S)-2,3-dihydroxy-1-phenylpropyl]-1-ethyl-5-fluoro-1,3-dihydro-2H-benzimidazol-2-one was prepared from 1-ethyl-5-fluoro-1,3-dihydro-2H-benzimidazol-2-one and [(2R,3R)-3-phenyloxiran-2-yl]methanol (EXAMPLE 117, step 4) as a white solid. MS (ES) m/z 331.1.

In an analogous manner to EXAMPLE 192, step 4 1-ethyl-5-fluoro-3-[(1S,2R)-2-hydroxy-3-(methylamino)-1-phenylpropyl]-1,3-dihydro-2H-benzimidazol-2-one hydrochloride was prepared from 3-[(1S,2S)-2,3-dihydroxy-1-phenylpropyl]-1-ethyl-5-fluoro-1,3-dihydro-2H-benzimidazol-2-one as a white solid. MS (ES) m/z 344.2; HRMS: calcd for $C_{19}H_{22}FN_3O_2+H+$, 344.17688. Found (ESI, [M+H]$^+$), 344.175.

Example 207

1-Ethyl-4-fluoro-3-[(1S,2R)-2-hydroxy-3-(methylamino)-1-phenylpropyl]-1,3-dihydro-2H-benzimidazol-2-one hydrochloride

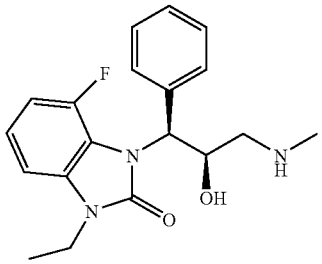

In an analogous manner to EXAMPLE 199, step 1 ethyl-(3-fluoro-2-nitro-phenyl)-amine was prepared from 1,3-difluoro-2-nitroaniline and ethylamine.

In an analogous manner to EXAMPLE 199, step 2 N-ethyl-3-fluoro-benzene-1,2-diamine was prepared from ethyl-(3-fluoro-2-nitro-phenyl)-amine.

In an analogous manner to EXAMPLE 199, step 3 1-ethyl-4-fluoro-1,3-dihydro-2H-benzimidazol-2-one was prepared from N-ethyl-3-fluoro-benzene-1,2-diamine. MS (ES) m/z 181.2.

In an analogous manner to EXAMPLE 192, step 3 3-[(1S,2S)-2,3-dihydroxy-1-phenylpropyl]-1-ethyl-4-fluoro-1,3-dihydro-2H-benzimidazol-2-one was prepared from 1-ethyl-4-fluoro-1,3-dihydro-2H-benzimidazol-2-one and [(2R,3R)-3-phenyloxiran-2-yl]methanol (EXAMPLE 117, step 4) as a white solid. MS (ES) m/z 331.1.

In an analogous manner to EXAMPLE 192, step 4 1-ethyl-4-fluoro-3-[(1S,2R)-2-hydroxy-3-(methylamino)-1-phenylpropyl]-1,3-dihydro-2H-benzimidazol-2-one hydrochloride was prepared from 3-[(1S,2S)-2,3-dihydroxy-1-phenylpropyl]-1-ethyl-4-fluoro-1,3-dihydro-2H-benzimidazol-2-one as a white solid. MS (ES) m/z 344.2; HRMS: calcd for $C_{19}H_{22}FN_3O_2+H^+$, 344.17688. Found (ESI, [M+H]$^+$), 344.1768.

Example 208

4-fluoro-3-[(1S,2R)-1-(3-fluorophenyl)-2-hydroxy-3-(methylamino)-propyl]-1-isopropyl-1,3-dihydro-2H-benzimidazol-2-one hydrochloride

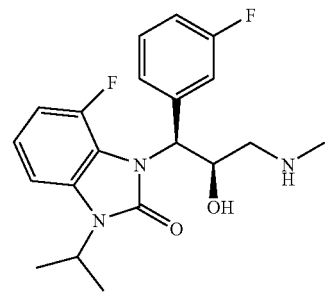

In an analogous manner to EXAMPLE 192, step 3 4-fluoro-3-[(1S,2S)-1-(3-fluoro-phenyl)-2,3-dihydroxy-propyl]-1-isopropyl-1,3-dihydro-benzimidazol-2-one was prepared from 4-fluoro-1-isopropyl-1,3-dihydro-benzimidazol-2-one (EXAMPLE 201, step 2) and [(2R,3R)-3-(3-fluorophenyl)-oxiran-2-yl]methanol (EXAMPLE 47, step 3) as an oil.

In an analogous manner to EXAMPLE 192, step 4 4-fluoro-3-[(1S,2R)-1-(3-fluorophenyl)-2-hydroxy-3-(methylamino)-propyl]-1-isopropyl-1,3-dihydro-2H-benzimidazol-2-one hydrochloride was prepared from 4-fluoro-3-[(1S,2S)-1-(3-fluorophenyl)-2,3-dihydroxy-propyl]-1-isopropyl-1,3-dihydro-benzimidazol-2-one as a white solid. MS (ES) m/z 376.2

Example 209

1-Ethyl-4-fluoro-3-[(1S,2R)-2-hydroxy-3-(methylamino)-1-(3-fluorophenyl)-propyl]-1,3-dihydro-2H-benzimidazol-2-one hydrochloride

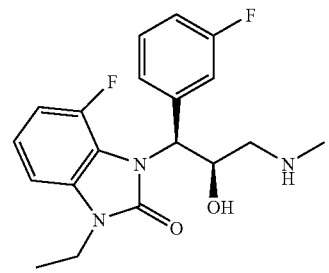

In an analogous manner to EXAMPLE 192, step 3 3-[(1S,2S)-2,3-dihydroxy-1-(3-fluorophenyl)-propyl]-1-ethyl-4-fluoro-1,3-dihydro-2H-benzimidazol-2-one was prepared from 1-ethyl-4-fluoro-1,3-dihydro-2H-benzimidazol-2-one (EXAMPLE 207, step 2) and [(2R,3R)-3-(3-fluorophenyl)-oxiran-2-yl]methanol (EXAMPLE 47, step 3) as clear oil. MS (ES) m/z 349.1.

In an analogous manner to EXAMPLE 192, step 4 1-ethyl-4-fluoro-3-[(1S,2R)-2-hydroxy-3-(methylamino)-1-(3-fluorophenyl)-propyl]-1,3-dihydro-2H-benzimidazol-2-one hydrochloride was prepared from 3-[(1S,2S)-2,3-dihydroxy-1-(3-fluorophenyl)-propyl]-1-ethyl-4-fluoro-1,3-dihydro-2H-benzimidazol-2-one as a white solid. MS (ES) m/z 362.1.

Example 210

1-[(1S,2R)-1-(3-fluorophenyl)-2-hydroxy-3-(methylamino)propyl]-3,3-dimethyl-1,3-dihydro-2H-indol-2-one hydrochloride

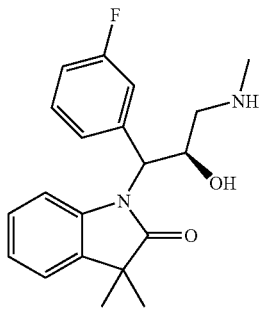

Step 1: In an analogous manner to EXAMPLE 101, step 1 (2S, 3S)-1-[1-(3-fluoro-phenyl)-2,3-dihydroxy-propyl]-3,3-dimethyl-1,3-dihydro-indol-2-one was prepared from 3,3-dimethyl-1,3-dihydro-indol-2-one[10] and [(2R,3R)-3-(3-fluorophenyl)oxiran-2-yl]methanol (EXAMPLE 47, step 3). MS (ESI) m/z 330 ([M+H]$^+$).

Step 2: In an analogous manner to EXAMPLE 1, step 2 (2S, 3S)-toluene-4-sulfonic acid 3-(3,3-dimethyl-2-oxo-2,3-dihydro-indol-1-yl)-3-(3-fluoro-phenyl)-2-hydroxy-propyl ester was prepared from (2S, 3S)-1-[1-(3-fluoro-phenyl)-2,3-dihydroxy-propyl]-3,3-dimethyl-1,3-dihydro-indol-2-one. MS (ESI) m/z 484 ([M+H]$^+$).

Step 3: In an analogous manner to EXAMPLE 5 1-[(1S,2R)-1-(3-fluorophenyl)-2-hydroxy-3-(methylamino)propyl]-3,3-dimethyl-1,3-dihydro-2H-indol-2-one hydrochloride was prepared from (2S,3S)-toluene-4-sulfonic acid 3-(3,3-dimethyl-2-oxo-2,3-dihydro-indol-1-yl)-3-(3-fluorophenyl)-2-hydroxy-propyl ester. MS (ESI) m/z 343 ([M+H]$^+$).

Example 211

(1S,2R)-1-[3-(2,3-difluorophenyl)-1H-indol-1-yl]-1-(3-fluorophenyl)-3-(methylamino)propan-2-ol hydrochloride

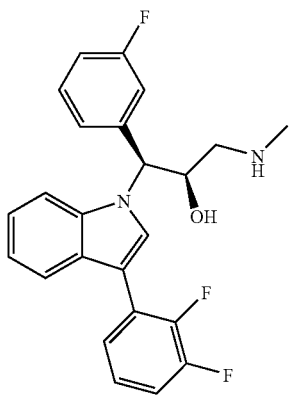

In an analogous manner to EXAMPLE 114, step 2, (2S, 3S)-3-(3-fluorophenyl)-[3-(2,3-difluorophenyl)-1H-indol-1-yl]propane-1,2-diol was prepared from (2S,3S)-3-(3-fluorophenyl)-3-(3-iodo-1H-indol-1-yl)propane-1,2-diol (EXAMPLE 114, step 1) and 2,3-difluorobenzeneboronic acid.

In an analogous manner to EXAMPLE 1, step 2, (2S,3S)-toluene-4-sulfonic acid 3-(3-fluorophenyl)-3-(2,3-difluorophenyl)-indol-1-yl]-2-hydroxy-propyl ester was prepared from (2S,3S)-3-(3-fluorophenyl)-3-[3-(2,3-difluorophenyl)-1H-indol-1-yl]propane-1,2-diol.

In an analogous manner to EXAMPLE 5, (1S,2R)-1-[3-(2,3-difluorophenyl)-1H-indol-1-yl]-1-(3-fluorophenyl)-3-(methylamino)propan-2-ol was prepared from (2S,3S)-toluene-4-sulfonic acid 3-(3-fluorophenyl)-3-(2,3-difluorophenyl)-indol-1-yl]-2-hydroxy-propyl ester. MS (ES) m/z 411.1; HRMS: calcd for C24H21F3N2O+H+, 411.16787. Found (ESI, [M+H]+), 411.1675.

Example 212

(1S,2R)-1-(3-fluorophenyl)-3-(methylamino)-1-[(2R)-2-phenyl-2,3-dihydro-4H-1,4-benzoxazin-4-yl]propan-2-ol hydrochloride

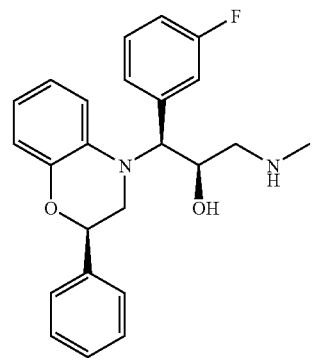

Step 1: Diastereomeric mixture of (1S,2R)-1-(3-fluorophenyl)-3-(methylamino)-1-(2-phenyl-2,3-dihydro-4H-1,4-benzoxazin-4-yl)propan-2-ol (EXAMPLE 168) was dissolved in methanol. The resulting solution was injected onto the Supercritical Fluid Chromatography instrument. The baseline resolved diastereomers, using the conditions described below, were collected.

| | |
|---|---|
| SFC Instrument: | Berger MultiGram Prep SFC (Berger Instruments, Inc. Newark, DE 19702. |
| Column: | Ethyl pyridine; 250 mm L x 20 mm ID (Princeton Chromatography Inc.) |
| Column temperature: | 35° C. |
| SFC Modifier: | 15% MeOH with 85% $CO_2$ |
| Flow rate: | 50 mL/min |
| Outlet Pressure: | 100 bar |
| Detector: | UV at 220 nm |

Step 2: (1S,2R)-1-(3-fluorophenyl)-3-(methylamino)-1-[(2R)-2-phenyl-2,3-dihydro-4H-1,4-benzoxazin-4-yl]propan-2-ol, isolated as peak 1, was subjected to hydrochloride salt formation in an analogous manner to EXAMPLE 144, step 2 to give (1S,2R)-1-(3-fluorophenyl)-3-(methylamino)-1-[(2R)-2-phenyl-2,3-dihydro-4H-1,4-benzoxazin-4-yl]propan-2-ol hydrochloride as a white powder. MS (ES) m/z 393.2 ([M+H]+); HRMS: calcd for $C_{24}H_{25}FN_2O_2+H^+$, 393.1973. Found (ESI, [M+H]+), 393.1992.

Example 213

(1S,2R)-1-(3-fluorophenyl)-3-(methylamino)-1-[(2S)-2-phenyl-2,3-dihydro-4H-1,4-benzoxazin-4-yl]propan-2-ol hydrochloride

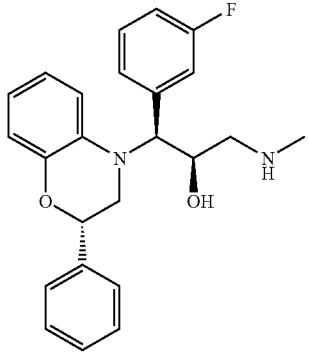

In an analogous manner to EXAMPLE 212, (1S,2R)-1-(3-fluorophenyl)-3-(methylamino)-1-[(2S)-2-phenyl-2,3-dihydro-4H-1,4-benzoxazin-4-yl]propan-2-ol hydrochloride was prepared as a white powder from (1S,2R)-1-(3-fluorophenyl)-3-(methylamino)-1-[(2S)-2-phenyl-2,3-dihydro-4H-1,4-benzoxazin-4-yl]propan-2-ol, which was isolated as peak 2 of the diastereomeric separation (EXAMPLE 212, step 1). MS (ES) m/z 393.2 ([M+H]+); HRMS: calcd for $C_{24}H_{25}FN_2O_2+H^+$, 393.1973. Found (ESI, [M+H]+), 393.1982.

Example 214

(1S,2R)-1-[3-(2-chlorophenyl)-1H-indol-1-yl]-1-(3-fluorophenyl)-3-(methylamino)propan-2-ol hydrochloride

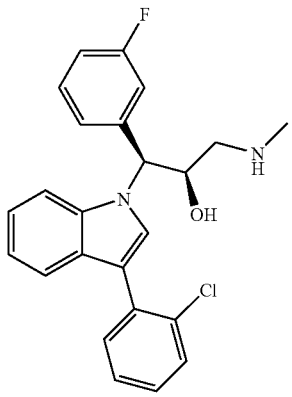

In an analogous manner to EXAMPLE 114, step 2, (2S,3S)-3-(3-fluorophenyl)-3-{3-[2-chlorophenyl]-1H-indol-1-yl}propane-1,2-diol was prepared from (2S,3S)-3-(3-fluorophenyl)-3-(3-iodo-1H-indol-1-yl)propane-1,2-diol (EXAMPLE 114, step 1) and 2-chlorobenzeneboronic acid.

In an analogous manner to EXAMPLE 1, step 2, (2S,3S)-toluene-4-sulfonic acid 3-(3-fluorophenyl)-3-[3-(2-chlorophenyl)-indol-1-yl]-2-hydroxy-propyl ester was prepared from (2S,3S)-3-(3-fluorophenyl)-3-{3-[2-chlorophenyl]-1H-indol-1-yl}propane-1,2-diol.

In an analogous manner to EXAMPLE 5, (1S,2R)-1-[3-(2-chlorophenyl)-1H-indol-1-yl]-1-(3-fluorophenyl)-3-(methylamino)propan-2-ol hydrochloride was prepared from (2S,3S)-toluene-4-sulfonic acid 3-(3-fluoro-phenyl)-3-[3-(2-chlorphenyl)-indol-1-yl]-2-hydroxy-propyl ester and methylamine (2N solution in methanol). MS (ESI) m/z 409.1; HRMS: calcd for C24H22ClFN2O+H+, 409.14774; found (ESI, [M+H]+), 409.146.

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 □g/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 pl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C). The reaction was terminated by decanting the supernatant from the plate. The plates containing cells were washed twice with 200 pl assay buffer (37° C.) to remove free radioligand. The plates were then inverted, left to dry for 2 minutes, then reinverted and air-dried for an additional 10 minutes. The cells were lysed in 25 µl of 0.25 N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. A stock solution of paroxetine (AHR-4389-1) was prepared in DMSO (10 mM) and delivered to triplicate wells containing cells for a final test concentration of 1 µM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 µl of assay buffer. The cells were incubated with the compound for 10 minutes (37° C.). To initiate the reaction, [$^3$H]hydroxytryptamine creatinine sulfate diluted in assay buffer was delivered in 25 µl aliquots to each well for a final test concentration of 15 nM. The cells were incubated with the reaction mixture for 5 minutes at 37° C. The 5-HT uptake reaction was terminated by decanting the assay buffer. The cells were washed twice with 200 µl assay buffer (37° C.) to remove free radioligand. The plates were inverted and left to dry for 2 minutes, then reinverted and air-dried for an additional 10 minutes. Subsequently, the cells were lysed in 25 µl of 0.25 N NaOH (4° C.) then placed on a shaker table and shaken vigorously for 5 minutes. After cell lysis, 75 µl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 µM desipramine (hNET) or 1 µM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment. The results are reported in Table 1.

TABLE 1

| Example | % Inhibition @ 1 µM (hNET) |
|---|---|
| 1 | 4.6 |
| 2 | 66.5 (@ 10 µM) |
| 3 | 17.6 |
| 4 | 24.5 |
| 5 | 58.1 |
| 6 | 13.1 |
| 7 | 25.6 |
| 8 | 53.4 |
| 9 | 79.2 (@ 10 µM) |
| 10 | 70.5 (@ 10 µM) |
| 11 | 94.5 |
| 12 | 70.6 |
| 13 | 34.3 |
| 14 | 24.4 |

TABLE 1-continued

| Example | % Inhibition @ 1 µM (hNET) |
|---|---|
| 15 | 8.5 |
| 16 | 96.8 |
| 17 | 71.0 |
| 18 | 11.3 |
| 19 | 31.6 |
| 20 | 85.0 |
| 21 | 97.5 |
| 22 | 83.8 |
| 23 | 89.7 |
| 24 | 57.2 |
| 25 | 37.5 |
| 26 | 54.0 |
| 27 | 75.4 |
| 28 | 30.1 |
| 29 | 89.5 |
| 30 | 79.7 |
| 31 | 98.9 |
| 33 | 99.4 |
| 34 | 78.4 |
| 35 | 94.3 |
| 36 | 82.3 |
| 37 | 21.4 |
| 38 | 71.9 |
| 39 | 57.4 |
| 40 | 57.6 |
| 41 | 32.4 |
| 42 | 95.7 |
| 43 | 99 |
| 44 | 98.2 |
| 47 | 99.9 |
| 48 | 96.6 |
| 49 | 101.2 |
| 50 | 91.8 |
| 51 | 87.0 |
| 52 | 94.3 |
| 53 | 57.4 |
| 54 | 68.6 |
| 55 | 61.1 |
| 56 | 12.3 |
| 57 | 17.5 |
| 58 | 26.5 |
| 59 | 93.2 |
| 60 | 100 |
| 61 | 99.8 |
| 62 | 99.7 |
| 63 | 91.9 |
| 64 | 99.9 |
| 65 | 100 |
| 66 | 86.6 |
| 67 | 90.9 |
| 68 | 99.6 |
| 69 | 87.5 |
| 70 | 77.7 |
| 71 | 44.9 |
| 72 | 24 |
| 73 | 21.8 |
| 74 | 67 |
| 75 | 88.4 |
| 76 | 75.2 |
| 77 | 77.3 |
| 78 | 70.9 |
| 79 | 66 |
| 80 | 83.5 |
| 81 | 58.0 |
| 82 | 53.9 |
| 83 | 99.5 |
| 84 | 40.9 |
| 85 | 97.4 |
| 86 | 52.7 |
| 87 | 99.7 |
| 90 | 73.1 |
| 91 | 90.8 |
| 92 | 85.8 |
| 93 | 96.3 |
| 94 | 94.9 |
| 95 | 97.6 |

TABLE 1-continued

| Example | % Inhibition @ 1 μM (hNET) |
|---|---|
| 96 | 98.2 |
| 97 | 99.6 |
| 98 | 99.1 |
| 99 | 98.1 |
| 100 | 94.2 |
| 101 | 98.6 |
| 102 | 95.3 |
| 103 | 86.1 |
| 104 | 99.4 |
| 105 | 92.6 |
| 106 | 85.8 |
| 107 | 96.6 |
| 108 | 98.7 |
| 109 | 94.7 |
| 110 | 86.4 |
| 111 | 42.7 |
| 112 | 100.3 |
| 113 | 99.7 |
| 114 | 100 |
| 115 | 23.9 |
| 116 | 97.3 |
| 117 | 95.3 |
| 118 | 67.9 |
| 119 | 96.3 |
| 120 | 68.6 |
| 121 | 21.2 |
| 122 | 97.4 |
| 123 | 65 |
| 124 | 91.5 |
| 125 | 94.3 |
| 126 | 92.9 |
| 127 | 95.7 |
| 128 | 45.6 |
| 129 | 71.8 |
| 130 | 76 |
| 131 | 63.1 |
| 132 | 93 |
| 133 | 96.4 |
| 134 | 68.5 |
| 135 | 99.5 |
| 136 | 97 |
| 137 | 99.1 |
| 138 | 97.9 |
| 139 | 94.9 |
| 140 | 96.7 |
| 143 | 96.8 |
| 146 | 97.1 |
| 147 | 91.7 |
| 148 | 97.8 |
| 149 | 100.4 |
| 150 | 98.3 |
| 151 | 94.3 |
| 152 | 96.2 |
| 153 | 97.4 |
| 154 | 96.1 |
| 155 | 98.9 |
| 157 | 99.6 |
| 158 | 99.6 |
| 159 | 93.8 |
| 160 | 99.3 |
| 161 | 99.4 |
| 162 | 99.2 |
| 163 | 99.7 |
| 164 | 98.6 |
| 169 | 72 |
| 170 | 96.4 |
| 171 | 98.3 |
| 172 | 88 |
| 173 | 67.5 |
| 174 | 99.1 |
| 175 | 99.6 |
| 176 | 100 |
| 177 | 29.9 |
| 178 | 69.2 |
| 179 | 99.8 |
| 180 | 70.4 |
| 181 | 96.9 |
| 182 | 97.1 |
| 183 | 100.5 |
| 184 | 99.7 |
| 185 | 80.8 |
| 186 | 96.6 |
| 187 | 52 |
| 188 | 71.6 |
| 189 | 99.3 |
| 190 | 53.7 |
| 191 | 63.9 |
| 192 | 54.6 |
| 193 | 98.4 |
| 194 | 79 |
| 195 | 91 |
| 196 | 94.6 |
| 197 | 97 |
| 198 | 97.7 |
| 199 | 99.1 |
| 200 | 97.9 |
| 201 | 98.8 |
| 202 | 92.7 |
| 203 | 98.9 |
| 204 | 47.4 |
| 205 | 82.9 |
| 206 | 96.9 |
| 207 | 98.3 |
| 208 | 99.8 |
| 209 | 99.3 |
| 210 | 96.3 |
| 211 | 99.8 |
| 214 | 99.9 |

When ranges are used herein for physical properties, such as molecular weight, or chemical properties, such as chemical formulae, all combinations and subcombinations of ranges specific embodiments therein are intended to be included.

The disclosure of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

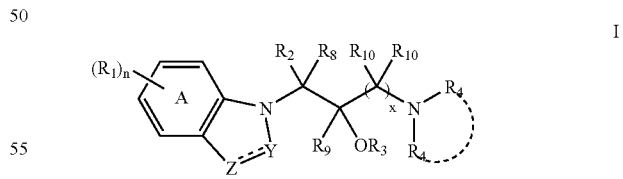

or a pharmaceutically acceptable salt thereof
wherein:
the dotted line between Y and Z represents an optional double bond;
the dotted line between the two $R_4$ groups represents an optional heterocyclic ring of 4 to 6 ring atoms that may be formed between the two $R_4$ groups, together with the nitrogen through which they are attached;
Y is $CR_6$, or C=O;
Z is N, $NR_7$, $CR_5$, or $C(R_5)_2$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$-$C_4$ alkyl, F, or $CF_3$;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H, or $C_1$-$C_4$ alkyl;

$R_9$ is H, or $C_1$-$C_4$ alkyl;

$R_{10}$ is, independently at each occurrence, H, or $C_1$-$C_4$ alkyl; or $R_{10}$ and $R_4$ together with the nitrogen to which $R_4$ is attached form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

2. A compound according to claim 1, wherein:
Y is $CR_6$.

3. A compound according to claim 2, wherein:
Y is CH.

4. A compound according to claim 1, wherein:
Z is $CR_5$.

5. A compound according to claim 1, wherein:
$R_1$ is halo.

6. A compound according to claim 5, wherein:
$R_1$ is fluoro or chloro.

7. A compound according to claim 1, wherein:
$R_2$ is aryl substituted with 0-3 $R_1$.

8. A compound according to claim 6, wherein:
$R_2$ is phenyl.

9. A compound according to claim 1, wherein:
$R_3$ is H or $C_1$ alkyl.

10. A compound according to claim 1, wherein:
$R_4$ is H or $C_1$-$C_4$ alkyl.

11. A compound according to claim 10, wherein:
$R_4$ is H, methyl, ethyl, or isopropyl.

12. A compound according to claim 1, wherein:
both $R_4$ groups, together with the nitrogen through which they are attached, form a pyridine, piperidine, piperazine, piperazine substituted with a methyl group, or morpholine ring.

13. A compound according to claim 1, wherein:
$R_5$ is, independently at each occurrence, H, $C_1$ alkyl, or cyano.

14. A compound according to claim 1, wherein:
$R_6$ is H, methyl, ethyl, or cyano.

15. A compound according to claim 1, wherein:
$R_7$ is H, methyl, ethyl, isopropyl, cyclopentyl, cyclohexyl, phenyl, tolyl, or xylyl.

16. A compound according to claim 1, wherein:
$R_8$ is H, methyl, or ethyl.

17. A compound according to claim 1, wherein:
$R_9$ is H, methyl, or ethyl.

18. A compound according to claim 1, wherein:
$R_{10}$ is H or methyl.

19. A compound according to claim 18, wherein:
n is 0 or 1.

20. A compound according to claim 1, wherein:
x is 1.

21. A compound according to claim 1, wherein:
Y is $CR_6$, or C=O;

Z is N, $NR_7$, $CR_5$, or $C(R_5)_2$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H $R_4$ is, independently at each occurrence, H, or $C_1$-$C_4$ alkyl, $R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, aryl substituted with 0-3 $R_1$;

$R_8$ is H;

$R_9$ is H;

$R_{10}$ is H;

n is an integer from 0 to 4;

x is 1;

$R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

22. A compound according to claim 1, wherein:
Y is $CR_6$;

Z is $CR_5$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

23. A compound according to claim 1, wherein:

Y is $CR_6$;

Z is $C(R_5)_2$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

24. A compound according to claim 1, wherein:

Y is C=O;

Z is $C(R_5)_2$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or when two $R_5$ are present, they form a carbocyclic ring of 3-7 carbons;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl; or $R_{10}$ and $R_4$, together with the nitrogen to which $R_4$ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

25. A compound according to claim 1, wherein:

Y is C=O;

Z is $NR_7$;

$R_1$ is, independently at each occurrence, alkyl, alkoxy, halo, $CF_3$, $OCF_3$, arylalkyloxy substituted with 0-3 $R_{11}$, aryloxy substituted with 0-3 $R_{11}$, aryl substituted with 0-3 $R_{11}$, heteroaryl substituted with 0-3 $R_{11}$, hydroxy, alkanoyloxy, nitro, nitrile, alkenyl, alkynyl, alkylsulfoxide, phenylsulfoxide substituted with 0-3 $R_{11}$, alkylsulfone, phenylsulfone substituted with 0-3 $R_{11}$, alkylsulfonamide, phenylsulfonamide substituted with 0-3 $R_{11}$, heteroaryloxy substituted with 0-3 $R_{11}$, heteroarylmethyloxy substituted with 0-3 $R_{11}$, alkylamido, or arylamido substituted with 0-3 $R_{11}$; or two adjacent $R_1$ also represent methylenedioxy;

$R_2$ is aryl substituted with 0-3 $R_1$ or heteroaryl substituted with 0-3 $R_1$;

$R_3$ is H or $C_1$-$C_4$ alkyl;

$R_4$ is, independently at each occurrence, H, $C_1$-$C_4$ alkyl, arylalkyl, heteroarylmethyl, cycloheptylmethyl, cyclohexylmethyl, cyclopentylmethyl, or cyclobutylmethyl;

$R_5$ is, independently at each occurrence, H, $C_1$-$C_4$ alkyl, aryl substituted with 0-3 $R_1$, or cyano; or in the cases where two $R_5$ substitutions are present, they may form a carbocyclic ring of $C_3$-$C_7$;

$R_6$ is H, $C_1$-$C_4$ alkyl, or cyano;

$R_7$ is H, $C_1$-$C_6$ alkyl, $C_3$-$C_6$ cycloalkyl, or aryl substituted with 0-3 $R_1$;

$R_8$ is H or $C_1$-$C_4$ alkyl;

$R_9$ is H or $C_1$-$C_4$ alkyl;

$R_{10}$ is, independently at each occurrence, H or $C_1$-$C_4$ alkyl;

$R_{10}$ is, independently at each occurrence, H or $C_1$-$C_4$ alkyl; or R₁₀ and R₄, together with the nitrogen to which R₄ is attached, form a nitrogen-containing ring containing 3-6 carbon atoms;

n is an integer from 0 to 4;

x is an integer from 1 to 2; and $R_{11}$ is alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido; or two adjacent $R_{11}$ also represent methylenedioxy;

wherein 1-3 carbon atoms in ring A may optionally be replaced with N.

26. A compound according to claim 1, wherein said compound is:

1-(1H-indol-1-yl)-3-(4-methylpiperazin-1-yl)-1-phenylpropan-2-ol;
1-(5-fluoro-1H-indol-1-yl)-3-(4-methylpiperazin-1-yl)-1-phenylpropan-2-ol;
1-(1H-indol-1-yl)-3-morpholin-4-yl-1-phenylpropan-2-ol;
3-(dimethylamino)-1-(1H-indol-1-yl)-1-phenylpropan-2-ol;
3-(ethylamino)-1-(1H-indol-1-yl)-1-phenylpropan-2-ol;
1-(1H-indol-1-yl)-3-(isopropylamino)-1-phenylpropan-2-ol;
3-(benzylamino)-1-(1H-indol-1-yl)-1-phenylpropan-2-ol;
3-[(cyclohexylmethyl)amino]-1-(1H-indol-1-yl)-1-phenylpropan-2-ol;
3-[(cyclohexylmethyl)amino]-1-(3-methyl-1H-indol-1-yl)-1-phenylpropan-2-ol;
3-(isopropylamino)-1-(3-methyl-1H-indol-1-yl)-1-phenylpropan-2-ol;
1-(1H-indol-1-yl)-3-(methylamino)-1-phenylpropan-2-ol;
3-(ethylamino)-1-(3-methyl-1H-indol-1-yl)-1-phenylpropan-2-ol;
1-(1H-indol-1-yl)-1-phenyl-3-piperazin-1-ylpropan-2-ol di;
1-(1H-indol-1-yl)-1-phenyl-3-[(pyridin-4-ylmethyl)amino]propan-2-ol;
1-(5-chloro-1H-indol-1-yl)-1-phenyl-3-piperidin-1-ylpropan-2-ol;
1-(1H-indol-1-yl)-3-(methylamino)-1-phenylpropan-2-ol;
3-amino-1-(1H-indol-1-yl)-1-phenylpropan-2-ol;
3-(ethylamino)-1-(5-fluoro-1H-indol-1-yl)-1-phenylpropan-2-ol;
3-amino-1-(5-fluoro-1H-indol-1-yl)-1-phenylpropan-2-ol;
1-(5-fluoro-1H-indol-1-yl)-3-(methylamino)-1-phenylpropan-2-ol;
3-(methylamino)-1-(3-methyl-1H-indol-1-yl)-1-phenylpropan-2-ol;
1-(1H-indol-1-yl)-3-(methylamino)-1-phenylpropan-2-ol;
1-(1H-indol-1-yl)-3-(methylamino)-1-phenylpropan-2-ol;
3-amino-1-(3-methyl-1H-indol-1-yl)-1-phenylpropan-2-ol;
3-[ethyl(methyl)amino]-1-(1H-indol-1-yl)-1-phenylpropan-2-ol;
1-(5-chloro-1H-indol-1-yl)-3-(methylamino)-1-phenylpropan-2-ol;
1-(5-chloro-1H-indol-1-yl)-3-(methylamino)-1-phenylpropan-1-ol;
1-[2-hydroxy-3-(methylamino)-1-phenylpropyl]-1H-indole-3-carbonitrile;
1-(1H-indol-1-yl)-3-(methylamino)-1-phenylpropan-2-ol;
1-(1H-indol-1-yl)-3-(methylamino)-1-phenylpropan-2-ol;
3-(methylamino)-1-(3-methyl-1H-indol-1-yl)-1-phenylpropan-2-ol;
1-(3-chlorophenyl)-1-(1H-indol-1-yl)-3-(methylamino)propan-2-ol;
1-(4-chlorophenyl)-1-(1H-indol-1-yl)-3-(methylamino)propan-2-ol;
1-(1H-indol-1-yl)-3-(methylamino)-1-[3-(trifluoromethoxy)phenyl]propan-2-ol;
1-(1H-indol-1-yl)-3-(methylamino)-1-[2-(trifluoromethoxy)phenyl]propan-2-ol;
1-(1H-indol-1-yl)-3-(methylamino)-1-[2-(trifluoromethoxy)phenyl]propan-2-ol;
1-(2-chlorophenyl)-1-(1H-indol-1-yl)-3-(methylamino)propan-2-ol;
1-(1H-indol-1-yl)-3-(methylamino)-1-[4-(trifluoromethoxy)phenyl]propan-2-ol;
1-(1H-indol-1-yl)-3-(methylamino)-1-[4-(trifluoromethoxy)phenyl]propan-2-ol;
1-(1H-indol-1-yl)-3-(methylamino)-1-[4-(trifluoromethoxy)phenyl]propan-2-ol;
4-amino-1-(3-chlorophenyl)-1-(1H-indol-1-yl)butan-2-ol
1-(3-bromophenyl)-1-(1H-indol-1-yl)-3-(methylamino)propan-2-ol;
3-[2-hydroxy-1-(1H-indol-1-yl)-3-(methylamino)propyl]benzonitrile
1-(3-fluorophenyl)-1-(1H-indol-1-yl)-3-(methylamino)propan-2-ol;
1-(3-fluorophenyl)-3-(methylamino)-1-[3-(3-methylphenyl)-1H-indol-1-yl]propan-2-ol;
1-(4-fluorophenyl)-3-(methylamino)-1-(3-methyl-1H-indol-1-yl)propan-2-ol;
1-(2-fluorophenyl)-1-(1H-indol-1-yl)-3-(methylamino)propan-2-ol;
1-(4-fluorophenyl)-1-(1H-indol-1-yl)-3-(methylamino)propan-2-ol;
1-(1H-indol-1-yl)-3-(methylamino)-1-(3-methylphenyl)propan-2-ol;
1-(1H-indol-1-yl)-3-(methylamino)-1-(2-methylphenyl)propan-2-ol;
1-(1H-indol-1-yl)-3-(methylamino)-1-(2-methylphenyl)propan-2-ol;
3-(ethylamino)-1-(3-fluorophenyl)-1-(1H-indol-1-yl)propan-2-ol;
1-(3-fluorophenyl)-1-(1H-indol-1-yl)-3-morpholin-4-ylpropan-2-ol;
1-(3-fluorophenyl)-1-(1H-indol-1-yl)-3-(propylamino)propan-2-ol;
1-(3-fluorophenyl)-1-(1H-indol-1-yl)-3-(4-methylpiperazin-1-yl)propan-2-ol;
1-(1H-indol-1-yl)-3-(methylamino)-1-(4-methylphenyl)propan-2-ol;
1-(2,3-dihydro-1H-indol-1-yl)-1-(3-fluorophenyl)-3-(methylamino)propan-2-ol;
1-(2,3-dihydro-1H-indol-1-yl)-3-(methylamino)-1-phenylpropan-2-ol;
1-(3-fluorophenyl)-3-(methylamino)-1-[3-(2-methylphenyl)-1H-indol-1-yl]propan-2-ol;
1-(3-fluorophenyl)-3-(methylamino)-1-(2-methyl-2,3-dihydro-1H-indol-1-yl)propan-2-ol;
1-(7-fluoro-3,3-dimethyl-2,3-dihydro-1H-indol-1-yl)-1-(3-fluorophenyl)-3-(methylamino)propan-2-ol;
1-(7-fluoro-3,3-dimethyl-2,3-dihydro-1H-indol-1-yl)-3-(methylamino)-1-phenylpropan-2-ol;
3-(methylamino)-1-(7-methyl-2,3-dihydro-1H-indol-1-yl)-1-phenylpropan-2-ol;
1-(3-fluorophenyl)-3-(methylamino)-1-(7-methyl-2,3-dihydro-1H-indol-1-yl)propan-2-ol;
1-(3-fluorophenyl)-3-(methylamino)-1-(5-methyl-2,3-dihydro-1H-indol-1-yl)propan-2-ol;

1-(1H-indol-1-yl)-1-(3-methoxyphenyl)-3-(methylamino)propan-2-ol;
1-(1H-indol-1-yl)-1-(4-methoxyphenyl)-3-(methylamino)propan-2-ol;
3-(methylamino)-1-(2-methyl-1H-indol-1-yl)-1-phenylpropan-2-ol;
1-(1H-benzimidazol-1-yl)-3-(methylamino)-1-phenylpropan-2-ol;
3-(methylamino)-1-(2-methyl-1H-benzimidazol-1-yl)-1-phenylpropan-2-ol;
1-(4-methoxy-1H-indol-1-yl)-3-(methylamino)-1-phenylpropan-2-ol;
1-(5-fluoro-1H-indol-1-yl)-3-(methylamino)-1-phenylpropan-2-ol;
1-(5-methoxy-1H-indol-1-yl)-3-(methylamino)-1-phenylpropan-2-ol;
1-(7-methoxy-1H-indol-1-yl)-3-(methylamino)-1-phenylpropan-2-ol;
1-(4-methoxy- 1H-indol-1-yl)-3-(methylamino)-1-phenylpropan-2-ol;
1-(6-methoxy-1H-indol-1-yl)-3-(methylamino)-1-phenylpropan-2-ol;
1-(5-methoxy-1H-indol-1-yl)-3-(methylamino)-1-phenylpropan-2-ol;
1-(3-fluorophenyl)-1-(6-methoxy-1H-indol-1-yl)-3-(methylamino)propan-2-ol;
3-(methylamino)-1-phenyl-1-(1H-pyrrolo[2,3-b]pyridin-1-yl)propan-2-ol;
1-(5-chloro-2,3-dihydro-1H-indol-1-yl)-1-(3-fluorophenyl)-3-(methylamino)propan-2-ol;
3-(methylamino)-1-phenyl-1-(1H-pyrrolo[2,3-c]pyridin-1-yl)propan-2-ol;
1-(5-fluoro-1H-indol-1-yl)-1-(3-fluorophenyl)-3-(methylamino)propan-2-ol;
3-(methylamino)-1-(3-fluorophenyl)-1-(1H-pyrrolo[2,3-c]pyridin-1-yl)propan-2-ol;
1-(5-chloro-2,3-dihydro-1H-indol-1-yl)-3-(methylamino)-1-phenylpropan-2-ol;
3-(methylamino)-1-(6-methyl-1H-indol-1-yl)-1-phenylpropan-2-ol;
3-(methylamino)-1-(7-methyl-1H-indol-1-yl)-1-phenylpropan-2-ol;
1-(3-fluorophenyl)-3-(methylamino)-1-(5-methyl-1H-indol-1-yl)propan-2-ol;
1-(3-fluorophenyl)-3-(methylamino)-1-(7-methyl-1H-indol-1-yl)propan-2-ol;
3-(methylamino)-1-(4-methyl-1H-indol-1-yl)-1-phenylpropan-2-ol;
3-(methylamino)-1-(5-methyl-1H-indol-1-yl)-1-phenylpropan-2-ol;
1-(3-fluorophenyl)-3-(methylamino)-1-(4-methyl-1H-indol-1-yl)propan-2-ol;
1-(3-ethyl-1H-indol-1-yl)-1-(3-fluorophenyl)-3-(methylamino)propan-2-ol;
1-(3-fluorophenyl)-3-(methylamino)-1-(3-phenyl-1H-indol-1-yl)propan-2-ol;
7-fluoro-1-[2hydroxy-3-(methylamino)-1-phenylpropyl]-3,3-dimethyl-1,3-dihydro-2H-indol-2-one;
1-[2hydroxy-3-(methylamino)-1-phenylpropyl]-3,3-dimethyl-1,3-dihydro-2H-indol-2-one;
7-fluoro-1-[1-(3-fluorophenyl)-2-hydroxy-3-(methylamino)propyl]-3,3-dimethyl-1,3-dihydro-2H-indol-2-one;
1-(1H-indol-1-yl)-3-(methylamino)-1-(2-thienyl)propan-2-ol;
1(1H-indol-1-yl)-3-(methylamino)-1-(2-thienyl)propan-2-ol;
1'-[2-hydroxy-3-(methylamino)-1-phenylpropyl]spiro[cyclohexane-1,3'-indol]-2'(1'H)-one;
2-(3-fluorophenyl)-2-(1H-indol-1-yl)-1-[(2S)-pyrrolidin-2-yl]ethanol;
2-(3-fluorophenyl)-2-(1H-indol-1-yl)-1-[pyrrolidin-2-yl]ethanol;
1'-[2hydroxy-3-(methylamino)-1-phenylpropyl]spiro[cyclobutane-1,3'-indol]-2'(1'H)-one;
1'-[2hydroxy-3-(methylamino)-1-phenylpropyl]spiro[cyclopentane-1,3'-indol]-2'(1'H)-one;
1'-[2hydroxy-3-(methylamino)-1-phenylpropyl]spiro[cyclopropane-1,3'-indol]-2'(1'H)-one;
5-fluoro-1-[2hydroxy-3-(methylamino)- 1-phenylpropyl]-3,3-dimethyl-1,3-dihydro-2H-indol-2-one;
3-(cyclopropylamino)-1-(3-fluorophenyl)-1-(1H-indol-1-yl)propan-2-ol;
7'-fluoro-1'-[2hydroxy-3-(methylamino)- 1-phenylpropyl]spiro[cyclohexane-1,3'-indol]-2'(1'H)-one;
5'-bromo-1'-[2hydroxy-3-(methylamino)-1-phenylpropyl]spiro[cyclohexane-1,3'-indol]-2'(1'H)-one;
1-(3-fluorophenyl)-1-[3-(2-fluorophenyl)-1H-indol-1-yl]-3-(methylamino)propan-2-ol;
1-[3-(3,4-dichlorophenyl)-1H-indol-1-yl]-1-(3-fluorophenyl)-3-(methylamino)propan-2-ol;
1-(3-fluorophenyl)-1-[3-(3-fluorophenyl)-1H-indol-1-yl]-3-(methylamino)propan-2-ol;
1-(5-fluoro-3-methyl-1H-indol-1-yl)-3-(methylamino)-1-phenylpropan-2-ol;
3-amino-1-(5-fluoro-3-methyl-1H-indol-1-yl)-1-phenylpropan-2-ol;
1-(5-chloro-3-methyl-1H-indol-1-yl)-3-(methylamino)-1-phenylpropan-2-ol;
3amino-1-(5-chloro-3-methyl-1H-indol-1-yl)-1-phenylpropan-2-ol;
[3-(5-chloro-3-methyl-1H-indol-1-yl)-2-methoxy-3-phenylpropyl]methylamine;
1-(7-chloro-3-methyl-1H-indol-1-yl)-3-(methylamino)-1-phenylpropan-2-ol;
[3-(5-fluoro-3-methyl-1H-indol-1-yl)-2-methoxy-3-phenylpropyl]methylamine;
1-(4-bromo-1H-indol-1-yl)-3-(methylamino)-1-phenylpropan-2-ol;
1-(4-bromo-1H-indol-1-yl)-1-(3-fluorophenyl)-3-(methylamino)propan-2-ol;
1-(5-bromo-1H-indol-1-yl)-3-(methylamino)- 1-phenylpropan-2-ol;
1-(5-bromo-1H-indol-1-yl)-1-(3-fluorophenyl)-3-(methylamino)propan-2-ol;
1-[2-hydroxy-3-(methylamino)-1-phenylpropyl]-1H-indole-4-carbonitrile;
1-(6-bromo-1H-indol-1-yl)-3-(methylamino)-1-phenylpropan-2-ol;
1-[2-hydroxy-3-(methylamino)-1-phenylpropyl]-1H-indole-5-carbonitrile;
1-[1-(3-fluorophenyl)-2-hydroxy-3-(methylamino)propyl]-1H-indole-4-carbonitrile;
1-(6-bromo-1H-indol-1-yl)-1-(3-fluorophenyl)-3-(methylamino)propan-2-ol;
1-(6-fluoro-1H-indol-1-yl)-1-(3-fluorophenyl)-3-(methylamino)propan-2-ol;
3-amino-1-(3-fluorophenyl)-1-(1H-indol-1-yl)propan-2-ol;
1-(7-bromo-1H-indol-1-yl)-1-(3-fluorophenyl)-3-(methylamino)propan-2-ol;
1-(1H-indol-1-yl)-3-(methylamino)-1-[3-(trifluoromethyl)phenyl]propan-2-ol;
1-(3-fluorophenyl)-3-(methylamino)-1-spiro[cyclohexane-1,3'-indol]-1'(2'H)-ylpropan-2-ol;
1-(2,3-dihydro-1H-indol-1-yl)-3-(methylamino)-1-[3-(trifluoromethyl)phenyl]propan-2-ol;
1-(3-fluorophenyl)-1-(1H-indol-1-yl)-3-(methylamino)propan-2-ol;

1-(3,4-difluorophenyl)-1-(1H-indol-1-yl)-3-(methylamino)propan-2-ol;
1-(3-fluorophenyl)-3-(methylamino)-1-(3-methyl-1H-indol-1-yl)propan-2-ol;
1-(4-chloro-1H-indol-1-yl)-3-(methylamino)-1-phenylpropan-2-ol;
1-(6-chloro-1H-indol-1-yl)-3-(methylamino)-1-phenylpropan-2-ol;
1-(7-chloro-1H-indol-1-yl)-3-(methylamino)-1-phenylpropan-2-ol;
1-(7-chloro-1H-indol-1-yl)-1-(3-fluorophenyl)-3-(methylamino)propan-2-ol;
1-(4-chloro-1H-indol-1-yl)-1-(3-fluorophenyl)-3-(methylamino)propan-2-ol;
1-(6-chloro-1H-indol-1-yl)-1-(3-fluorophenyl)-3-(methylamino)propan-2-ol;
1-(5-chloro-1H-indol-1-yl)-3-(methylamino)-1-phenylpropan-2-ol;
1-(5-chloro-1H-indol-1-yl)-1-(3-fluorophenyl)-3-(methylamino)propan-2-ol;
1-(3-isopropyl-1H-indol-1-yl)-3-(methylamino)-1-phenylpropan-2-ol;
1-(3-fluorophenyl)-1-(3-isopropyl-1H-indol-1-yl)-3-(methylamino)propan-2-ol;
1-(3,5-difluorophenyl)-1-(1H-indol-1-yl)-3-(methylamino)propan-2-ol;
1-(3,5-difluorophenyl)-1-(2,3-dihydro-1H-indol-1-yl)-3-(methylamino)propan-2-ol;
4-amino-1-(3-fluorophenyl)-1-(1H-indol-1-yl)butan-2-ol;
1-(3,3-dimethyl-2,3-dihydro-1H-indol-1-yl)-1-(3-fluorophenyl)-3-(methylamino)propan-2-ol;
1-(3,5-difluorophenyl)-1-(3,3-dimethyl-2,3-dihydro-1H-indol-1-yl)-3-(methylamino)propan-2-ol;
1-(3,3-dimethyl-2,3-dihydro-1H-indol-1-yl)-3-(methylamino)-1-phenylpropan-2-ol;
1-(3-fluorophenyl)-3-(methylamino)-1-(3-methyl-2,3-dihydro-1H-indol-1-yl)propan-2-ol;
1-(3-fluorophenyl)-3-(methylamino)-1-spiro[cyclopentane-1,3'-indol]-1'(2'H)-ylpropan-2-ol;
1-(3-fluorophenyl)-1-[3-(4-methoxyphenyl)-1H-indol-1-yl]-3-(methylamino)propan-2-ol;
1-(3-fluorophenyl)-3-(methylamino)-1-[3-(4-methylphenyl)-1H-indol-1-yl]propan-2-ol;
1-[3-(4-tert-butylphenyl)-1H-indol-1-yl]-1-(3-fluorophenyl)-3-(methylamino)propan-2-ol;
1-(3-fluorophenyl)-1-[3-(3-methoxyphenyl)-1H-indol-1-yl]-3-(methylamino)propan-2-ol;
1-(3-fluorophenyl)-3-(methylamino)-1-{3-[4-(trifluoromethyl)phenyl]-1H-indol-1-yl}propan-2-ol;
1-(3,5-difluorophenyl)-1-(6-fluoro-2,3-dihydro-1H-indol-1-yl)-3-(methylamino)propan-2-ol;
1-(3-fluorophenyl)-3-(methylamino)-1-{3-[2-(trifluoromethyl)phenyl]-1H-indol-1-yl}propan-2-ol;
1-(3-fluorophenyl)-1-[3-(2-methoxyphenyl)-1H-indol-1-yl]-3-(methylamino)propan-2-ol;
1-(3-fluorophenyl)-3-(methylamino)-1-{3-[3-(trifluoromethyl)phenyl]-1H-indol-1-yl}propan-2-ol;
3-amino-1-(3-methyl-1H-indol-1-yl)-1-phenylpropan-2-ol;
1-(7-fluoro-3-methyl-1H-indol-1-yl)-3-(methylamino)-1-phenylpropan-2-ol;
3-amino-1-(7-fluoro-3-methyl-1H-indol-1-yl)-1-phenylpropan-2-ol;
1-(7-fluoro-1H-indol-1-yl)-3-(methylamino)-1-phenylpropan-2-ol;
1-(4-fluoro-1H-indol-1-yl)-3-(methylamino)-1-phenylpropan-2-ol;
1-(7-fluoro-1H-indol-1-yl)-1-(3-fluorophenyl)-3-(methylamino)propan-2-ol;
1-(4-fluoro-1H-indol-1-yl)-1-(3-fluorophenyl)-3-(methylamino)propan-2-ol;
1-(3-fluorophenyl)-3-(methylamino)-1-[5-(trifluoromethyl)-1H-indol-1-yl]propan-2-ol;
1-(6-fluoro-1H-indol-1-yl)-3-(methylamino)-1-phenylpropan-2-ol;
3-(methylamino)-1-phenyl-1-[6-(trifluoromethyl)-1H-indol-1-yl]propan-2-ol;
3-(methylamino)-1-phenyl-1-[5-(trifluoromethyl)-1H-indol-1-yl]propan-2-ol;
1-(3-tert-butyl-1H-indol-1-yl)-1-(3-fluorophenyl)-3-(methylamino)propan-2-ol;
1-(1H-indol-1-yl)-2-methyl-3-(methylamino)-1-phenylpropan-2-ol;
3-(1H-indol-1-yl)-1-(methylamino)-3-phenylbutan-2-ol;
1-tert-butyl-3-[2hydroxy-3-(methylamino)-1-phenylpropyl]-1,3-dihydro-2H-benzimidazol-2-one;
1-[2-hydroxy-3-(methylamino)-1-phenylpropyl]-3-propyl-1,3-dihydro-2H-benzimidazol-2-one;
5-bromo-1-[2hydroxy-3-(methylamino)-1-phenylpropyl]-3,3-dimethyl-1,3-dihydro-2H-indol-2-one;
6-fluoro-1-[2hydroxy-3-(methylamino)-1-phenylpropyl]-3,3-dimethyl-1,3-dihydro-2H-indol-2-one;
4-fluoro-1-[2hydroxy-3-(methylamino)-1-phenylpropyl]-3,3-dimethyl-1,3-dihydro-2H-indol-2-one;
1-cyclobutyl-3-[2hydroxy-3-(methylamino)-1-phenylpropyl]-1,3-dihydro-2H-benzimidazol-2-one;
5-fluoro-3-[2hydroxy-3-(methylamino)-1-phenylpropyl]-1-propyl-1,3-dihydro-2H-benzimidazol-2-one;
1-ethyl-3-[1-(3-fluorophenyl)-2-hydroxy-3-(methylamino)propyl]-1,3-dihydro-2H-benzimidazol-2-one;
1-ethyl-3-[2hydroxy-3-(methylamino)-1-phenylpropyl]-1,3-dihydro-2H-benzimidazol-2-one;
4-fluoro-3-[2hydroxy-3-(methylamino)-1-phenylpropyl]-1-isopropyl-1,3-dihydro-2H-benzimidazol-2-one;
1-cyclopentyl-3-[2hydroxy-3-(methylamino)-1-phenylpropyl]-1,3-dihydro-2H-benzimidazol-2-one;
1-[2hydroxy-3-(methylamino)-1-phenylpropyl]-3-isopropyl-1,3-dihydro-2H-benzimidazol-2-one;
3-[3(ethylamino)-2-hydroxy-1-phenylpropyl]-5-fluoro-1-isopropyl-1,3-dihydro-2H-benzimidazol-2-one;
1-[2hydroxy-3-(methylamino)-1-phenylpropyl]-3-methyl-1,3-dihydro-2H-benzimidazol-2-one;
1-ethyl-5-fluoro-3-[2-hydroxy-3-(methylamino)-1-phenylpropyl]-1,3-dihydro-2H-benzimidazol-2-one;
1-ethyl-4-fluoro-3-[2-hydroxy-3-(methylamino)-1-phenylpropyl]-1,3-dihydro-2H-benzimidazol-2-one;
4-fluoro-3-[1-(3-fluorophenyl)-2-hydroxy-3-(methylamino)propyl]-1-isopropyl-1,3-dihydro-2H-benzimidazol-2-one;
1-ethyl-4-fluoro-3-[2hydroxy-3-(methylamino)-1-(3-fluorophenyl)-propyl]-1,3-dihydro-2H-benzimidazol-2-one;
1-[1-(3-fluorophenyl)-2-hydroxy-3-(methylamino)propyl]-3,3-dimethyl-1,3-dihydro-2H-indol-2-one;
1-[3-(2,3-difluorophenyl)-1H-indol-1-yl]-1-(3-fluorophenyl)-3-(methylamino)propan-2-ol;
1-[3-(2-chlorophenyl)-1H-indol-1-yl]-1-(3-fluorophenyl)-3-(methylamino)propan-2-ol; or a pharmaceutically acceptable salt thereof.

27. A compound according to claim 1, wherein said compound is:
(1RS,2SR)-1-(1H-indol-1-yl)-3-(4-methylpiperazin-1-yl)-1-phenylpropan-2-ol;
(1RS,2SR)-1-(5-fluoro-1H-indol-1-yl)-3-(4-methylpiperazin-1-yl)-1-phenylpropan-2-ol;
(1RS,2SR)-1-(1H-indol-1-yl)-3-morpholin-4-yl-1-phenylpropan-2-ol;
(1RS,2SR)-3-(dimethylamino)-1-(1H-indol-1-yl)-1-phenylpropan-2-ol;

(1RS,2SR)-3-(ethylamino)-1-(1H-indol-1-yl)-1-phenylpropan-2-ol;
(1RS,2SR)-1-(1H-indol-1-yl)-3-(isopropylamino)-1-phenylpropan-2-ol;
(1RS,2SR)-3-(benzylamino)-1-(1H-indol-1-yl)-1-phenylpropan-2-ol;
(1RS,2SR)-3-[(cyclohexylmethyl)amino]-1-(1H-indol-1-yl)-1-phenylpropan-2-ol;
(1RS,2SR)-3-[(cyclohexylmethyl)amino]-1-(3-methyl-1H-indol-1-yl)-1-phenylpropan-2-ol;
(1RS,2SR)-3-(isopropylamino)-1-(3-methyl-1H-indol-1-yl)-1-phenylpropan-2-ol;
(1RS,2SR)-1-(1H-indol-1-yl)-3-(methylamino)-1-phenylpropan-2-ol;
(1RS,2SR)-3-(ethylamino)-1-(3-methyl-1H-indol-1-yl)-1-phenylpropan-2-ol;
(1RS,2SR)-1-(1H-indol-1yl)-1-phenyl-3-piperazin-1-ylpropan-2-ol;
(1RS,2SR)-1-(1H-indol-1-yl)-1-phenyl-3-[(pyridin-4-ylmethyl) amino]propan-2-ol;
(1RS,2SR)-1-(5-chloro-1H-indol-1-yl)-1-phenyl-3-piperidin-1-ylpropan-2-ol;
(1RS,2RS)-1-(1H-indol-1-yl)-3-(methylamino)-1-phenylpropan-2-ol;
(1RS,2SR)-3-amino-1-(1H-indol-1-yl)-1-phenylpropan-2-ol;
(1RS,2SR)-3-(ethylamino)-1-(5-fluoro-1H-indol-1-yl)-1-phenylpropan-2-ol;
(1RS,2SR)-3-amino-1-(5-fluoro-1H-indol-1-yl)-1-phenylpropan-2-ol;
(1RS,2SR)-1-(5-fluoro-1H-indol-1-yl)-3-(methylamino)-1-phenylpropan-2-ol;
(1RS,2SR)-3-(methylamino)-1-(3-methyl-1H-indol-1-yl)-1-phenylpropan-2-ol;
(1R,2S)-1-(1H-indol-1-yl)-3-(methylamino)-1-phenylpropan-2-ol;
(1S,2R)-1-(1H-indol-1-yl)-3-(methylamino)-1-phenylpropan-2-ol;
(1RS,2SR)-3-amino-1-(3-methyl-1H-indol-1-yl)-1-phenylpropan-2-ol;
(1RS,2SR)-3-[ethyl(methyl)amino]-1-(1H-indol-1-yl)-1-phenylpropan-2-ol;
(1RS,2SR)-1-(5-chloro-1H-indol-1-yl)-3-(methylamino)-1-phenylpropan-2-ol;
(1RS,2RS)-1-(5-chloro-1H-indol-1-yl)-3-(methylamino)-1-phenylpropan-1-ol;
1-[(1RS,2SR)-2-hydroxy-3-(methylamino)-1-phenylpropyl]-1H-indole-3-carbonitrile;
(1R,2R)-1-(1H-indol-1-yl)-3-(methylamino)-1-phenylpropan-2-ol;
(1S,2S)-1-(1H-indol-1-yl)-3-(methylamino)-1-phenylpropan-2-ol;
(1S,2R)-3-(methylamino)-1-(3-methyl-1H-indol-1-yl)-1-phenylpropan-2-ol;
(1S,2R)-1-(3-chlorophenyl)-1-(1H-indol-1-yl)-3-(methylamino)propan-2-ol;
(1S,2R)-1-(4-chlorophenyl)-1-(1H-indol-1-yl)-3-(methylamino)propan-2-ol;
(1S,2R)-1-(1H-indol-1-yl)-3-(methylamino)-1-[3-(trifluoromethoxy)phenyl]propan-2-ol;
(1S,2R)-1-(1H-indol-1-yl)-3-(methylamino)-1-[2-(trifluoromethoxy)phenyl]propan-2-ol;
(1R,2S)-1-(1H-indol-1-yl)-3-(methylamino)-1-[2-(trifluoromethoxy)phenyl]propan-2-ol;
(1S,2R)-1-(2-chlorophenyl)-1-(1H-indol-1yl)-3-(methylamino)propan-2-ol;
(1SR,2RS)-1-(1H-indol-1-yl)-3-(methylamino)-1-[4-(trifluoromethoxy)phenyl]propan-2-ol;
(1S,2R)-1-(1H-indol-1-yl)-3-(methylamino)-1-[4-(trifluoromethoxy)phenyl]propan-2-ol;
(1R,2S)-1-(1H-indol-1-yl)-3-(methylamino)-1-[4-(trifluoromethoxy)phenyl]propan-2-ol;
(1S,2R)-4-amino-1-(3-chlorophenyl)-1-(1H-indol-1-yl)butan-2-ol
(1S,2R)-1-(3-bromophenyl)-1-(1H-indol-1-yl)-3-(methylamino)propan-2-ol;
3-[(1S,2R)-2-hydroxy-1-(1H-indol-1-yl)-3-(methylamino)propyl]benzonitrile
(1S,2R)-1-(3-fluorophenyl)-1-(1H-indol-1-yl)-3-(methylamino)propan-2-ol;
(1S,2R)-1-(3-fluorophenyl)-3-(methylamino)-1-[3-(3-methylphenyl)-1H-indol-1-yl]propan-2-ol;
(1S,2R)-1-(4-fluorophenyl)-3-(methylamino)-1-(3-methyl-1H-indol-1-yl)propan-2-ol;
(1S,2R)-1-(2-fluorophenyl)-1-(1H-indol-1-yl)-3-(methylamino)propan-2-ol;
(1S,2R)-1-(4-fluorophenyl)-1-(1H-indol-1-yl)-3-(methylamino)propan-2-ol;
(1S,2R)-1-(1H-indol-1-yl)-3-(methylamino)-1-(3-methylphenyl)propan-2-ol;
(1S,2R)-1-(1H-indol-1-yl)-3-(methylamino)-1-(2-methylphenyl)propan-2-ol;
(1R,2S)-1-(1H-indol-1-yl)-3-(methylamino)-1-(2-methylphenyl)propan-2-ol;
(1S,2R)-3-(ethylamino)-1-(3-fluorophenyl)-1-(1H-indol-1-yl)propan-2-ol;
(1S,2R)-1-(3-fluorophenyl)-1-(1H-indol-1-yl)-3-morpholin-4-ylpropan-2-ol;
(1S,2R)-1-(3-fluorophenyl)-1-(1H-indol-1-yl)-3-(propylamino)propan-2-ol;
(1S,2R)-1-(3-fluorophenyl)-1-(1H-indol-1-yl)-3-(4-methylpiperazin-1-yl)propan-2-ol;
(1S,2R)-1-(1H-indol-1-yl)-3-(methylamino)-1-(4-methylphenyl)propan-2-ol;
(1S,2R)-1-(2,3-dihydro-1H-indol-1-yl)-1-(3-fluorophenyl)-3-(methylamino)propan-2-ol;
(1S,2R)-1-(2,3-dihydro-1H-indol-1-yl)-3-(methylamino)-1-phenylpropan-2-ol;
(1S,2R)-1-(3-fluorophenyl)-3-(methylamino)-1-[3-(2-methylphenyl)-1H-indol-1-yl]propan-2-ol;
(1S,2R)-1-(3-fluorophenyl)-3-(methylamino)-1-(2-methyl-2,3-dihydro-1H-indol-1-yl)propan-2-ol;
(1S,2R)-1-(7-fluoro-3,3-dimethyl-2,3-dihydro-1H-indol-1-yl)-1-(3-fluorophenyl)-3-(methylamino)propan-2-ol;
(1S,2R)-1-(7-fluoro-3,3-dimethyl-2,3-dihydro-1H-indol-1-yl)-3-(methylamino)-1-phenylpropan-2-ol;
(1S,2R)-3-(methylamino)-1-(7-methyl-2,3-dihydro-1H-indol-1-yl)-1-phenylpropan-2-ol;
(1S,2R)-1-(3-fluorophenyl)-3-(methylamino)-1-(7-methyl-2,3-dihydro-1H-indol-1-yl)propan-2-ol;
(1S,2R)-1-(3-fluorophenyl)-3-(methylamino)-1-(5-methyl-2,3-dihydro-1H-indol-1-yl)propan-2-ol;
(1S,2R)-1-(1H-indol-1-yl)-1-(3-methoxyphenyl)-3-(methylamino)propan-2-ol;
(1SR,2RS)-1-(1H-indol-1-yl)-1-(4-methoxyphenyl)-3-(methylamino)propan-2-ol;
(1RS,2SR)-3-(methylamino)-1-(2-methyl-1H-indol-1-yl)-1-phenylpropan-2-ol;
(1RS,2SR)-1-(1H-benzimidazol-1-yl)-3-(methylamino)-1-phenylpropan-2-ol;
(1RS,2SR)-3-(methylamino)-1-(2-methyl-1H-benzimidazol-1-yl)-1-phenylpropan-2-ol;
(1RS,2SR)-1-(4-methoxy-1H-indol-1-yl)-3-(methylamino)-1-phenylpropan-2-ol;
(1S,2R)-1-(5-fluoro-1H-indol-1-yl)-3-(methylamino)-1-phenylpropan-2-ol;
(1S,2R)-1-(5-methoxy-1H-indol-1-yl)-3-(methylamino)-1-phenylpropan-2-ol;
(1S,2R)-1-(7-methoxy-1H-indol-1-yl)-3-(methylamino)-1-phenylpropan-2-ol;

(1S,2R)-1-(4-methoxy-1H-indol-1-yl)-3-(methylamino)-1-phenylpropan-2-ol;
(1S,2R)-1-(6-methoxy-1H-indol-1-yl)-3-(methylamino)-1-phenylpropan-2-ol;
(1RS,2SR)-1-(5-methoxy-1H-indol-1-yl)-3-(methylamino)-1-phenylpropan-2-ol;
(1S,2R)-1-(3-fluorophenyl)-1-(6-methoxy-1H-indol-1-yl)-3-(methylamino)propan-2-ol;
(1S,2R)-3-(methylamino)-1-phenyl-1-(1H-pyrrolo[2,3-b]pyridin-1-yl)propan-2-ol;
(1S,2R)-1-(5-chloro-2,3-dihydro-1H-indol-1-yl)-1-(3-fluorophenyl)-3-(methylamino)propan-2-ol;
(1S,2R)-3-(methylamino)-1-phenyl-1-(1H-pyrrolo[2,3-c]pyridin-1-yl)propan-2-ol;
(1S,2R)-1-(5-fluoro-1H-indol-1-yl)-1-(3-fluorophenyl)-3-(methylamino)propan-2-ol;
(1S,2R)-3-(methylamino)-1-(3-fluorophenyl)-1-(1H-pyrrolo[2,3-c]pyridin-1-yl)propan-2-ol;
(1S,2R)-1-(5-chloro-2,3-dihydro-1H-indol-1-yl)-3-(methylamino)-1-phenylpropan-2-ol;
(1S,2R)-3-(methylamino)-1-(6-methyl-1H-indol-1-yl)-1-phenylpropan-2-ol;
(1S,2R)-3-(methylamino)-1-(7-methyl-1H-indol-1-yl)-1-phenylpropan-2-ol;
(1S,2R)-1-(3-fluorophenyl)-3-(methylamino)-1-(5-methyl-1H-indol-1-yl)propan-2-ol;
(1S,2R)-1-(3-fluorophenyl)-3-(methylamino)-1-(7-methyl-1H-indol-1-yl)propan-2-ol;
(1S,2R)-3-(methylamino)-1-(4-methyl-1H-indol-1-yl)-1-phenylpropan-2-ol;
(1S,2R)-3-(methylamino)-1-(5-methyl-1H-indol-1-yl)-1-phenylpropan-2-ol;
(1S,2R)-1-(3-fluorophenyl)-3-(methylamino)-1-(4-methyl-1H-indol-1-yl)propan-2-ol;
(1S,2R)-1-(3-ethyl-1H-indol-1-yl)-1-(3-fluorophenyl)-3-(methylamino)propan-2-ol;
(1S,2R)-1-(3-fluorophenyl)-3-(methylamino)-1-(3-phenyl-1H-indol-1-yl)propan-2-ol;
7-fluoro-1-[(1S,2R)-2-hydroxy-3-(methylamino)-1-phenylpropyl]-3,3-dimethyl-1,3-dihydro-2H-indol-2-one;
1-[(1S,2R)-2-hydroxy-3-(methylamino)-1-phenylpropyl]-3,3-dimethyl-1,3-dihydro-2H-indol-2-one;
7-fluoro-1-[(1S,2R)-1-(3-fluorophenyl)-2-hydroxy-3-(methylamino)propyl]-3,3-dimethyl-1,3-dihydro-2H-indol-2-one;
(1S,2R)-1-(1H-indol-1-yl)-3-(methylamino)-1-(2-thienyl)propan-2-ol;
(1R,2R)-1-(1H-indol-1-yl)-3-(methylamino)-1-(2-thienyl)propan-2-ol;
1'-[(1S,2R)-2-hydroxy-3-(methylamino)-1-phenylpropyl]spiro[cyclohexane-1,3'-indol]-2'(1'H)-one;
(1S,2R)-2-(3-fluorophenyl)-2-(1H-indol-1-yl)-1-[(2S)-pyrrolidin-2-yl]ethanol;
(1R,2S)-2-(3-fluorophenyl)-2-(1H-indol-1-yl)-1-[(2S)-pyrrolidin-2-yl]ethanol;
1'-[(1S,2R)-2-hydroxy-3-(methylamino)-1-phenylpropyl]spiro[cyclobutane-1,3'-indol]-2'(1'H)-one;
1'-[(1S,2R)-2-hydroxy-3-(methylamino)-1-phenylpropyl]spiro[cyclopentane-1,3'-indol]-2'(1'H)-one;
1'-[(1S,2R)-2-hydroxy-3-(methylamino)-1-phenylpropyl]spiro[cyclopropane-1,3'-indol]-2'(1'H)-one;
5-fluoro-1-[(1S,2R)-2-hydroxy-3-(methylamino)-1-phenylpropyl]-3,3-dimethyl-1,3-dihydro-2H-indol-2-one;
(1S,2R)-3-(cyclopropylamino)-1-(3-fluorophenyl)-1-(1H-indol-1-yl)propan-2-ol;
7'-fluoro-1'-[(1S,2R)-2-hydroxy-3-(methylamino)-1-phenylpropyl]spiro[cyclohexane-1,3'-indol]-2'(1'H)-one;
5'-bromo-1'-[(1S,2R)-2-hydroxy-3-(methylamino)-1-phenylpropyl]spiro[cyclohexane-1,3'-indol]-2'(1'H)-one;

(1S,2R)-1-(3-fluorophenyl)-1-[3-(2-fluorophenyl)-1H-indol-1-yl]-3-(methylamino)propan-2-ol;
(1S,2R)-1-[3-(3,4-dichlorophenyl)-1H-indol-1-yl]-1-(3-fluorophenyl)-3-(methylamino)propan-2-ol;
(1S,2R)-1-(3-fluorophenyl)-1-[3-(3-fluorophenyl)-1H-indol-1-yl]-3-(methylamino)propan-2-ol;
(1S,2R)-1-(5-fluoro-3-methyl-1H-indol-1-yl)-3-(methylamino)-1-phenylpropan-2-ol;
(1S*,2R*)-3-amino-1-(5-fluoro-3-methyl-1H-indol-1-yl)-1-phenylpropan-2-ol;
(1S,2R)-1-(5-chloro-3-methyl-1H-indol-1-yl)-3-(methylamino)-1-phenylpropan-2-ol;
(1S,2R)-3-amino-1-(5-chloro-3-methyl-1H-indol-1-yl)-1-phenylpropan-2-ol;
[(2R,3 S)-3-(5-chloro-3-methyl-1H-indol-1-yl)-2-methoxy-3-phenylpropyl]methylamine;
(1S,2R)-1-(7-chloro-3-methyl-1H-indol-1-yl)-3-(methylamino)-1-phenylpropan-2-ol;
[(2R,3S)-3-(5-fluoro-3-methyl-1H-indol-1-yl)-2-methoxy-3-phenylpropyl]methylamine;
(1S,2R)-1-(4-bromo-1H-indol-1-yl)-3-(methylamino)-1-phenylpropan-2-ol;
(1S,2R)-1-(4-bromo-1H-indol-1-yl)-1-(3-fluorophenyl)-3-(methylamino)propan-2-ol;
(1S,2R)-1-(5-bromo-1H-indol-1-yl)-3-(methylamino)-1-phenylpropan-2-ol;
(1S,2R)-1-(5-bromo-1H-indol-1-yl)-1-(3-fluorophenyl)-3-(methylamino)propan-2-ol;
1-[(1S,2R)-2-hydroxy-3-(methylamino)-1-phenylpropyl]-1H-indole-4-carbonitrile;
(1S,2R)-1-(6-bromo-1H-indol-1-yl)-3-(methylamino)-1-phenylpropan-2-ol;
1-[(1S,2R)-2-hydroxy-3-(methylamino)-1-phenylpropyl]-1H-indole-5-carbonitrile;
1-[(1S,2R)-1-(3-fluorophenyl)-2-hydroxy-3-(methylamino)propyl]-1H-indole-4-carbonitrile;
(1S,2R)-1-(6-bromo-1H-indol-1-yl)-1-(3-fluorophenyl)-3-(methylamino)propan-2-ol;
(1S,2R)-1-(6-fluoro-1H-indol-1-yl)-1-(3-fluorophenyl)-3-(methylamino)propan-2-ol;
(1S,2R)-3-amino-1-(3-fluorophenyl)-1-(1H-indol-1-yl)propan-2-ol;
(1S,2R)-1-(7-bromo-1H-indol-1-yl)-1-(3-fluorophenyl)-3-(methylamino)propan-2-ol;
(1S,2R)-1-(1H-indol-1-yl)-3-(methylamino)-1-[3-(trifluoromethyl)phenyl]propan-2-ol;
(1S,2R)-1-(3-fluorophenyl)-3-(methylamino)-1-spiro[cyclohexane-1,3'-indol]-1'(2'H)-ylpropan-2-ol;
(1S,2R)-1-(2,3-dihydro-1H-indol-1-yl)-3-(methylamino)-1-[3-(trifluoromethyl)phenyl]propan-2-ol;
(1S,2S)-1-(3-fluorophenyl)-1-(1H-indol-1-yl)-3-(methylamino)propan-2-ol;
(1S,2R)-1-(3,4-difluorophenyl)-1-(1H-indol-1-yl)-3-(methylamino)propan-2-ol;
(1S,2R)-1-(3-fluorophenyl)-3-(methylamino)-1-(3-methyl-1H-indol-1-yl)propan-2-ol;
(1S,2R)-1-(4-chloro-1H-indol-1-yl)-3-(methylamino)-1-phenylpropan-2-ol;
(1S,2R)-1-(6-chloro-1H-indol-1-yl)-3-(methylamino)-1-phenylpropan-2-ol;
(1S,2R)-1-(7-chloro-1H-indol-1-yl)-3-(methylamino)-1-phenylpropan-2-ol;
(1S,2R)-1-(7-chloro-1H-indol-1-yl)-1-(3-fluorophenyl)-3-(methylamino)propan-2-ol;
(1S,2R)-1-(4-chloro-1H-indol-1-yl)-1-(3-fluorophenyl)-3-(methylamino)propan-2-ol;
(1S,2R)-1-(6-chloro-1H-indol-1-yl)-1-(3-fluorophenyl)-3-(methylamino)propan-2-ol;
(1S,2R)-1-(5-chloro-1H-indol-1-yl)-3-(methylamino)-1-phenylpropan-2-ol;

(1S,2R)-1-(5-chloro-1H-indol-1-yl)-1-(3-fluorophenyl)-3-(methylamino)propan-2-ol;
(1S,2R)-1-(3-isopropyl-1H-indol-1-yl)-3-(methylamino)-1-phenylpropan-2-ol;
(1S,2R)-1-(3-fluorophenyl)-1-(3-isopropyl-1H-indol-1-yl)-3-(methylamino)propan-2-ol;
(1S,2R)-1-(3,5-difluorophenyl)-1-(1H-indol-1-yl)-3-(methylamino)propan-2-ol;
(1S,2R)-1-(3,5-difluorophenyl)-1-(2,3-dihydro-1H-indol-1-yl)-3-(methylamino)propan-2-ol;
(1S,2R)-4-amino-1-(3-fluorophenyl)-1-(1H-indol-1-yl)butan-2-ol;
(1S,2R)-1-(3,3-dimethyl-2,3-dihydro-1H-indol-1-yl)-1-(3-fluorophenyl)-3-(methylamino)propan-2-ol;
(1S,2R)-1-(3,5-difluorophenyl)-1-(3,3-dimethyl-2,3-dihydro-1H-indol-1-yl)-3-(methylamino)propan-2-ol;
(1S,2R)-1-(3,3-dimethyl-2,3-dihydro-1H-indol-1-yl)-3-(methylamino)-1-phenylpropan-2-ol;
(1,2R)-1-(3-fluorophenyl)-3-(methylamino)-1-(3-methyl-2,3-dihydro-1H-indol-1-yl)propan-2-ol;
(1S,2R)-1-(3-fluorophenyl)-3-(methylamino)-1-spiro[cyclopentane-1,3'-indol]-1'(2'H)-ylpropan-2-ol;
(1S,2R)-1-(3-fluorophenyl)-1-[3-(4-methoxyphenyl)-1H-indol-1-yl]-3-(methylamino)propan-2-ol;
(1S,2R)-1-(3-fluorophenyl)-3-(methylamino)-1-[3-(4-methylphenyl)-1H-indol-1-yl]propan-2-ol;
(1S,2R)-1-[3-(4-tert-butylphenyl)-1H-indol-1-yl]-1-(3-fluorophenyl)-3-(methylamino)propan-2-ol;
(1S,2R)-1-(3-fluorophenyl)-1-[3-(3-methoxyphenyl)-1H-indol-1-yl]-3-(methylamino)propan-2-ol;
(1S,2R)-1-(3-fluorophenyl)-3-(methylamino)-1-{3-[4-(trifluoromethyl)phenyl]-1H-indol-1-yl}propan-2-ol;
(1S,2R)-1-(3,5-difluorophenyl)-1-(6-fluoro-2,3-dihydro-1H-indol-1-yl)-3-(methylamino)propan-2-ol;
(1S,2R)-1-(3-fluorophenyl)-3-(methylamino)-1-{3-[2-(trifluoromethyl)phenyl]-1H-indol-1-yl}propan-2-ol;
(1S,2R)-1-(3-fluorophenyl)-1-[3-(2-methoxyphenyl)-1H-indol-1-yl]-3-(methylamino)propan-2-ol;
(1S,2R)-1-(3-fluorophenyl)-3-(methylamino)-1-{3-[3-(trifluoromethyl)phenyl]-1H-indol-1-yl}propan-2-ol;
(1S,2R)-3-amino-1-(3-methyl-1H-indol-1-yl)-1-phenylpropan-2-ol;
(1S,2R)-1-(7-fluoro-3-methyl-1H-indol-1-yl)-3-(methylamino)-1-phenylpropan-2-ol;
(1S,2R)-3-amino-1-(7-fluoro-3-methyl-1H-indol-1-yl)-1-phenylpropan-2-ol;
(1S,2R)-1-(7-fluoro-1H-indol-1-yl)-3-(methylamino)-1-phenylpropan-2-ol;
(1S,2R)-1-(4-fluoro-1H-indol-1-yl)-3-(methylamino)-1-phenylpropan-2-ol;
(1S,2R)-1-(7-fluoro-1H-indol-1-yl)-1-(3-fluorophenyl)-3-(methylamino)propan-2-ol;
(1S,2R)-1-(4-fluoro-1H-indol-1-yl)-1-(3-fluorophenyl)-3-(methylamino)propan-2-ol;
(1S,2R)-1-(3-fluorophenyl)-3-(methylamino)-1-[5-(trifluoromethyl)-1H-indol-1-yl]propan-2-ol;
(1S,2R)-1-(6-fluoro-1H-indol-1-yl)-3-(methylamino)-1-phenylpropan-2-ol;
(1S,2R)-3-(methylamino)-1-phenyl-1-[6-(trifluoromethyl)-1H-indol-1-yl]propan-2-ol;
(1S,2R)-3-(methylamino)-1-phenyl-1-[5-(trifluoromethyl)-1H-indol-1-yl]propan-2-ol;
(1S,2R)-1-(3-tert-butyl-1H-indol-1-yl)-1-(3-fluorophenyl)-3-(methylamino)propan-2-ol;
(1S,2R)-1-(1H-indol-1-yl)-2-methyl-3-(methylamino)-1-phenylpropan-2-ol;
(2R,3S)-3-(1H-indol-1-yl)-1-(methylamino)-3-phenylbutan-2-ol;
1-tert-butyl-3-[(1S,2R)-2-hydroxy-3-(methylamino)-1-phenylpropyl]-1,3-dihydro-2H-benzimidazol-2-one;
1-[(1S,2R)-2-hydroxy-3-(methylamino)-1-phenylpropyl]-3-propyl-1,3-dihydro-2H-benzimidazol-2-one;
5-bromo-1-[(1S,2R)-2-hydroxy-3-(methylamino)-1-phenylpropyl]-3,3-dimethyl-1,3-dihydro-2H-indol-2-one;
6-fluoro-1-[(1S,2R)-2-hydroxy-3-(methylamino)-1-phenylpropyl]-3,3-dimethyl-1,3-dihydro-2H-indol-2-one;
4-fluoro-1-[(1S,2R)-2-hydroxy-3-(methylamino)-1-phenylpropyl]-3,3-dimethyl-1,3-dihydro-2H-indol-2-one;
1-cyclobutyl-3-[(1S,2R)-2-hydroxy-3-(methylamino)-1-phenylpropyl]-1,3-dihydro-2H-benzimidazol-2-one;
5-fluoro-3-[(1S,2R)-2-hydroxy-3-(methylamino)-1-phenylpropyl]-1-propyl-1,3-dihydro-2H-benzimidazol-2-one;
1-ethyl-3-[(1S,2R)-1-(3-fluorophenyl)-2-hydroxy-3-(methylamino)propyl]-1,3-dihydro-2H-benzimidazol-2-one;
1-ethyl-3-[(1S,2R)-2-hydroxy-3-(methylamino)-1-phenylpropyl]-1,3-dihydro-2H-benzimidazol-2-one;
4-fluoro-3-[(1S,2R)-2-hydroxy-3-(methylamino)-1-phenylpropyl]-1-isopropyl-1,3-dihydro-2H-benzimidazol-2-one;
1-cyclopentyl-3-[(1S,2R)-2-hydroxy-3-(methylamino)-1-phenylpropyl]-1,3-dihydro-2H-benzimidazol-2-one;
1-[(1S,2R)-2-hydroxy-3-(methylamino)-1-phenylpropyl]-3-isopropyl-1,3-dihydro-2H-benzimidazol-2-one;
3-[(1S,2R)-3-(ethylamino)-2-hydroxy-1-phenylpropyl]-5-fluoro-1-isopropyl-1,3-dihydro-2H-benzimidazol-2-one;
1-[(1S,2R)-2-hydroxy-3-(methylamino)-1-phenylpropyl]-3-methyl-1,3-dihydro-2H-benzimidazol-2-one;
1-ethyl-5-fluoro-3-[(1S,2R)-2-hydroxy-3-(methylamino)-1-phenylpropyl]-1,3-dihydro-2H-benzimidazol-2-one;
1-ethyl-4-fluoro-3-[(1S,2R)-2-hydroxy-3-(methylamino)-1-phenylpropyl]-1,3-dihydro-2H-benzimidazol-2-one;
4-fluoro-3-[(1S,2R)-1-(3-fluorophenyl)-2-hydroxy-3-(methylamino)propyl]-1-isopropyl-1,3-dihydro-2H-benzimidazol-2-one;
1-ethyl-4-fluoro-3-[(1S,2R)-2-hydroxy-3 -(methylamino)-1-(3-fluorophenyl)-propyl ]-1,3-dihydro-2H-benzimidazol-2-one;
1-[(1S,2R)-1-(3-fluorophenyl)-2-hydroxy-3-(methylamino)propyl]-3,3-dimethyl-1,3-dihydro-2H-indol-2-one;
(1S,2R)-1-[3-(2,3-difluorophenyl)-1H-indol-1-yl]-1-(3-fluorophenyl)-3-(methylamino)propan-2-ol;
(1S,2R)-1-[3-(2-chlorophenyl)-1H-indol-1-yl]-1-(3-fluorophenyl)-3-(methylamino)propan-2-ol; or a pharmaceutically acceptable salt thereof.

28. A composition, comprising:
at least one compound according to claim 1; and
at least one pharmaceutically acceptable carrier.

* * * * *